US011926676B2

United States Patent
Sagert et al.

(10) Patent No.: US 11,926,676 B2
(45) Date of Patent: Mar. 12, 2024

(54) MASKED CHIMERIC ANTIGEN RECEPTOR SPECIFIC TO TYROSINE-PROTEIN KINASE LIKE 7 (PTK7) AND IMMUNE CELLS EXPRESSING SUCH

(71) Applicant: CRISPR THERAPEUTICS AG, Zug (CH)

(72) Inventors: Jason Sagert, Cambridge, MA (US); Jui Dutta-Simmons, Cambridge, MA (US); Jonathan Alexander Terrett, Cambridge, MA (US)

(73) Assignee: CRISPR THERAPEUTICS AG, Zug (CH)

( * ) Notice: Subject to any disclaimer, the term of this patent is extended or adjusted under 35 U.S.C. 154(b) by 153 days.

(21) Appl. No.: 17/313,121

(22) Filed: May 6, 2021

(65) Prior Publication Data

US 2021/0347913 A1 Nov. 11, 2021

Related U.S. Application Data

(60) Provisional application No. 63/020,794, filed on May 6, 2020.

(51) Int. Cl.

| | |
|---|---|
| *C07K 16/40* | (2006.01) |
| *A61K 35/17* | (2015.01) |
| *A61K 38/00* | (2006.01) |
| *A61K 39/00* | (2006.01) |
| *A61P 35/00* | (2006.01) |
| *C07K 7/08* | (2006.01) |
| *C07K 14/47* | (2006.01) |
| *C07K 14/705* | (2006.01) |
| *C07K 14/725* | (2006.01) |
| *C12N 5/0783* | (2010.01) |

(52) U.S. Cl.
CPC .............. *C07K 16/40* (2013.01); *A61K 35/17* (2013.01); *A61P 35/00* (2018.01); *C07K 7/08* (2013.01); *C07K 14/47* (2013.01); *C07K 14/7051* (2013.01); *C07K 14/70517* (2013.01); *C07K 14/70521* (2013.01); *C07K 14/70578* (2013.01); *C12N 5/0636* (2013.01); *A61K 38/00* (2013.01); *A61K 2039/505* (2013.01); *A61K 2039/5156* (2013.01); *A61K 2039/5158* (2013.01); *C07K 2317/622* (2013.01); *C07K 2317/72* (2013.01); *C07K 2317/73* (2013.01); *C07K 2317/76* (2013.01); *C07K 2317/92* (2013.01); *C07K 2319/02* (2013.01); *C07K 2319/03* (2013.01); *C07K 2319/30* (2013.01); *C07K 2319/33* (2013.01); *C07K 2319/50* (2013.01); *C12N 2510/00* (2013.01)

(58) Field of Classification Search
CPC .......... C07K 16/40; C07K 7/08; C07K 14/47; C07K 14/7051; C07K 14/70517; C07K 14/70521; C07K 14/7058; C07K 2317/622; C07K 2137/72; C07K 2137/73; C07K 2317/76; C07K 231/92; C07K 2319/02; C07K 2319/03; C07K 2319/30; C07K 2319/33; A61K 35/17; A61K 38/00; A61K 2039/505; A61K 2039/5156; A61K 2039/5158; A61P 35/00; C12N 5/0636

See application file for complete search history.

(56) References Cited

U.S. PATENT DOCUMENTS

| | | | |
|---|---|---|---|
| 9,102,738 B2 * | 8/2015 | Terrett | ................... A61P 35/00 |
| 2015/0315293 A1 | 11/2015 | Damelin et al. | |
| 2018/0148508 A1 * | 5/2018 | Wang | ................. C07K 16/3023 |

FOREIGN PATENT DOCUMENTS

| | | | | |
|---|---|---|---|---|
| CA | 3101510 A1 | 12/2019 | | |
| WO | WO 2018/107125 A1 | 6/2018 | | |
| WO | WO 2018/213335 A1 | 11/2018 | | |
| WO | WO-2019232503 A1 * | 12/2019 | ............. | A61K 35/17 |
| WO | WO 2020/060593 A1 | 3/2020 | | |

OTHER PUBLICATIONS

GenBank AB977471.1; submitted Jul. 22, 2014. (Year: 2014).*
Chen et al., Selective antibody activation through protease-activated pro-antibodies that mask binding sites with inhibitory domains. Sci Rep. Sep. 14, 2017;7(1):11587(1-12).
Damelin et al., A PTK7-targeted antibody-drug conjugate reduces tumor-initiating cells and induces sustained tumor regressions. Sci Transl Med. Jan. 11, 2017;9(372):eaag2611(1-11).
Han et al., Masked Chimeric Antigen Receptor for Tumor-Specific Activation. Mol Ther. Jan. 4, 2017;25(1):274-284. Epub Jan. 4, 2017.
Zabel et al., The making and function of CAR cells. Immunol Lett. Aug. 2019;212:53-69. Epub Jun. 7, 2019.

* cited by examiner

*Primary Examiner* — Taeyoon Kim
*Assistant Examiner* — Eric J Rogers
(74) *Attorney, Agent, or Firm* — Casimir Jones, S.C.; J. Mitchell Jones

(57) ABSTRACT

Masked chimeric antigen receptor (CAR) constructs comprising an extracellular antigen binding domain specific tyrosine-protein kinase-like 7 (PTK7), which is linked to a mask peptide that blocks binding of masked CAR from binding to PTK7. Also provided herein are genetically engineered T cells expressing a masked CAR specific to PTK7 and therapeutic uses thereof.

30 Claims, 14 Drawing Sheets

Specification includes a Sequence Listing.

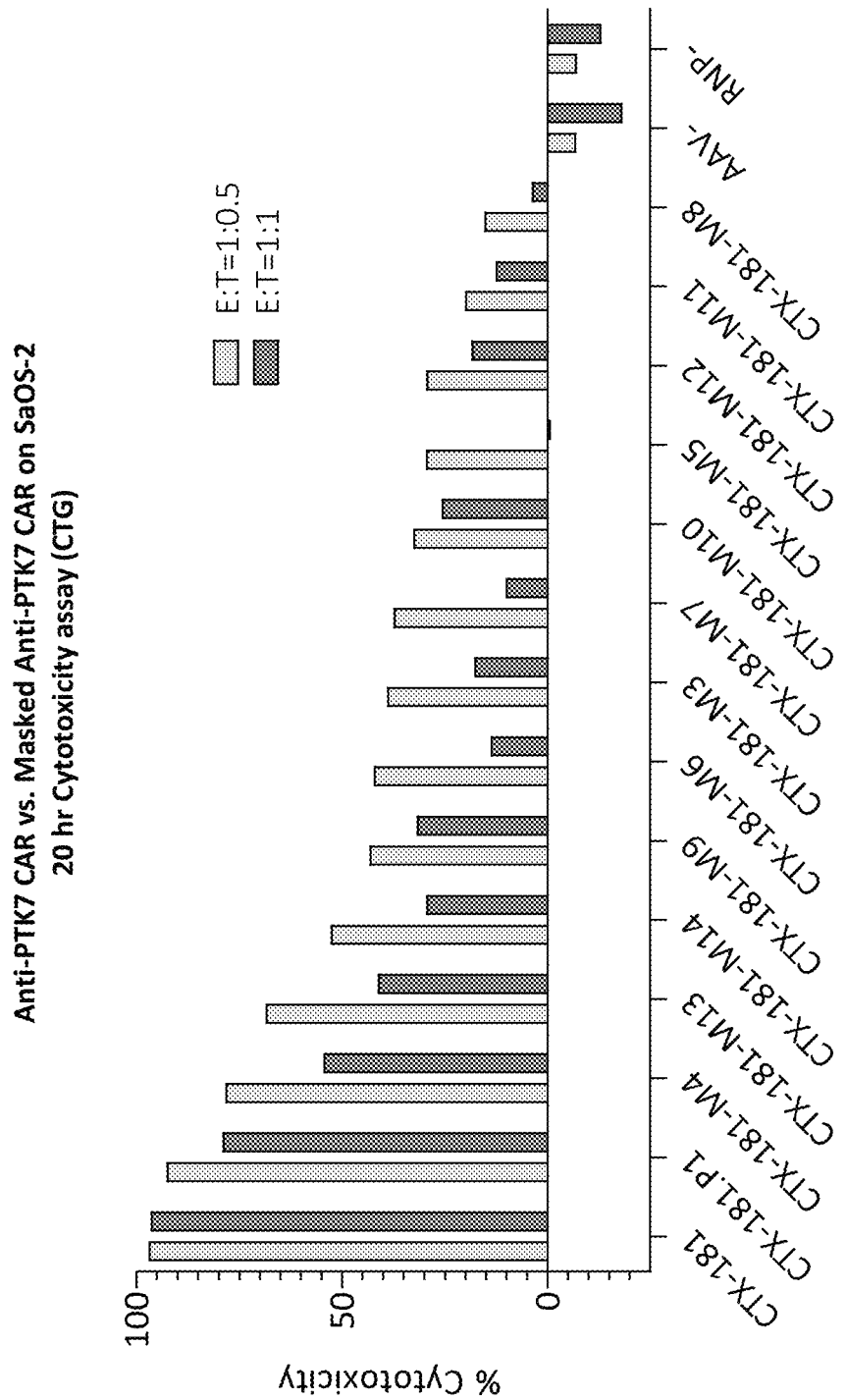

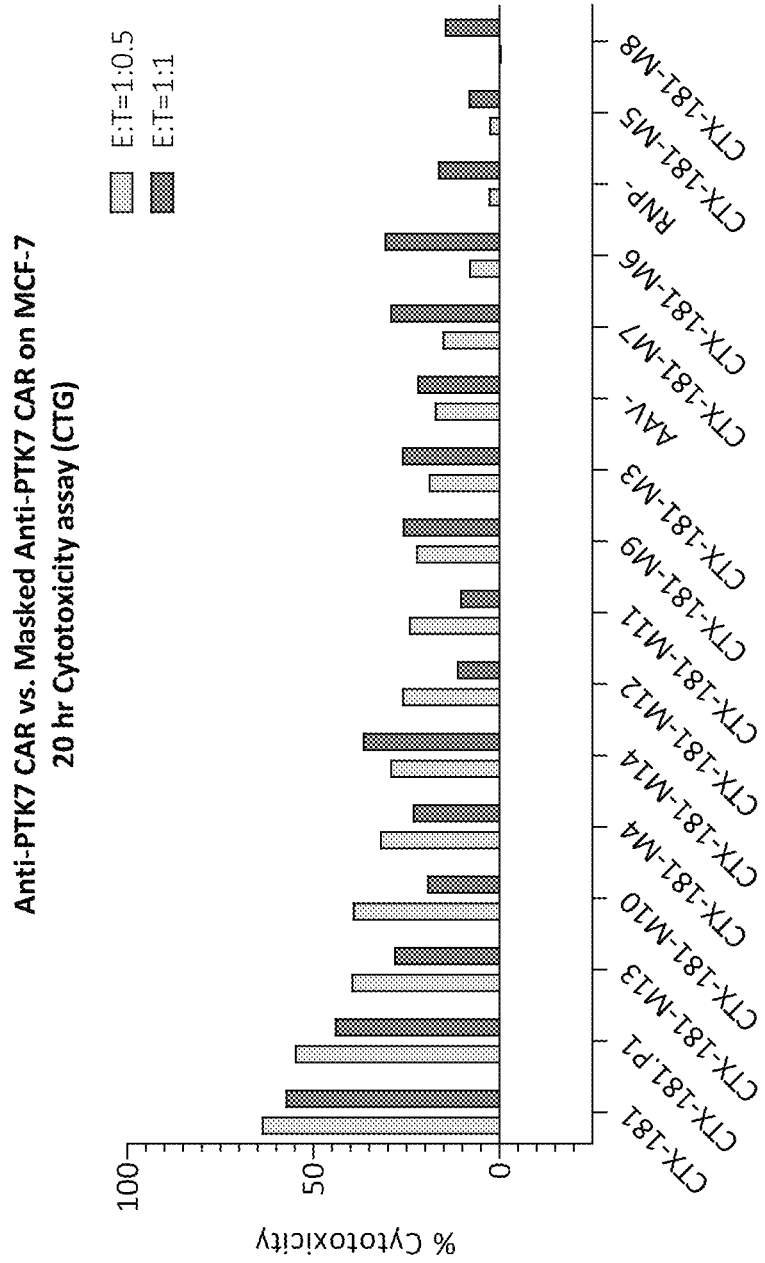

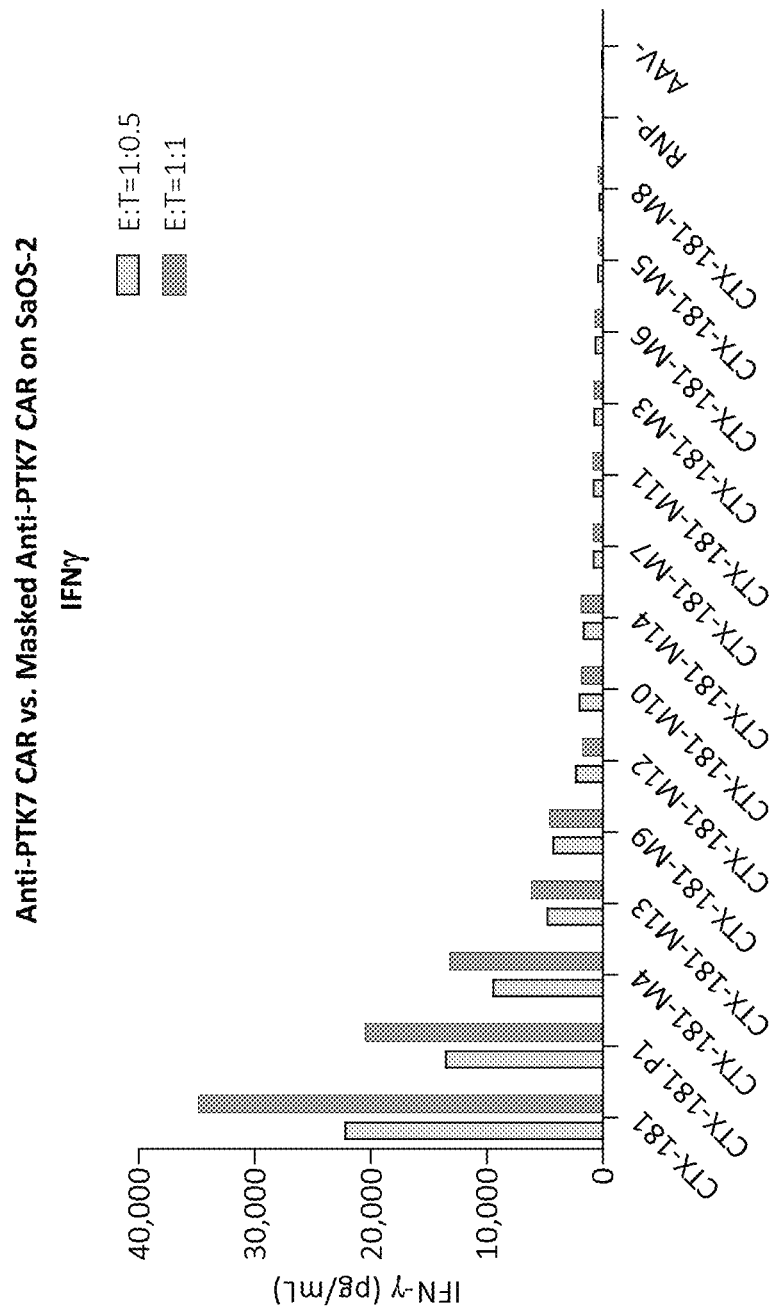

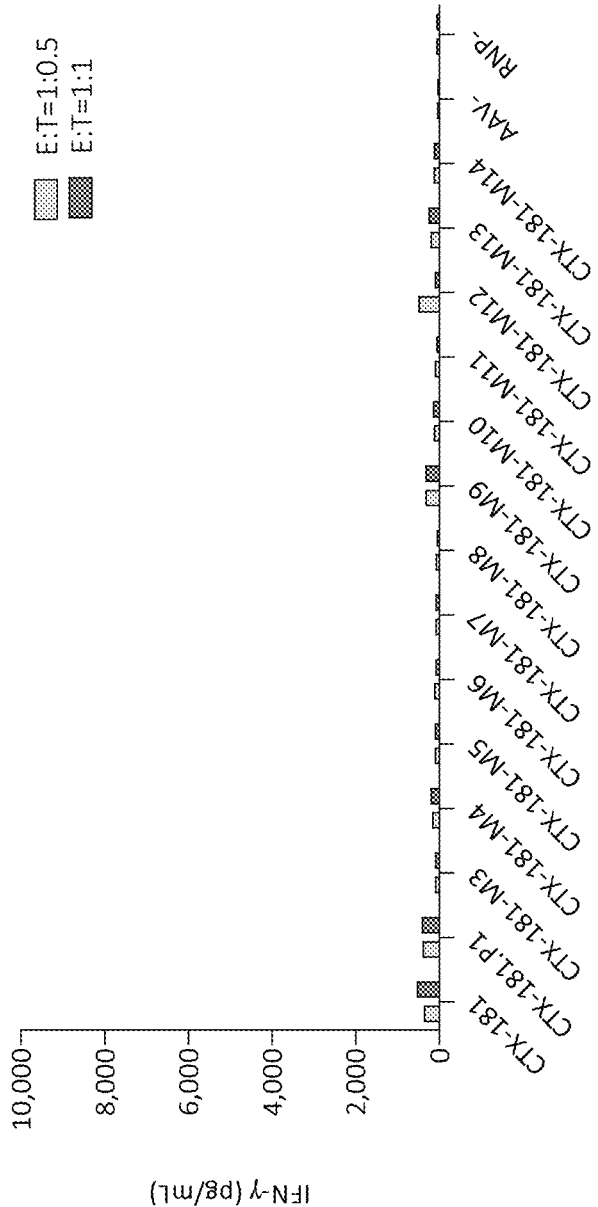

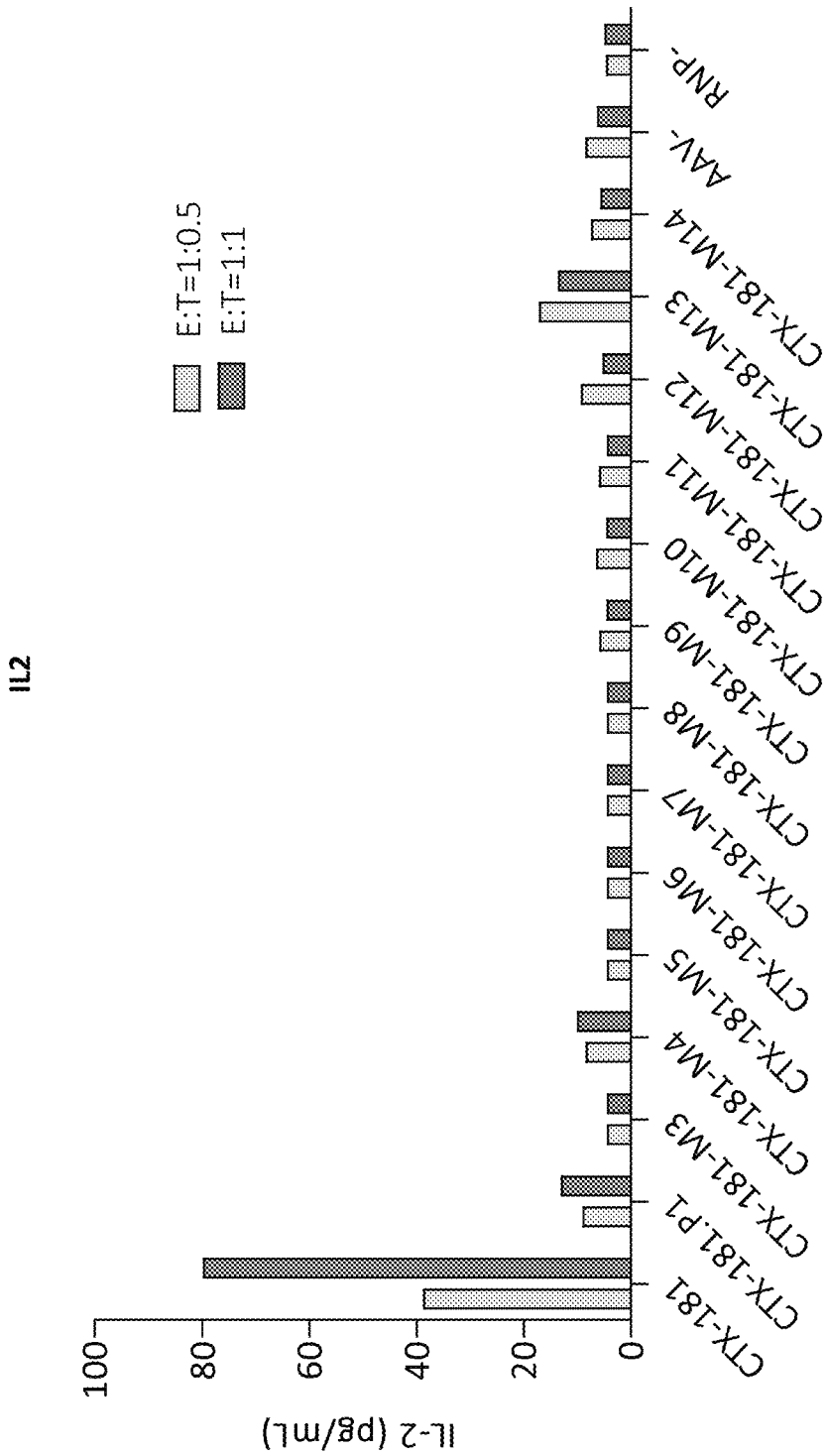

SEQUENCE LISTING

```
<160> NUMBER OF SEQ ID NOS: 134

<210> SEQ ID NO 1
<211> LENGTH: 20
<212> TYPE: PRT
<213> ORGANISM: Artificial Sequence
<220> FEATURE:
<223> OTHER INFORMATION: Synthetic

<400> SEQUENCE: 1

Glu Val Ala Pro Gly Lys Arg Trp Phe Tyr Asn His Val Lys Gln Val
1               5                   10                  15

Pro His Leu Val
            20

<210> SEQ ID NO 2
<211> LENGTH: 23
<212> TYPE: PRT
<213> ORGANISM: Artificial Sequence
<220> FEATURE:
```

<223> OTHER INFORMATION: Synthetic

<400> SEQUENCE: 2

His Glu Glu Val His Met Arg Pro Asn Lys Leu Ser Leu Thr Trp Ala
1               5                   10                  15

Tyr Thr Gly Pro Gln Leu Arg
            20

<210> SEQ ID NO 3
<211> LENGTH: 13
<212> TYPE: PRT
<213> ORGANISM: Artificial Sequence
<220> FEATURE:
<223> OTHER INFORMATION: Synthetic

<400> SEQUENCE: 3

Cys Thr Met Pro Pro Ser Pro Arg Ser Lys Val Ile Cys
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetic

<400> SEQUENCE: 4

Cys Thr Phe Pro Asn Thr Thr Met Gln Arg Thr Phe Cys
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic

<400> SEQUENCE: 5

Cys Thr Tyr Pro Ser Trp Val Ala Tyr Ile Arg Phe Cys
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthetic

<400> SEQUENCE: 6

Val Cys Thr Tyr Pro Pro Ala His Arg Thr Arg Phe Cys
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetic

<400> SEQUENCE: 7

Cys Thr Met Pro Tyr His Ile His Ser Ile Gly Leu Cys
1               5                   10

<210> SEQ ID NO 8
<211> LENGTH: 13
<212> TYPE: PRT

```
<213> ORGANISM: Artificial Sequence
<220> FEATURE:
<223> OTHER INFORMATION: Synthetic

<400> SEQUENCE: 8

Trp Cys Thr Ile Pro Ser Ser Met Ser Ile Arg Leu Cys
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic

<400> SEQUENCE: 9

Cys His Ile Gly Lys Arg Pro Val Pro Cys Leu Trp Ile
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Synthetic

<400> SEQUENCE: 10

Cys Tyr Ile Gly Leu Arg Met Val Pro Cys Phe His Met
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Synthetic

<400> SEQUENCE: 11

Cys Thr Met Pro Ser His Ala Val Ala Ser Phe Leu Cys
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic

<400> SEQUENCE: 12

Cys Thr Met Pro Val His Thr Tyr Ser Gln Trp Leu Cys
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Synthetic

<400> SEQUENCE: 13

Cys Thr Tyr Pro Pro Arg Phe His Met His Trp Leu Cys
1               5                   10

<210> SEQ ID NO 14
<211> LENGTH: 13
<212> TYPE: PRT
<213> ORGANISM: Artificial Sequence
```

```
<220> FEATURE:
<223> OTHER INFORMATION: Synthetic

<400> SEQUENCE: 14

Cys Thr His Val Ala Gln Trp Ala Ile Lys Ala Phe Cys
1               5                   10

<210> SEQ ID NO 15
<211> LENGTH: 5
<212> TYPE: PRT
<213> ORGANISM: Artificial Sequence
<220> FEATURE:
<223> OTHER INFORMATION: Synthetic

<400> SEQUENCE: 15

Pro Leu Gly Leu Ala
1               5

<210> SEQ ID NO 16
<211> LENGTH: 22
<212> TYPE: PRT
<213> ORGANISM: Artificial Sequence
<220> FEATURE:
<223> OTHER INFORMATION: Synthetic

<400> SEQUENCE: 16

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 17
<211> LENGTH: 21
<212> TYPE: PRT
<213> ORGANISM: Artificial Sequence
<220> FEATURE:
<223> OTHER INFORMATION: Synthetic

<400> SEQUENCE: 17

Met Ala Leu Pro Val Thr Ala Leu Leu Leu Pro Leu Ala Leu Leu Leu
1               5                   10                  15

His Ala Ala Arg Pro
            20

<210> SEQ ID NO 18
<211> LENGTH: 8
<212> TYPE: PRT
<213> ORGANISM: Artificial Sequence
<220> FEATURE:
<223> OTHER INFORMATION: Synthetic

<400> SEQUENCE: 18

Leu Ser Gly Arg Ser Asp Asn His
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic

<400> SEQUENCE: 19

Thr Gly Arg Gly Pro Ser Trp Val
1               5
```

<210> SEQ ID NO 20
<211> LENGTH: 15
<212> TYPE: PRT
<213> ORGANISM: Artificial Sequence
<220> FEATURE:
<223> OTHER INFORMATION: Synthetic

<400> SEQUENCE: 20

Gly Ser Ser Gly Gly Ser Gly Gly Ser Gly Gly Ser Gly Gly Gly
1               5                   10                  15

<210> SEQ ID NO 21
<211> LENGTH: 5
<212> TYPE: PRT
<213> ORGANISM: Artificial Sequence
<220> FEATURE:
<223> OTHER INFORMATION: Synthetic

<400> SEQUENCE: 21

Gly Gly Ser Ser Gly
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic

<400> SEQUENCE: 22

Gly Gly Gly Gly Ser
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic

<400> SEQUENCE: 23

Ser Tyr Gly Met His
1               5

<210> SEQ ID NO 24
<211> LENGTH: 17
<212> TYPE: PRT
<213> ORGANISM: Artificial Sequence
<220> FEATURE:
<223> OTHER INFORMATION: Synthetic

<400> SEQUENCE: 24

Val Ile Trp Asp Asp Gly Ser Asn Lys Tyr Tyr Val Asp Ser Val Lys
1               5                   10                  15

Gly

<210> SEQ ID NO 25
<211> LENGTH: 17
<212> TYPE: PRT
<213> ORGANISM: Artificial Sequence
<220> FEATURE:
<223> OTHER INFORMATION: Synthetic

<400> SEQUENCE: 25

Asp Asp Tyr Tyr Gly Ser Gly Ser Phe Asn Ser Tyr Tyr Gly Thr Asp
1               5                   10                  15

Val

<210> SEQ ID NO 26
<211> LENGTH: 11
<212> TYPE: PRT
<213> ORGANISM: Artificial Sequence
<220> FEATURE:
<223> OTHER INFORMATION: Synthetic

<400> SEQUENCE: 26

Arg Ala Ser Gln Ser Val Ser Ile Tyr Leu Ala
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Synthetic

<400> SEQUENCE: 27

Asp Ala Ser Asn Arg Ala Thr
1               5

<210> SEQ ID NO 28
<211> LENGTH: 10
<212> TYPE: PRT
<213> ORGANISM: Artificial Sequence
<220> FEATURE:
<223> OTHER INFORMATION: Synthetic

<400> SEQUENCE: 28

Gln Gln Arg Ser Asn Trp Pro Pro Phe Thr
1               5                   10

<210> SEQ ID NO 29
<211> LENGTH: 126
<212> TYPE: PRT
<213> ORGANISM: Artificial Sequence
<220> FEATURE:
<223> OTHER INFORMATION: Synthetic

<400> SEQUENCE: 29

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Asp Asp Gly Ser Asn Lys Tyr Tyr Val Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Tyr Tyr Gly Ser Gly Ser Phe Asn Ser Tyr Tyr Gly
            100                 105                 110

Thr Asp Val Trp Gly Gln Gly Thr Thr Val Thr Val Ser Ser
        115                 120                 125

<210> SEQ ID NO 30
<211> LENGTH: 108

```
<212> TYPE: PRT
<213> ORGANISM: Artificial Sequence
<220> FEATURE:
<223> OTHER INFORMATION: Synthetic

<400> SEQUENCE: 30

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ile Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys
            100                 105

<210> SEQ ID NO 31
<211> LENGTH: 249
<212> TYPE: PRT
<213> ORGANISM: Artificial Sequence
<220> FEATURE:
<223> OTHER INFORMATION: Synthetic

<400> SEQUENCE: 31

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Asn Lys Tyr Tyr Val Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Tyr Tyr Gly Ser Gly Ser Phe Asn Ser Tyr Tyr Gly
            100                 105                 110

Thr Asp Val Trp Gly Gln Gly Thr Thr Val Thr Val Ser Ser Gly Gly
        115                 120                 125

Gly Gly Ser Gly Gly Gly Gly Ser Gly Gly Gly Gly Ser Glu Ile Val
    130                 135                 140

Leu Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ile Tyr Leu Ala Trp
                165                 170                 175

Tyr Gln Gln Lys Pro Gly Gln Ala Pro Arg Leu Leu Ile Tyr Asp Ala
            180                 185                 190

Ser Asn Arg Ala Thr Gly Ile Pro Ala Arg Phe Ser Gly Ser Gly Ser
        195                 200                 205

Gly Thr Asp Phe Thr Leu Thr Ile Ser Ser Leu Glu Pro Glu Asp Phe
    210                 215                 220
```

```
Ala Val Tyr Tyr Cys Gln Gln Arg Ser Asn Trp Pro Pro Phe Thr Phe
225                 230                 235                 240

Gly Pro Gly Thr Lys Val Asp Ile Lys
                245

<210> SEQ ID NO 32
<211> LENGTH: 510
<212> TYPE: PRT
<213> ORGANISM: Artificial Sequence
<220> FEATURE:
<223> OTHER INFORMATION: Synthetic

<400> SEQUENCE: 32

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
                20                  25                  30

Val Gln Pro Gly Arg Ser Leu Arg Leu Ser Cys Ala Ala Ser Gly Phe
            35                  40                  45

Thr Phe Ser Ser Tyr Gly Met His Trp Val Arg Gln Ala Pro Gly Lys
    50                  55                  60

Gly Leu Glu Trp Val Ala Val Ile Trp Asp Asp Gly Ser Asn Lys Tyr
65                  70                  75                  80

Tyr Val Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Asp Asp Tyr Tyr Gly Ser Gly Ser Phe
        115                 120                 125

Asn Ser Tyr Tyr Gly Thr Asp Val Trp Gly Gln Gly Thr Thr Val Thr
130                 135                 140

Val Ser Ser Gly Gly Gly Gly Ser Gly Gly Gly Gly Ser Gly Gly Gly
145                 150                 155                 160

Gly Ser Glu Ile Val Leu Thr Gln Ser Pro Ala Thr Leu Ser Leu Ser
                165                 170                 175

Pro Gly Glu Arg Ala Thr Leu Ser Cys Arg Ala Ser Gln Ser Val Ser
            180                 185                 190

Ile Tyr Leu Ala Trp Tyr Gln Gln Lys Pro Gly Gln Ala Pro Arg Leu
        195                 200                 205

Leu Ile Tyr Asp Ala Ser Asn Arg Ala Thr Gly Ile Pro Ala Arg Phe
    210                 215                 220

Ser Gly Ser Gly Ser Gly Thr Asp Phe Thr Leu Thr Ile Ser Ser Leu
225                 230                 235                 240

Glu Pro Glu Asp Phe Ala Val Tyr Tyr Cys Gln Gln Arg Ser Asn Trp
                245                 250                 255

Pro Pro Phe Thr Phe Gly Pro Gly Thr Lys Val Asp Ile Lys Ser Ala
            260                 265                 270

Ala Ala Phe Val Pro Val Phe Leu Pro Ala Lys Pro Thr Thr Thr Pro
        275                 280                 285

Ala Pro Arg Pro Pro Thr Pro Ala Pro Thr Ile Ala Ser Gln Pro Leu
    290                 295                 300

Ser Leu Arg Pro Glu Ala Cys Arg Pro Ala Ala Gly Gly Ala Val His
305                 310                 315                 320

Thr Arg Gly Leu Asp Phe Ala Cys Asp Ile Tyr Ile Trp Ala Pro Leu
                325                 330                 335
```

```
Ala Gly Thr Cys Gly Val Leu Leu Ser Leu Val Ile Thr Leu Tyr
            340                 345                 350

Cys Asn His Arg Asn Arg Ser Lys Arg Ser Arg Leu Leu His Ser Asp
        355                 360                 365

Tyr Met Asn Met Thr Pro Arg Arg Pro Gly Pro Thr Arg Lys His Tyr
370                 375                 380

Gln Pro Tyr Ala Pro Pro Arg Asp Phe Ala Ala Tyr Arg Ser Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
        420                 425                 430

Leu Asp Lys Arg Arg Gly Arg Asp Pro Glu Met Gly Gly Lys Pro Arg
            435                 440                 445

Arg Lys Asn Pro Gln Glu Gly Leu Tyr Asn Glu Leu Gln Lys Asp Lys
        450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
                500                 505                 510

<210> SEQ ID NO 33
<211> LENGTH: 512
<212> TYPE: PRT
<213> ORGANISM: Artificial Sequence
<220> FEATURE:
<223> OTHER INFORMATION: Synthetic

<400> SEQUENCE: 33

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
                20                  25                  30

Val Gln Pro Gly Arg Ser Leu Arg Leu Ser Cys Ala Ala Ser Gly Phe
            35                  40                  45

Thr Phe Ser Ser Tyr Gly Met His Trp Val Arg Gln Ala Pro Gly Lys
        50                  55                  60

Gly Leu Glu Trp Val Ala Val Ile Trp Asp Asp Gly Ser Asn Lys Tyr
65                  70                  75                  80

Tyr Val Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Asp Asp Tyr Gly Ser Gly Ser Phe
        115                 120                 125

Asn Ser Tyr Tyr Gly Thr Asp Val Trp Gly Gln Gly Thr Thr Val Thr
    130                 135                 140

Val Ser Ser Gly Gly Gly Gly Ser Gly Gly Gly Gly Ser Gly Gly Gly
145                 150                 155                 160

Gly Ser Glu Ile Val Leu Thr Gln Ser Pro Ala Thr Leu Ser Leu Ser
                165                 170                 175

Pro Gly Glu Arg Ala Thr Leu Ser Cys Arg Ala Ser Gln Ser Val Ser
            180                 185                 190
```

-continued

Ile Tyr Leu Ala Trp Tyr Gln Gln Lys Pro Gly Gln Ala Pro Arg Leu
            195                 200                 205

Leu Ile Tyr Asp Ala Ser Asn Arg Ala Thr Gly Ile Pro Ala Arg Phe
    210                 215                 220

Ser Gly Ser Gly Ser Gly Thr Asp Phe Thr Leu Thr Ile Ser Ser Leu
225                 230                 235                 240

Glu Pro Glu Asp Phe Ala Val Tyr Tyr Cys Gln Gln Arg Ser Asn Trp
                245                 250                 255

Pro Pro Phe Thr Phe Gly Pro Gly Thr Lys Val Asp Ile Lys Ser Ala
            260                 265                 270

Ala Ala Phe Val Pro Val Phe Leu Pro Ala Lys Pro Thr Thr Thr Pro
            275                 280                 285

Ala Pro Arg Pro Pro Thr Pro Ala Pro Thr Ile Ala Ser Gln Pro Leu
        290                 295                 300

Ser Leu Arg Pro Glu Ala Cys Arg Pro Ala Ala Gly Gly Ala Val His
305                 310                 315                 320

Thr Arg Gly Leu Asp Phe Ala Cys Asp Ile Tyr Ile Trp Ala Pro Leu
                325                 330                 335

Ala Gly Thr Cys Gly Val Leu Leu Leu Ser Leu Val Ile Thr Leu Tyr
            340                 345                 350

Cys Asn His Arg Asn Arg Lys Arg Gly Arg Lys Lys Leu Leu Tyr Ile
            355                 360                 365

Phe Lys Gln Pro Phe Met Arg Pro Val Gln Thr Thr Gln Glu Glu Asp
        370                 375                 380

Gly Cys Ser Cys Arg Phe Pro Glu Glu Glu Glu Gly Gly Cys Glu Leu
385                 390                 395                 400

Arg Val Lys Phe Ser Arg Ser Ala Asp Ala Pro Ala Tyr Gln Gln Gly
                405                 410                 415

Gln Asn Gln Leu Tyr Asn Glu Leu Asn Leu Gly Arg Arg Glu Glu Tyr
            420                 425                 430

Asp Val Leu Asp Lys Arg Arg Gly Arg Asp Pro Glu Met Gly Gly Lys
        435                 440                 445

Pro Arg Arg Lys Asn Pro Gln Glu Gly Leu Tyr Asn Glu Leu Gln Lys
        450                 455                 460

Asp Lys Met Ala Glu Ala Tyr Ser Glu Ile Gly Met Lys Gly Glu Arg
465                 470                 475                 480

Arg Arg Gly Lys Gly His Asp Gly Leu Tyr Gln Gly Leu Ser Thr Ala
                485                 490                 495

Thr Lys Asp Thr Tyr Asp Ala Leu His Met Gln Ala Leu Pro Pro Arg
            500                 505                 510

<210> SEQ ID NO 34
<211> LENGTH: 21
<212> TYPE: PRT
<213> ORGANISM: Artificial Sequence
<220> FEATURE:
<223> OTHER INFORMATION: Synthetic

<400> SEQUENCE: 34

Met Ala Leu Pro Val Thr Ala Leu Leu Leu Pro Leu Ala Leu Leu Leu
1               5                   10                  15

His Ala Ala Arg Pro
            20

<210> SEQ ID NO 35

```
<211> LENGTH: 88
<212> TYPE: PRT
<213> ORGANISM: Artificial Sequence
<220> FEATURE:
<223> OTHER INFORMATION: Synthetic

<400> SEQUENCE: 35

Ser Ala Ala Ala Phe Val Pro Val Phe Leu Pro Ala Lys Pro Thr Thr
1               5                   10                  15

Thr Pro Ala Pro Arg Pro Pro Thr Pro Ala Pro Thr Ile Ala Ser Gln
            20                  25                  30

Pro Leu Ser Leu Arg Pro Glu Ala Cys Arg Pro Ala Ala Gly Gly Ala
        35                  40                  45

Val His Thr Arg Gly Leu Asp Phe Ala Cys Asp Ile Tyr Ile Trp Ala
    50                  55                  60

Pro Leu Ala Gly Thr Cys Gly Val Leu Leu Leu Ser Leu Val Ile Thr
65                  70                  75                  80

Leu Tyr Cys Asn His Arg Asn Arg
                85

<210> SEQ ID NO 36
<211> LENGTH: 84
<212> TYPE: PRT
<213> ORGANISM: Artificial Sequence
<220> FEATURE:
<223> OTHER INFORMATION: Synthetic

<400> SEQUENCE: 36

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Arg

<210> SEQ ID NO 37
<211> LENGTH: 40
<212> TYPE: PRT
<213> ORGANISM: Artificial Sequence
<220> FEATURE:
<223> OTHER INFORMATION: Synthetic

<400> SEQUENCE: 37

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser
        35                  40

<210> SEQ ID NO 38
<211> LENGTH: 42
<212> TYPE: PRT
<213> ORGANISM: Artificial Sequence
<220> FEATURE:
<223> OTHER INFORMATION: Synthetic
```

-continued

<400> SEQUENCE: 38

Lys Arg Gly Arg Lys Lys Leu Leu Tyr Ile Phe Lys Gln Pro Phe Met
1               5                   10                  15

Arg Pro Val Gln Thr Thr Gln Glu Asp Gly Cys Ser Cys Arg Phe
            20                  25                  30

Pro Glu Glu Glu Gly Gly Cys Glu Leu
        35                  40

<210> SEQ ID NO 39
<211> LENGTH: 112
<212> TYPE: PRT
<213> ORGANISM: Artificial Sequence
<220> FEATURE:
<223> OTHER INFORMATION: Synthetic

<400> SEQUENCE: 39

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 40
<211> LENGTH: 20
<212> TYPE: DNA
<213> ORGANISM: Artificial Sequence
<220> FEATURE:
<223> OTHER INFORMATION: Synthetic

<400> SEQUENCE: 40
agagcaacag tgctgtggcc                                              20

<210> SEQ ID NO 41
<211> LENGTH: 23
<212> TYPE: DNA
<213> ORGANISM: Artificial Sequence
<220> FEATURE:
<223> OTHER INFORMATION: Synthetic

<400> SEQUENCE: 41
agagcaacag tgctgtggcc tgg                                          23

<210> SEQ ID NO 42
<211> LENGTH: 100
<212> TYPE: RNA
<213> ORGANISM: Artificial Sequence
<220> FEATURE:
<223> OTHER INFORMATION: Synthetic

<400> SEQUENCE: 42
agagcaacag ugcuguggcc guuuuagagc uagaaauagc aaguuaaaau aaggcuaguc    60
cguuaucaac uugaaaaagu ggcaccgagu cggugcuuuu           100

<210> SEQ ID NO 43
<211> LENGTH: 20
<212> TYPE: RNA
<213> ORGANISM: Artificial Sequence
<220> FEATURE:
<223> OTHER INFORMATION: Synthetic

<400> SEQUENCE: 43
agagcaacag ugcuguggcc                                  20

<210> SEQ ID NO 44
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 44
agagcaacag ugcuguggcc                                  20

<210> SEQ ID NO 45
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 45
agagcaacag ugcuguggcc guuuuagagc uagaaauagc aaguuaaaau aaggcuaguc    60
cguuaucaac uugaaaaagu ggcaccgagu cggugcuuuu                         100

<210> SEQ ID NO 46
<211> LENGTH: 19
<212> TYPE: DNA
<213> ORGANISM: Artificial Sequence
<220> FEATURE:
<223> OTHER INFORMATION: Synthetic

<400> SEQUENCE: 46
aagagcaaca aatctgact                                   19

<210> SEQ ID NO 47
<211> LENGTH: 58
<212> TYPE: DNA
<213> ORGANISM: Artificial Sequence
<220> FEATURE:
<223> OTHER INFORMATION: Synthetic

<400> SEQUENCE: 47
aagagcaaca gtgctgtgcc tggagcaaca aatctgacta agagcaacaa atctgact      58

<210> SEQ ID NO 48
<211> LENGTH: 52

```
<212> TYPE: DNA
<213> ORGANISM: Artificial Sequence
<220> FEATURE:
<223> OTHER INFORMATION: Synthetic

<400> SEQUENCE: 48
aagagcaaca gtgctggagc aacaaatctg actaagagca acaaatctga ct            52

<210> SEQ ID NO 49
<211> LENGTH: 53
<212> TYPE: DNA
<213> ORGANISM: Artificial Sequence
<220> FEATURE:
<223> OTHER INFORMATION: Synthetic

<400> SEQUENCE: 49
aagagcaaca gtgcctggag caacaaatct gactaagagc aacaaatctg act           53

<210> SEQ ID NO 50
<211> LENGTH: 38
<212> TYPE: DNA
<213> ORGANISM: Artificial Sequence
<220> FEATURE:
<223> OTHER INFORMATION: Synthetic

<400> SEQUENCE: 50
aagagcaaca gtgctgacta agagcaacaa atctgact                            38

<210> SEQ ID NO 51
<211> LENGTH: 60
<212> TYPE: DNA
<213> ORGANISM: Artificial Sequence
<220> FEATURE:
<223> OTHER INFORMATION: Synthetic

<400> SEQUENCE: 51
aagagcaaca gtgctgtggg cctggagcaa caaatctgac taagagcaac aaatctgact    60

<210> SEQ ID NO 52
<211> LENGTH: 57
<212> TYPE: DNA
<213> ORGANISM: Artificial Sequence
<220> FEATURE:
<223> OTHER INFORMATION: Synthetic

<400> SEQUENCE: 52
aagagcaaca gtgctggcct ggagcaacaa atctgactaa gagcaacaaa tctgact       57

<210> SEQ ID NO 53
<211> LENGTH: 60
<212> TYPE: DNA
<213> ORGANISM: Artificial Sequence
<220> FEATURE:
<223> OTHER INFORMATION: Synthetic

<400> SEQUENCE: 53
aagagcaaca gtgctgtgtg cctggagcaa caaatctgac taagagcaac aaatctgact    60

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
```
gctactctct ctttctggcc                                                  20

<210> SEQ ID NO 55
<211> LENGTH: 23
<212> TYPE: DNA
<213> ORGANISM: Artificial Sequence
<220> FEATURE:
<223> OTHER INFORMATION: Synthetic

<400> SEQUENCE: 55
gctactctct ctttctggcc tgg                                              23

<210> SEQ ID NO 56
<211> LENGTH: 20
<212> TYPE: RNA
<213> ORGANISM: Artificial Sequence
<220> FEATURE:
<223> OTHER INFORMATION: Synthetic

<400> SEQUENCE: 56
gcuacucucu cuuucuggcc                                                  20

<210> SEQ ID NO 57
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 57
gcuacucucu cuuucuggcc                                                  20

<210> SEQ ID NO 58
<211> LENGTH: 100
<212> TYPE: RNA
<213> ORGANISM: Artificial Sequence
<220> FEATURE:
<223> OTHER INFORMATION: Synthetic

<400> SEQUENCE: 58
gcuacucucu cuuucuggcc guuuuagagc uagaaauagc aaguuaaaau aaggcuaguc       60
cguuaucaac uugaaaaagu ggcaccgagu cggugcuuuu                           100

<210> SEQ ID NO 59
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 59
gcuacucucu cuuucuggcc guuuuagagc uagaaauagc aaguuaaaau aaggcuaguc       60
cguuaucaac uugaaaaagu ggcaccgagu cggugcuuuu                           100

<210> SEQ ID NO 60
<211> LENGTH: 79
<212> TYPE: DNA
<213> ORGANISM: Artificial Sequence
<220> FEATURE:
<223> OTHER INFORMATION: Synthetic

<400> SEQUENCE: 60
cgtggcctta gctgtgctcg cgctactctc tctttctgcc tggaggctat ccagcgtgag    60
tctctcctac cctcccgct                                                 79

<210> SEQ ID NO 61
<211> LENGTH: 78
<212> TYPE: DNA
<213> ORGANISM: Artificial Sequence
<220> FEATURE:
<223> OTHER INFORMATION: Synthetic

<400> SEQUENCE: 61
cgtggcctta gctgtgctcg cgctactctc tctttcgcct ggaggctatc cagcgtgagt    60
ctctcctacc ctcccgct                                                  78

<210> SEQ ID NO 62
<211> LENGTH: 75
<212> TYPE: DNA
<213> ORGANISM: Artificial Sequence
<220> FEATURE:
<223> OTHER INFORMATION: Synthetic

<400> SEQUENCE: 62
cgtggcctta gctgtgctcg cgctactctc tctttctgga ggctatccag cgtgagtctc    60
tcctaccctc ccgct                                                     75

<210> SEQ ID NO 63
<211> LENGTH: 84
<212> TYPE: DNA
<213> ORGANISM: Artificial Sequence
<220> FEATURE:
<223> OTHER INFORMATION: Synthetic

<400> SEQUENCE: 63
cgtggcctta gctgtgctcg cgctactctc tctttctgga tagcctggag gctatccagc    60
gtgagtctct cctaccctcc cgct                                           84

<210> SEQ ID NO 64
<211> LENGTH: 55
<212> TYPE: DNA
<213> ORGANISM: Artificial Sequence
<220> FEATURE:
<223> OTHER INFORMATION: Synthetic

<400> SEQUENCE: 64
cgtggcctta gctgtgctcg cgctatccag cgtgagtctc tcctaccctc ccgct         55

<210> SEQ ID NO 65
<211> LENGTH: 82
<212> TYPE: DNA
<213> ORGANISM: Artificial Sequence
<220> FEATURE:
<223> OTHER INFORMATION: Synthetic

<400> SEQUENCE: 65
cgtggcctta gctgtgctcg cgctactctc tctttctgtg gcctggaggc tatccagcgt    60

```
gagtctctcc taccctcccg ct                                              82
```

<210> SEQ ID NO 66
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n is a, c, g, or u

<400> SEQUENCE: 66

```
nnnnnnnnnn nnnnnnnnnn guuuuagagc uagaaauagc aaguuaaaau aaggcuaguc     60
cguuaucaac uugaaaaagu ggcaccgagu cggugcuuuu                          100
```

<210> SEQ ID NO 67
<211> LENGTH: 96
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n is a, c, g, or u

<400> SEQUENCE: 67

```
nnnnnnnnnn nnnnnnnnnn guuuuagagc uagaaauagc aaguuaaaau aaggcuaguc     60
cguuaucaac uugaaaaagu ggcaccgagu cggugc                               96
```

<210> SEQ ID NO 68
<211> LENGTH: 114
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(17)
<223> OTHER INFORMATION: n is a, c, g, or u
<220> FEATURE:
<221> NAME/KEY: misc_feature
<222> LOCATION: (18)..(30)
<223> OTHER INFORMATION: n is a, c, g, or u, or absent
<220> FEATURE:
<221> NAME/KEY: misc_feature
<222> LOCATION: (108)..(114)
<223> OTHER INFORMATION: n is a, c, g, or u, or absent

<400> SEQUENCE: 68

```
nnnnnnnnnn nnnnnnnnnn nnnnnnnnnn guuuuagagc uagaaauagc aaguuaaaau     60
aaggcuaguc cguuaucaac uugaaaaagu ggcaccgagu cggugcuuuu uuuu          114
```

<210> SEQ ID NO 69
<211> LENGTH: 1368
<212> TYPE: PRT
<213> ORGANISM: Artificial Sequence
<220> FEATURE:
<223> OTHER INFORMATION: Synthetic

<400> SEQUENCE: 69

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30
```

```
Lys Val Leu Gly Asn Thr Asp Arg His Ser Ile Lys Lys Asn Leu Ile
         35                  40                  45

Gly Ala Leu Leu Phe Asp Ser Gly Glu Thr Ala Glu Ala Thr Arg Leu
         50                  55                  60

Lys Arg Thr Ala Arg Arg Arg Tyr Thr Arg Arg Lys Asn Arg Ile Cys
65                   70                  75                  80

Tyr Leu Gln Glu Ile Phe Ser Asn Glu Met Ala Lys Val Asp Asp Ser
                 85                  90                  95

Phe Phe His Arg Leu Glu Glu Ser Phe Leu Val Glu Glu Asp Lys Lys
             100                 105                 110

His Glu Arg His Pro Ile Phe Gly Asn Ile Val Asp Glu Val Ala Tyr
             115                 120                 125

His Glu Lys Tyr Pro Thr Ile Tyr His Leu Arg Lys Lys Leu Val Asp
             130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                 165                 170                 175

Asp Asn Ser Asp Val Asp Lys Leu Phe Ile Gln Leu Val Gln Thr Tyr
             180                 185                 190

Asn Gln Leu Phe Glu Glu Asn Pro Ile Asn Ala Ser Gly Val Asp Ala
             195                 200                 205

Lys Ala Ile Leu Ser Ala Arg Leu Ser Lys Ser Arg Arg Leu Glu Asn
             210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                 245                 250                 255

Asp Leu Ala Glu Asp Ala Lys Leu Gln Leu Ser Lys Asp Thr Tyr Asp
             260                 265                 270

Asp Asp Leu Asp Asn Leu Leu Ala Gln Ile Gly Asp Gln Tyr Ala Asp
             275                 280                 285

Leu Phe Leu Ala Ala Lys Asn Leu Ser Asp Ala Ile Leu Leu Ser Asp
             290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                 325                 330                 335

Ala Leu Val Arg Gln Gln Leu Pro Glu Lys Tyr Lys Glu Ile Phe Phe
             340                 345                 350

Asp Gln Ser Lys Asn Gly Tyr Ala Gly Tyr Ile Asp Gly Gly Ala Ser
             355                 360                 365

Gln Glu Glu Phe Tyr Lys Phe Ile Lys Pro Ile Leu Glu Lys Met Asp
             370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
             405                 410                 415

Gly Glu Leu His Ala Ile Leu Arg Arg Gln Glu Asp Phe Tyr Pro Phe
             420                 425                 430

Leu Lys Asp Asn Arg Glu Lys Ile Glu Lys Ile Leu Thr Phe Arg Ile
             435                 440                 445
```

-continued

```
Pro Tyr Tyr Val Gly Pro Leu Ala Arg Gly Asn Ser Arg Phe Ala Trp
450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
                515                 520                 525
Tyr Val Thr Glu Gly Met Arg Lys Pro Ala Phe Leu Ser Gly Glu Gln
530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
                580                 585                 590
Thr Tyr His Asp Leu Leu Lys Ile Ile Lys Asp Lys Asp Phe Leu Asp
                595                 600                 605
Asn Glu Glu Asn Glu Asp Ile Leu Glu Asp Ile Val Leu Thr Leu Thr
610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
                660                 665                 670
Lys Gln Ser Gly Lys Thr Ile Leu Asp Phe Leu Lys Ser Asp Gly Phe
                675                 680                 685
Ala Asn Arg Asn Phe Met Gln Leu Ile His Asp Asp Ser Leu Thr Phe
690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
                740                 745                 750
Arg His Lys Pro Glu Asn Ile Val Ile Glu Met Ala Arg Glu Asn Gln
                755                 760                 765
Thr Thr Gln Lys Gly Gln Lys Asn Ser Arg Glu Arg Met Lys Arg Ile
770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
                820                 825                 830
Leu Ser Asp Tyr Asp Val Asp His Ile Val Pro Gln Ser Phe Leu Lys
                835                 840                 845
Asp Asp Ser Ile Asp Asn Lys Val Leu Thr Arg Ser Asp Lys Asn Arg
850                 855                 860
Gly Lys Ser Asp Asn Val Pro Ser Glu Glu Val Val Lys Lys Met Lys
```

-continued

```
               865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
                915                 920                 925
Lys His Val Ala Gln Ile Leu Asp Ser Arg Met Asn Thr Lys Tyr Asp
                930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
                995                1000                1005
Val Tyr Gly Asp Tyr Lys Val Tyr Asp Val Arg Lys Met Ile Ala
                1010                1015                1020
Lys Ser Glu Gln Glu Ile Gly Lys Ala Thr Ala Lys Tyr Phe Phe
                1025                1030                1035
Tyr Ser Asn Ile Met Asn Phe Phe Lys Thr Glu Ile Thr Leu Ala
                1040                1045                1050
Asn Gly Glu Ile Arg Lys Arg Pro Leu Ile Glu Thr Asn Gly Glu
                1055                1060                1065
Thr Gly Glu Ile Val Trp Asp Lys Gly Arg Asp Phe Ala Thr Val
                1070                1075                1080
Arg Lys Val Leu Ser Met Pro Gln Val Asn Ile Val Lys Lys Thr
                1085                1090                1095
Glu Val Gln Thr Gly Gly Phe Ser Lys Glu Ser Ile Leu Pro Lys
                1100                1105                1110
Arg Asn Ser Asp Lys Leu Ile Ala Arg Lys Lys Asp Trp Asp Pro
                1115                1120                1125
Lys Lys Tyr Gly Gly Phe Asp Ser Pro Thr Val Ala Tyr Ser Val
                1130                1135                1140
Leu Val Val Ala Lys Val Glu Lys Gly Lys Ser Lys Lys Leu Lys
                1145                1150                1155
Ser Val Lys Glu Leu Leu Gly Ile Thr Ile Met Glu Arg Ser Ser
                1160                1165                1170
Phe Glu Lys Asn Pro Ile Asp Phe Leu Glu Ala Lys Gly Tyr Lys
                1175                1180                1185
Glu Val Lys Lys Asp Leu Ile Ile Lys Leu Pro Lys Tyr Ser Leu
                1190                1195                1200
Phe Glu Leu Glu Asn Gly Arg Lys Arg Met Leu Ala Ser Ala Gly
                1205                1210                1215
Glu Leu Gln Lys Gly Asn Glu Leu Ala Leu Pro Ser Lys Tyr Val
                1220                1225                1230
Asn Phe Leu Tyr Leu Ala Ser His Tyr Glu Lys Leu Lys Gly Ser
                1235                1240                1245
Pro Glu Asp Asn Glu Gln Lys Gln Leu Phe Val Glu Gln His Lys
                1250                1255                1260
His Tyr Leu Asp Glu Ile Ile Glu Gln Ile Ser Glu Phe Ser Lys
                1265                1270                1275
```

```
Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365
```

<210> SEQ ID NO 70
<211> LENGTH: 800
<212> TYPE: DNA
<213> ORGANISM: Artificial Sequence
<220> FEATURE:
<223> OTHER INFORMATION: Synthetic

<400> SEQUENCE: 70

```
gagatgtaag gagctgctgt gacttgctca aggccttata tcgagtaaac ggtagtgctg      60
gggcttagac gcaggtgttc tgatttatag ttcaaaacct ctatcaatga gagagcaatc     120
tcctggtaat gtgatagatt tcccaactta atgccaacat accataaacc tcccattctg     180
ctaatgccca gcctaagttg gggagaccac tccagattcc aagatgtaca gtttgctttg     240
ctgggccttt ttcccatgcc tgcctttact ctgccagagt tatattgctg ggttttgaa      300
gaagatccta ttaaataaaa gaataagcag tattattaag tagccctgca tttcaggttt     360
ccttgagtgg caggccaggc ctggccgtga acgttcactg aaatcatggc ctcttggcca     420
agattgatag cttgtgcctg tccctgagtc ccagtccatc acgagcagct ggtttctaag     480
atgctatttc ccgtataaag catgagaccg tgacttgcca gccccacaga gccccgccct     540
tgtccatcac tggcatctgg actccagcct gggttgggc aaagagggaa atgagatcat      600
gtcctaaccc tgatcctctt gtcccacaga tatccagaac cctgaccctg ccgtgtacca     660
gctgagagac tctaaatcca gtgacaagtc tgtctgccta ttcaccgatt ttgattctca     720
aacaaatgtg tcacaaagta aggattctga tgtgtatatc acagacaaaa ctgtgctaga     780
catgaggtct atggacttca                                                 800
```

<210> SEQ ID NO 71
<211> LENGTH: 1178
<212> TYPE: DNA
<213> ORGANISM: Artificial Sequence
<220> FEATURE:
<223> OTHER INFORMATION: Synthetic

<400> SEQUENCE: 71

```
ggctccggtg cccgtcagtg ggcagagcgc acatcgccca cagtccccga gaagttgggg      60
ggaggggtcg gcaattgaac cggtgcctag agaaggtggc gcggggtaaa ctgggaaagt     120
gatgtcgtgt actggctccg cctttttccc gagggtgggg gagaaccgta tataagtgca     180
gtagtcgccg tgaacgttct ttttcgcaac gggtttgccg ccagaacaca ggtaagtgcc     240
gtgtgtggtt cccgcgggcc tggcctcttt acgggttatg cccttgcgt gccttgaatt      300
acttccactg gctgcagtac gtgattcttg atcccgagct tcgggttgga agtgggtggg     360
```

```
agagttcgag gccttgcgct taaggagccc cttcgcctcg tgcttgagtt gaggcctggc    420
ctgggcgctg gggccgccgc gtgcgaatct ggtggcacct tcgcgcctgt ctcgctgctt    480
tcgataagtc tctagccatt taaaattttt gatgacctgc tgcgacgctt ttttctggc     540
aagatagtct tgtaaatgcg ggccaagatc tgcacactgg tatttcggtt tttggggccg    600
cgggcggcga cggggcccgt gcgtcccagc gcacatgttc ggcgaggcgg ggcctgcgag    660
cgcggccacc gagaatcgga cggggtagt ctcaagctgg ccggcctgct ctggtgcctg     720
gcctcgcgcc gccgtgtatc gccccgccct gggcggcaag gctggcccgg tcggcaccag    780
ttgcgtgagc ggaaagatgg ccgcttcccg gccctgctgc agggagctca aaatggagga    840
cgcggcgctc gggagagcgg gcgggtgagt cacccacaca aaggaaaagg gcctttccgt    900
cctcagccgt cgcttcatgt gactccacgg agtaccgggc gccgtccagg cacctcgatt    960
agttctcgag cttttggagt acgtcgtctt taggttgggg ggaggggttt tatgcgatgg   1020
agtttcccca cactgagtgg gtggagactg aagttaggcc agcttggcac ttgatgtaat   1080
tctccttgga atttgcccttt tttgagtttg gatcttggtt cattctcaag cctcagacag   1140
tggttcaaag ttttttttctt ccatttcagg tgtcgtga                          1178

<210> SEQ ID NO 72
<211> LENGTH: 49
<212> TYPE: DNA
<213> ORGANISM: Artificial Sequence
<220> FEATURE:
<223> OTHER INFORMATION: Synthetic

<400> SEQUENCE: 72
aataaaatcg ctatccatcg aagatggatg tgtgttggtt ttttgtgtg                 49

<210> SEQ ID NO 73
<211> LENGTH: 804
<212> TYPE: DNA
<213> ORGANISM: Artificial Sequence
<220> FEATURE:
<223> OTHER INFORMATION: Synthetic

<400> SEQUENCE: 73
tggagcaaca aatctgactt tgcatgtgca aacgccttca acaacagcat tattccagaa     60
gacaccttct tccccagccc aggtaagggc agctttggtg ccttcgcagg ctgtttcctt    120
gcttcaggaa tggccaggtt ctgcccagag ctctggtcaa tgatgtctaa aactcctctg    180
attggtggtc tcggccttat ccattgccac caaaaccctc ttttttactaa gaaacagtga    240
gccttgttct ggcagtccag agaatgacac gggaaaaaag cagatgaaga gaaggtggca    300
ggagagggca cgtggcccag cctcagtctc tccaactgag ttcctgcctg cctgcctttg    360
ctcagactgt ttgcccctta ctgctcttct aggcctcatt ctaagcccct tctccaagtt    420
gcctctcctt atttctccct gtctgccaaa aaatctttcc cagctcacta agtcagtctc    480
acgcagtcac tcattaaccc accaatcact gattgtgccg gcacatgaat gcaccaggtg    540
ttgaagtgga ggaattaaaa agtcagatga ggggtgtgcc cagaggaagc accattctag    600
ttgggggagc ccatctgtca gctgggaaaa gtccaaataa cttcgattg gaatgtgttt     660
taactcaggg ttgagaaaac agctaccttc aggacaaaag tcagggaagg gctctctgaa    720
gaaatgctac ttgaagatac cagccctacc aagggcaggg agaggaccct atagaggcct    780
gggacaggag ctcaatgaga aagg                                            804
```

```
<210> SEQ ID NO 74
<211> LENGTH: 215
<212> TYPE: PRT
<213> ORGANISM: Artificial Sequence
<220> FEATURE:
<223> OTHER INFORMATION: Synthetic

<400> SEQUENCE: 74

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ile Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 75
<211> LENGTH: 456
<212> TYPE: PRT
<213> ORGANISM: Artificial Sequence
<220> FEATURE:
<223> OTHER INFORMATION: Synthetic

<400> SEQUENCE: 75

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Asn Lys Tyr Tyr Val Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Asp Asp Tyr Tyr Gly Ser Gly Ser Phe Asn Ser Tyr Tyr Gly
        100                 105                 110

Thr Asp Val Trp Gly Gln Gly Thr Thr Val Thr Val Ser Ser Ala Ser
    115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
        180                 185                 190

Ser Val Val Thr Val Pro Ser Ser Ser Leu Gly Thr Gln Thr Tyr Ile
    195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
        260                 265                 270

Val Asp Val Ser His Glu Asp Pro Glu Val Lys Phe Asn Trp Tyr Val
    275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
        340                 345                 350

Arg Glu Pro Gln Val Tyr Thr Leu Pro Pro Ser Arg Asp Glu Leu Thr
    355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
        420                 425                 430

Ser Cys Ser Val Met His Glu Ala Leu His Asn His Tyr Thr Gln Lys
    435                 440                 445

Ser Leu Ser Leu Ser Pro Gly Lys
    450                 455

<210> SEQ ID NO 76
<211> LENGTH: 501
<212> TYPE: PRT
<213> ORGANISM: Artificial Sequence
<220> FEATURE:
<223> OTHER INFORMATION: Synthetic

<400> SEQUENCE: 76
```

```
Glu Val Ala Pro Gly Lys Arg Trp Phe Tyr Asn His Val Lys Gln Val
1               5                   10                  15

Pro His Leu Val Gly Ser Ser Gly Gly Ser Gly Gly Ser Gly Gly Ser
            20                  25                  30

Gly Gly Gly Pro Leu Gly Leu Ala Gly Gly Ser Ser Gly Gln Val Gln
        35                  40                  45

Leu Val Glu Ser Gly Gly Gly Val Val Gln Pro Gly Arg Ser Leu Arg
    50                  55                  60

Leu Ser Cys Ala Ala Ser Gly Phe Thr Phe Ser Ser Tyr Gly Met His
65                  70                  75                  80

Trp Val Arg Gln Ala Pro Gly Lys Gly Leu Glu Trp Val Ala Val Ile
                85                  90                  95

Trp Asp Asp Gly Ser Asn Lys Tyr Tyr Val Asp Ser Val Lys Gly Arg
            100                 105                 110

Phe Thr Ile Ser Arg Asp Asn Ser Lys Asn Thr Leu Tyr Leu Gln Met
        115                 120                 125

Asn Ser Leu Arg Ala Glu Asp Thr Ala Val Tyr Tyr Cys Ala Arg Asp
    130                 135                 140

Asp Tyr Tyr Gly Ser Gly Ser Phe Asn Ser Tyr Tyr Gly Thr Asp Val
145                 150                 155                 160

Trp Gly Gln Gly Thr Thr Val Thr Val Ser Ser Ala Ser Thr Lys Gly
                165                 170                 175

Pro Ser Val Phe Pro Leu Ala Pro Ser Ser Lys Ser Thr Ser Gly Gly
            180                 185                 190

Thr Ala Ala Leu Gly Cys Leu Val Lys Asp Tyr Phe Pro Glu Pro Val
        195                 200                 205

Thr Val Ser Trp Asn Ser Gly Ala Leu Thr Ser Gly Val His Thr Phe
    210                 215                 220

Pro Ala Val Leu Gln Ser Ser Gly Leu Tyr Ser Leu Ser Ser Val Val
225                 230                 235                 240

Thr Val Pro Ser Ser Ser Leu Gly Thr Gln Thr Tyr Ile Cys Asn Val
                245                 250                 255

Asn His Lys Pro Ser Asn Thr Lys Val Asp Lys Lys Val Glu Pro Lys
            260                 265                 270

Ser Cys Asp Lys Thr His Thr Cys Pro Pro Cys Pro Ala Pro Glu Leu
    275                 280                 285

Leu Gly Gly Pro Ser Val Phe Leu Phe Pro Pro Lys Pro Lys Asp Thr
290                 295                 300

Leu Met Ile Ser Arg Thr Pro Glu Val Thr Cys Val Val Val Asp Val
305                 310                 315                 320

Ser His Glu Asp Pro Glu Val Lys Phe Asn Trp Tyr Val Asp Gly Val
                325                 330                 335

Glu Val His Asn Ala Lys Thr Lys Pro Arg Glu Glu Gln Tyr Asn Ser
            340                 345                 350

Thr Tyr Arg Val Val Ser Val Leu Thr Val Leu His Gln Asp Trp Leu
        355                 360                 365

Asn Gly Lys Glu Tyr Lys Cys Lys Val Ser Asn Lys Ala Leu Pro Ala
    370                 375                 380

Pro Ile Glu Lys Thr Ile Ser Lys Ala Lys Gly Gln Pro Arg Glu Pro
385                 390                 395                 400

Gln Val Tyr Thr Leu Pro Pro Ser Arg Asp Glu Leu Thr Lys Asn Gln
                405                 410                 415

Val Ser Leu Thr Cys Leu Val Lys Gly Phe Tyr Pro Ser Asp Ile Ala
```

```
            420                 425                 430
Val Glu Trp Glu Ser Asn Gly Gln Pro Glu Asn Asn Tyr Lys Thr Thr
            435                 440                 445

Pro Pro Val Leu Asp Ser Asp Gly Ser Phe Phe Leu Tyr Ser Lys Leu
450                 455                 460

Thr Val Asp Lys Ser Arg Trp Gln Gln Gly Asn Val Phe Ser Cys Ser
465                 470                 475                 480

Val Met His Glu Ala Leu His Asn His Tyr Thr Gln Lys Ser Leu Ser
                485                 490                 495

Leu Ser Pro Gly Lys
                500

<210> SEQ ID NO 77
<211> LENGTH: 504
<212> TYPE: PRT
<213> ORGANISM: Artificial Sequence
<220> FEATURE:
<223> OTHER INFORMATION: Synthetic

<400> SEQUENCE: 77

His Glu Glu Val His Met Arg Pro Asn Lys Leu Ser Leu Thr Trp Ala
1               5                   10                  15

Tyr Thr Gly Pro Gln Leu Arg Gly Ser Ser Gly Gly Ser Gly Gly Ser
                20                  25                  30

Gly Gly Ser Gly Gly Gly Pro Leu Gly Leu Ala Gly Gly Ser Ser Gly
            35                  40                  45

Gln Val Gln Leu Val Glu Ser Gly Gly Gly Val Val Gln Pro Gly Arg
50                  55                  60

Ser Leu Arg Leu Ser Cys Ala Ala Ser Gly Phe Thr Phe Ser Ser Tyr
65                  70                  75                  80

Gly Met His Trp Val Arg Gln Ala Pro Gly Lys Gly Leu Glu Trp Val
                85                  90                  95

Ala Val Ile Trp Asp Asp Gly Ser Asn Lys Tyr Tyr Val Asp Ser Val
            100                 105                 110

Lys Gly Arg Phe Thr Ile Ser Arg Asp Asn Ser Lys Asn Thr Leu Tyr
        115                 120                 125

Leu Gln Met Asn Ser Leu Arg Ala Glu Asp Thr Ala Val Tyr Tyr Cys
    130                 135                 140

Ala Arg Asp Asp Tyr Tyr Gly Ser Gly Ser Phe Asn Ser Tyr Tyr Gly
145                 150                 155                 160

Thr Asp Val Trp Gly Gln Gly Thr Thr Val Thr Val Ser Ser Ala Ser
                165                 170                 175

Thr Lys Gly Pro Ser Val Phe Pro Leu Ala Pro Ser Ser Lys Ser Thr
            180                 185                 190

Ser Gly Gly Thr Ala Ala Leu Gly Cys Leu Val Lys Asp Tyr Phe Pro
        195                 200                 205

Glu Pro Val Thr Val Ser Trp Asn Ser Gly Ala Leu Thr Ser Gly Val
    210                 215                 220

His Thr Phe Pro Ala Val Leu Gln Ser Ser Gly Leu Tyr Ser Leu Ser
225                 230                 235                 240

Ser Val Val Thr Val Pro Ser Ser Ser Leu Gly Thr Gln Thr Tyr Ile
                245                 250                 255

Cys Asn Val Asn His Lys Pro Ser Asn Thr Lys Val Asp Lys Lys Val
            260                 265                 270

Glu Pro Lys Ser Cys Asp Lys Thr His Thr Cys Pro Pro Cys Pro Ala
```

```
            275                 280                 285
Pro Glu Leu Leu Gly Gly Pro Ser Val Phe Leu Phe Pro Pro Lys Pro
290                 295                 300

Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
                325                 330                 335

Asp Gly Val Glu Val His Asn Ala Lys Thr Lys Pro Arg Glu Glu Gln
            340                 345                 350

Tyr Asn Ser Thr Tyr Arg Val Val Ser Val Leu Thr Val Leu His Gln
        355                 360                 365

Asp Trp Leu Asn Gly Lys Glu Tyr Lys Cys Lys Val Ser Asn Lys Ala
    370                 375                 380

Leu Pro Ala Pro Ile Glu Lys Thr Ile Ser Lys Ala Lys Gly Gln Pro
385                 390                 395                 400

Arg Glu Pro Gln Val Tyr Thr Leu Pro Pro Ser Arg Asp Glu Leu Thr
                405                 410                 415

Lys Asn Gln Val Ser Leu Thr Cys Leu Val Lys Gly Phe Tyr Pro Ser
            420                 425                 430

Asp Ile Ala Val Glu Trp Glu Ser Asn Gly Gln Pro Glu Asn Asn Tyr
        435                 440                 445

Lys Thr Thr Pro Pro Val Leu Asp Ser Asp Gly Ser Phe Phe Leu Tyr
    450                 455                 460

Ser Lys Leu Thr Val Asp Lys Ser Arg Trp Gln Gln Gly Asn Val Phe
465                 470                 475                 480

Ser Cys Ser Val Met His Glu Ala Leu His Asn His Tyr Thr Gln Lys
                485                 490                 495

Ser Leu Ser Leu Ser Pro Gly Lys
            500

<210> SEQ ID NO 78
<211> LENGTH: 496
<212> TYPE: PRT
<213> ORGANISM: Artificial Sequence
<220> FEATURE:
<223> OTHER INFORMATION: Synthetic

<400> SEQUENCE: 78

Gln Gly Cys Thr Met Pro Pro Ser Pro Arg Ser Lys Val Ile Cys Gly
1               5                   10                  15

Ser Ser Gly Gly Ser Gly Gly Ser Gly Gly Ser Gly Gly Gly Pro Leu
            20                  25                  30

Gly Leu Ala Gly Gly Ser Ser Gly Gln Val Gln Leu Val Glu Ser Gly
        35                  40                  45

Gly Gly Val Val Gln Pro Gly Arg Ser Leu Arg Leu Ser Cys Ala Ala
    50                  55                  60

Ser Gly Phe Thr Phe Ser Ser Tyr Gly Met His Trp Val Arg Gln Ala
65                  70                  75                  80

Pro Gly Lys Gly Leu Glu Trp Val Ala Val Ile Trp Asp Asp Gly Ser
                85                  90                  95

Asn Lys Tyr Tyr Val Asp Ser Val Lys Gly Arg Phe Thr Ile Ser Arg
            100                 105                 110

Asp Asn Ser Lys Asn Thr Leu Tyr Leu Gln Met Asn Ser Leu Arg Ala
        115                 120                 125

Glu Asp Thr Ala Val Tyr Tyr Cys Ala Arg Asp Asp Tyr Tyr Gly Ser
```

```
            130                 135                 140
Gly Ser Phe Asn Ser Tyr Tyr Gly Thr Asp Val Trp Gly Gln Gly Thr
145                 150                 155                 160

Thr Val Thr Val Ser Ser Ala Ser Thr Lys Gly Pro Ser Val Phe Pro
                165                 170                 175

Leu Ala Pro Ser Ser Lys Ser Thr Ser Gly Gly Thr Ala Ala Leu Gly
                180                 185                 190

Cys Leu Val Lys Asp Tyr Phe Pro Glu Pro Val Thr Val Ser Trp Asn
                195                 200                 205

Ser Gly Ala Leu Thr Ser Gly Val His Thr Phe Pro Ala Val Leu Gln
210                 215                 220

Ser Ser Gly Leu Tyr Ser Leu Ser Ser Val Val Thr Val Pro Ser Ser
225                 230                 235                 240

Ser Leu Gly Thr Gln Thr Tyr Ile Cys Asn Val Asn His Lys Pro Ser
                245                 250                 255

Asn Thr Lys Val Asp Lys Lys Val Glu Pro Lys Ser Cys Asp Lys Thr
                260                 265                 270

His Thr Cys Pro Pro Cys Pro Ala Pro Glu Leu Leu Gly Gly Pro Ser
                275                 280                 285

Val Phe Leu Phe Pro Pro Lys Pro Lys Asp Thr Leu Met Ile Ser Arg
290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
                340                 345                 350

Ser Val Leu Thr Val Leu His Gln Asp Trp Leu Asn Gly Lys Glu Tyr
                355                 360                 365

Lys Cys Lys Val Ser Asn Lys Ala Leu Pro Ala Pro Ile Glu Lys Thr
370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
                405                 410                 415

Leu Val Lys Gly Phe Tyr Pro Ser Asp Ile Ala Val Glu Trp Glu Ser
                420                 425                 430

Asn Gly Gln Pro Glu Asn Asn Tyr Lys Thr Thr Pro Pro Val Leu Asp
                435                 440                 445

Ser Asp Gly Ser Phe Phe Leu Tyr Ser Lys Leu Thr Val Asp Lys Ser
450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495

<210> SEQ ID NO 79
<211> LENGTH: 496
<212> TYPE: PRT
<213> ORGANISM: Artificial Sequence
<220> FEATURE:
<223> OTHER INFORMATION: Synthetic

<400> SEQUENCE: 79

Gln Gly Cys Thr Phe Pro Asn Thr Thr Met Gln Arg Thr Phe Cys Gly
```

```
1               5                   10                  15
Ser Ser Gly Gly Ser Gly Gly Ser Gly Gly Ser Gly Gly Pro Leu
                20                  25                  30
Gly Leu Ala Gly Gly Ser Ser Gly Gln Val Gln Leu Val Glu Ser Gly
                35                  40                  45
Gly Gly Val Val Gln Pro Gly Arg Ser Leu Arg Leu Ser Cys Ala Ala
        50                  55                  60
Ser Gly Phe Thr Phe Ser Ser Tyr Gly Met His Trp Val Arg Gln Ala
65                  70                  75                  80
Pro Gly Lys Gly Leu Glu Trp Val Ala Val Ile Trp Asp Asp Gly Ser
                85                  90                  95
Asn Lys Tyr Tyr Val Asp Ser Val Lys Gly Arg Phe Thr Ile Ser Arg
                100                 105                 110
Asp Asn Ser Lys Asn Thr Leu Tyr Leu Gln Met Asn Ser Leu Arg Ala
                115                 120                 125
Glu Asp Thr Ala Val Tyr Tyr Cys Ala Arg Asp Asp Tyr Tyr Gly Ser
        130                 135                 140
Gly Ser Phe Asn Ser Tyr Tyr Gly Thr Asp Val Trp Gly Gln Gly Thr
145                 150                 155                 160
Thr Val Thr Val Ser Ser Ala Ser Thr Lys Gly Pro Ser Val Phe Pro
                165                 170                 175
Leu Ala Pro Ser Ser Lys Ser Thr Ser Gly Gly Thr Ala Ala Leu Gly
                180                 185                 190
Cys Leu Val Lys Asp Tyr Phe Pro Glu Pro Val Thr Val Ser Trp Asn
                195                 200                 205
Ser Gly Ala Leu Thr Ser Gly Val His Thr Phe Pro Ala Val Leu Gln
        210                 215                 220
Ser Ser Gly Leu Tyr Ser Leu Ser Ser Val Val Thr Val Pro Ser Ser
225                 230                 235                 240
Ser Leu Gly Thr Gln Thr Tyr Ile Cys Asn Val Asn His Lys Pro Ser
                245                 250                 255
Asn Thr Lys Val Asp Lys Lys Val Glu Pro Lys Ser Cys Asp Lys Thr
                260                 265                 270
His Thr Cys Pro Pro Cys Pro Ala Pro Glu Leu Leu Gly Gly Pro Ser
                275                 280                 285
Val Phe Leu Phe Pro Pro Lys Pro Lys Asp Thr Leu Met Ile Ser Arg
        290                 295                 300
Thr Pro Glu Val Thr Cys Val Val Val Asp Val Ser His Glu Asp Pro
305                 310                 315                 320
Glu Val Lys Phe Asn Trp Tyr Val Asp Gly Val Glu Val His Asn Ala
                325                 330                 335
Lys Thr Lys Pro Arg Glu Glu Gln Tyr Asn Ser Thr Tyr Arg Val Val
                340                 345                 350
Ser Val Leu Thr Val Leu His Gln Asp Trp Leu Asn Gly Lys Glu Tyr
                355                 360                 365
Lys Cys Lys Val Ser Asn Lys Ala Leu Pro Ala Pro Ile Glu Lys Thr
        370                 375                 380
Ile Ser Lys Ala Lys Gly Gln Pro Arg Glu Pro Gln Val Tyr Thr Leu
385                 390                 395                 400
Pro Pro Ser Arg Asp Glu Leu Thr Lys Asn Gln Val Ser Leu Thr Cys
                405                 410                 415
Leu Val Lys Gly Phe Tyr Pro Ser Asp Ile Ala Val Glu Trp Glu Ser
                420                 425                 430
```

-continued

Asn Gly Gln Pro Glu Asn Asn Tyr Lys Thr Thr Pro Pro Val Leu Asp
        435                 440                 445

Ser Asp Gly Ser Phe Phe Leu Tyr Ser Lys Leu Thr Val Asp Lys Ser
    450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495

<210> SEQ ID NO 80
<211> LENGTH: 496
<212> TYPE: PRT
<213> ORGANISM: Artificial Sequence
<220> FEATURE:
<223> OTHER INFORMATION: Synthetic

<400> SEQUENCE: 80

Gln Gly Cys Thr Tyr Pro Ser Trp Val Ala Tyr Ile Arg Phe Cys Gly
1               5                   10                  15

Ser Ser Gly Gly Ser Gly Gly Ser Gly Gly Ser Gly Gly Gly Pro Leu
            20                  25                  30

Gly Leu Ala Gly Gly Ser Ser Gly Gln Val Gln Leu Val Glu Ser Gly
        35                  40                  45

Gly Gly Val Val Gln Pro Gly Arg Ser Leu Arg Leu Ser Cys Ala Ala
    50                  55                  60

Ser Gly Phe Thr Phe Ser Ser Tyr Gly Met His Trp Val Arg Gln Ala
65                  70                  75                  80

Pro Gly Lys Gly Leu Glu Trp Val Ala Val Ile Trp Asp Asp Gly Ser
                85                  90                  95

Asn Lys Tyr Tyr Val Asp Ser Val Lys Gly Arg Phe Thr Ile Ser Arg
            100                 105                 110

Asp Asn Ser Lys Asn Thr Leu Tyr Leu Gln Met Asn Ser Leu Arg Ala
        115                 120                 125

Glu Asp Thr Ala Val Tyr Tyr Cys Ala Arg Asp Asp Tyr Tyr Gly Ser
    130                 135                 140

Gly Ser Phe Asn Ser Tyr Tyr Gly Thr Asp Val Trp Gly Gln Gly Thr
145                 150                 155                 160

Thr Val Thr Val Ser Ser Ala Ser Thr Lys Gly Pro Ser Val Phe Pro
                165                 170                 175

Leu Ala Pro Ser Ser Lys Ser Thr Ser Gly Gly Thr Ala Ala Leu Gly
            180                 185                 190

Cys Leu Val Lys Asp Tyr Phe Pro Glu Pro Val Thr Val Ser Trp Asn
        195                 200                 205

Ser Gly Ala Leu Thr Ser Gly Val His Thr Phe Pro Ala Val Leu Gln
    210                 215                 220

Ser Ser Gly Leu Tyr Ser Leu Ser Ser Val Val Thr Val Pro Ser Ser
225                 230                 235                 240

Ser Leu Gly Thr Gln Thr Tyr Ile Cys Asn Val Asn His Lys Pro Ser
                245                 250                 255

Asn Thr Lys Val Asp Lys Lys Val Glu Pro Lys Ser Cys Asp Lys Thr
            260                 265                 270

His Thr Cys Pro Pro Cys Pro Ala Pro Glu Leu Leu Gly Gly Pro Ser
        275                 280                 285

Val Phe Leu Phe Pro Pro Lys Pro Lys Asp Thr Leu Met Ile Ser Arg
    290                 295                 300

```
Thr Pro Glu Val Thr Cys Val Val Asp Val Ser His Glu Asp Pro
305                 310                 315                 320

Glu Val Lys Phe Asn Trp Tyr Val Asp Gly Val Glu Val His Asn Ala
            325                 330                 335

Lys Thr Lys Pro Arg Glu Glu Gln Tyr Asn Ser Thr Tyr Arg Val Val
        340                 345                 350

Ser Val Leu Thr Val Leu His Gln Asp Trp Leu Asn Gly Lys Glu Tyr
        355                 360                 365

Lys Cys Lys Val Ser Asn Lys Ala Leu Pro Ala Pro Ile Glu Lys Thr
370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
            405                 410                 415

Leu Val Lys Gly Phe Tyr Pro Ser Asp Ile Ala Val Glu Trp Glu Ser
        420                 425                 430

Asn Gly Gln Pro Glu Asn Asn Tyr Lys Thr Thr Pro Pro Val Leu Asp
        435                 440                 445

Ser Asp Gly Ser Phe Phe Leu Tyr Ser Lys Leu Thr Val Asp Lys Ser
450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
            485                 490                 495

<210> SEQ ID NO 81
<211> LENGTH: 496
<212> TYPE: PRT
<213> ORGANISM: Artificial Sequence
<220> FEATURE:
<223> OTHER INFORMATION: Synthetic

<400> SEQUENCE: 81

Gln Gly Val Cys Thr Tyr Pro Pro Ala His Arg Thr Arg Phe Cys Gly
1               5                   10                  15

Ser Ser Gly Gly Ser Gly Gly Ser Gly Gly Ser Gly Gly Gly Pro Leu
            20                  25                  30

Gly Leu Ala Gly Gly Ser Ser Gly Gln Val Gln Leu Val Glu Ser Gly
        35                  40                  45

Gly Gly Val Val Gln Pro Gly Arg Ser Leu Arg Leu Ser Cys Ala Ala
    50                  55                  60

Ser Gly Phe Thr Phe Ser Ser Tyr Gly Met His Trp Val Arg Gln Ala
65                  70                  75                  80

Pro Gly Lys Gly Leu Glu Trp Val Ala Val Ile Trp Asp Asp Gly Ser
                85                  90                  95

Asn Lys Tyr Tyr Val Asp Ser Val Lys Gly Arg Phe Thr Ile Ser Arg
            100                 105                 110

Asp Asn Ser Lys Asn Thr Leu Tyr Leu Gln Met Asn Ser Leu Arg Ala
        115                 120                 125

Glu Asp Thr Ala Val Tyr Tyr Cys Ala Arg Asp Tyr Tyr Gly Ser
    130                 135                 140

Gly Ser Phe Asn Ser Tyr Tyr Gly Thr Asp Val Trp Gly Gln Gly Thr
145                 150                 155                 160

Thr Val Thr Val Ser Ser Ala Ser Thr Lys Gly Pro Ser Val Phe Pro
                165                 170                 175
```

Leu Ala Pro Ser Ser Lys Ser Thr Ser Gly Gly Thr Ala Ala Leu Gly
            180                 185                 190

Cys Leu Val Lys Asp Tyr Phe Pro Glu Pro Val Thr Val Ser Trp Asn
        195                 200                 205

Ser Gly Ala Leu Thr Ser Gly Val His Thr Phe Pro Ala Val Leu Gln
    210                 215                 220

Ser Ser Gly Leu Tyr Ser Leu Ser Ser Val Val Thr Val Pro Ser Ser
225                 230                 235                 240

Ser Leu Gly Thr Gln Thr Tyr Ile Cys Asn Val Asn His Lys Pro Ser
                245                 250                 255

Asn Thr Lys Val Asp Lys Lys Val Glu Pro Lys Ser Cys Asp Lys Thr
            260                 265                 270

His Thr Cys Pro Pro Cys Pro Ala Pro Glu Leu Leu Gly Gly Pro Ser
        275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Ala Leu Pro Ala Pro Ile Glu Lys Thr
    370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
                405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
        435                 440                 445

Ser Asp Gly Ser Phe Phe Leu Tyr Ser Lys Leu Thr Val Asp Lys Ser
    450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495

<210> SEQ ID NO 82
<211> LENGTH: 496
<212> TYPE: PRT
<213> ORGANISM: Artificial Sequence
<220> FEATURE:
<223> OTHER INFORMATION: Synthetic

<400> SEQUENCE: 82

Gln Gly Cys Thr Met Pro Tyr His Ile His Ser Ile Gly Leu Cys Gly
1               5                   10                  15

Ser Ser Gly Gly Ser Gly Gly Ser Gly Gly Gly Gly Pro Leu
            20                  25                  30

Gly Leu Ala Gly Gly Ser Ser Gly Gln Val Gln Leu Val Glu Ser Gly
        35                  40                  45

```
Gly Gly Val Val Gln Pro Gly Arg Ser Leu Arg Leu Ser Cys Ala Ala
 50                  55                  60

Ser Gly Phe Thr Phe Ser Ser Tyr Gly Met His Trp Val Arg Gln Ala
 65                  70                  75                  80

Pro Gly Lys Gly Leu Glu Trp Val Ala Val Ile Trp Asp Asp Gly Ser
                 85                  90                  95

Asn Lys Tyr Tyr Val Asp Ser Val Lys Gly Arg Phe Thr Ile Ser Arg
                100                 105                 110

Asp Asn Ser Lys Asn Thr Leu Tyr Leu Gln Met Asn Ser Leu Arg Ala
            115                 120                 125

Glu Asp Thr Ala Val Tyr Tyr Cys Ala Arg Asp Tyr Tyr Gly Ser
        130                 135                 140

Gly Ser Phe Asn Ser Tyr Tyr Gly Thr Asp Val Trp Gly Gln Gly Thr
145                 150                 155                 160

Thr Val Thr Val Ser Ser Ala Ser Thr Lys Gly Pro Ser Val Phe Pro
                165                 170                 175

Leu Ala Pro Ser Ser Lys Ser Thr Ser Gly Gly Thr Ala Ala Leu Gly
            180                 185                 190

Cys Leu Val Lys Asp Tyr Phe Pro Glu Pro Val Thr Val Ser Trp Asn
            195                 200                 205

Ser Gly Ala Leu Thr Ser Gly Val His Thr Phe Pro Ala Val Leu Gln
210                 215                 220

Ser Ser Gly Leu Tyr Ser Leu Ser Ser Val Val Thr Val Pro Ser Ser
225                 230                 235                 240

Ser Leu Gly Thr Gln Thr Tyr Ile Cys Asn Val Asn His Lys Pro Ser
                245                 250                 255

Asn Thr Lys Val Asp Lys Lys Val Glu Pro Lys Ser Cys Asp Lys Thr
            260                 265                 270

His Thr Cys Pro Pro Cys Pro Ala Pro Glu Leu Leu Gly Gly Pro Ser
            275                 280                 285

Val Phe Leu Phe Pro Pro Lys Pro Lys Asp Thr Leu Met Ile Ser Arg
            290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
            355                 360                 365

Lys Cys Lys Val Ser Asn Lys Ala Leu Pro Ala Pro Ile Glu Lys Thr
            370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
                405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
            435                 440                 445

Ser Asp Gly Ser Phe Phe Leu Tyr Ser Lys Leu Thr Val Asp Lys Ser
450                 455                 460
```

```
Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
            485                 490                 495
```

<210> SEQ ID NO 83
<211> LENGTH: 496
<212> TYPE: PRT
<213> ORGANISM: Artificial Sequence
<220> FEATURE:
<223> OTHER INFORMATION: Synthetic

<400> SEQUENCE: 83

```
Gln Gly Trp Cys Thr Ile Pro Ser Ser Met Ser Ile Arg Leu Cys Gly
1               5                   10                  15

Ser Ser Gly Gly Ser Gly Gly Ser Gly Gly Ser Gly Gly Gly Pro Leu
            20                  25                  30

Gly Leu Ala Gly Gly Ser Ser Gly Gln Val Gln Leu Val Glu Ser Gly
        35                  40                  45

Gly Gly Val Val Gln Pro Gly Arg Ser Leu Arg Leu Ser Cys Ala Ala
    50                  55                  60

Ser Gly Phe Thr Phe Ser Ser Tyr Gly Met His Trp Val Arg Gln Ala
65                  70                  75                  80

Pro Gly Lys Gly Leu Glu Trp Val Ala Val Ile Trp Asp Asp Gly Ser
            85                  90                  95

Asn Lys Tyr Tyr Val Asp Ser Val Lys Gly Arg Phe Thr Ile Ser Arg
            100                 105                 110

Asp Asn Ser Lys Asn Thr Leu Tyr Leu Gln Met Asn Ser Leu Arg Ala
        115                 120                 125

Glu Asp Thr Ala Val Tyr Tyr Cys Ala Arg Asp Asp Tyr Tyr Gly Ser
    130                 135                 140

Gly Ser Phe Asn Ser Tyr Tyr Gly Thr Asp Val Trp Gly Gln Gly Thr
145                 150                 155                 160

Thr Val Thr Val Ser Ser Ala Ser Thr Lys Gly Pro Ser Val Phe Pro
                165                 170                 175

Leu Ala Pro Ser Ser Lys Ser Thr Ser Gly Gly Thr Ala Ala Leu Gly
            180                 185                 190

Cys Leu Val Lys Asp Tyr Phe Pro Glu Pro Val Thr Val Ser Trp Asn
        195                 200                 205

Ser Gly Ala Leu Thr Ser Gly Val His Thr Phe Pro Ala Val Leu Gln
    210                 215                 220

Ser Ser Gly Leu Tyr Ser Leu Ser Ser Val Val Thr Val Pro Ser Ser
225                 230                 235                 240

Ser Leu Gly Thr Gln Thr Tyr Ile Cys Asn Val Asn His Lys Pro Ser
                245                 250                 255

Asn Thr Lys Val Asp Lys Lys Val Glu Pro Lys Ser Cys Asp Lys Thr
            260                 265                 270

His Thr Cys Pro Pro Cys Pro Ala Pro Glu Leu Leu Gly Gly Pro Ser
        275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335
```

```
Lys Thr Lys Pro Arg Glu Glu Gln Tyr Asn Ser Thr Tyr Arg Val Val
                340                 345                 350

Ser Val Leu Thr Val Leu His Gln Asp Trp Leu Asn Gly Lys Glu Tyr
            355                 360                 365

Lys Cys Lys Val Ser Asn Lys Ala Leu Pro Ala Pro Ile Glu Lys Thr
        370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
                405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
        435                 440                 445

Ser Asp Gly Ser Phe Phe Leu Tyr Ser Lys Leu Thr Val Asp Lys Ser
    450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495

<210> SEQ ID NO 84
<211> LENGTH: 496
<212> TYPE: PRT
<213> ORGANISM: Artificial Sequence
<220> FEATURE:
<223> OTHER INFORMATION: Synthetic

<400> SEQUENCE: 84

Gln Gly Cys His Ile Gly Lys Arg Pro Val Pro Cys Leu Trp Ile Gly
1               5                   10                  15

Ser Ser Gly Gly Ser Gly Gly Ser Gly Gly Ser Gly Gly Gly Pro Leu
                20                  25                  30

Gly Leu Ala Gly Gly Ser Ser Gly Gln Val Gln Leu Val Glu Ser Gly
            35                  40                  45

Gly Gly Val Val Gln Pro Gly Arg Ser Leu Arg Leu Ser Cys Ala Ala
        50                  55                  60

Ser Gly Phe Thr Phe Ser Ser Tyr Gly Met His Trp Val Arg Gln Ala
65                  70                  75                  80

Pro Gly Lys Gly Leu Glu Trp Val Ala Val Ile Trp Asp Asp Gly Ser
                85                  90                  95

Asn Lys Tyr Tyr Val Asp Ser Val Lys Gly Arg Phe Thr Ile Ser Arg
            100                 105                 110

Asp Asn Ser Lys Asn Thr Leu Tyr Leu Gln Met Asn Ser Leu Arg Ala
        115                 120                 125

Glu Asp Thr Ala Val Tyr Tyr Cys Ala Arg Asp Asp Tyr Tyr Gly Ser
    130                 135                 140

Gly Ser Phe Asn Ser Tyr Tyr Gly Thr Asp Val Trp Gly Gln Gly Thr
145                 150                 155                 160

Thr Val Thr Val Ser Ser Ala Ser Thr Lys Gly Pro Ser Val Phe Pro
                165                 170                 175

Leu Ala Pro Ser Ser Lys Ser Thr Ser Gly Gly Thr Ala Ala Leu Gly
            180                 185                 190

Cys Leu Val Lys Asp Tyr Phe Pro Glu Pro Val Thr Val Ser Trp Asn
        195                 200                 205
```

```
Ser Gly Ala Leu Thr Ser Gly Val His Thr Phe Pro Ala Val Leu Gln
    210                 215                 220

Ser Ser Gly Leu Tyr Ser Leu Ser Ser Val Val Thr Val Pro Ser Ser
225                 230                 235                 240

Ser Leu Gly Thr Gln Thr Tyr Ile Cys Asn Val Asn His Lys Pro Ser
            245                 250                 255

Asn Thr Lys Val Asp Lys Lys Val Glu Pro Lys Ser Cys Asp Lys Thr
            260                 265                 270

His Thr Cys Pro Pro Cys Pro Ala Pro Glu Leu Leu Gly Gly Pro Ser
            275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Ala Leu Pro Ala Pro Ile Glu Lys Thr
    370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
                405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
        435                 440                 445

Ser Asp Gly Ser Phe Phe Leu Tyr Ser Lys Leu Thr Val Asp Lys Ser
    450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495

<210> SEQ ID NO 85
<211> LENGTH: 496
<212> TYPE: PRT
<213> ORGANISM: Artificial Sequence
<220> FEATURE:
<223> OTHER INFORMATION: Synthetic

<400> SEQUENCE: 85

Gln Gly Cys Tyr Ile Gly Leu Arg Met Val Pro Cys Phe His Met Gly
1               5                   10                  15

Ser Ser Gly Gly Ser Gly Gly Ser Gly Gly Gly Pro Leu
                20                  25                  30

Gly Leu Ala Gly Gly Ser Ser Gly Gln Val Gln Leu Val Glu Ser Gly
            35                  40                  45

Gly Gly Val Val Gln Pro Gly Arg Ser Leu Arg Leu Ser Cys Ala Ala
        50                  55                  60

Ser Gly Phe Thr Phe Ser Ser Tyr Gly Met His Trp Val Arg Gln Ala
65                  70                  75                  80
```

-continued

```
Pro Gly Lys Gly Leu Glu Trp Val Ala Val Ile Trp Asp Asp Gly Ser
                85                  90                  95

Asn Lys Tyr Tyr Val Asp Ser Val Lys Gly Arg Phe Thr Ile Ser Arg
            100                 105                 110

Asp Asn Ser Lys Asn Thr Leu Tyr Leu Gln Met Asn Ser Leu Arg Ala
        115                 120                 125

Glu Asp Thr Ala Val Tyr Tyr Cys Ala Arg Asp Asp Tyr Tyr Gly Ser
    130                 135                 140

Gly Ser Phe Asn Ser Tyr Tyr Gly Thr Asp Val Trp Gly Gln Gly Thr
145                 150                 155                 160

Thr Val Thr Val Ser Ser Ala Ser Thr Lys Gly Pro Ser Val Phe Pro
                165                 170                 175

Leu Ala Pro Ser Ser Lys Ser Thr Ser Gly Gly Thr Ala Ala Leu Gly
            180                 185                 190

Cys Leu Val Lys Asp Tyr Phe Pro Glu Pro Val Thr Val Ser Trp Asn
        195                 200                 205

Ser Gly Ala Leu Thr Ser Gly Val His Thr Phe Pro Ala Val Leu Gln
    210                 215                 220

Ser Ser Gly Leu Tyr Ser Leu Ser Ser Val Val Thr Val Pro Ser Ser
225                 230                 235                 240

Ser Leu Gly Thr Gln Thr Tyr Ile Cys Asn Val Asn His Lys Pro Ser
                245                 250                 255

Asn Thr Lys Val Asp Lys Lys Val Glu Pro Lys Ser Cys Asp Lys Thr
            260                 265                 270

His Thr Cys Pro Pro Cys Pro Ala Pro Glu Leu Leu Gly Gly Pro Ser
        275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Ala Leu Pro Ala Pro Ile Glu Lys Thr
    370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
                405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
        435                 440                 445

Ser Asp Gly Ser Phe Phe Leu Tyr Ser Lys Leu Thr Val Asp Lys Ser
    450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495
```

```
<210> SEQ ID NO 86
<211> LENGTH: 496
<212> TYPE: PRT
<213> ORGANISM: Artificial Sequence
<220> FEATURE:
<223> OTHER INFORMATION: Synthetic

<400> SEQUENCE: 86

Gln Gly Cys Thr Met Pro Ser His Ala Val Ala Ser Phe Leu Cys Gly
1               5                   10                  15

Ser Ser Gly Gly Ser Gly Gly Ser Gly Ser Gly Gly Gly Pro Leu
            20                  25                  30

Gly Leu Ala Gly Gly Ser Ser Gly Gln Val Gln Leu Val Glu Ser Gly
            35                  40                  45

Gly Gly Val Val Gln Pro Gly Arg Ser Leu Arg Leu Ser Cys Ala Ala
        50                  55                  60

Ser Gly Phe Thr Phe Ser Ser Tyr Gly Met His Trp Val Arg Gln Ala
65                  70                  75                  80

Pro Gly Lys Gly Leu Glu Trp Val Ala Val Ile Trp Asp Asp Gly Ser
                85                  90                  95

Asn Lys Tyr Tyr Val Asp Ser Val Lys Gly Arg Phe Thr Ile Ser Arg
            100                 105                 110

Asp Asn Ser Lys Asn Thr Leu Tyr Leu Gln Met Asn Ser Leu Arg Ala
        115                 120                 125

Glu Asp Thr Ala Val Tyr Tyr Cys Ala Arg Asp Asp Tyr Tyr Gly Ser
130                 135                 140

Gly Ser Phe Asn Ser Tyr Tyr Gly Thr Asp Val Trp Gly Gln Gly Thr
145                 150                 155                 160

Thr Val Thr Val Ser Ser Ala Ser Thr Lys Gly Pro Ser Val Phe Pro
                165                 170                 175

Leu Ala Pro Ser Ser Lys Ser Thr Ser Gly Gly Thr Ala Ala Leu Gly
            180                 185                 190

Cys Leu Val Lys Asp Tyr Phe Pro Glu Pro Val Thr Val Ser Trp Asn
        195                 200                 205

Ser Gly Ala Leu Thr Ser Gly Val His Thr Phe Pro Ala Val Leu Gln
210                 215                 220

Ser Ser Gly Leu Tyr Ser Leu Ser Ser Val Val Thr Val Pro Ser Ser
225                 230                 235                 240

Ser Leu Gly Thr Gln Thr Tyr Ile Cys Asn Val Asn His Lys Pro Ser
                245                 250                 255

Asn Thr Lys Val Asp Lys Lys Val Glu Pro Lys Ser Cys Asp Lys Thr
            260                 265                 270

His Thr Cys Pro Pro Cys Pro Ala Pro Glu Leu Leu Gly Gly Pro Ser
        275                 280                 285

Val Phe Leu Phe Pro Pro Lys Pro Lys Asp Thr Leu Met Ile Ser Arg
290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Ala Leu Pro Ala Pro Ile Glu Lys Thr
```

```
            370                 375                 380
Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
                405                 410                 415

Leu Val Lys Gly Phe Tyr Pro Ser Asp Ile Ala Val Glu Trp Glu Ser
                420                 425                 430

Asn Gly Gln Pro Glu Asn Asn Tyr Lys Thr Thr Pro Pro Val Leu Asp
                435                 440                 445

Ser Asp Gly Ser Phe Phe Leu Tyr Ser Lys Leu Thr Val Asp Lys Ser
            450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495

<210> SEQ ID NO 87
<211> LENGTH: 496
<212> TYPE: PRT
<213> ORGANISM: Artificial Sequence
<220> FEATURE:
<223> OTHER INFORMATION: Synthetic

<400> SEQUENCE: 87

Gln Gly Cys Thr Met Pro Val His Thr Tyr Ser Gln Trp Leu Cys Gly
1               5                   10                  15

Ser Ser Gly Gly Ser Gly Gly Ser Gly Gly Ser Gly Gly Gly Pro Leu
                20                  25                  30

Gly Leu Ala Gly Gly Ser Ser Gly Gln Val Gln Leu Val Glu Ser Gly
            35                  40                  45

Gly Gly Val Val Gln Pro Gly Arg Ser Leu Arg Leu Ser Cys Ala Ala
        50                  55                  60

Ser Gly Phe Thr Phe Ser Ser Tyr Gly Met His Trp Val Arg Gln Ala
65                  70                  75                  80

Pro Gly Lys Gly Leu Glu Trp Val Ala Val Ile Trp Asp Asp Gly Ser
                85                  90                  95

Asn Lys Tyr Tyr Val Asp Ser Val Lys Gly Arg Phe Thr Ile Ser Arg
                100                 105                 110

Asp Asn Ser Lys Asn Thr Leu Tyr Leu Gln Met Asn Ser Leu Arg Ala
            115                 120                 125

Glu Asp Thr Ala Val Tyr Tyr Cys Ala Arg Asp Asp Tyr Tyr Gly Ser
        130                 135                 140

Gly Ser Phe Asn Ser Tyr Tyr Gly Thr Asp Val Trp Gly Gln Gly Thr
145                 150                 155                 160

Thr Val Thr Val Ser Ser Ala Ser Thr Lys Gly Pro Ser Val Phe Pro
                165                 170                 175

Leu Ala Pro Ser Ser Lys Ser Thr Ser Gly Gly Thr Ala Ala Leu Gly
                180                 185                 190

Cys Leu Val Lys Asp Tyr Phe Pro Glu Pro Val Thr Val Ser Trp Asn
            195                 200                 205

Ser Gly Ala Leu Thr Ser Gly Val His Thr Phe Pro Ala Val Leu Gln
        210                 215                 220

Ser Ser Gly Leu Tyr Ser Leu Ser Ser Val Val Thr Val Pro Ser Ser
225                 230                 235                 240

Ser Leu Gly Thr Gln Thr Tyr Ile Cys Asn Val Asn His Lys Pro Ser
```

```
                    245                 250                 255
Asn Thr Lys Val Asp Lys Val Glu Pro Lys Ser Cys Asp Lys Thr
            260                 265                 270

His Thr Cys Pro Pro Cys Pro Ala Pro Glu Leu Leu Gly Gly Pro Ser
        275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Ala Leu Pro Ala Pro Ile Glu Lys Thr
    370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
                405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
        435                 440                 445

Ser Asp Gly Ser Phe Phe Leu Tyr Ser Lys Leu Thr Val Asp Lys Ser
    450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495

<210> SEQ ID NO 88
<211> LENGTH: 496
<212> TYPE: PRT
<213> ORGANISM: Artificial Sequence
<220> FEATURE:
<223> OTHER INFORMATION: Synthetic

<400> SEQUENCE: 88

Gln Gly Cys Thr Tyr Pro Pro Arg Phe His Met His Trp Leu Cys Gly
1               5                   10                  15

Ser Ser Gly Gly Ser Gly Gly Ser Gly Gly Ser Gly Gly Gly Pro Leu
            20                  25                  30

Gly Leu Ala Gly Gly Ser Ser Gly Gln Val Gln Leu Val Glu Ser Gly
        35                  40                  45

Gly Gly Val Val Gln Pro Gly Arg Ser Leu Arg Leu Ser Cys Ala Ala
    50                  55                  60

Ser Gly Phe Thr Phe Ser Ser Tyr Gly Met His Trp Val Arg Gln Ala
65                  70                  75                  80

Pro Gly Lys Gly Leu Glu Trp Val Ala Val Ile Trp Asp Asp Gly Ser
                85                  90                  95

Asn Lys Tyr Tyr Val Asp Ser Val Lys Gly Arg Phe Thr Ile Ser Arg
            100                 105                 110

Asp Asn Ser Lys Asn Thr Leu Tyr Leu Gln Met Asn Ser Leu Arg Ala
```

```
                115                 120                 125
Glu Asp Thr Ala Val Tyr Tyr Cys Ala Arg Asp Asp Tyr Tyr Gly Ser
130                 135                 140

Gly Ser Phe Asn Ser Tyr Tyr Gly Thr Asp Val Trp Gly Gln Gly Thr
145                 150                 155                 160

Thr Val Thr Val Ser Ser Ala Ser Thr Lys Gly Pro Ser Val Phe Pro
                165                 170                 175

Leu Ala Pro Ser Ser Lys Ser Thr Ser Gly Gly Thr Ala Ala Leu Gly
                180                 185                 190

Cys Leu Val Lys Asp Tyr Phe Pro Glu Pro Val Thr Val Ser Trp Asn
                195                 200                 205

Ser Gly Ala Leu Thr Ser Gly Val His Thr Phe Pro Ala Val Leu Gln
210                 215                 220

Ser Ser Gly Leu Tyr Ser Leu Ser Ser Val Val Thr Val Pro Ser Ser
225                 230                 235                 240

Ser Leu Gly Thr Gln Thr Tyr Ile Cys Asn Val Asn His Lys Pro Ser
                245                 250                 255

Asn Thr Lys Val Asp Lys Lys Val Glu Pro Lys Ser Cys Asp Lys Thr
                260                 265                 270

His Thr Cys Pro Pro Cys Pro Ala Pro Glu Leu Leu Gly Gly Pro Ser
                275                 280                 285

Val Phe Leu Phe Pro Pro Lys Pro Lys Asp Thr Leu Met Ile Ser Arg
290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
                340                 345                 350

Ser Val Leu Thr Val Leu His Gln Asp Trp Leu Asn Gly Lys Glu Tyr
                355                 360                 365

Lys Cys Lys Val Ser Asn Lys Ala Leu Pro Ala Pro Ile Glu Lys Thr
370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
                405                 410                 415

Leu Val Lys Gly Phe Tyr Pro Ser Asp Ile Ala Val Glu Trp Glu Ser
                420                 425                 430

Asn Gly Gln Pro Glu Asn Asn Tyr Lys Thr Thr Pro Pro Val Leu Asp
                435                 440                 445

Ser Asp Gly Ser Phe Phe Leu Tyr Ser Lys Leu Thr Val Asp Lys Ser
                450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495

<210> SEQ ID NO 89
<211> LENGTH: 496
<212> TYPE: PRT
<213> ORGANISM: Artificial Sequence
<220> FEATURE:
<223> OTHER INFORMATION: Synthetic
```

```
<400> SEQUENCE: 89

Gln Gly Cys Thr His Val Ala Gln Trp Ala Ile Lys Ala Phe Cys Gly
1               5                   10                  15

Ser Ser Gly Gly Ser Gly Gly Ser Gly Gly Ser Gly Gly Gly Pro Leu
            20                  25                  30

Gly Leu Ala Gly Gly Ser Ser Gly Gln Val Gln Leu Val Glu Ser Gly
        35                  40                  45

Gly Gly Val Val Gln Pro Gly Arg Ser Leu Arg Leu Ser Cys Ala Ala
    50                  55                  60

Ser Gly Phe Thr Phe Ser Ser Tyr Gly Met His Trp Val Arg Gln Ala
65                  70                  75                  80

Pro Gly Lys Gly Leu Glu Trp Val Ala Val Ile Trp Asp Asp Gly Ser
                85                  90                  95

Asn Lys Tyr Tyr Val Asp Ser Val Lys Gly Arg Phe Thr Ile Ser Arg
            100                 105                 110

Asp Asn Ser Lys Asn Thr Leu Tyr Leu Gln Met Asn Ser Leu Arg Ala
        115                 120                 125

Glu Asp Thr Ala Val Tyr Tyr Cys Ala Arg Asp Asp Tyr Tyr Gly Ser
130                 135                 140

Gly Ser Phe Asn Ser Tyr Tyr Gly Thr Asp Val Trp Gly Gln Gly Thr
145                 150                 155                 160

Thr Val Thr Val Ser Ser Ala Ser Thr Lys Gly Pro Ser Val Phe Pro
                165                 170                 175

Leu Ala Pro Ser Ser Lys Ser Thr Ser Gly Gly Thr Ala Ala Leu Gly
            180                 185                 190

Cys Leu Val Lys Asp Tyr Phe Pro Glu Pro Val Thr Val Ser Trp Asn
        195                 200                 205

Ser Gly Ala Leu Thr Ser Gly Val His Thr Phe Pro Ala Val Leu Gln
210                 215                 220

Ser Ser Gly Leu Tyr Ser Leu Ser Ser Val Val Thr Val Pro Ser Ser
225                 230                 235                 240

Ser Leu Gly Thr Gln Thr Tyr Ile Cys Asn Val Asn His Lys Pro Ser
                245                 250                 255

Asn Thr Lys Val Asp Lys Lys Val Glu Pro Lys Ser Cys Asp Lys Thr
            260                 265                 270

His Thr Cys Pro Pro Cys Pro Ala Pro Glu Leu Leu Gly Gly Pro Ser
        275                 280                 285

Val Phe Leu Phe Pro Pro Lys Pro Lys Asp Thr Leu Met Ile Ser Arg
290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Ala Leu Pro Ala Pro Ile Glu Lys Thr
370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
                405                 410                 415
```

-continued

```
Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
        435                 440                 445

Ser Asp Gly Ser Phe Phe Leu Tyr Ser Lys Leu Thr Val Asp Lys Ser
450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495

<210> SEQ ID NO 90
<211> LENGTH: 512
<212> TYPE: PRT
<213> ORGANISM: Artificial Sequence
<220> FEATURE:
<223> OTHER INFORMATION: Synthetic

<400> SEQUENCE: 90

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ala Val Ile Trp Asp Asp Gly Ser Asn Lys Tyr
65                  70                  75                  80

Tyr Val Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Asp Asp Tyr Tyr Gly Ser Gly Ser Phe
        115                 120                 125

Asn Ser Tyr Tyr Gly Thr Asp Val Trp Gly Gln Gly Thr Thr Val Thr
    130                 135                 140

Val Ser Ser Gly Gly Gly Ser Gly Gly Gly Ser Gly Gly Gly Gly
145                 150                 155                 160

Gly Ser Glu Ile Val Leu Thr Gln Ser Pro Ala Thr Leu Ser Leu Ser
                165                 170                 175

Pro Gly Glu Arg Ala Thr Leu Ser Cys Arg Ala Ser Gln Ser Val Ser
            180                 185                 190

Ile Tyr Leu Ala Trp Tyr Gln Gln Lys Pro Gly Gln Ala Pro Arg Leu
        195                 200                 205

Leu Ile Tyr Asp Ala Ser Asn Arg Ala Thr Gly Ile Pro Ala Arg Phe
    210                 215                 220

Ser Gly Ser Gly Ser Gly Thr Asp Phe Thr Leu Thr Ile Ser Ser Leu
225                 230                 235                 240

Glu Pro Glu Asp Phe Ala Val Tyr Tyr Cys Gln Gln Arg Ser Asn Trp
                245                 250                 255

Pro Pro Phe Thr Phe Gly Pro Gly Thr Lys Val Asp Ile Lys Ser Ala
            260                 265                 270

Ala Ala Phe Val Pro Val Phe Leu Pro Ala Lys Pro Thr Thr Thr Pro
        275                 280                 285
```

Ala Pro Arg Pro Pro Thr Pro Ala Pro Thr Ile Ala Ser Gln Pro Leu
            290                 295                 300

Ser Leu Arg Pro Glu Ala Cys Arg Pro Ala Ala Gly Gly Ala Val His
305                 310                 315                 320

Thr Arg Gly Leu Asp Phe Ala Cys Asp Ile Tyr Ile Trp Ala Pro Leu
                325                 330                 335

Ala Gly Thr Cys Gly Val Leu Leu Ser Leu Val Ile Thr Leu Tyr
            340                 345                 350

Cys Asn His Arg Asn Arg Lys Arg Gly Arg Lys Lys Leu Leu Tyr Ile
            355                 360                 365

Phe Lys Gln Pro Phe Met Arg Pro Val Gln Thr Thr Gln Glu Glu Asp
370                 375                 380

Gly Cys Ser Cys Arg Phe Pro Glu Glu Glu Gly Gly Cys Glu Leu
385                 390                 395                 400

Arg Val Lys Phe Ser Arg Ser Ala Asp Ala Pro Ala Tyr Gln Gln Gly
                405                 410                 415

Gln Asn Gln Leu Tyr Asn Glu Leu Asn Leu Gly Arg Arg Glu Glu Tyr
            420                 425                 430

Asp Val Leu Asp Lys Arg Gly Arg Asp Pro Glu Met Gly Gly Lys
            435                 440                 445

Pro Arg Arg Lys Asn Pro Gln Glu Gly Leu Tyr Asn Glu Leu Gln Lys
450                 455                 460

Asp Lys Met Ala Glu Ala Tyr Ser Glu Ile Gly Met Lys Gly Glu Arg
465                 470                 475                 480

Arg Arg Gly Lys Gly His Asp Gly Leu Tyr Gln Gly Leu Ser Thr Ala
                485                 490                 495

Thr Lys Asp Thr Tyr Asp Ala Leu His Met Gln Ala Leu Pro Pro Arg
                500                 505                 510

<210> SEQ ID NO 91
<211> LENGTH: 557
<212> TYPE: PRT
<213> ORGANISM: Artificial Sequence
<220> FEATURE:
<223> OTHER INFORMATION: Synthetic

<400> SEQUENCE: 91

Met Ala Leu Pro Val Thr Ala Leu Leu Leu Pro Leu Ala Leu Leu Leu
1               5                   10                  15

His Ala Ala Arg Pro Glu Val Ala Pro Gly Lys Arg Trp Phe Tyr Asn
                20                  25                  30

His Val Lys Gln Val Pro His Leu Val Gly Ser Ser Gly Gly Ser Gly
            35                  40                  45

Gly Ser Gly Gly Ser Gly Gly Pro Leu Gly Ala Gly Gly Ser
        50                  55                  60

Ser Gly Gln Val Gln Leu Val Glu Ser Gly Gly Val Val Gln Pro
65                  70                  75                  80

Gly Arg Ser Leu Arg Leu Ser Cys Ala Ala Ser Gly Phe Thr Phe Ser
                85                  90                  95

Ser Tyr Gly Met His Trp Val Arg Gln Ala Pro Gly Lys Gly Leu Glu
            100                 105                 110

Trp Val Ala Val Ile Trp Asp Asp Gly Ser Asn Lys Tyr Tyr Val Asp
        115                 120                 125

Ser Val Lys Gly Arg Phe Thr Ile Ser Arg Asp Asn Ser Lys Asn Thr
    130                 135                 140

```
Leu Tyr Leu Gln Met Asn Ser Leu Arg Ala Glu Asp Thr Ala Val Tyr
145                 150                 155                 160

Tyr Cys Ala Arg Asp Asp Tyr Gly Ser Gly Ser Phe Asn Ser Tyr
            165                 170                 175

Tyr Gly Thr Asp Val Trp Gly Gln Gly Thr Thr Val Thr Val Ser Ser
            180                 185                 190

Gly Gly Gly Gly Ser Gly Gly Gly Gly Ser Gly Gly Gly Gly Ser Glu
            195                 200                 205

Ile Val Leu Thr Gln Ser Pro Ala Thr Leu Ser Leu Ser Pro Gly Glu
            210                 215                 220

Arg Ala Thr Leu Ser Cys Arg Ala Ser Gln Ser Val Ser Ile Tyr Leu
225                 230                 235                 240

Ala Trp Tyr Gln Gln Lys Pro Gly Gln Ala Pro Arg Leu Leu Ile Tyr
                245                 250                 255

Asp Ala Ser Asn Arg Ala Thr Gly Ile Pro Ala Arg Phe Ser Gly Ser
            260                 265                 270

Gly Ser Gly Thr Asp Phe Thr Leu Thr Ile Ser Ser Leu Glu Pro Glu
            275                 280                 285

Asp Phe Ala Val Tyr Tyr Cys Gln Gln Arg Ser Asn Trp Pro Pro Phe
290                 295                 300

Thr Phe Gly Pro Gly Thr Lys Val Asp Ile Lys Ser Ala Ala Ala Phe
305                 310                 315                 320

Val Pro Val Phe Leu Pro Ala Lys Pro Thr Thr Pro Ala Pro Arg
            325                 330                 335

Pro Pro Thr Pro Ala Pro Thr Ile Ala Ser Gln Pro Leu Ser Leu Arg
            340                 345                 350

Pro Glu Ala Cys Arg Pro Ala Ala Gly Gly Ala Val His Thr Arg Gly
            355                 360                 365

Leu Asp Phe Ala Cys Asp Ile Tyr Ile Trp Ala Pro Leu Ala Gly Thr
370                 375                 380

Cys Gly Val Leu Leu Leu Ser Leu Val Ile Thr Leu Tyr Cys Asn His
385                 390                 395                 400

Arg Asn Arg Lys Arg Gly Arg Lys Lys Leu Leu Tyr Ile Phe Lys Gln
            405                 410                 415

Pro Phe Met Arg Pro Val Gln Thr Thr Gln Glu Glu Asp Gly Cys Ser
            420                 425                 430

Cys Arg Phe Pro Glu Glu Glu Gly Gly Cys Glu Leu Arg Val Lys
            435                 440                 445

Phe Ser Arg Ser Ala Asp Ala Pro Ala Tyr Gln Gln Gly Gln Asn Gln
450                 455                 460

Leu Tyr Asn Glu Leu Asn Leu Gly Arg Arg Glu Glu Tyr Asp Val Leu
465                 470                 475                 480

Asp Lys Arg Arg Gly Arg Asp Pro Glu Met Gly Gly Lys Pro Arg Arg
            485                 490                 495

Lys Asn Pro Gln Glu Gly Leu Tyr Asn Glu Leu Gln Lys Asp Lys Met
            500                 505                 510

Ala Glu Ala Tyr Ser Glu Ile Gly Met Lys Gly Glu Arg Arg Arg Gly
            515                 520                 525

Lys Gly His Asp Gly Leu Tyr Gln Gly Leu Ser Thr Ala Thr Lys Asp
            530                 535                 540

Thr Tyr Asp Ala Leu His Met Gln Ala Leu Pro Pro Arg
545                 550                 555
```

```
<210> SEQ ID NO 92
<211> LENGTH: 556
<212> TYPE: PRT
<213> ORGANISM: Artificial Sequence
<220> FEATURE:
<223> OTHER INFORMATION: Synthetic

<400> SEQUENCE: 92

Met Ala Leu Pro Val Thr Ala Leu Leu Leu Pro Leu Ala Leu Leu Leu
1               5                   10                  15

His Ala Ala Arg Pro His Glu Glu Val His Met Arg Pro Asn Lys Leu
            20                  25                  30

Ser Leu Thr Trp Ala Tyr Thr Gly Pro Gln Leu Arg Gly Ser Ser Gly
        35                  40                  45

Gly Ser Gly Gly Ser Gly Gly Gly Ser Gly Pro Leu Gly Leu Ala Gly
    50                  55                  60

Gly Gly Ser Gln Val Gln Leu Val Glu Ser Gly Gly Val Val Gln
65                  70                  75                  80

Pro Gly Arg Ser Leu Arg Leu Ser Cys Ala Ala Ser Gly Phe Thr Phe
                85                  90                  95

Ser Ser Tyr Gly Met His Trp Val Arg Gln Ala Pro Lys Gly Leu
            100                 105                 110

Glu Trp Val Ala Val Ile Trp Asp Asp Gly Ser Asn Lys Tyr Tyr Val
        115                 120                 125

Asp Ser Val Lys Gly Arg Phe Thr Ile Ser Arg Asp Asn Ser Lys Asn
    130                 135                 140

Thr Leu Tyr Leu Gln Met Asn Ser Leu Arg Ala Glu Asp Thr Ala Val
145                 150                 155                 160

Tyr Tyr Cys Ala Arg Asp Asp Tyr Tyr Gly Ser Gly Ser Phe Asn Ser
                165                 170                 175

Tyr Tyr Gly Thr Asp Val Trp Gly Gln Gly Thr Thr Val Thr Val Ser
            180                 185                 190

Ser Gly Gly Gly Gly Ser Gly Gly Gly Ser Gly Gly Gly Gly Ser
        195                 200                 205

Glu Ile Val Leu Thr Gln Ser Pro Ala Thr Leu Ser Leu Ser Pro Gly
    210                 215                 220

Glu Arg Ala Thr Leu Ser Cys Arg Ala Ser Gln Ser Val Ser Ile Tyr
225                 230                 235                 240

Leu Ala Trp Tyr Gln Gln Lys Pro Gly Gln Ala Pro Arg Leu Leu Ile
                245                 250                 255

Tyr Asp Ala Ser Asn Arg Ala Thr Gly Ile Pro Ala Arg Phe Ser Gly
            260                 265                 270

Ser Gly Ser Gly Thr Asp Phe Thr Leu Thr Ile Ser Ser Leu Glu Pro
        275                 280                 285

Glu Asp Phe Ala Val Tyr Tyr Cys Gln Gln Arg Ser Asn Trp Pro Pro
    290                 295                 300

Phe Thr Phe Gly Pro Gly Thr Lys Val Asp Ile Lys Ser Ala Ala Ala
305                 310                 315                 320

Phe Val Pro Val Phe Leu Pro Ala Lys Pro Thr Thr Thr Pro Ala Pro
                325                 330                 335

Arg Pro Pro Thr Pro Ala Pro Thr Ile Ala Ser Gln Pro Leu Ser Leu
            340                 345                 350

Arg Pro Glu Ala Cys Arg Pro Ala Ala Gly Gly Ala Val His Thr Arg
        355                 360                 365
```

Gly Leu Asp Phe Ala Cys Asp Ile Tyr Ile Trp Ala Pro Leu Ala Gly
    370                 375                 380

Thr Cys Gly Val Leu Leu Leu Ser Leu Val Ile Thr Leu Tyr Cys Asn
385                 390                 395                 400

His Arg Asn Arg Ser Lys Arg Ser Arg Leu Leu His Ser Asp Tyr Met
                405                 410                 415

Asn Met Thr Pro Arg Arg Pro Gly Pro Thr Arg Lys His Tyr Gln Pro
            420                 425                 430

Tyr Ala Pro Pro Arg Asp Phe Ala Ala Tyr Arg Ser Arg Val Lys Phe
            435                 440                 445

Ser Arg Ser Ala Asp Ala Pro Ala Tyr Gln Gln Gly Gln Asn Gln Leu
450                 455                 460

Tyr Asn Glu Leu Asn Leu Gly Arg Arg Glu Glu Tyr Asp Val Leu Asp
465                 470                 475                 480

Lys Arg Arg Gly Arg Asp Pro Glu Met Gly Gly Lys Pro Arg Arg Lys
                485                 490                 495

Asn Pro Gln Glu Gly Leu Tyr Asn Glu Leu Gln Lys Asp Lys Met Ala
            500                 505                 510

Glu Ala Tyr Ser Glu Ile Gly Met Lys Gly Glu Arg Arg Arg Gly Lys
            515                 520                 525

Gly His Asp Gly Leu Tyr Gln Gly Leu Ser Thr Ala Thr Lys Asp Thr
        530                 535                 540

Tyr Asp Ala Leu His Met Gln Ala Leu Pro Pro Arg
545                 550                 555

<210> SEQ ID NO 93
<211> LENGTH: 550
<212> TYPE: PRT
<213> ORGANISM: Artificial Sequence
<220> FEATURE:
<223> OTHER INFORMATION: Synthetic

<400> SEQUENCE: 93

Met Ala Leu Pro Val Thr Ala Leu Leu Leu Pro Leu Ala Leu Leu Leu
1               5                   10                  15

His Ala Ala Arg Pro Gln Gly Cys Thr Met Pro Ser Pro Arg Ser
                20                  25                  30

Lys Val Ile Cys Gly Ser Ser Gly Ser Gly Ser Gly Gly Ser
                35                  40                  45

Gly Gly Gly Pro Leu Gly Leu Ala Gly Ser Ser Gly Gln Val Gln
            50                  55                  60

Leu Val Glu Ser Gly Gly Val Val Gln Pro Gly Arg Ser Leu Arg
65                  70                  75                  80

Leu Ser Cys Ala Ala Ser Gly Phe Thr Phe Ser Ser Tyr Gly Met His
                85                  90                  95

Trp Val Arg Gln Ala Pro Gly Lys Gly Leu Glu Trp Val Ala Val Ile
                100                 105                 110

Trp Asp Asp Gly Ser Asn Lys Tyr Tyr Val Asp Ser Val Lys Gly Arg
            115                 120                 125

Phe Thr Ile Ser Arg Asp Asn Ser Lys Asn Thr Leu Tyr Leu Gln Met
        130                 135                 140

Asn Ser Leu Arg Ala Glu Asp Thr Ala Val Tyr Tyr Cys Ala Arg Asp
145                 150                 155                 160

Asp Tyr Tyr Gly Ser Gly Ser Phe Asn Ser Tyr Tyr Gly Thr Asp Val
                165                 170                 175

Trp Gly Gln Gly Thr Thr Val Thr Val Ser Ser Gly Gly Gly Gly Ser
            180                 185                 190

Gly Gly Gly Gly Ser Gly Gly Gly Ser Glu Ile Val Leu Thr Gln
        195                 200                 205

Ser Pro Ala Thr Leu Ser Leu Ser Pro Gly Glu Arg Ala Thr Leu Ser
    210                 215                 220

Cys Arg Ala Ser Gln Ser Val Ser Ile Tyr Leu Ala Trp Tyr Gln Gln
225                 230                 235                 240

Lys Pro Gly Gln Ala Pro Arg Leu Leu Ile Tyr Asp Ala Ser Asn Arg
                245                 250                 255

Ala Thr Gly Ile Pro Ala Arg Phe Ser Gly Ser Gly Ser Gly Thr Asp
            260                 265                 270

Phe Thr Leu Thr Ile Ser Ser Leu Glu Pro Glu Asp Phe Ala Val Tyr
        275                 280                 285

Tyr Cys Gln Gln Arg Ser Asn Trp Pro Pro Phe Thr Phe Gly Pro Gly
    290                 295                 300

Thr Lys Val Asp Ile Lys Ser Ala Ala Ala Phe Val Pro Val Phe Leu
305                 310                 315                 320

Pro Ala Lys Pro Thr Thr Thr Pro Ala Pro Arg Pro Pro Thr Pro Ala
                325                 330                 335

Pro Thr Ile Ala Ser Gln Pro Leu Ser Leu Arg Pro Glu Ala Cys Arg
            340                 345                 350

Pro Ala Ala Gly Gly Ala Val His Thr Arg Gly Leu Asp Phe Ala Cys
        355                 360                 365

Asp Ile Tyr Ile Trp Ala Pro Leu Ala Gly Thr Cys Gly Val Leu Leu
    370                 375                 380

Leu Ser Leu Val Ile Thr Leu Tyr Cys Asn His Arg Asn Arg Ser Lys
385                 390                 395                 400

Arg Ser Arg Leu Leu His Ser Asp Tyr Met Asn Met Thr Pro Arg Arg
                405                 410                 415

Pro Gly Pro Thr Arg Lys His Tyr Gln Pro Tyr Ala Pro Pro Arg Asp
            420                 425                 430

Phe Ala Ala Tyr Arg Ser Arg Val Lys Phe Ser Arg Ser Ala Asp Ala
        435                 440                 445

Pro Ala Tyr Gln Gln Gly Gln Asn Gln Leu Tyr Asn Glu Leu Asn Leu
    450                 455                 460

Gly Arg Arg Glu Glu Tyr Asp Val Leu Asp Lys Arg Arg Gly Arg Asp
465                 470                 475                 480

Pro Glu Met Gly Gly Lys Pro Arg Arg Lys Asn Pro Gln Glu Gly Leu
                485                 490                 495

Tyr Asn Glu Leu Gln Lys Asp Lys Met Ala Glu Ala Tyr Ser Glu Ile
            500                 505                 510

Gly Met Lys Gly Glu Arg Arg Gly Lys Gly His Asp Gly Leu Tyr
        515                 520                 525

Gln Gly Leu Ser Thr Ala Thr Lys Asp Thr Tyr Asp Ala Leu His Met
    530                 535                 540

Gln Ala Leu Pro Pro Arg
545                 550

<210> SEQ ID NO 94
<211> LENGTH: 550
<212> TYPE: PRT
<213> ORGANISM: Artificial Sequence
<220> FEATURE:
<223> OTHER INFORMATION: Synthetic

<400> SEQUENCE: 94

Met Ala Leu Pro Val Thr Ala Leu Leu Pro Leu Ala Leu Leu Leu
1               5                   10                  15

His Ala Ala Arg Pro Gln Gly Cys Thr Phe Pro Asn Thr Thr Met Gln
            20                  25                  30

Arg Thr Phe Cys Gly Ser Ser Gly Ser Gly Ser Gly Gly Ser
        35                  40                  45

Gly Gly Gly Pro Leu Gly Leu Ala Gly Gly Ser Gly Gln Val Gln
    50                  55                  60

Leu Val Glu Ser Gly Gly Gly Val Val Gln Pro Gly Arg Ser Leu Arg
65                  70                  75                  80

Leu Ser Cys Ala Ala Ser Gly Phe Thr Phe Ser Ser Tyr Gly Met His
                85                  90                  95

Trp Val Arg Gln Ala Pro Gly Lys Gly Leu Glu Trp Val Ala Val Ile
            100                 105                 110

Trp Asp Asp Gly Ser Asn Lys Tyr Tyr Val Asp Ser Val Lys Gly Arg
        115                 120                 125

Phe Thr Ile Ser Arg Asp Asn Ser Lys Asn Thr Leu Tyr Leu Gln Met
130                 135                 140

Asn Ser Leu Arg Ala Glu Asp Thr Ala Val Tyr Tyr Cys Ala Arg Asp
145                 150                 155                 160

Asp Tyr Tyr Gly Ser Gly Ser Phe Asn Ser Tyr Tyr Gly Thr Asp Val
                165                 170                 175

Trp Gly Gln Gly Thr Thr Val Thr Val Ser Ser Gly Gly Gly Gly Ser
            180                 185                 190

Gly Gly Gly Gly Ser Gly Gly Gly Gly Ser Glu Ile Val Leu Thr Gln
        195                 200                 205

Ser Pro Ala Thr Leu Ser Leu Ser Pro Gly Glu Arg Ala Thr Leu Ser
210                 215                 220

Cys Arg Ala Ser Gln Ser Val Ser Ile Tyr Leu Ala Trp Tyr Gln Gln
225                 230                 235                 240

Lys Pro Gly Gln Ala Pro Arg Leu Leu Ile Tyr Asp Ala Ser Asn Arg
                245                 250                 255

Ala Thr Gly Ile Pro Ala Arg Phe Ser Gly Ser Gly Ser Gly Thr Asp
            260                 265                 270

Phe Thr Leu Thr Ile Ser Ser Leu Glu Pro Glu Asp Phe Ala Val Tyr
        275                 280                 285

Tyr Cys Gln Gln Arg Ser Asn Trp Pro Pro Phe Thr Phe Gly Pro Gly
290                 295                 300

Thr Lys Val Asp Ile Lys Ser Ala Ala Ala Phe Val Pro Val Phe Leu
305                 310                 315                 320

Pro Ala Lys Pro Thr Thr Thr Pro Ala Pro Arg Pro Pro Thr Pro Ala
                325                 330                 335

Pro Thr Ile Ala Ser Gln Pro Leu Ser Leu Arg Pro Glu Ala Cys Arg
            340                 345                 350

Pro Ala Ala Gly Gly Ala Val His Thr Arg Gly Leu Asp Phe Ala Cys
        355                 360                 365

Asp Ile Tyr Ile Trp Ala Pro Leu Ala Gly Thr Cys Gly Val Leu Leu
370                 375                 380

Leu Ser Leu Val Ile Thr Leu Tyr Cys Asn His Arg Asn Arg Ser Lys
385                 390                 395                 400

Arg Ser Arg Leu Leu His Ser Asp Tyr Met Asn Met Thr Pro Arg Arg

```
                    405                 410                 415
Pro Gly Pro Thr Arg Lys His Tyr Gln Pro Tyr Ala Pro Pro Arg Asp
            420                 425                 430

Phe Ala Ala Tyr Arg Ser Arg Val Lys Phe Ser Arg Ser Ala Asp Ala
            435                 440                 445

Pro Ala Tyr Gln Gln Gly Gln Asn Gln Leu Tyr Asn Glu Leu Asn Leu
            450                 455                 460

Gly Arg Arg Glu Glu Tyr Asp Val Leu Asp Lys Arg Arg Gly Arg Asp
465                 470                 475                 480

Pro Glu Met Gly Gly Lys Pro Arg Arg Lys Asn Pro Gln Glu Gly Leu
                485                 490                 495

Tyr Asn Glu Leu Gln Lys Asp Lys Met Ala Glu Ala Tyr Ser Glu Ile
            500                 505                 510

Gly Met Lys Gly Glu Arg Arg Arg Gly Lys Gly His Asp Gly Leu Tyr
            515                 520                 525

Gln Gly Leu Ser Thr Ala Thr Lys Asp Thr Tyr Asp Ala Leu His Met
            530                 535                 540

Gln Ala Leu Pro Pro Arg
545                 550

<210> SEQ ID NO 95
<211> LENGTH: 550
<212> TYPE: PRT
<213> ORGANISM: Artificial Sequence
<220> FEATURE:
<223> OTHER INFORMATION: Synthetic

<400> SEQUENCE: 95

Met Ala Leu Pro Val Thr Ala Leu Leu Leu Pro Leu Ala Leu Leu Leu
1               5                   10                  15

His Ala Ala Arg Pro Gln Gly Cys Thr Tyr Pro Ser Trp Val Ala Tyr
            20                  25                  30

Ile Arg Phe Cys Gly Ser Ser Gly Gly Ser Gly Gly Ser
            35                  40                  45

Gly Gly Gly Pro Leu Gly Leu Ala Gly Gly Ser Ser Gly Gln Val Gln
        50                  55                  60

Leu Val Glu Ser Gly Gly Gly Val Val Gln Pro Gly Arg Ser Leu Arg
65                  70                  75                  80

Leu Ser Cys Ala Ala Ser Gly Phe Thr Phe Ser Ser Tyr Gly Met His
            85                  90                  95

Trp Val Arg Gln Ala Pro Gly Lys Gly Leu Glu Trp Val Ala Val Ile
            100                 105                 110

Trp Asp Asp Gly Ser Asn Lys Tyr Tyr Val Asp Ser Val Lys Gly Arg
            115                 120                 125

Phe Thr Ile Ser Arg Asp Asn Ser Lys Asn Thr Leu Tyr Leu Gln Met
            130                 135                 140

Asn Ser Leu Arg Ala Glu Asp Thr Ala Val Tyr Tyr Cys Ala Arg Asp
145                 150                 155                 160

Asp Tyr Tyr Gly Ser Gly Ser Phe Asn Ser Tyr Tyr Gly Thr Asp Val
            165                 170                 175

Trp Gly Gln Gly Thr Thr Val Thr Val Ser Ser Gly Gly Gly Gly Ser
            180                 185                 190

Gly Gly Gly Gly Ser Gly Gly Gly Ser Glu Ile Val Leu Thr Gln
            195                 200                 205

Ser Pro Ala Thr Leu Ser Leu Ser Pro Gly Glu Arg Ala Thr Leu Ser
```

```
                210                 215                 220
Cys Arg Ala Ser Gln Ser Val Ser Ile Tyr Leu Ala Trp Tyr Gln Gln
225                 230                 235                 240

Lys Pro Gly Gln Ala Pro Arg Leu Leu Ile Tyr Asp Ala Ser Asn Arg
                245                 250                 255

Ala Thr Gly Ile Pro Ala Arg Phe Ser Gly Ser Gly Ser Gly Thr Asp
                260                 265                 270

Phe Thr Leu Thr Ile Ser Ser Leu Glu Pro Glu Asp Phe Ala Val Tyr
                275                 280                 285

Tyr Cys Gln Gln Arg Ser Asn Trp Pro Pro Phe Thr Phe Gly Pro Gly
                290                 295                 300

Thr Lys Val Asp Ile Lys Ser Ala Ala Ala Phe Val Pro Val Phe Leu
305                 310                 315                 320

Pro Ala Lys Pro Thr Thr Thr Pro Ala Pro Arg Pro Pro Thr Pro Ala
                325                 330                 335

Pro Thr Ile Ala Ser Gln Pro Leu Ser Leu Arg Pro Glu Ala Cys Arg
                340                 345                 350

Pro Ala Ala Gly Gly Ala Val His Thr Arg Gly Leu Asp Phe Ala Cys
                355                 360                 365

Asp Ile Tyr Ile Trp Ala Pro Leu Ala Gly Thr Cys Gly Val Leu Leu
                370                 375                 380

Leu Ser Leu Val Ile Thr Leu Tyr Cys Asn His Arg Asn Arg Ser Lys
385                 390                 395                 400

Arg Ser Arg Leu Leu His Ser Asp Tyr Met Asn Met Thr Pro Arg Arg
                405                 410                 415

Pro Gly Pro Thr Arg Lys His Tyr Gln Pro Tyr Ala Pro Pro Arg Asp
                420                 425                 430

Phe Ala Ala Tyr Arg Ser Arg Val Lys Phe Ser Arg Ser Ala Asp Ala
                435                 440                 445

Pro Ala Tyr Gln Gln Gly Gln Asn Gln Leu Tyr Asn Glu Leu Asn Leu
                450                 455                 460

Gly Arg Arg Glu Glu Tyr Asp Val Leu Asp Lys Arg Arg Gly Arg Asp
465                 470                 475                 480

Pro Glu Met Gly Gly Lys Pro Arg Arg Lys Asn Pro Gln Glu Gly Leu
                485                 490                 495

Tyr Asn Glu Leu Gln Lys Asp Lys Met Ala Glu Ala Tyr Ser Glu Ile
                500                 505                 510

Gly Met Lys Gly Glu Arg Arg Arg Gly Lys Gly His Asp Gly Leu Tyr
                515                 520                 525

Gln Gly Leu Ser Thr Ala Thr Lys Asp Thr Tyr Asp Ala Leu His Met
                530                 535                 540

Gln Ala Leu Pro Pro Arg
545                 550

<210> SEQ ID NO 96
<211> LENGTH: 550
<212> TYPE: PRT
<213> ORGANISM: Artificial Sequence
<220> FEATURE:
<223> OTHER INFORMATION: Synthetic

<400> SEQUENCE: 96

Met Ala Leu Pro Val Thr Ala Leu Leu Leu Pro Leu Ala Leu Leu Leu
1               5                   10                  15

His Ala Ala Arg Pro Gln Gly Val Cys Thr Tyr Pro Pro Ala His Arg
```

```
                    20                  25                  30
Thr Arg Phe Cys Gly Ser Ser Gly Gly Ser Gly Gly Ser Gly Gly Ser
                35                  40                  45
Gly Gly Gly Pro Leu Gly Leu Ala Gly Gly Ser Ser Gly Gln Val Gln
                50                  55                  60
Leu Val Glu Ser Gly Gly Val Val Gln Pro Gly Arg Ser Leu Arg
 65                  70                  75                  80
Leu Ser Cys Ala Ala Ser Gly Phe Thr Phe Ser Ser Tyr Gly Met His
                85                  90                  95
Trp Val Arg Gln Ala Pro Gly Lys Gly Leu Glu Trp Val Ala Val Ile
               100                 105                 110
Trp Asp Asp Gly Ser Asn Lys Tyr Tyr Val Asp Ser Val Lys Gly Arg
               115                 120                 125
Phe Thr Ile Ser Arg Asp Asn Ser Lys Asn Thr Leu Tyr Leu Gln Met
               130                 135                 140
Asn Ser Leu Arg Ala Glu Asp Thr Ala Val Tyr Tyr Cys Ala Arg Asp
145                 150                 155                 160
Asp Tyr Tyr Gly Ser Gly Ser Phe Asn Ser Tyr Tyr Gly Thr Asp Val
               165                 170                 175
Trp Gly Gln Gly Thr Thr Val Thr Val Ser Ser Gly Gly Gly Gly Ser
               180                 185                 190
Gly Gly Gly Gly Ser Gly Gly Gly Ser Glu Ile Val Leu Thr Gln
               195                 200                 205
Ser Pro Ala Thr Leu Ser Leu Ser Pro Gly Glu Arg Ala Thr Leu Ser
               210                 215                 220
Cys Arg Ala Ser Gln Ser Val Ser Ile Tyr Leu Ala Trp Tyr Gln Gln
225                 230                 235                 240
Lys Pro Gly Gln Ala Pro Arg Leu Leu Ile Tyr Asp Ala Ser Asn Arg
               245                 250                 255
Ala Thr Gly Ile Pro Ala Arg Phe Ser Gly Ser Gly Ser Gly Thr Asp
               260                 265                 270
Phe Thr Leu Thr Ile Ser Ser Leu Glu Pro Glu Asp Phe Ala Val Tyr
               275                 280                 285
Tyr Cys Gln Gln Arg Ser Asn Trp Pro Pro Phe Thr Phe Gly Pro Gly
               290                 295                 300
Thr Lys Val Asp Ile Lys Ser Ala Ala Ala Phe Val Pro Val Phe Leu
305                 310                 315                 320
Pro Ala Lys Pro Thr Thr Thr Pro Ala Pro Arg Pro Pro Thr Pro Ala
               325                 330                 335
Pro Thr Ile Ala Ser Gln Pro Leu Ser Leu Arg Pro Glu Ala Cys Arg
               340                 345                 350
Pro Ala Ala Gly Gly Ala Val His Thr Arg Gly Leu Asp Phe Ala Cys
               355                 360                 365
Asp Ile Tyr Ile Trp Ala Pro Leu Ala Gly Thr Cys Gly Val Leu Leu
               370                 375                 380
Leu Ser Leu Val Ile Thr Leu Tyr Cys Asn His Arg Asn Arg Ser Lys
385                 390                 395                 400
Arg Ser Arg Leu Leu His Ser Asp Tyr Met Asn Met Thr Pro Arg Arg
               405                 410                 415
Pro Gly Pro Thr Arg Lys His Tyr Gln Pro Tyr Ala Pro Pro Arg Asp
               420                 425                 430
Phe Ala Ala Tyr Arg Ser Arg Val Lys Phe Ser Arg Ser Ala Asp Ala
               435                 440                 445
```

```
Pro Ala Tyr Gln Gln Gly Gln Asn Gln Leu Tyr Asn Glu Leu Asn Leu
    450                 455                 460

Gly Arg Arg Glu Glu Tyr Asp Val Leu Asp Lys Arg Arg Gly Arg Asp
465                 470                 475                 480

Pro Glu Met Gly Gly Lys Pro Arg Arg Lys Asn Pro Gln Glu Gly Leu
                485                 490                 495

Tyr Asn Glu Leu Gln Lys Asp Lys Met Ala Glu Ala Tyr Ser Glu Ile
            500                 505                 510

Gly Met Lys Gly Glu Arg Arg Arg Gly Lys Gly His Asp Gly Leu Tyr
        515                 520                 525

Gln Gly Leu Ser Thr Ala Thr Lys Asp Thr Tyr Asp Ala Leu His Met
    530                 535                 540

Gln Ala Leu Pro Pro Arg
545                 550

<210> SEQ ID NO 97
<211> LENGTH: 550
<212> TYPE: PRT
<213> ORGANISM: Artificial Sequence
<220> FEATURE:
<223> OTHER INFORMATION: Synthetic

<400> SEQUENCE: 97

Met Ala Leu Pro Val Thr Ala Leu Leu Leu Pro Leu Ala Leu Leu Leu
1               5                   10                  15

His Ala Ala Arg Pro Gln Gly Cys Thr Met Pro Tyr His Ile His Ser
            20                  25                  30

Ile Gly Leu Cys Gly Ser Ser Gly Ser Gly Ser Gly Gly Ser
        35                  40                  45

Gly Gly Gly Pro Leu Gly Leu Ala Gly Gly Ser Gly Gln Val Gln
    50                  55                  60

Leu Val Glu Ser Gly Gly Gly Val Val Gln Pro Gly Arg Ser Leu Arg
65                  70                  75                  80

Leu Ser Cys Ala Ala Ser Gly Phe Thr Phe Ser Ser Tyr Gly Met His
                85                  90                  95

Trp Val Arg Gln Ala Pro Gly Lys Gly Leu Glu Trp Val Ala Val Ile
            100                 105                 110

Trp Asp Asp Gly Ser Asn Lys Tyr Tyr Val Asp Ser Val Lys Gly Arg
        115                 120                 125

Phe Thr Ile Ser Arg Asp Asn Ser Lys Asn Thr Leu Tyr Leu Gln Met
    130                 135                 140

Asn Ser Leu Arg Ala Glu Asp Thr Ala Val Tyr Tyr Cys Ala Arg Asp
145                 150                 155                 160

Asp Tyr Tyr Gly Ser Gly Ser Phe Asn Ser Tyr Tyr Gly Thr Asp Val
                165                 170                 175

Trp Gly Gln Gly Thr Thr Val Thr Val Ser Ser Gly Gly Gly Gly Ser
            180                 185                 190

Gly Gly Gly Gly Ser Gly Gly Gly Ser Glu Ile Val Leu Thr Gln
        195                 200                 205

Ser Pro Ala Thr Leu Ser Leu Ser Pro Gly Glu Arg Ala Thr Leu Ser
    210                 215                 220

Cys Arg Ala Ser Gln Ser Val Ser Ile Tyr Leu Ala Trp Tyr Gln Gln
225                 230                 235                 240

Lys Pro Gly Gln Ala Pro Arg Leu Leu Ile Tyr Asp Ala Ser Asn Arg
                245                 250                 255
```

```
Ala Thr Gly Ile Pro Ala Arg Phe Ser Gly Ser Gly Ser Gly Thr Asp
            260                 265                 270

Phe Thr Leu Thr Ile Ser Ser Leu Glu Pro Glu Asp Phe Ala Val Tyr
            275                 280                 285

Tyr Cys Gln Gln Arg Ser Asn Trp Pro Pro Phe Thr Phe Gly Pro Gly
290                 295                 300

Thr Lys Val Asp Ile Lys Ser Ala Ala Ala Phe Val Pro Val Phe Leu
305                 310                 315                 320

Pro Ala Lys Pro Thr Thr Pro Ala Pro Arg Pro Pro Thr Pro Ala
                325                 330                 335

Pro Thr Ile Ala Ser Gln Pro Leu Ser Leu Arg Pro Glu Ala Cys Arg
                340                 345                 350

Pro Ala Ala Gly Gly Ala Val His Thr Arg Gly Leu Asp Phe Ala Cys
                355                 360                 365

Asp Ile Tyr Ile Trp Ala Pro Leu Ala Gly Thr Cys Gly Val Leu Leu
            370                 375                 380

Leu Ser Leu Val Ile Thr Leu Tyr Cys Asn His Arg Asn Arg Ser Lys
385                 390                 395                 400

Arg Ser Arg Leu Leu His Ser Asp Tyr Met Asn Met Thr Pro Arg Arg
                405                 410                 415

Pro Gly Pro Thr Arg Lys His Tyr Gln Pro Tyr Ala Pro Pro Arg Asp
                420                 425                 430

Phe Ala Ala Tyr Arg Ser Arg Val Lys Phe Ser Arg Ser Ala Asp Ala
            435                 440                 445

Pro Ala Tyr Gln Gln Gly Gln Asn Gln Leu Tyr Asn Glu Leu Asn Leu
            450                 455                 460

Gly Arg Arg Glu Glu Tyr Asp Val Leu Asp Lys Arg Arg Gly Arg Asp
465                 470                 475                 480

Pro Glu Met Gly Gly Lys Pro Arg Arg Lys Asn Pro Gln Glu Gly Leu
                485                 490                 495

Tyr Asn Glu Leu Gln Lys Asp Lys Met Ala Glu Ala Tyr Ser Glu Ile
                500                 505                 510

Gly Met Lys Gly Glu Arg Arg Arg Gly Lys Gly His Asp Gly Leu Tyr
            515                 520                 525

Gln Gly Leu Ser Thr Ala Thr Lys Asp Thr Tyr Asp Ala Leu His Met
            530                 535                 540

Gln Ala Leu Pro Pro Arg
545                 550

<210> SEQ ID NO 98
<211> LENGTH: 550
<212> TYPE: PRT
<213> ORGANISM: Artificial Sequence
<220> FEATURE:
<223> OTHER INFORMATION: Synthetic

<400> SEQUENCE: 98

Met Ala Leu Pro Val Thr Ala Leu Leu Leu Pro Leu Ala Leu Leu Leu
1               5                   10                  15

His Ala Ala Arg Pro Gln Gly Trp Cys Thr Ile Pro Ser Ser Met Ser
                20                  25                  30

Ile Arg Leu Cys Gly Ser Ser Gly Ser Gly Gly Ser Gly Gly Ser
            35                  40                  45

Gly Gly Gly Pro Leu Gly Leu Ala Gly Gly Ser Ser Gln Val Gln
        50                  55                  60
```

-continued

```
Leu Val Glu Ser Gly Gly Val Val Gln Pro Gly Arg Ser Leu Arg
 65                  70                  75                  80

Leu Ser Cys Ala Ala Ser Gly Phe Thr Phe Ser Ser Tyr Gly Met His
                 85                  90                  95

Trp Val Arg Gln Ala Pro Gly Lys Gly Leu Glu Trp Val Ala Val Ile
            100                 105                 110

Trp Asp Asp Gly Ser Asn Lys Tyr Tyr Val Asp Ser Val Lys Gly Arg
        115                 120                 125

Phe Thr Ile Ser Arg Asp Asn Ser Lys Asn Thr Leu Tyr Leu Gln Met
130                 135                 140

Asn Ser Leu Arg Ala Glu Asp Thr Ala Val Tyr Tyr Cys Ala Arg Asp
145                 150                 155                 160

Asp Tyr Tyr Gly Ser Gly Ser Phe Asn Ser Tyr Tyr Gly Thr Asp Val
                165                 170                 175

Trp Gly Gln Gly Thr Thr Val Thr Val Ser Ser Gly Gly Gly Gly Ser
            180                 185                 190

Gly Gly Gly Gly Ser Gly Gly Gly Ser Glu Ile Val Leu Thr Gln
        195                 200                 205

Ser Pro Ala Thr Leu Ser Leu Ser Pro Gly Glu Arg Ala Thr Leu Ser
210                 215                 220

Cys Arg Ala Ser Gln Ser Val Ser Ile Tyr Leu Ala Trp Tyr Gln Gln
225                 230                 235                 240

Lys Pro Gly Gln Ala Pro Arg Leu Leu Ile Tyr Asp Ala Ser Asn Arg
                245                 250                 255

Ala Thr Gly Ile Pro Ala Arg Phe Ser Gly Ser Gly Ser Gly Thr Asp
            260                 265                 270

Phe Thr Leu Thr Ile Ser Ser Leu Glu Pro Glu Asp Phe Ala Val Tyr
        275                 280                 285

Tyr Cys Gln Gln Arg Ser Asn Trp Pro Pro Phe Thr Phe Gly Pro Gly
290                 295                 300

Thr Lys Val Asp Ile Lys Ser Ala Ala Ala Phe Val Pro Val Phe Leu
305                 310                 315                 320

Pro Ala Lys Pro Thr Thr Thr Pro Ala Pro Arg Pro Pro Thr Pro Ala
                325                 330                 335

Pro Thr Ile Ala Ser Gln Pro Leu Ser Leu Arg Pro Glu Ala Cys Arg
            340                 345                 350

Pro Ala Ala Gly Gly Ala Val His Thr Arg Gly Leu Asp Phe Ala Cys
        355                 360                 365

Asp Ile Tyr Ile Trp Ala Pro Leu Ala Gly Thr Cys Gly Val Leu Leu
370                 375                 380

Leu Ser Leu Val Ile Thr Leu Tyr Cys Asn His Arg Asn Arg Ser Lys
385                 390                 395                 400

Arg Ser Arg Leu Leu His Ser Asp Tyr Met Asn Met Thr Pro Arg Arg
                405                 410                 415

Pro Gly Pro Thr Arg Lys His Tyr Gln Pro Tyr Ala Pro Pro Arg Asp
            420                 425                 430

Phe Ala Ala Tyr Arg Ser Arg Val Lys Phe Ser Arg Ser Ala Asp Ala
        435                 440                 445

Pro Ala Tyr Gln Gln Gly Gln Asn Gln Leu Tyr Asn Glu Leu Asn Leu
450                 455                 460

Gly Arg Arg Glu Glu Tyr Asp Val Leu Asp Lys Arg Arg Gly Arg Asp
465                 470                 475                 480
```

```
Pro Glu Met Gly Gly Lys Pro Arg Arg Lys Asn Pro Gln Glu Gly Leu
                485                 490                 495

Tyr Asn Glu Leu Gln Lys Asp Lys Met Ala Glu Ala Tyr Ser Glu Ile
            500                 505                 510

Gly Met Lys Gly Glu Arg Arg Arg Gly Lys Gly His Asp Gly Leu Tyr
            515                 520                 525

Gln Gly Leu Ser Thr Ala Thr Lys Asp Thr Tyr Asp Ala Leu His Met
            530                 535                 540

Gln Ala Leu Pro Pro Arg
545             550

<210> SEQ ID NO 99
<211> LENGTH: 550
<212> TYPE: PRT
<213> ORGANISM: Artificial Sequence
<220> FEATURE:
<223> OTHER INFORMATION: Synthetic

<400> SEQUENCE: 99

Met Ala Leu Pro Val Thr Ala Leu Leu Leu Pro Leu Ala Leu Leu Leu
1               5                   10                  15

His Ala Ala Arg Pro Gln Gly Cys His Ile Gly Lys Arg Pro Val Pro
            20                  25                  30

Cys Leu Trp Ile Gly Ser Ser Gly Ser Gly Gly Ser Gly Gly Ser
        35                  40                  45

Gly Gly Gly Pro Leu Gly Leu Ala Gly Ser Ser Gly Gln Val Gln
    50                  55                  60

Leu Val Glu Ser Gly Gly Val Val Gln Pro Gly Arg Ser Leu Arg
65                  70                  75                  80

Leu Ser Cys Ala Ala Ser Gly Phe Thr Phe Ser Ser Tyr Gly Met His
            85                  90                  95

Trp Val Arg Gln Ala Pro Gly Lys Gly Leu Glu Trp Val Ala Val Ile
            100                 105                 110

Trp Asp Asp Gly Ser Asn Lys Tyr Tyr Val Asp Ser Val Lys Gly Arg
        115                 120                 125

Phe Thr Ile Ser Arg Asp Asn Ser Lys Asn Thr Leu Tyr Leu Gln Met
    130                 135                 140

Asn Ser Leu Arg Ala Glu Asp Thr Ala Val Tyr Tyr Cys Ala Arg Asp
145                 150                 155                 160

Asp Tyr Tyr Gly Ser Gly Ser Phe Asn Ser Tyr Tyr Gly Thr Asp Val
            165                 170                 175

Trp Gly Gln Gly Thr Thr Val Thr Val Ser Ser Gly Gly Gly Gly Ser
            180                 185                 190

Gly Gly Gly Gly Ser Gly Gly Gly Ser Glu Ile Val Leu Thr Gln
    195                 200                 205

Ser Pro Ala Thr Leu Ser Leu Ser Pro Gly Glu Arg Ala Thr Leu Ser
    210                 215                 220

Cys Arg Ala Ser Gln Ser Val Ser Ile Tyr Leu Ala Trp Tyr Gln Gln
225                 230                 235                 240

Lys Pro Gly Gln Ala Pro Arg Leu Leu Ile Tyr Asp Ala Ser Asn Arg
            245                 250                 255

Ala Thr Gly Ile Pro Ala Arg Phe Ser Gly Ser Gly Ser Gly Thr Asp
            260                 265                 270

Phe Thr Leu Thr Ile Ser Ser Leu Glu Pro Glu Asp Phe Ala Val Tyr
        275                 280                 285
```

```
Tyr Cys Gln Gln Arg Ser Asn Trp Pro Pro Phe Thr Phe Gly Pro Gly
290                 295                 300
Thr Lys Val Asp Ile Lys Ser Ala Ala Ala Phe Val Pro Val Phe Leu
305                 310                 315                 320
Pro Ala Lys Pro Thr Thr Thr Pro Ala Pro Arg Pro Pro Thr Pro Ala
                325                 330                 335
Pro Thr Ile Ala Ser Gln Pro Leu Ser Leu Arg Pro Glu Ala Cys Arg
            340                 345                 350
Pro Ala Ala Gly Gly Ala Val His Thr Arg Gly Leu Asp Phe Ala Cys
            355                 360                 365
Asp Ile Tyr Ile Trp Ala Pro Leu Ala Gly Thr Cys Gly Val Leu Leu
370                 375                 380
Leu Ser Leu Val Ile Thr Leu Tyr Cys Asn His Arg Asn Arg Ser Lys
385                 390                 395                 400
Arg Ser Arg Leu Leu His Ser Asp Tyr Met Asn Met Thr Pro Arg Arg
                405                 410                 415
Pro Gly Pro Thr Arg Lys His Tyr Gln Pro Tyr Ala Pro Pro Arg Asp
            420                 425                 430
Phe Ala Ala Tyr Arg Ser Arg Val Lys Phe Ser Arg Ser Ala Asp Ala
435                 440                 445
Pro Ala Tyr Gln Gln Gly Gln Asn Gln Leu Tyr Asn Glu Leu Asn Leu
450                 455                 460
Gly Arg Arg Glu Glu Tyr Asp Val Leu Asp Lys Arg Arg Gly Arg Asp
465                 470                 475                 480
Pro Glu Met Gly Gly Lys Pro Arg Arg Lys Asn Pro Gln Glu Gly Leu
                485                 490                 495
Tyr Asn Glu Leu Gln Lys Asp Lys Met Ala Glu Ala Tyr Ser Glu Ile
            500                 505                 510
Gly Met Lys Gly Glu Arg Arg Arg Gly Lys Gly His Asp Gly Leu Tyr
            515                 520                 525
Gln Gly Leu Ser Thr Ala Thr Lys Asp Thr Tyr Asp Ala Leu His Met
530                 535                 540
Gln Ala Leu Pro Pro Arg
545                 550

<210> SEQ ID NO 100
<211> LENGTH: 550
<212> TYPE: PRT
<213> ORGANISM: Artificial Sequence
<220> FEATURE:
<223> OTHER INFORMATION: Synthetic

<400> SEQUENCE: 100

Met Ala Leu Pro Val Thr Ala Leu Leu Leu Pro Leu Ala Leu Leu Leu
1               5                   10                  15
His Ala Ala Arg Pro Gln Gly Cys Tyr Ile Gly Leu Arg Met Val Pro
                20                  25                  30
Cys Phe His Met Gly Ser Ser Gly Ser Gly Gly Ser Gly Gly Gly Ser
            35                  40                  45
Gly Gly Gly Pro Leu Gly Leu Ala Gly Gly Ser Ser Gly Gln Val Gln
        50                  55                  60
Leu Val Glu Ser Gly Gly Gly Val Val Gln Pro Gly Arg Ser Leu Arg
65                  70                  75                  80
Leu Ser Cys Ala Ala Ser Gly Phe Thr Phe Ser Ser Tyr Gly Met His
                85                  90                  95
```

-continued

```
Trp Val Arg Gln Ala Pro Gly Lys Gly Leu Glu Trp Val Ala Val Ile
            100                 105                 110
Trp Asp Asp Gly Ser Asn Lys Tyr Tyr Val Asp Ser Val Lys Gly Arg
            115                 120                 125
Phe Thr Ile Ser Arg Asp Asn Ser Lys Asn Thr Leu Tyr Leu Gln Met
        130                 135                 140
Asn Ser Leu Arg Ala Glu Asp Thr Ala Val Tyr Tyr Cys Ala Arg Asp
145                 150                 155                 160
Asp Tyr Tyr Gly Ser Gly Ser Phe Asn Ser Tyr Tyr Gly Thr Asp Val
                165                 170                 175
Trp Gly Gln Gly Thr Thr Val Thr Val Ser Ser Gly Gly Gly Gly Ser
            180                 185                 190
Gly Gly Gly Gly Ser Gly Gly Gly Ser Glu Ile Val Leu Thr Gln
        195                 200                 205
Ser Pro Ala Thr Leu Ser Leu Ser Pro Gly Glu Arg Ala Thr Leu Ser
    210                 215                 220
Cys Arg Ala Ser Gln Ser Val Ser Ile Tyr Leu Ala Trp Tyr Gln Gln
225                 230                 235                 240
Lys Pro Gly Gln Ala Pro Arg Leu Leu Ile Tyr Asp Ala Ser Asn Arg
                245                 250                 255
Ala Thr Gly Ile Pro Ala Arg Phe Ser Gly Ser Gly Ser Gly Thr Asp
            260                 265                 270
Phe Thr Leu Thr Ile Ser Ser Leu Glu Pro Glu Asp Phe Ala Val Tyr
        275                 280                 285
Tyr Cys Gln Gln Arg Ser Asn Trp Pro Pro Phe Thr Phe Gly Pro Gly
290                 295                 300
Thr Lys Val Asp Ile Lys Ser Ala Ala Ala Phe Val Pro Val Phe Leu
305                 310                 315                 320
Pro Ala Lys Pro Thr Thr Thr Pro Ala Pro Arg Pro Pro Thr Pro Ala
                325                 330                 335
Pro Thr Ile Ala Ser Gln Pro Leu Ser Leu Arg Pro Glu Ala Cys Arg
            340                 345                 350
Pro Ala Ala Gly Gly Ala Val His Thr Arg Gly Leu Asp Phe Ala Cys
        355                 360                 365
Asp Ile Tyr Ile Trp Ala Pro Leu Ala Gly Thr Cys Gly Val Leu Leu
370                 375                 380
Leu Ser Leu Val Ile Thr Leu Tyr Cys Asn His Arg Asn Arg Ser Lys
385                 390                 395                 400
Arg Ser Arg Leu Leu His Ser Asp Tyr Met Asn Met Thr Pro Arg Arg
                405                 410                 415
Pro Gly Pro Thr Arg Lys His Tyr Gln Pro Tyr Ala Pro Pro Arg Asp
            420                 425                 430
Phe Ala Ala Tyr Arg Ser Arg Val Lys Phe Ser Arg Ser Ala Asp Ala
        435                 440                 445
Pro Ala Tyr Gln Gln Gly Gln Asn Gln Leu Tyr Asn Glu Leu Asn Leu
450                 455                 460
Gly Arg Arg Glu Glu Tyr Asp Val Leu Asp Lys Arg Arg Gly Arg Asp
465                 470                 475                 480
Pro Glu Met Gly Gly Lys Pro Arg Arg Lys Asn Pro Gln Glu Gly Leu
                485                 490                 495
Tyr Asn Glu Leu Gln Lys Asp Lys Met Ala Glu Ala Tyr Ser Glu Ile
            500                 505                 510
Gly Met Lys Gly Glu Arg Arg Arg Gly Lys Gly His Asp Gly Leu Tyr
```

```
            515                 520                 525
Gln Gly Leu Ser Thr Ala Thr Lys Asp Thr Tyr Asp Ala Leu His Met
    530                 535                 540

Gln Ala Leu Pro Pro Arg
545                 550

<210> SEQ ID NO 101
<211> LENGTH: 550
<212> TYPE: PRT
<213> ORGANISM: Artificial Sequence
<220> FEATURE:
<223> OTHER INFORMATION: Synthetic

<400> SEQUENCE: 101

Met Ala Leu Pro Val Thr Ala Leu Leu Leu Pro Leu Ala Leu Leu Leu
1               5                   10                  15

His Ala Ala Arg Pro Gln Gly Cys Thr Met Pro Ser His Ala Val Ala
                20                  25                  30

Ser Phe Leu Cys Gly Ser Ser Gly Gly Ser Gly Gly Ser
            35                  40                  45

Gly Gly Gly Pro Leu Gly Leu Ala Gly Ser Ser Gly Gln Val Gln
    50                  55                  60

Leu Val Glu Ser Gly Gly Val Val Gln Pro Gly Arg Ser Leu Arg
65                  70                  75                  80

Leu Ser Cys Ala Ala Ser Gly Phe Thr Phe Ser Ser Tyr Gly Met His
                85                  90                  95

Trp Val Arg Gln Ala Pro Gly Lys Gly Leu Glu Trp Val Ala Val Ile
                100                 105                 110

Trp Asp Asp Gly Ser Asn Lys Tyr Tyr Val Asp Ser Val Lys Gly Arg
            115                 120                 125

Phe Thr Ile Ser Arg Asp Asn Ser Lys Asn Thr Leu Tyr Leu Gln Met
            130                 135                 140

Asn Ser Leu Arg Ala Glu Asp Thr Ala Val Tyr Tyr Cys Ala Arg Asp
145                 150                 155                 160

Asp Tyr Tyr Gly Ser Gly Ser Phe Asn Ser Tyr Tyr Gly Thr Asp Val
                165                 170                 175

Trp Gly Gln Gly Thr Thr Val Thr Val Ser Ser Gly Gly Gly Gly Ser
            180                 185                 190

Gly Gly Gly Gly Ser Gly Gly Gly Ser Glu Ile Val Leu Thr Gln
        195                 200                 205

Ser Pro Ala Thr Leu Ser Leu Ser Pro Gly Glu Arg Ala Thr Leu Ser
    210                 215                 220

Cys Arg Ala Ser Gln Ser Val Ser Ile Tyr Leu Ala Trp Tyr Gln Gln
225                 230                 235                 240

Lys Pro Gly Gln Ala Pro Arg Leu Leu Ile Tyr Asp Ala Ser Asn Arg
                245                 250                 255

Ala Thr Gly Ile Pro Ala Arg Phe Ser Gly Ser Gly Ser Gly Thr Asp
            260                 265                 270

Phe Thr Leu Thr Ile Ser Ser Leu Glu Pro Glu Asp Phe Ala Val Tyr
        275                 280                 285

Tyr Cys Gln Gln Arg Ser Asn Trp Pro Pro Phe Thr Phe Gly Pro Gly
        290                 295                 300

Thr Lys Val Asp Ile Lys Ser Ala Ala Ala Phe Val Pro Val Phe Leu
305                 310                 315                 320

Pro Ala Lys Pro Thr Thr Thr Pro Ala Pro Arg Pro Pro Thr Pro Ala
```

```
                    325                 330                 335
Pro Thr Ile Ala Ser Gln Pro Leu Ser Leu Arg Pro Glu Ala Cys Arg
                340                 345                 350

Pro Ala Ala Gly Gly Ala Val His Thr Arg Gly Leu Asp Phe Ala Cys
            355                 360                 365

Asp Ile Tyr Ile Trp Ala Pro Leu Ala Gly Thr Cys Gly Val Leu Leu
        370                 375                 380

Leu Ser Leu Val Ile Thr Leu Tyr Cys Asn His Arg Asn Arg Ser Lys
385                 390                 395                 400

Arg Ser Arg Leu Leu His Ser Asp Tyr Met Asn Met Thr Pro Arg Arg
                405                 410                 415

Pro Gly Pro Thr Arg Lys His Tyr Gln Pro Tyr Ala Pro Pro Arg Asp
            420                 425                 430

Phe Ala Ala Tyr Arg Ser Arg Val Lys Phe Ser Arg Ser Ala Asp Ala
        435                 440                 445

Pro Ala Tyr Gln Gln Gly Gln Asn Gln Leu Tyr Asn Glu Leu Asn Leu
    450                 455                 460

Gly Arg Arg Glu Glu Tyr Asp Val Leu Asp Lys Arg Arg Gly Arg Asp
465                 470                 475                 480

Pro Glu Met Gly Gly Lys Pro Arg Arg Lys Asn Pro Gln Glu Gly Leu
                485                 490                 495

Tyr Asn Glu Leu Gln Lys Asp Lys Met Ala Glu Ala Tyr Ser Glu Ile
            500                 505                 510

Gly Met Lys Gly Glu Arg Arg Arg Gly Lys Gly His Asp Gly Leu Tyr
        515                 520                 525

Gln Gly Leu Ser Thr Ala Thr Lys Asp Thr Tyr Asp Ala Leu His Met
    530                 535                 540

Gln Ala Leu Pro Pro Arg
545                 550

<210> SEQ ID NO 102
<211> LENGTH: 550
<212> TYPE: PRT
<213> ORGANISM: Artificial Sequence
<220> FEATURE:
<223> OTHER INFORMATION: Synthetic

<400> SEQUENCE: 102

Met Ala Leu Pro Val Thr Ala Leu Leu Leu Pro Leu Ala Leu Leu Leu
1               5                   10                  15

His Ala Ala Arg Pro Gln Gly Cys Thr Met Pro Val His Thr Tyr Ser
                20                  25                  30

Gln Trp Leu Cys Gly Ser Ser Gly Ser Gly Gly Ser Gly Gly Ser
            35                  40                  45

Gly Gly Gly Pro Leu Gly Leu Ala Gly Gly Ser Gly Gln Val Gln
        50                  55                  60

Leu Val Glu Ser Gly Gly Val Val Gln Pro Gly Arg Ser Leu Arg
65                  70                  75                  80

Leu Ser Cys Ala Ala Ser Gly Phe Thr Phe Ser Ser Tyr Gly Met His
                85                  90                  95

Trp Val Arg Gln Ala Pro Gly Lys Gly Leu Glu Trp Val Ala Val Ile
                100                 105                 110

Trp Asp Asp Gly Ser Asn Lys Tyr Tyr Val Asp Ser Val Lys Gly Arg
            115                 120                 125

Phe Thr Ile Ser Arg Asp Asn Ser Lys Asn Thr Leu Tyr Leu Gln Met
```

-continued

```
            130                 135                 140
Asn Ser Leu Arg Ala Glu Asp Thr Ala Val Tyr Tyr Cys Ala Arg Asp
145                 150                 155                 160

Asp Tyr Tyr Gly Ser Gly Ser Phe Asn Ser Tyr Tyr Gly Thr Asp Val
                    165                 170                 175

Trp Gly Gln Gly Thr Thr Val Thr Val Ser Ser Gly Gly Gly Gly Ser
                180                 185                 190

Gly Gly Gly Gly Ser Gly Gly Gly Ser Glu Ile Val Leu Thr Gln
                195                 200                 205

Ser Pro Ala Thr Leu Ser Leu Ser Pro Gly Glu Arg Ala Thr Leu Ser
210                 215                 220

Cys Arg Ala Ser Gln Ser Val Ser Ile Tyr Leu Ala Trp Tyr Gln Gln
225                 230                 235                 240

Lys Pro Gly Gln Ala Pro Arg Leu Leu Ile Tyr Asp Ala Ser Asn Arg
                245                 250                 255

Ala Thr Gly Ile Pro Ala Arg Phe Ser Gly Ser Gly Ser Gly Thr Asp
                260                 265                 270

Phe Thr Leu Thr Ile Ser Ser Leu Glu Pro Glu Asp Phe Ala Val Tyr
                275                 280                 285

Tyr Cys Gln Gln Arg Ser Asn Trp Pro Pro Phe Thr Phe Gly Pro Gly
290                 295                 300

Thr Lys Val Asp Ile Lys Ser Ala Ala Ala Phe Val Pro Val Phe Leu
305                 310                 315                 320

Pro Ala Lys Pro Thr Thr Thr Pro Ala Pro Arg Pro Pro Thr Pro Ala
                325                 330                 335

Pro Thr Ile Ala Ser Gln Pro Leu Ser Leu Arg Pro Glu Ala Cys Arg
                340                 345                 350

Pro Ala Ala Gly Gly Ala Val His Thr Arg Gly Leu Asp Phe Ala Cys
                355                 360                 365

Asp Ile Tyr Ile Trp Ala Pro Leu Ala Gly Thr Cys Gly Val Leu Leu
                370                 375                 380

Leu Ser Leu Val Ile Thr Leu Tyr Cys Asn His Arg Asn Arg Ser Lys
385                 390                 395                 400

Arg Ser Arg Leu Leu His Ser Asp Tyr Met Asn Met Thr Pro Arg Arg
                405                 410                 415

Pro Gly Pro Thr Arg Lys His Tyr Gln Pro Tyr Ala Pro Pro Arg Asp
                420                 425                 430

Phe Ala Ala Tyr Arg Ser Arg Val Lys Phe Ser Arg Ser Ala Asp Ala
                435                 440                 445

Pro Ala Tyr Gln Gln Gly Gln Asn Gln Leu Tyr Asn Glu Leu Asn Leu
450                 455                 460

Gly Arg Arg Glu Glu Tyr Asp Val Leu Asp Lys Arg Arg Gly Arg Asp
465                 470                 475                 480

Pro Glu Met Gly Gly Lys Pro Arg Arg Lys Asn Pro Gln Glu Gly Leu
                485                 490                 495

Tyr Asn Glu Leu Gln Lys Asp Lys Met Ala Glu Ala Tyr Ser Glu Ile
                500                 505                 510

Gly Met Lys Gly Glu Arg Arg Arg Gly Lys Gly His Asp Gly Leu Tyr
                515                 520                 525

Gln Gly Leu Ser Thr Ala Thr Lys Asp Thr Tyr Asp Ala Leu His Met
530                 535                 540

Gln Ala Leu Pro Pro Arg
545                 550
```

<210> SEQ ID NO 103
<211> LENGTH: 550
<212> TYPE: PRT
<213> ORGANISM: Artificial Sequence
<220> FEATURE:
<223> OTHER INFORMATION: Synthetic

<400> SEQUENCE: 103

```
Met Ala Leu Pro Val Thr Ala Leu Leu Leu Pro Leu Ala Leu Leu Leu
1               5                   10                  15

His Ala Ala Arg Pro Gln Gly Cys Thr Tyr Pro Pro Arg Phe His Met
            20                  25                  30

His Trp Leu Cys Gly Ser Ser Gly Ser Gly Gly Ser Gly Gly Ser
        35                  40                  45

Gly Gly Gly Pro Leu Gly Leu Ala Gly Gly Ser Ser Gly Gln Val Gln
        50                  55                  60

Leu Val Glu Ser Gly Gly Gly Val Val Gln Pro Gly Arg Ser Leu Arg
65                  70                  75                  80

Leu Ser Cys Ala Ala Ser Gly Phe Thr Phe Ser Ser Tyr Gly Met His
                85                  90                  95

Trp Val Arg Gln Ala Pro Gly Lys Gly Leu Glu Trp Val Ala Val Ile
            100                 105                 110

Trp Asp Asp Gly Ser Asn Lys Tyr Tyr Val Asp Ser Val Lys Gly Arg
        115                 120                 125

Phe Thr Ile Ser Arg Asp Asn Ser Lys Asn Thr Leu Tyr Leu Gln Met
    130                 135                 140

Asn Ser Leu Arg Ala Glu Asp Thr Ala Val Tyr Tyr Cys Ala Arg Asp
145                 150                 155                 160

Asp Tyr Tyr Gly Ser Gly Ser Phe Asn Ser Tyr Gly Thr Asp Val
                165                 170                 175

Trp Gly Gln Gly Thr Thr Val Thr Val Ser Ser Gly Gly Gly Gly Ser
            180                 185                 190

Gly Gly Gly Gly Ser Gly Gly Gly Ser Glu Ile Val Leu Thr Gln
        195                 200                 205

Ser Pro Ala Thr Leu Ser Leu Ser Pro Gly Glu Arg Ala Thr Leu Ser
    210                 215                 220

Cys Arg Ala Ser Gln Ser Val Ser Ile Tyr Leu Ala Trp Tyr Gln Gln
225                 230                 235                 240

Lys Pro Gly Gln Ala Pro Arg Leu Leu Ile Tyr Asp Ala Ser Asn Arg
                245                 250                 255

Ala Thr Gly Ile Pro Ala Arg Phe Ser Gly Ser Gly Ser Gly Thr Asp
            260                 265                 270

Phe Thr Leu Thr Ile Ser Ser Leu Glu Pro Glu Asp Phe Ala Val Tyr
        275                 280                 285

Tyr Cys Gln Gln Arg Ser Asn Trp Pro Pro Phe Thr Phe Gly Pro Gly
    290                 295                 300

Thr Lys Val Asp Ile Lys Ser Ala Ala Ala Phe Val Pro Val Phe Leu
305                 310                 315                 320

Pro Ala Lys Pro Thr Thr Thr Pro Ala Pro Arg Pro Pro Thr Pro Ala
                325                 330                 335

Pro Thr Ile Ala Ser Gln Pro Leu Ser Leu Arg Pro Glu Ala Cys Arg
            340                 345                 350

Pro Ala Ala Gly Gly Ala Val His Thr Arg Gly Leu Asp Phe Ala Cys
        355                 360                 365
```

```
Asp Ile Tyr Ile Trp Ala Pro Leu Ala Gly Thr Cys Gly Val Leu Leu
            370                 375                 380

Leu Ser Leu Val Ile Thr Leu Tyr Cys Asn His Arg Asn Arg Ser Lys
385                 390                 395                 400

Arg Ser Arg Leu Leu His Ser Asp Tyr Met Asn Met Thr Pro Arg Arg
                405                 410                 415

Pro Gly Pro Thr Arg Lys His Tyr Gln Pro Tyr Ala Pro Pro Arg Asp
            420                 425                 430

Phe Ala Ala Tyr Arg Ser Arg Val Lys Phe Ser Arg Ser Ala Asp Ala
            435                 440                 445

Pro Ala Tyr Gln Gln Gly Gln Asn Gln Leu Tyr Asn Glu Leu Asn Leu
            450                 455                 460

Gly Arg Arg Glu Glu Tyr Asp Val Leu Asp Lys Arg Arg Gly Arg Asp
465                 470                 475                 480

Pro Glu Met Gly Gly Lys Pro Arg Arg Lys Asn Pro Gln Glu Gly Leu
            485                 490                 495

Tyr Asn Glu Leu Gln Lys Asp Lys Met Ala Glu Ala Tyr Ser Glu Ile
                500                 505                 510

Gly Met Lys Gly Glu Arg Arg Arg Gly Lys Gly His Asp Gly Leu Tyr
            515                 520                 525

Gln Gly Leu Ser Thr Ala Thr Lys Asp Thr Tyr Asp Ala Leu His Met
            530                 535                 540

Gln Ala Leu Pro Pro Arg
545                 550

<210> SEQ ID NO 104
<211> LENGTH: 550
<212> TYPE: PRT
<213> ORGANISM: Artificial Sequence
<220> FEATURE:
<223> OTHER INFORMATION: Synthetic

<400> SEQUENCE: 104

Met Ala Leu Pro Val Thr Ala Leu Leu Leu Pro Leu Ala Leu Leu Leu
1               5                   10                  15

His Ala Ala Arg Pro Gln Gly Cys Thr His Val Ala Gln Trp Ala Ile
                20                  25                  30

Lys Ala Phe Cys Gly Ser Ser Gly Gly Ser Gly Gly Ser Gly Gly Ser
            35                  40                  45

Gly Gly Gly Pro Leu Gly Leu Ala Gly Gly Ser Ser Gly Gln Val Gln
        50                  55                  60

Leu Val Glu Ser Gly Gly Gly Val Val Gln Pro Gly Arg Ser Leu Arg
65                  70                  75                  80

Leu Ser Cys Ala Ala Ser Gly Phe Thr Phe Ser Ser Tyr Gly Met His
                85                  90                  95

Trp Val Arg Gln Ala Pro Gly Lys Gly Leu Glu Trp Val Ala Val Ile
            100                 105                 110

Trp Asp Asp Gly Ser Asn Lys Tyr Tyr Val Asp Ser Val Lys Gly Arg
        115                 120                 125

Phe Thr Ile Ser Arg Asp Asn Ser Lys Asn Thr Leu Tyr Leu Gln Met
    130                 135                 140

Asn Ser Leu Arg Ala Glu Asp Thr Ala Val Tyr Tyr Cys Ala Arg Asp
145                 150                 155                 160

Asp Tyr Tyr Gly Ser Gly Ser Phe Asn Ser Tyr Tyr Gly Thr Asp Val
                165                 170                 175
```

Trp Gly Gln Gly Thr Val Thr Val Ser Ser Gly Gly Gly Ser
            180                 185                 190

Gly Gly Gly Gly Ser Gly Gly Gly Ser Glu Ile Val Leu Thr Gln
            195                 200                 205

Ser Pro Ala Thr Leu Ser Leu Ser Pro Gly Glu Arg Ala Thr Leu Ser
210                 215                 220

Cys Arg Ala Ser Gln Ser Val Ser Ile Tyr Leu Ala Trp Tyr Gln Gln
225                 230                 235                 240

Lys Pro Gly Gln Ala Pro Arg Leu Leu Ile Tyr Asp Ala Ser Asn Arg
            245                 250                 255

Ala Thr Gly Ile Pro Ala Arg Phe Ser Gly Ser Gly Ser Gly Thr Asp
            260                 265                 270

Phe Thr Leu Thr Ile Ser Ser Leu Glu Pro Glu Asp Phe Ala Val Tyr
            275                 280                 285

Tyr Cys Gln Gln Arg Ser Asn Trp Pro Pro Phe Thr Phe Gly Pro Gly
290                 295                 300

Thr Lys Val Asp Ile Lys Ser Ala Ala Ala Phe Val Pro Val Phe Leu
305                 310                 315                 320

Pro Ala Lys Pro Thr Thr Thr Pro Ala Pro Arg Pro Pro Thr Pro Ala
            325                 330                 335

Pro Thr Ile Ala Ser Gln Pro Leu Ser Leu Arg Pro Glu Ala Cys Arg
            340                 345                 350

Pro Ala Ala Gly Gly Ala Val His Thr Arg Gly Leu Asp Phe Ala Cys
            355                 360                 365

Asp Ile Tyr Ile Trp Ala Pro Leu Ala Gly Thr Cys Gly Val Leu Leu
            370                 375                 380

Leu Ser Leu Val Ile Thr Leu Tyr Cys Asn His Arg Asn Arg Ser Lys
385                 390                 395                 400

Arg Ser Arg Leu Leu His Ser Asp Tyr Met Asn Met Thr Pro Arg Arg
            405                 410                 415

Pro Gly Pro Thr Arg Lys His Tyr Gln Pro Tyr Ala Pro Pro Arg Asp
            420                 425                 430

Phe Ala Ala Tyr Arg Ser Arg Val Lys Phe Ser Arg Ser Ala Asp Ala
            435                 440                 445

Pro Ala Tyr Gln Gln Gly Gln Asn Gln Leu Tyr Asn Glu Leu Asn Leu
450                 455                 460

Gly Arg Arg Glu Glu Tyr Asp Val Leu Asp Lys Arg Gly Arg Asp
465                 470                 475                 480

Pro Glu Met Gly Gly Lys Pro Arg Arg Lys Asn Pro Gln Glu Gly Leu
            485                 490                 495

Tyr Asn Glu Leu Gln Lys Asp Lys Met Ala Glu Ala Tyr Ser Glu Ile
            500                 505                 510

Gly Met Lys Gly Glu Arg Arg Arg Gly Lys Gly His Asp Gly Leu Tyr
            515                 520                 525

Gln Gly Leu Ser Thr Ala Thr Lys Asp Thr Tyr Asp Ala Leu His Met
            530                 535                 540

Gln Ala Leu Pro Pro Arg
545                 550

<210> SEQ ID NO 105
<211> LENGTH: 491
<212> TYPE: PRT
<213> ORGANISM: Artificial Sequence
<220> FEATURE:

<223> OTHER INFORMATION: Synthetic

<400> SEQUENCE: 105

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Tyr Tyr Gly Ser Gly Ser Phe Asn Ser Tyr Tyr Gly
            100                 105                 110

Thr Asp Val Trp Gly Gln Gly Thr Thr Val Thr Val Ser Gly Gly
        115                 120                 125

Gly Gly Ser Gly Gly Gly Ser Gly Gly Gly Ser Glu Ile Val
130                 135                 140

Leu Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ile Tyr Leu Ala Trp
            165                 170                 175

Tyr Gln Gln Lys Pro Gly Gln Ala Pro Arg Leu Leu Ile Tyr Asp Ala
            180                 185                 190

Ser Asn Arg Ala Thr Gly Ile Pro Ala Arg Phe Ser Gly Ser Gly Ser
            195                 200                 205

Gly Thr Asp Phe Thr Leu Thr Ile Ser Ser Leu Glu Pro Glu Asp Phe
210                 215                 220

Ala Val Tyr Tyr Cys Gln Gln Arg Ser Asn Trp Pro Pro Phe Thr Phe
225                 230                 235                 240

Gly Pro Gly Thr Lys Val Asp Ile Lys Ser Ala Ala Ala Phe Val Pro
            245                 250                 255

Val Phe Leu Pro Ala Lys Pro Thr Thr Thr Pro Ala Pro Arg Pro Pro
            260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
            290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Asn His Arg Asn
                325                 330                 335

Arg Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
            355                 360                 365

Phe Pro Glu Glu Glu Glu Gly Gly Cys Glu Leu Arg Val Lys Phe Ser
            370                 375                 380

Arg Ser Ala Asp Ala Pro Ala Tyr Gln Gln Gly Gln Asn Gln Leu Tyr
385                 390                 395                 400

```
Asn Glu Leu Asn Leu Gly Arg Arg Glu Tyr Asp Val Leu Asp Lys
                405                 410                 415

Arg Arg Gly Arg Asp Pro Glu Met Gly Gly Lys Pro Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490
```

```
<210> SEQ ID NO 106
<211> LENGTH: 536
<212> TYPE: PRT
<213> ORGANISM: Artificial Sequence
<220> FEATURE:
<223> OTHER INFORMATION: Synthetic

<400> SEQUENCE: 106

Glu Val Ala Pro Gly Lys Arg Trp Phe Tyr Asn His Val Lys Gln Val
1               5                   10                  15

Pro His Leu Val Gly Ser Ser Gly Ser Gly Gly Ser Gly Gly Ser
            20                  25                  30

Gly Gly Gly Pro Leu Gly Leu Ala Gly Gly Ser Ser Gly Gln Val Gln
        35                  40                  45

Leu Val Glu Ser Gly Gly Gly Val Val Gln Pro Gly Arg Ser Leu Arg
    50                  55                  60

Leu Ser Cys Ala Ala Ser Gly Phe Thr Phe Ser Ser Tyr Gly Met His
65                  70                  75                  80

Trp Val Arg Gln Ala Pro Gly Lys Gly Leu Glu Trp Val Ala Val Ile
                85                  90                  95

Trp Asp Asp Gly Ser Asn Lys Tyr Tyr Val Asp Ser Val Lys Gly Arg
            100                 105                 110

Phe Thr Ile Ser Arg Asp Asn Ser Lys Asn Thr Leu Tyr Leu Gln Met
        115                 120                 125

Asn Ser Leu Arg Ala Glu Asp Thr Ala Val Tyr Tyr Cys Ala Arg Asp
    130                 135                 140

Asp Tyr Tyr Gly Ser Gly Ser Phe Asn Ser Tyr Tyr Gly Thr Asp Val
145                 150                 155                 160

Trp Gly Gln Gly Thr Thr Val Thr Val Ser Ser Gly Gly Gly Gly Ser
                165                 170                 175

Gly Gly Gly Gly Ser Gly Gly Gly Ser Glu Ile Val Leu Thr Gln
            180                 185                 190

Ser Pro Ala Thr Leu Ser Leu Ser Pro Gly Glu Arg Ala Thr Leu Ser
        195                 200                 205

Cys Arg Ala Ser Gln Ser Val Ser Ile Tyr Leu Ala Trp Tyr Gln Gln
    210                 215                 220

Lys Pro Gly Gln Ala Pro Arg Leu Leu Ile Tyr Asp Ala Ser Asn Arg
225                 230                 235                 240

Ala Thr Gly Ile Pro Ala Arg Phe Ser Gly Ser Gly Ser Gly Thr Asp
                245                 250                 255

Phe Thr Leu Thr Ile Ser Ser Leu Glu Pro Glu Asp Phe Ala Val Tyr
            260                 265                 270
```

```
Tyr Cys Gln Gln Arg Ser Asn Trp Pro Pro Phe Thr Phe Gly Pro Gly
            275                 280                 285

Thr Lys Val Asp Ile Lys Ser Ala Ala Ala Phe Val Pro Val Phe Leu
290                 295                 300

Pro Ala Lys Pro Thr Thr Thr Pro Ala Pro Arg Pro Pro Thr Pro Ala
305                 310                 315                 320

Pro Thr Ile Ala Ser Gln Pro Leu Ser Leu Arg Pro Glu Ala Cys Arg
            325                 330                 335

Pro Ala Ala Gly Gly Ala Val His Thr Arg Gly Leu Asp Phe Ala Cys
            340                 345                 350

Asp Ile Tyr Ile Trp Ala Pro Leu Ala Gly Thr Cys Gly Val Leu Leu
            355                 360                 365

Leu Ser Leu Val Ile Thr Leu Tyr Cys Asn His Arg Asn Arg Lys Arg
370                 375                 380

Gly Arg Lys Lys Leu Leu Tyr Ile Phe Lys Gln Pro Phe Met Arg Pro
385                 390                 395                 400

Val Gln Thr Thr Gln Glu Glu Asp Gly Cys Ser Cys Arg Phe Pro Glu
            405                 410                 415

Glu Glu Glu Gly Gly Cys Glu Leu Arg Val Lys Phe Ser Arg Ser Ala
            420                 425                 430

Asp Ala Pro Ala Tyr Gln Gln Gly Gln Asn Gln Leu Tyr Asn Glu Leu
435                 440                 445

Asn Leu Gly Arg Arg Glu Glu Tyr Asp Val Leu Asp Lys Arg Arg Gly
            450                 455                 460

Arg Asp Pro Glu Met Gly Gly Lys Pro Arg Arg Lys Asn Pro Gln Glu
465                 470                 475                 480

Gly Leu Tyr Asn Glu Leu Gln Lys Asp Lys Met Ala Glu Ala Tyr Ser
            485                 490                 495

Glu Ile Gly Met Lys Gly Glu Arg Arg Arg Gly Lys Gly His Asp Gly
            500                 505                 510

Leu Tyr Gln Gly Leu Ser Thr Ala Thr Lys Asp Thr Tyr Asp Ala Leu
            515                 520                 525

His Met Gln Ala Leu Pro Pro Arg
            530                 535

<210> SEQ ID NO 107
<211> LENGTH: 535
<212> TYPE: PRT
<213> ORGANISM: Artificial Sequence
<220> FEATURE:
<223> OTHER INFORMATION: Synthetic

<400> SEQUENCE: 107

His Glu Glu Val His Met Arg Pro Asn Lys Leu Ser Leu Thr Trp Ala
1               5                   10                  15

Tyr Thr Gly Pro Gln Leu Arg Gly Ser Ser Gly Gly Ser Gly Gly Ser
            20                  25                  30

Gly Gly Gly Ser Gly Pro Leu Gly Leu Ala Gly Gly Ser Gln Val
            35                  40                  45

Gln Leu Val Glu Ser Gly Gly Val Val Gln Pro Gly Arg Ser Leu
50                  55                  60

Arg Leu Ser Cys Ala Ala Ser Gly Phe Thr Phe Ser Ser Tyr Gly Met
65                  70                  75                  80

His Trp Val Arg Gln Ala Pro Gly Lys Gly Leu Glu Trp Val Ala Val
            85                  90                  95
```

```
Ile Trp Asp Asp Gly Ser Asn Lys Tyr Tyr Val Asp Ser Val Lys Gly
            100                 105                 110

Arg Phe Thr Ile Ser Arg Asp Asn Ser Lys Asn Thr Leu Tyr Leu Gln
            115                 120                 125

Met Asn Ser Leu Arg Ala Glu Asp Thr Ala Val Tyr Tyr Cys Ala Arg
            130                 135                 140

Asp Asp Tyr Tyr Gly Ser Gly Ser Phe Asn Ser Tyr Tyr Gly Thr Asp
145                 150                 155                 160

Val Trp Gly Gln Gly Thr Thr Val Thr Val Ser Ser Gly Gly Gly Gly
                165                 170                 175

Ser Gly Gly Gly Gly Ser Gly Gly Gly Gly Ser Glu Ile Val Leu Thr
            180                 185                 190

Gln Ser Pro Ala Thr Leu Ser Leu Ser Pro Gly Glu Arg Ala Thr Leu
            195                 200                 205

Ser Cys Arg Ala Ser Gln Ser Val Ser Ile Tyr Leu Ala Trp Tyr Gln
            210                 215                 220

Gln Lys Pro Gly Gln Ala Pro Arg Leu Leu Ile Tyr Asp Ala Ser Asn
225                 230                 235                 240

Arg Ala Thr Gly Ile Pro Ala Arg Phe Ser Gly Ser Gly Ser Gly Thr
                245                 250                 255

Asp Phe Thr Leu Thr Ile Ser Ser Leu Glu Pro Glu Asp Phe Ala Val
            260                 265                 270

Tyr Tyr Cys Gln Gln Arg Ser Asn Trp Pro Pro Phe Thr Phe Gly Pro
            275                 280                 285

Gly Thr Lys Val Asp Ile Lys Ser Ala Ala Phe Val Pro Val Phe
            290                 295                 300

Leu Pro Ala Lys Pro Thr Thr Thr Pro Ala Pro Arg Pro Pro Thr Pro
305                 310                 315                 320

Ala Pro Thr Ile Ala Ser Gln Pro Leu Ser Leu Arg Pro Glu Ala Cys
                325                 330                 335

Arg Pro Ala Ala Gly Gly Ala Val His Thr Arg Gly Leu Asp Phe Ala
            340                 345                 350

Cys Asp Ile Tyr Ile Trp Ala Pro Leu Ala Gly Thr Cys Gly Val Leu
            355                 360                 365

Leu Leu Ser Leu Val Ile Thr Leu Tyr Cys Asn His Arg Asn Arg Ser
370                 375                 380

Lys Arg Ser Arg Leu Leu His Ser Asp Tyr Met Asn Met Thr Pro Arg
385                 390                 395                 400

Arg Pro Gly Pro Thr Arg Lys His Tyr Gln Pro Tyr Ala Pro Pro Arg
                405                 410                 415

Asp Phe Ala Ala Tyr Arg Ser Arg Val Lys Phe Ser Arg Ser Ala Asp
            420                 425                 430

Ala Pro Ala Tyr Gln Gln Gly Gln Asn Gln Leu Tyr Asn Glu Leu Asn
            435                 440                 445

Leu Gly Arg Arg Glu Glu Tyr Asp Val Leu Asp Lys Arg Arg Gly Arg
450                 455                 460

Asp Pro Glu Met Gly Gly Lys Pro Arg Arg Lys Asn Pro Gln Glu Gly
465                 470                 475                 480

Leu Tyr Asn Glu Leu Gln Lys Asp Lys Met Ala Glu Ala Tyr Ser Glu
                485                 490                 495

Ile Gly Met Lys Gly Glu Arg Arg Arg Gly Lys Gly His Asp Gly Leu
            500                 505                 510

Tyr Gln Gly Leu Ser Thr Ala Thr Lys Asp Thr Tyr Asp Ala Leu His
```

```
            515                 520                 525
Met Gln Ala Leu Pro Pro Arg
    530                 535

<210> SEQ ID NO 108
<211> LENGTH: 529
<212> TYPE: PRT
<213> ORGANISM: Artificial Sequence
<220> FEATURE:
<223> OTHER INFORMATION: Synthetic

<400> SEQUENCE: 108

Gln Gly Cys Thr Met Pro Pro Ser Pro Arg Ser Lys Val Ile Cys Gly
1               5                   10                  15

Ser Ser Gly Gly Ser Gly Gly Ser Gly Gly Ser Gly Gly Gly Pro Leu
            20                  25                  30

Gly Leu Ala Gly Gly Ser Ser Gly Gln Val Gln Leu Val Glu Ser Gly
        35                  40                  45

Gly Gly Val Val Gln Pro Gly Arg Ser Leu Arg Leu Ser Cys Ala Ala
    50                  55                  60

Ser Gly Phe Thr Phe Ser Ser Tyr Gly Met His Trp Val Arg Gln Ala
65                  70                  75                  80

Pro Gly Lys Gly Leu Glu Trp Val Ala Val Ile Trp Asp Asp Gly Ser
                85                  90                  95

Asn Lys Tyr Tyr Val Asp Ser Val Lys Gly Arg Phe Thr Ile Ser Arg
            100                 105                 110

Asp Asn Ser Lys Asn Thr Leu Tyr Leu Gln Met Asn Ser Leu Arg Ala
        115                 120                 125

Glu Asp Thr Ala Val Tyr Tyr Cys Ala Arg Asp Asp Tyr Tyr Gly Ser
    130                 135                 140

Gly Ser Phe Asn Ser Tyr Tyr Gly Thr Asp Val Trp Gly Gln Gly Thr
145                 150                 155                 160

Thr Val Thr Val Ser Ser Gly Gly Gly Ser Gly Gly Gly Gly Gly Ser
                165                 170                 175

Gly Gly Gly Gly Ser Glu Ile Val Leu Thr Gln Ser Pro Ala Thr Leu
            180                 185                 190

Ser Leu Ser Pro Gly Glu Arg Ala Thr Leu Ser Cys Arg Ala Ser Gln
        195                 200                 205

Ser Val Ser Ile Tyr Leu Ala Trp Tyr Gln Gln Lys Pro Gly Gln Ala
    210                 215                 220

Pro Arg Leu Leu Ile Tyr Asp Ala Ser Asn Arg Ala Thr Gly Ile Pro
225                 230                 235                 240

Ala Arg Phe Ser Gly Ser Gly Ser Gly Thr Asp Phe Thr Leu Thr Ile
                245                 250                 255

Ser Ser Leu Glu Pro Glu Asp Phe Ala Val Tyr Tyr Cys Gln Gln Arg
            260                 265                 270

Ser Asn Trp Pro Pro Phe Thr Phe Gly Pro Gly Thr Lys Val Asp Ile
        275                 280                 285

Lys Ser Ala Ala Ala Phe Val Pro Val Phe Leu Pro Ala Lys Pro Thr
    290                 295                 300

Thr Thr Pro Ala Pro Arg Pro Pro Thr Pro Ala Pro Thr Ile Ala Ser
305                 310                 315                 320

Gln Pro Leu Ser Leu Arg Pro Glu Ala Cys Arg Pro Ala Ala Gly Gly
                325                 330                 335

Ala Val His Thr Arg Gly Leu Asp Phe Ala Cys Asp Ile Tyr Ile Trp
```

```
            340                 345                 350
Ala Pro Leu Ala Gly Thr Cys Gly Val Leu Leu Ser Leu Val Ile
        355                 360                 365

Thr Leu Tyr Cys Asn His Arg Asn Arg Ser Lys Arg Ser Arg Leu Leu
    370                 375                 380

His Ser Asp Tyr Met Asn Met Thr Pro Arg Arg Pro Gly Pro Thr Arg
385                 390                 395                 400

Lys His Tyr Gln Pro Tyr Ala Pro Pro Arg Asp Phe Ala Ala Tyr Arg
                405                 410                 415

Ser Arg Val Lys Phe Ser Arg Ser Ala Asp Ala Pro Ala Tyr Gln Gln
            420                 425                 430

Gly Gln Asn Gln Leu Tyr Asn Glu Leu Asn Leu Gly Arg Arg Glu Glu
        435                 440                 445

Tyr Asp Val Leu Asp Lys Arg Arg Gly Arg Asp Pro Glu Met Gly Gly
    450                 455                 460

Lys Pro Arg Arg Lys Asn Pro Gln Glu Gly Leu Tyr Asn Glu Leu Gln
465                 470                 475                 480

Lys Asp Lys Met Ala Glu Ala Tyr Ser Glu Ile Gly Met Lys Gly Glu
                485                 490                 495

Arg Arg Arg Gly Lys Gly His Asp Gly Leu Tyr Gln Gly Leu Ser Thr
            500                 505                 510

Ala Thr Lys Asp Thr Tyr Asp Ala Leu His Met Gln Ala Leu Pro Pro
        515                 520                 525

Arg

<210> SEQ ID NO 109
<211> LENGTH: 529
<212> TYPE: PRT
<213> ORGANISM: Artificial Sequence
<220> FEATURE:
<223> OTHER INFORMATION: Synthetic

<400> SEQUENCE: 109

Gln Gly Cys Thr Phe Pro Asn Thr Thr Met Gln Arg Thr Phe Cys Gly
1               5                   10                  15

Ser Ser Gly Gly Ser Gly Gly Ser Gly Gly Ser Gly Gly Gly Pro Leu
            20                  25                  30

Gly Leu Ala Gly Gly Ser Ser Gly Gln Val Gln Leu Val Glu Ser Gly
        35                  40                  45

Gly Gly Val Val Gln Pro Gly Arg Ser Leu Arg Leu Ser Cys Ala Ala
    50                  55                  60

Ser Gly Phe Thr Phe Ser Ser Tyr Gly Met His Trp Val Arg Gln Ala
65                  70                  75                  80

Pro Gly Lys Gly Leu Glu Trp Val Ala Val Ile Trp Asp Asp Gly Ser
                85                  90                  95

Asn Lys Tyr Tyr Val Asp Ser Val Lys Gly Arg Phe Thr Ile Ser Arg
            100                 105                 110

Asp Asn Ser Lys Asn Thr Leu Tyr Leu Gln Met Asn Ser Leu Arg Ala
        115                 120                 125

Glu Asp Thr Ala Val Tyr Tyr Cys Ala Arg Asp Tyr Tyr Gly Ser
    130                 135                 140

Gly Ser Phe Asn Ser Tyr Tyr Gly Thr Asp Val Trp Gly Gln Gly Thr
145                 150                 155                 160

Thr Val Thr Val Ser Ser Gly Gly Gly Gly Ser Gly Gly Gly Gly Ser
                165                 170                 175
```

Gly Gly Gly Gly Ser Glu Ile Val Leu Thr Gln Ser Pro Ala Thr Leu
            180                 185                 190

Ser Leu Ser Pro Gly Glu Arg Ala Thr Leu Ser Cys Arg Ala Ser Gln
        195                 200                 205

Ser Val Ser Ile Tyr Leu Ala Trp Tyr Gln Gln Lys Pro Gly Gln Ala
    210                 215                 220

Pro Arg Leu Leu Ile Tyr Asp Ala Ser Asn Arg Ala Thr Gly Ile Pro
225                 230                 235                 240

Ala Arg Phe Ser Gly Ser Gly Ser Gly Thr Asp Phe Thr Leu Thr Ile
                245                 250                 255

Ser Ser Leu Glu Pro Glu Asp Phe Ala Val Tyr Tyr Cys Gln Gln Arg
            260                 265                 270

Ser Asn Trp Pro Pro Phe Thr Phe Gly Pro Gly Thr Lys Val Asp Ile
        275                 280                 285

Lys Ser Ala Ala Ala Phe Val Pro Val Phe Leu Pro Ala Lys Pro Thr
    290                 295                 300

Thr Thr Pro Ala Pro Arg Pro Pro Thr Pro Ala Pro Thr Ile Ala Ser
305                 310                 315                 320

Gln Pro Leu Ser Leu Arg Pro Glu Ala Cys Arg Pro Ala Ala Gly Gly
                325                 330                 335

Ala Val His Thr Arg Gly Leu Asp Phe Ala Cys Asp Ile Tyr Ile Trp
            340                 345                 350

Ala Pro Leu Ala Gly Thr Cys Gly Val Leu Leu Ser Leu Val Ile
        355                 360                 365

Thr Leu Tyr Cys Asn His Arg Asn Arg Ser Lys Arg Ser Arg Leu Leu
    370                 375                 380

His Ser Asp Tyr Met Asn Met Thr Pro Arg Arg Pro Gly Pro Thr Arg
385                 390                 395                 400

Lys His Tyr Gln Pro Tyr Ala Pro Pro Arg Asp Phe Ala Ala Tyr Arg
                405                 410                 415

Ser Arg Val Lys Phe Ser Arg Ser Ala Asp Ala Pro Ala Tyr Gln Gln
            420                 425                 430

Gly Gln Asn Gln Leu Tyr Asn Glu Leu Asn Leu Gly Arg Arg Glu Glu
        435                 440                 445

Tyr Asp Val Leu Asp Lys Arg Gly Arg Asp Pro Glu Met Gly Gly
    450                 455                 460

Lys Pro Arg Arg Lys Asn Pro Gln Glu Gly Leu Tyr Asn Glu Leu Gln
465                 470                 475                 480

Lys Asp Lys Met Ala Glu Ala Tyr Ser Glu Ile Gly Met Lys Gly Glu
                485                 490                 495

Arg Arg Arg Gly Lys Gly His Asp Gly Leu Tyr Gln Gly Leu Ser Thr
            500                 505                 510

Ala Thr Lys Asp Thr Tyr Asp Ala Leu His Met Gln Ala Leu Pro Pro
        515                 520                 525

Arg

<210> SEQ ID NO 110
<211> LENGTH: 529
<212> TYPE: PRT
<213> ORGANISM: Artificial Sequence
<220> FEATURE:
<223> OTHER INFORMATION: Synthetic

<400> SEQUENCE: 110

```
Gln Gly Cys Thr Tyr Pro Ser Trp Val Ala Tyr Ile Arg Phe Cys Gly
1               5                   10                  15
Ser Ser Gly Gly Ser Gly Gly Ser Gly Gly Gly Pro Leu
        20              25              30
Gly Leu Ala Gly Gly Ser Ser Gly Gln Val Gln Leu Val Glu Ser Gly
            35              40                  45
Gly Gly Val Val Gln Pro Gly Arg Ser Leu Arg Leu Ser Cys Ala Ala
        50              55              60
Ser Gly Phe Thr Phe Ser Ser Tyr Gly Met His Trp Val Arg Gln Ala
65              70                  75                  80
Pro Gly Lys Gly Leu Glu Trp Val Ala Val Ile Trp Asp Asp Gly Ser
                85                  90                  95
Asn Lys Tyr Tyr Val Asp Ser Val Lys Gly Arg Phe Thr Ile Ser Arg
            100             105                 110
Asp Asn Ser Lys Asn Thr Leu Tyr Leu Gln Met Asn Ser Leu Arg Ala
            115             120                 125
Glu Asp Thr Ala Val Tyr Tyr Cys Ala Arg Asp Asp Tyr Tyr Gly Ser
    130             135                 140
Gly Ser Phe Asn Ser Tyr Tyr Gly Thr Asp Val Trp Gly Gln Gly Thr
145             150                 155                 160
Thr Val Thr Val Ser Ser Gly Gly Gly Ser Gly Gly Gly Gly Gly Ser
                165             170                 175
Gly Gly Gly Gly Ser Glu Ile Val Leu Thr Gln Ser Pro Ala Thr Leu
            180             185                 190
Ser Leu Ser Pro Gly Glu Arg Ala Thr Leu Ser Cys Arg Ala Ser Gln
    195             200                 205
Ser Val Ser Ile Tyr Leu Ala Trp Tyr Gln Gln Lys Pro Gly Gln Ala
    210             215                 220
Pro Arg Leu Leu Ile Tyr Asp Ala Ser Asn Arg Ala Thr Gly Ile Pro
225             230                 235                 240
Ala Arg Phe Ser Gly Ser Gly Ser Gly Thr Asp Phe Thr Leu Thr Ile
                245             250                 255
Ser Ser Leu Glu Pro Glu Asp Phe Ala Val Tyr Tyr Cys Gln Gln Arg
            260             265                 270
Ser Asn Trp Pro Pro Phe Thr Phe Gly Pro Gly Thr Lys Val Asp Ile
    275             280                 285
Lys Ser Ala Ala Ala Phe Val Pro Val Phe Leu Pro Ala Lys Pro Thr
    290             295                 300
Thr Thr Pro Ala Pro Arg Pro Pro Thr Pro Ala Pro Thr Ile Ala Ser
305             310                 315                 320
Gln Pro Leu Ser Leu Arg Pro Glu Ala Cys Arg Pro Ala Ala Gly Gly
            325             330                 335
Ala Val His Thr Arg Gly Leu Asp Phe Ala Cys Asp Ile Tyr Ile Trp
            340             345                 350
Ala Pro Leu Ala Gly Thr Cys Gly Val Leu Leu Leu Ser Leu Val Ile
            355             360                 365
Thr Leu Tyr Cys Asn His Arg Asn Arg Ser Lys Arg Ser Arg Leu Leu
    370             375                 380
His Ser Asp Tyr Met Asn Met Thr Pro Arg Arg Pro Gly Pro Thr Arg
385             390                 395                 400
Lys His Tyr Gln Pro Tyr Ala Pro Pro Arg Asp Phe Ala Ala Tyr Arg
            405             410                 415
Ser Arg Val Lys Phe Ser Arg Ser Ala Asp Ala Pro Ala Tyr Gln Gln
```

```
                    420                 425                 430
Gly Gln Asn Gln Leu Tyr Asn Glu Leu Asn Leu Gly Arg Arg Glu Glu
                435                 440                 445

Tyr Asp Val Leu Asp Lys Arg Arg Gly Arg Asp Pro Glu Met Gly Gly
            450                 455                 460

Lys Pro Arg Arg Lys Asn Pro Gln Glu Gly Leu Tyr Asn Glu Leu Gln
465                 470                 475                 480

Lys Asp Lys Met Ala Glu Ala Tyr Ser Glu Ile Gly Met Lys Gly Glu
                485                 490                 495

Arg Arg Arg Gly Lys Gly His Asp Gly Leu Tyr Gln Gly Leu Ser Thr
            500                 505                 510

Ala Thr Lys Asp Thr Tyr Asp Ala Leu His Met Gln Ala Leu Pro Pro
            515                 520                 525

Arg

<210> SEQ ID NO 111
<211> LENGTH: 529
<212> TYPE: PRT
<213> ORGANISM: Artificial Sequence
<220> FEATURE:
<223> OTHER INFORMATION: Synthetic

<400> SEQUENCE: 111

Gln Gly Val Cys Thr Tyr Pro Pro Ala His Arg Thr Arg Phe Cys Gly
1               5                   10                  15

Ser Ser Gly Gly Ser Gly Gly Ser Gly Gly Gly Gly Pro Leu
                20                  25                  30

Gly Leu Ala Gly Gly Ser Ser Gly Gln Val Gln Leu Val Glu Ser Gly
            35                  40                  45

Gly Gly Val Val Gln Pro Gly Arg Ser Leu Arg Leu Ser Cys Ala Ala
        50                  55                  60

Ser Gly Phe Thr Phe Ser Ser Tyr Gly Met His Trp Val Arg Gln Ala
65                  70                  75                  80

Pro Gly Lys Gly Leu Glu Trp Val Ala Val Ile Trp Asp Asp Gly Ser
                85                  90                  95

Asn Lys Tyr Tyr Val Asp Ser Val Lys Gly Arg Phe Thr Ile Ser Arg
                100                 105                 110

Asp Asn Ser Lys Asn Thr Leu Tyr Leu Gln Met Asn Ser Leu Arg Ala
            115                 120                 125

Glu Asp Thr Ala Val Tyr Tyr Cys Ala Arg Asp Asp Tyr Tyr Gly Ser
        130                 135                 140

Gly Ser Phe Asn Ser Tyr Tyr Gly Thr Asp Val Trp Gly Gln Gly Thr
145                 150                 155                 160

Thr Val Thr Val Ser Ser Gly Gly Gly Ser Gly Gly Gly Gly Ser
                165                 170                 175

Gly Gly Gly Gly Ser Glu Ile Val Leu Thr Gln Ser Pro Ala Thr Leu
            180                 185                 190

Ser Leu Ser Pro Gly Glu Arg Ala Thr Leu Ser Cys Arg Ala Ser Gln
        195                 200                 205

Ser Val Ser Ile Tyr Leu Ala Trp Tyr Gln Gln Lys Pro Gly Gln Ala
    210                 215                 220

Pro Arg Leu Leu Ile Tyr Asp Ala Ser Asn Arg Ala Thr Gly Ile Pro
225                 230                 235                 240

Ala Arg Phe Ser Gly Ser Gly Ser Gly Thr Asp Phe Thr Leu Thr Ile
                245                 250                 255
```

```
Ser Ser Leu Glu Pro Glu Asp Phe Ala Val Tyr Tyr Cys Gln Gln Arg
            260                 265                 270

Ser Asn Trp Pro Pro Phe Thr Phe Gly Pro Gly Thr Lys Val Asp Ile
            275                 280                 285

Lys Ser Ala Ala Ala Phe Val Pro Val Phe Leu Pro Ala Lys Pro Thr
            290                 295                 300

Thr Thr Pro Ala Pro Arg Pro Pro Thr Pro Ala Pro Thr Ile Ala Ser
305                 310                 315                 320

Gln Pro Leu Ser Leu Arg Pro Glu Ala Cys Arg Pro Ala Ala Gly Gly
            325                 330                 335

Ala Val His Thr Arg Gly Leu Asp Phe Ala Cys Asp Ile Tyr Ile Trp
            340                 345                 350

Ala Pro Leu Ala Gly Thr Cys Gly Val Leu Leu Leu Ser Leu Val Ile
            355                 360                 365

Thr Leu Tyr Cys Asn His Arg Asn Arg Ser Lys Arg Ser Arg Leu Leu
            370                 375                 380

His Ser Asp Tyr Met Asn Met Thr Pro Arg Arg Pro Gly Pro Thr Arg
385                 390                 395                 400

Lys His Tyr Gln Pro Tyr Ala Pro Pro Arg Asp Phe Ala Ala Tyr Arg
            405                 410                 415

Ser Arg Val Lys Phe Ser Arg Ser Ala Asp Ala Pro Ala Tyr Gln Gln
            420                 425                 430

Gly Gln Asn Gln Leu Tyr Asn Glu Leu Asn Leu Gly Arg Arg Glu Glu
            435                 440                 445

Tyr Asp Val Leu Asp Lys Arg Gly Arg Asp Pro Glu Met Gly Gly
450                 455                 460

Lys Pro Arg Arg Lys Asn Pro Gln Glu Gly Leu Tyr Asn Glu Leu Gln
465                 470                 475                 480

Lys Asp Lys Met Ala Glu Ala Tyr Ser Glu Ile Gly Met Lys Gly Glu
            485                 490                 495

Arg Arg Arg Gly Lys Gly His Asp Gly Leu Tyr Gln Gly Leu Ser Thr
            500                 505                 510

Ala Thr Lys Asp Thr Tyr Asp Ala Leu His Met Gln Ala Leu Pro Pro
            515                 520                 525

Arg

<210> SEQ ID NO 112
<211> LENGTH: 529
<212> TYPE: PRT
<213> ORGANISM: Artificial Sequence
<220> FEATURE:
<223> OTHER INFORMATION: Synthetic

<400> SEQUENCE: 112

Gln Gly Cys Thr Met Pro Tyr His Ile His Ser Ile Gly Leu Cys Gly
1               5                   10                  15

Ser Ser Gly Gly Ser Gly Gly Ser Gly Ser Gly Gly Gly Pro Leu
            20                  25                  30

Gly Leu Ala Gly Gly Ser Ser Gly Gln Val Gln Leu Val Glu Ser Gly
            35                  40                  45

Gly Gly Val Val Gln Pro Gly Arg Ser Leu Arg Leu Ser Cys Ala Ala
            50                  55                  60

Ser Gly Phe Thr Phe Ser Ser Tyr Gly Met His Trp Val Arg Gln Ala
65                  70                  75                  80
```

-continued

Pro Gly Lys Gly Leu Glu Trp Val Ala Val Ile Trp Asp Asp Gly Ser
            85                  90                  95

Asn Lys Tyr Tyr Val Asp Ser Val Lys Gly Arg Phe Thr Ile Ser Arg
        100                 105                 110

Asp Asn Ser Lys Asn Thr Leu Tyr Leu Gln Met Asn Ser Leu Arg Ala
        115                 120                 125

Glu Asp Thr Ala Val Tyr Tyr Cys Ala Arg Asp Asp Tyr Tyr Gly Ser
    130                 135                 140

Gly Ser Phe Asn Ser Tyr Tyr Gly Thr Asp Val Trp Gly Gln Gly Thr
145                 150                 155                 160

Thr Val Thr Val Ser Ser Gly Gly Gly Ser Gly Gly Gly Gly Gly Ser
                165                 170                 175

Gly Gly Gly Gly Ser Glu Ile Val Leu Thr Gln Ser Pro Ala Thr Leu
            180                 185                 190

Ser Leu Ser Pro Gly Glu Arg Ala Thr Leu Ser Cys Arg Ala Ser Gln
        195                 200                 205

Ser Val Ser Ile Tyr Leu Ala Trp Tyr Gln Gln Lys Pro Gly Gln Ala
        210                 215                 220

Pro Arg Leu Leu Ile Tyr Asp Ala Ser Asn Arg Ala Thr Gly Ile Pro
225                 230                 235                 240

Ala Arg Phe Ser Gly Ser Gly Ser Gly Thr Asp Phe Thr Leu Thr Ile
                245                 250                 255

Ser Ser Leu Glu Pro Glu Asp Phe Ala Val Tyr Tyr Cys Gln Gln Arg
            260                 265                 270

Ser Asn Trp Pro Pro Phe Thr Phe Gly Pro Gly Thr Lys Val Asp Ile
        275                 280                 285

Lys Ser Ala Ala Ala Phe Val Pro Val Phe Leu Pro Ala Lys Pro Thr
290                 295                 300

Thr Thr Pro Ala Pro Arg Pro Pro Thr Pro Ala Pro Thr Ile Ala Ser
305                 310                 315                 320

Gln Pro Leu Ser Leu Arg Pro Glu Ala Cys Arg Pro Ala Ala Gly Gly
                325                 330                 335

Ala Val His Thr Arg Gly Leu Asp Phe Ala Cys Asp Ile Tyr Ile Trp
            340                 345                 350

Ala Pro Leu Ala Gly Thr Cys Gly Val Leu Leu Leu Ser Leu Val Ile
        355                 360                 365

Thr Leu Tyr Cys Asn His Arg Asn Arg Ser Lys Arg Ser Arg Leu Leu
    370                 375                 380

His Ser Asp Tyr Met Asn Met Thr Pro Arg Arg Pro Gly Pro Thr Arg
385                 390                 395                 400

Lys His Tyr Gln Pro Tyr Ala Pro Pro Arg Asp Phe Ala Ala Tyr Arg
                405                 410                 415

Ser Arg Val Lys Phe Ser Arg Ser Ala Asp Ala Pro Ala Tyr Gln Gln
            420                 425                 430

Gly Gln Asn Gln Leu Tyr Asn Glu Leu Asn Leu Gly Arg Arg Glu Glu
        435                 440                 445

Tyr Asp Val Leu Asp Lys Arg Arg Gly Arg Asp Pro Glu Met Gly Gly
    450                 455                 460

Lys Pro Arg Arg Lys Asn Pro Gln Glu Gly Leu Tyr Asn Glu Leu Gln
465                 470                 475                 480

Lys Asp Lys Met Ala Glu Ala Tyr Ser Glu Ile Gly Met Lys Gly Glu
                485                 490                 495

Arg Arg Arg Gly Lys Gly His Asp Gly Leu Tyr Gln Gly Leu Ser Thr

```
                    500                 505                 510
Ala Thr Lys Asp Thr Tyr Asp Ala Leu His Met Gln Ala Leu Pro Pro
            515                 520                 525
Arg
```

```
<210> SEQ ID NO 113
<211> LENGTH: 529
<212> TYPE: PRT
<213> ORGANISM: Artificial Sequence
<220> FEATURE:
<223> OTHER INFORMATION: Synthetic

<400> SEQUENCE: 113

Gln Gly Trp Cys Thr Ile Pro Ser Ser Met Ser Ile Arg Leu Cys Gly
1               5                   10                  15

Ser Ser Gly Gly Ser Gly Gly Ser Gly Gly Ser Gly Gly Gly Pro Leu
            20                  25                  30

Gly Leu Ala Gly Gly Ser Ser Gly Gln Val Gln Leu Val Glu Ser Gly
        35                  40                  45

Gly Gly Val Val Gln Pro Gly Arg Ser Leu Arg Leu Ser Cys Ala Ala
    50                  55                  60

Ser Gly Phe Thr Phe Ser Ser Tyr Gly Met His Trp Val Arg Gln Ala
65                  70                  75                  80

Pro Gly Lys Gly Leu Glu Trp Val Ala Val Ile Trp Asp Asp Gly Ser
                85                  90                  95

Asn Lys Tyr Tyr Val Asp Ser Val Lys Gly Arg Phe Thr Ile Ser Arg
            100                 105                 110

Asp Asn Ser Lys Asn Thr Leu Tyr Leu Gln Met Asn Ser Leu Arg Ala
        115                 120                 125

Glu Asp Thr Ala Val Tyr Tyr Cys Ala Arg Asp Asp Tyr Tyr Gly Ser
    130                 135                 140

Gly Ser Phe Asn Ser Tyr Tyr Gly Thr Asp Val Trp Gly Gln Gly Thr
145                 150                 155                 160

Thr Val Thr Val Ser Ser Gly Gly Gly Ser Gly Gly Gly Gly Gly Ser
                165                 170                 175

Gly Gly Gly Gly Ser Glu Ile Val Leu Thr Gln Ser Pro Ala Thr Leu
            180                 185                 190

Ser Leu Ser Pro Gly Glu Arg Ala Thr Leu Ser Cys Arg Ala Ser Gln
        195                 200                 205

Ser Val Ser Ile Tyr Leu Ala Trp Tyr Gln Gln Lys Pro Gly Gln Ala
    210                 215                 220

Pro Arg Leu Leu Ile Tyr Asp Ala Ser Asn Arg Ala Thr Gly Ile Pro
225                 230                 235                 240

Ala Arg Phe Ser Gly Ser Gly Ser Gly Thr Asp Phe Thr Leu Thr Ile
                245                 250                 255

Ser Ser Leu Glu Pro Glu Asp Phe Ala Val Tyr Tyr Cys Gln Gln Arg
            260                 265                 270

Ser Asn Trp Pro Pro Phe Thr Phe Gly Pro Gly Thr Lys Val Asp Ile
        275                 280                 285

Lys Ser Ala Ala Ala Phe Val Pro Val Phe Leu Pro Ala Lys Pro Thr
    290                 295                 300

Thr Thr Pro Ala Pro Arg Pro Pro Thr Pro Ala Pro Thr Ile Ala Ser
305                 310                 315                 320

Gln Pro Leu Ser Leu Arg Pro Glu Ala Cys Arg Pro Ala Ala Gly Gly
                325                 330                 335
```

```
Ala Val His Thr Arg Gly Leu Asp Phe Ala Cys Asp Ile Tyr Ile Trp
            340                 345                 350

Ala Pro Leu Ala Gly Thr Cys Gly Val Leu Leu Leu Ser Leu Val Ile
            355                 360                 365

Thr Leu Tyr Cys Asn His Arg Asn Arg Ser Lys Arg Ser Arg Leu Leu
    370                 375                 380

His Ser Asp Tyr Met Asn Met Thr Pro Arg Arg Pro Gly Pro Thr Arg
385                 390                 395                 400

Lys His Tyr Gln Pro Tyr Ala Pro Pro Arg Asp Phe Ala Ala Tyr Arg
                405                 410                 415

Ser Arg Val Lys Phe Ser Arg Ser Ala Asp Ala Pro Ala Tyr Gln Gln
            420                 425                 430

Gly Gln Asn Gln Leu Tyr Asn Glu Leu Asn Leu Gly Arg Arg Glu Glu
            435                 440                 445

Tyr Asp Val Leu Asp Lys Arg Gly Arg Asp Pro Glu Met Gly Gly
            450                 455                 460

Lys Pro Arg Arg Lys Asn Pro Gln Glu Gly Leu Tyr Asn Glu Leu Gln
465                 470                 475                 480

Lys Asp Lys Met Ala Glu Ala Tyr Ser Glu Ile Gly Met Lys Gly Glu
                485                 490                 495

Arg Arg Arg Gly Lys Gly His Asp Gly Leu Tyr Gln Gly Leu Ser Thr
            500                 505                 510

Ala Thr Lys Asp Thr Tyr Asp Ala Leu His Met Gln Ala Leu Pro Pro
            515                 520                 525

Arg

<210> SEQ ID NO 114
<211> LENGTH: 528
<212> TYPE: PRT
<213> ORGANISM: Artificial Sequence
<220> FEATURE:
<223> OTHER INFORMATION: Synthetic

<400> SEQUENCE: 114

Gln Gly Cys His Ile Gly Lys Arg Pro Val Pro Cys Leu Trp Ile Gly
1               5                   10                  15

Ser Ser Gly Gly Ser Gly Gly Ser Gly Gly Ser Gly Gly Gly Pro Leu
            20                  25                  30

Gly Leu Ala Gly Gly Ser Ser Gly Gln Val Gln Leu Val Glu Ser Gly
            35                  40                  45

Gly Gly Val Val Gln Pro Gly Arg Ser Leu Arg Leu Ser Cys Ala Ala
        50                  55                  60

Ser Gly Phe Thr Phe Ser Ser Tyr Gly Met His Trp Val Arg Gln Ala
65                  70                  75                  80

Pro Gly Lys Gly Leu Glu Trp Val Ala Val Ile Trp Asp Asp Gly Ser
                85                  90                  95

Asn Lys Tyr Tyr Val Asp Ser Val Lys Gly Arg Phe Thr Ile Ser Arg
            100                 105                 110

Asp Asn Ser Lys Asn Thr Leu Tyr Leu Gln Met Asn Ser Leu Arg Ala
        115                 120                 125

Glu Asp Thr Ala Val Tyr Tyr Cys Ala Arg Asp Asp Tyr Tyr Gly Ser
    130                 135                 140

Gly Ser Phe Asn Ser Tyr Tyr Gly Thr Asp Val Trp Gly Gln Gly Thr
145                 150                 155                 160
```

```
Thr Val Thr Val Ser Ser Gly Gly Gly Ser Gly Gly Gly Ser
            165                 170                 175

Gly Gly Gly Gly Ser Glu Ile Val Leu Thr Gln Ser Pro Ala Thr Leu
            180                 185                 190

Ser Leu Ser Pro Gly Glu Arg Ala Thr Leu Ser Cys Arg Ala Ser Gln
            195                 200                 205

Ser Val Ser Ile Tyr Leu Ala Trp Tyr Gln Gln Lys Pro Gly Gln Ala
210                 215                 220

Pro Arg Leu Leu Ile Tyr Asp Ala Ser Asn Arg Ala Thr Gly Ile Pro
225                 230                 235                 240

Ala Arg Phe Ser Gly Ser Gly Ser Gly Thr Asp Phe Thr Leu Thr Ile
            245                 250                 255

Ser Ser Leu Glu Pro Glu Asp Phe Ala Val Tyr Tyr Cys Gln Gln Arg
            260                 265                 270

Ser Asn Trp Pro Pro Phe Thr Phe Gly Pro Gly Thr Lys Val Asp Ile
            275                 280                 285

Ser Ala Ala Ala Phe Val Pro Val Phe Leu Pro Ala Lys Pro Thr Thr
            290                 295                 300

Thr Pro Ala Pro Arg Pro Pro Thr Pro Ala Pro Thr Ile Ala Ser Gln
305                 310                 315                 320

Pro Leu Ser Leu Arg Pro Glu Ala Cys Arg Pro Ala Ala Gly Gly Ala
            325                 330                 335

Val His Thr Arg Gly Leu Asp Phe Ala Cys Asp Ile Tyr Ile Trp Ala
            340                 345                 350

Pro Leu Ala Gly Thr Cys Gly Val Leu Leu Leu Ser Leu Val Ile Thr
            355                 360                 365

Leu Tyr Cys Asn His Arg Asn Arg Ser Lys Arg Ser Arg Leu Leu His
370                 375                 380

Ser Asp Tyr Met Asn Met Thr Pro Arg Arg Pro Gly Pro Thr Arg Lys
385                 390                 395                 400

His Tyr Gln Pro Tyr Ala Pro Pro Arg Asp Phe Ala Ala Tyr Arg Ser
            405                 410                 415

Arg Val Lys Phe Ser Arg Ser Ala Asp Ala Pro Ala Tyr Gln Gln Gly
            420                 425                 430

Gln Asn Gln Leu Tyr Asn Glu Leu Asn Leu Gly Arg Arg Glu Glu Tyr
            435                 440                 445

Asp Val Leu Asp Lys Arg Arg Gly Arg Asp Pro Glu Met Gly Gly Lys
            450                 455                 460

Pro Arg Arg Lys Asn Pro Gln Glu Gly Leu Tyr Asn Glu Leu Gln Lys
465                 470                 475                 480

Asp Lys Met Ala Glu Ala Tyr Ser Glu Ile Gly Met Lys Gly Glu Arg
            485                 490                 495

Arg Arg Gly Lys Gly His Asp Gly Leu Tyr Gln Gly Leu Ser Thr Ala
            500                 505                 510

Thr Lys Asp Thr Tyr Asp Ala Leu His Met Gln Ala Leu Pro Pro Arg
            515                 520                 525

<210> SEQ ID NO 115
<211> LENGTH: 529
<212> TYPE: PRT
<213> ORGANISM: Artificial Sequence
<220> FEATURE:
<223> OTHER INFORMATION: Synthetic

<400> SEQUENCE: 115
```

```
Gln Gly Cys Tyr Ile Gly Leu Arg Met Val Pro Cys Phe His Met Gly
 1               5                  10                  15

Ser Ser Gly Gly Ser Gly Ser Gly Gly Ser Gly Gly Gly Pro Leu
             20                  25                  30

Gly Leu Ala Gly Gly Ser Ser Gly Gln Val Gln Leu Val Glu Ser Gly
             35                  40                  45

Gly Gly Val Val Gln Pro Gly Arg Ser Leu Arg Leu Ser Cys Ala Ala
 50                  55                  60

Ser Gly Phe Thr Phe Ser Ser Tyr Gly Met His Trp Val Arg Gln Ala
 65                  70                  75                  80

Pro Gly Lys Gly Leu Glu Trp Val Ala Val Ile Trp Asp Asp Gly Ser
             85                  90                  95

Asn Lys Tyr Tyr Val Asp Ser Val Lys Gly Arg Phe Thr Ile Ser Arg
             100                 105                 110

Asp Asn Ser Lys Asn Thr Leu Tyr Leu Gln Met Asn Ser Leu Arg Ala
             115                 120                 125

Glu Asp Thr Ala Val Tyr Tyr Cys Ala Arg Asp Asp Tyr Tyr Gly Ser
             130                 135                 140

Gly Ser Phe Asn Ser Tyr Tyr Gly Thr Asp Val Trp Gly Gln Gly Thr
145                 150                 155                 160

Thr Val Thr Val Ser Ser Gly Gly Gly Ser Gly Gly Gly Gly Ser
             165                 170                 175

Gly Gly Gly Gly Ser Glu Ile Val Leu Thr Gln Ser Pro Ala Thr Leu
             180                 185                 190

Ser Leu Ser Pro Gly Glu Arg Ala Thr Leu Ser Cys Arg Ala Ser Gln
             195                 200                 205

Ser Val Ser Ile Tyr Leu Ala Trp Tyr Gln Gln Lys Pro Gly Gln Ala
             210                 215                 220

Pro Arg Leu Leu Ile Tyr Asp Ala Ser Asn Arg Ala Thr Gly Ile Pro
225                 230                 235                 240

Ala Arg Phe Ser Gly Ser Gly Ser Gly Thr Asp Phe Thr Leu Thr Ile
             245                 250                 255

Ser Ser Leu Glu Pro Glu Asp Phe Ala Val Tyr Tyr Cys Gln Gln Arg
             260                 265                 270

Ser Asn Trp Pro Pro Phe Thr Phe Gly Pro Gly Thr Lys Val Asp Ile
             275                 280                 285

Lys Ser Ala Ala Ala Phe Val Pro Val Phe Leu Pro Ala Lys Pro Thr
             290                 295                 300

Thr Thr Pro Ala Pro Arg Pro Pro Thr Pro Ala Pro Thr Ile Ala Ser
305                 310                 315                 320

Gln Pro Leu Ser Leu Arg Pro Glu Ala Cys Arg Pro Ala Ala Gly Gly
             325                 330                 335

Ala Val His Thr Arg Gly Leu Asp Phe Ala Cys Asp Ile Tyr Ile Trp
             340                 345                 350

Ala Pro Leu Ala Gly Thr Cys Gly Val Leu Leu Leu Ser Leu Val Ile
             355                 360                 365

Thr Leu Tyr Cys Asn His Arg Asn Arg Ser Lys Arg Ser Arg Leu Leu
             370                 375                 380

His Ser Asp Tyr Met Asn Met Thr Pro Arg Arg Pro Gly Pro Thr Arg
385                 390                 395                 400

Lys His Tyr Gln Pro Tyr Ala Pro Pro Arg Asp Phe Ala Ala Tyr Arg
             405                 410                 415

Ser Arg Val Lys Phe Ser Arg Ser Ala Asp Ala Pro Ala Tyr Gln Gln
```

-continued

```
                420                 425                 430
Gly Gln Asn Gln Leu Tyr Asn Glu Leu Asn Leu Gly Arg Arg Glu Glu
            435                 440                 445

Tyr Asp Val Leu Asp Lys Arg Arg Gly Arg Asp Pro Glu Met Gly Gly
450                 455                 460

Lys Pro Arg Arg Lys Asn Pro Gln Glu Gly Leu Tyr Asn Glu Leu Gln
465                 470                 475                 480

Lys Asp Lys Met Ala Glu Ala Tyr Ser Glu Ile Gly Met Lys Gly Glu
                485                 490                 495

Arg Arg Arg Gly Lys Gly His Asp Gly Leu Tyr Gln Gly Leu Ser Thr
            500                 505                 510

Ala Thr Lys Asp Thr Tyr Asp Ala Leu His Met Gln Ala Leu Pro Pro
            515                 520                 525

Arg

<210> SEQ ID NO 116
<211> LENGTH: 529
<212> TYPE: PRT
<213> ORGANISM: Artificial Sequence
<220> FEATURE:
<223> OTHER INFORMATION: Synthetic

<400> SEQUENCE: 116

Gln Gly Cys Thr Met Pro Ser His Ala Val Ala Ser Phe Leu Cys Gly
1               5                   10                  15

Ser Ser Gly Gly Ser Gly Gly Ser Gly Gly Ser Gly Gly Gly Pro Leu
            20                  25                  30

Gly Leu Ala Gly Gly Ser Ser Gly Gln Val Gln Leu Val Glu Ser Gly
        35                  40                  45

Gly Gly Val Val Gln Pro Gly Arg Ser Leu Arg Leu Ser Cys Ala Ala
    50                  55                  60

Ser Gly Phe Thr Phe Ser Ser Tyr Gly Met His Trp Val Arg Gln Ala
65                  70                  75                  80

Pro Gly Lys Gly Leu Glu Trp Val Ala Val Ile Trp Asp Asp Gly Ser
                85                  90                  95

Asn Lys Tyr Tyr Val Asp Ser Val Lys Gly Arg Phe Thr Ile Ser Arg
            100                 105                 110

Asp Asn Ser Lys Asn Thr Leu Tyr Leu Gln Met Asn Ser Leu Arg Ala
        115                 120                 125

Glu Asp Thr Ala Val Tyr Tyr Cys Ala Arg Asp Asp Tyr Tyr Gly Ser
    130                 135                 140

Gly Ser Phe Asn Ser Tyr Tyr Gly Thr Asp Val Trp Gly Gln Gly Thr
145                 150                 155                 160

Thr Val Thr Val Ser Ser Gly Gly Gly Ser Gly Gly Gly Gly Gly Ser
                165                 170                 175

Gly Gly Gly Gly Ser Glu Ile Val Leu Thr Gln Ser Pro Ala Thr Leu
            180                 185                 190

Ser Leu Ser Pro Gly Glu Arg Ala Thr Leu Ser Cys Arg Ala Ser Gln
        195                 200                 205

Ser Val Ser Ile Tyr Leu Ala Trp Tyr Gln Gln Lys Pro Gly Gln Ala
    210                 215                 220

Pro Arg Leu Leu Ile Tyr Asp Ala Ser Asn Arg Ala Thr Gly Ile Pro
225                 230                 235                 240

Ala Arg Phe Ser Gly Ser Gly Ser Gly Thr Asp Phe Thr Leu Thr Ile
                245                 250                 255
```

Ser Ser Leu Glu Pro Glu Asp Phe Ala Val Tyr Tyr Cys Gln Gln Arg
                260                 265                 270

Ser Asn Trp Pro Pro Phe Thr Phe Gly Pro Gly Thr Lys Val Asp Ile
            275                 280                 285

Lys Ser Ala Ala Ala Phe Val Pro Val Phe Leu Pro Ala Lys Pro Thr
        290                 295                 300

Thr Thr Pro Ala Pro Arg Pro Pro Thr Pro Ala Pro Thr Ile Ala Ser
305                 310                 315                 320

Gln Pro Leu Ser Leu Arg Pro Glu Ala Cys Arg Pro Ala Ala Gly Gly
                325                 330                 335

Ala Val His Thr Arg Gly Leu Asp Phe Ala Cys Asp Ile Tyr Ile Trp
            340                 345                 350

Ala Pro Leu Ala Gly Thr Cys Gly Val Leu Leu Leu Ser Leu Val Ile
        355                 360                 365

Thr Leu Tyr Cys Asn His Arg Asn Arg Ser Lys Arg Ser Arg Leu Leu
370                 375                 380

His Ser Asp Tyr Met Asn Met Thr Pro Arg Arg Pro Gly Pro Thr Arg
385                 390                 395                 400

Lys His Tyr Gln Pro Tyr Ala Pro Pro Arg Asp Phe Ala Ala Tyr Arg
                405                 410                 415

Ser Arg Val Lys Phe Ser Arg Ser Ala Asp Ala Pro Ala Tyr Gln Gln
            420                 425                 430

Gly Gln Asn Gln Leu Tyr Asn Glu Leu Asn Leu Gly Arg Arg Glu Glu
        435                 440                 445

Tyr Asp Val Leu Asp Lys Arg Gly Arg Asp Pro Glu Met Gly Gly
450                 455                 460

Lys Pro Arg Arg Lys Asn Pro Gln Glu Gly Leu Tyr Asn Glu Leu Gln
465                 470                 475                 480

Lys Asp Lys Met Ala Glu Ala Tyr Ser Glu Ile Gly Met Lys Gly Glu
                485                 490                 495

Arg Arg Arg Gly Lys Gly His Asp Gly Leu Tyr Gln Gly Leu Ser Thr
            500                 505                 510

Ala Thr Lys Asp Thr Tyr Asp Ala Leu His Met Gln Ala Leu Pro Pro
        515                 520                 525

Arg

<210> SEQ ID NO 117
<211> LENGTH: 529
<212> TYPE: PRT
<213> ORGANISM: Artificial Sequence
<220> FEATURE:
<223> OTHER INFORMATION: Synthetic

<400> SEQUENCE: 117

Gln Gly Cys Thr Met Pro Val His Thr Tyr Ser Gln Trp Leu Cys Gly
1               5                   10                  15

Ser Ser Gly Gly Ser Gly Gly Ser Gly Gly Gly Gly Pro Leu
            20                  25                  30

Gly Leu Ala Gly Gly Ser Ser Gly Gln Val Gln Leu Val Glu Ser Gly
        35                  40                  45

Gly Gly Val Val Gln Pro Gly Arg Ser Leu Arg Leu Ser Cys Ala Ala
    50                  55                  60

Ser Gly Phe Thr Phe Ser Ser Tyr Gly Met His Trp Val Arg Gln Ala
65                  70                  75                  80

```
Pro Gly Lys Gly Leu Glu Trp Val Ala Val Ile Trp Asp Asp Gly Ser
                 85                  90                  95

Asn Lys Tyr Tyr Val Asp Ser Val Lys Gly Arg Phe Thr Ile Ser Arg
            100                 105                 110

Asp Asn Ser Lys Asn Thr Leu Tyr Leu Gln Met Asn Ser Leu Arg Ala
            115                 120                 125

Glu Asp Thr Ala Val Tyr Tyr Cys Ala Arg Asp Tyr Tyr Gly Ser
130             135                 140

Gly Ser Phe Asn Ser Tyr Tyr Gly Thr Asp Val Trp Gly Gln Gly Thr
145                 150                 155                 160

Thr Val Thr Val Ser Ser Gly Gly Gly Ser Gly Gly Gly Gly Ser
                165                 170                 175

Gly Gly Gly Gly Ser Glu Ile Val Leu Thr Gln Ser Pro Ala Thr Leu
            180                 185                 190

Ser Leu Ser Pro Gly Glu Arg Ala Thr Leu Ser Cys Arg Ala Ser Gln
        195                 200                 205

Ser Val Ser Ile Tyr Leu Ala Trp Tyr Gln Gln Lys Pro Gly Gln Ala
    210                 215                 220

Pro Arg Leu Leu Ile Tyr Asp Ala Ser Asn Arg Ala Thr Gly Ile Pro
225                 230                 235                 240

Ala Arg Phe Ser Gly Ser Gly Ser Gly Thr Asp Phe Thr Leu Thr Ile
                245                 250                 255

Ser Ser Leu Glu Pro Glu Asp Phe Ala Val Tyr Tyr Cys Gln Gln Arg
            260                 265                 270

Ser Asn Trp Pro Pro Phe Thr Phe Gly Pro Gly Thr Lys Val Asp Ile
        275                 280                 285

Lys Ser Ala Ala Ala Phe Val Pro Val Phe Leu Pro Ala Lys Pro Thr
    290                 295                 300

Thr Thr Pro Ala Pro Arg Pro Pro Thr Pro Ala Pro Thr Ile Ala Ser
305                 310                 315                 320

Gln Pro Leu Ser Leu Arg Pro Glu Ala Cys Arg Pro Ala Ala Gly Gly
                325                 330                 335

Ala Val His Thr Arg Gly Leu Asp Phe Ala Cys Asp Ile Tyr Ile Trp
            340                 345                 350

Ala Pro Leu Ala Gly Thr Cys Gly Val Leu Leu Leu Ser Leu Val Ile
        355                 360                 365

Thr Leu Tyr Cys Asn His Arg Asn Arg Ser Lys Arg Ser Arg Leu Leu
    370                 375                 380

His Ser Asp Tyr Met Asn Met Thr Pro Arg Arg Pro Gly Pro Thr Arg
385                 390                 395                 400

Lys His Tyr Gln Pro Tyr Ala Pro Pro Arg Asp Phe Ala Ala Tyr Arg
                405                 410                 415

Ser Arg Val Lys Phe Ser Arg Ser Ala Asp Ala Pro Ala Tyr Gln Gln
            420                 425                 430

Gly Gln Asn Gln Leu Tyr Asn Glu Leu Asn Leu Gly Arg Arg Glu Glu
        435                 440                 445

Tyr Asp Val Leu Asp Lys Arg Arg Gly Arg Asp Pro Glu Met Gly Gly
    450                 455                 460

Lys Pro Arg Arg Lys Asn Pro Gln Glu Gly Leu Tyr Asn Glu Leu Gln
465                 470                 475                 480

Lys Asp Lys Met Ala Glu Ala Tyr Ser Glu Ile Gly Met Lys Gly Glu
                485                 490                 495

Arg Arg Arg Gly Lys Gly His Asp Gly Leu Tyr Gln Gly Leu Ser Thr
```

```
                      500                 505                 510
Ala Thr Lys Asp Thr Tyr Asp Ala Leu His Met Gln Ala Leu Pro Pro
                515                 520                 525
Arg

<210> SEQ ID NO 118
<211> LENGTH: 529
<212> TYPE: PRT
<213> ORGANISM: Artificial Sequence
<220> FEATURE:
<223> OTHER INFORMATION: Synthetic

<400> SEQUENCE: 118

Gln Gly Cys Thr Tyr Pro Pro Arg Phe His Met His Trp Leu Cys Gly
1               5                   10                  15

Ser Ser Gly Gly Ser Gly Gly Ser Gly Gly Ser Gly Gly Gly Pro Leu
                20                  25                  30

Gly Leu Ala Gly Gly Ser Ser Gly Gln Val Gln Leu Val Glu Ser Gly
            35                  40                  45

Gly Gly Val Val Gln Pro Gly Arg Ser Leu Arg Leu Ser Cys Ala Ala
        50                  55                  60

Ser Gly Phe Thr Phe Ser Ser Tyr Gly Met His Trp Val Arg Gln Ala
65                  70                  75                  80

Pro Gly Lys Gly Leu Glu Trp Val Ala Val Ile Trp Asp Asp Gly Ser
                85                  90                  95

Asn Lys Tyr Tyr Val Asp Ser Val Lys Gly Arg Phe Thr Ile Ser Arg
                100                 105                 110

Asp Asn Ser Lys Asn Thr Leu Tyr Leu Gln Met Asn Ser Leu Arg Ala
            115                 120                 125

Glu Asp Thr Ala Val Tyr Tyr Cys Ala Arg Asp Asp Tyr Tyr Gly Ser
        130                 135                 140

Gly Ser Phe Asn Ser Tyr Tyr Gly Thr Asp Val Trp Gly Gln Gly Thr
145                 150                 155                 160

Thr Val Thr Val Ser Ser Gly Gly Gly Ser Gly Gly Gly Gly Gly Ser
                165                 170                 175

Gly Gly Gly Gly Ser Glu Ile Val Leu Thr Gln Ser Pro Ala Thr Leu
                180                 185                 190

Ser Leu Ser Pro Gly Glu Arg Ala Thr Leu Ser Cys Arg Ala Ser Gln
            195                 200                 205

Ser Val Ser Ile Tyr Leu Ala Trp Tyr Gln Gln Lys Pro Gly Gln Ala
        210                 215                 220

Pro Arg Leu Leu Ile Tyr Asp Ala Ser Asn Arg Ala Thr Gly Ile Pro
225                 230                 235                 240

Ala Arg Phe Ser Gly Ser Gly Ser Gly Thr Asp Phe Thr Leu Thr Ile
                245                 250                 255

Ser Ser Leu Glu Pro Glu Asp Phe Ala Val Tyr Tyr Cys Gln Gln Arg
                260                 265                 270

Ser Asn Trp Pro Pro Phe Thr Phe Gly Pro Gly Thr Lys Val Asp Ile
            275                 280                 285

Lys Ser Ala Ala Ala Phe Val Pro Val Phe Leu Pro Ala Lys Pro Thr
        290                 295                 300

Thr Thr Pro Ala Pro Arg Pro Pro Thr Pro Ala Pro Thr Ile Ala Ser
305                 310                 315                 320

Gln Pro Leu Ser Leu Arg Pro Glu Ala Cys Arg Pro Ala Ala Gly Gly
                325                 330                 335
```

```
Ala Val His Thr Arg Gly Leu Asp Phe Ala Cys Asp Ile Tyr Ile Trp
            340                 345                 350
Ala Pro Leu Ala Gly Thr Cys Gly Val Leu Leu Leu Ser Leu Val Ile
            355                 360                 365
Thr Leu Tyr Cys Asn His Arg Asn Arg Ser Lys Arg Ser Arg Leu Leu
        370                 375                 380
His Ser Asp Tyr Met Asn Met Thr Pro Arg Arg Pro Gly Pro Thr Arg
385                 390                 395                 400
Lys His Tyr Gln Pro Tyr Ala Pro Pro Arg Asp Phe Ala Ala Tyr Arg
                405                 410                 415
Ser Arg Val Lys Phe Ser Arg Ser Ala Asp Ala Pro Ala Tyr Gln Gln
            420                 425                 430
Gly Gln Asn Gln Leu Tyr Asn Glu Leu Asn Leu Gly Arg Arg Glu Glu
                435                 440                 445
Tyr Asp Val Leu Asp Lys Arg Gly Arg Asp Pro Glu Met Gly Gly
    450                 455                 460
Lys Pro Arg Arg Lys Asn Pro Gln Glu Gly Leu Tyr Asn Glu Leu Gln
465                 470                 475                 480
Lys Asp Lys Met Ala Glu Ala Tyr Ser Glu Ile Gly Met Lys Gly Glu
                485                 490                 495
Arg Arg Arg Gly Lys Gly His Asp Gly Leu Tyr Gln Gly Leu Ser Thr
            500                 505                 510
Ala Thr Lys Asp Thr Tyr Asp Ala Leu His Met Gln Ala Leu Pro Pro
            515                 520                 525
Arg

<210> SEQ ID NO 119
<211> LENGTH: 529
<212> TYPE: PRT
<213> ORGANISM: Artificial Sequence
<220> FEATURE:
<223> OTHER INFORMATION: Synthetic

<400> SEQUENCE: 119

Gln Gly Cys Thr His Val Ala Gln Trp Ala Ile Lys Ala Phe Cys Gly
1               5                   10                  15
Ser Ser Gly Gly Ser Gly Gly Ser Gly Gly Ser Gly Gly Gly Pro Leu
            20                  25                  30
Gly Leu Ala Gly Gly Ser Ser Gly Gln Val Gln Leu Val Glu Ser Gly
            35                  40                  45
Gly Gly Val Val Gln Pro Gly Arg Ser Leu Arg Leu Ser Cys Ala Ala
        50                  55                  60
Ser Gly Phe Thr Phe Ser Ser Tyr Gly Met His Trp Val Arg Gln Ala
65                  70                  75                  80
Pro Gly Lys Gly Leu Glu Trp Val Ala Val Ile Trp Asp Asp Gly Ser
                85                  90                  95
Asn Lys Tyr Tyr Val Asp Ser Val Lys Gly Arg Phe Thr Ile Ser Arg
            100                 105                 110
Asp Asn Ser Lys Asn Thr Leu Tyr Leu Gln Met Asn Ser Leu Arg Ala
        115                 120                 125
Glu Asp Thr Ala Val Tyr Tyr Cys Ala Arg Asp Asp Tyr Tyr Gly Ser
    130                 135                 140
Gly Ser Phe Asn Ser Tyr Tyr Gly Thr Asp Val Trp Gly Gln Gly Thr
145                 150                 155                 160
```

Thr Val Thr Val Ser Ser Gly Gly Gly Ser Gly Gly Gly Ser
                165                 170                 175

Gly Gly Gly Gly Ser Glu Ile Val Leu Thr Gln Ser Pro Ala Thr Leu
            180                 185                 190

Ser Leu Ser Pro Gly Glu Arg Ala Thr Leu Ser Cys Arg Ala Ser Gln
        195                 200                 205

Ser Val Ser Ile Tyr Leu Ala Trp Tyr Gln Gln Lys Pro Gly Gln Ala
    210                 215                 220

Pro Arg Leu Leu Ile Tyr Asp Ala Ser Asn Arg Ala Thr Gly Ile Pro
225                 230                 235                 240

Ala Arg Phe Ser Gly Ser Gly Ser Gly Thr Asp Phe Thr Leu Thr Ile
                245                 250                 255

Ser Ser Leu Glu Pro Glu Asp Phe Ala Val Tyr Tyr Cys Gln Gln Arg
            260                 265                 270

Ser Asn Trp Pro Pro Phe Thr Phe Gly Pro Gly Thr Lys Val Asp Ile
        275                 280                 285

Lys Ser Ala Ala Ala Phe Val Pro Val Phe Leu Pro Ala Lys Pro Thr
    290                 295                 300

Thr Thr Pro Ala Pro Arg Pro Pro Thr Pro Ala Pro Thr Ile Ala Ser
305                 310                 315                 320

Gln Pro Leu Ser Leu Arg Pro Glu Ala Cys Arg Pro Ala Ala Gly Gly
                325                 330                 335

Ala Val His Thr Arg Gly Leu Asp Phe Ala Cys Asp Ile Tyr Ile Trp
            340                 345                 350

Ala Pro Leu Ala Gly Thr Cys Gly Val Leu Leu Leu Ser Leu Val Ile
        355                 360                 365

Thr Leu Tyr Cys Asn His Arg Asn Arg Ser Lys Arg Ser Arg Leu Leu
    370                 375                 380

His Ser Asp Tyr Met Asn Met Thr Pro Arg Arg Pro Gly Pro Thr Arg
385                 390                 395                 400

Lys His Tyr Gln Pro Tyr Ala Pro Pro Arg Asp Phe Ala Ala Tyr Arg
                405                 410                 415

Ser Arg Val Lys Phe Ser Arg Ser Ala Asp Ala Pro Ala Tyr Gln Gln
            420                 425                 430

Gly Gln Asn Gln Leu Tyr Asn Glu Leu Asn Leu Gly Arg Arg Glu Glu
        435                 440                 445

Tyr Asp Val Leu Asp Lys Arg Arg Gly Arg Asp Pro Glu Met Gly Gly
    450                 455                 460

Lys Pro Arg Arg Lys Asn Pro Gln Glu Gly Leu Tyr Asn Glu Leu Gln
465                 470                 475                 480

Lys Asp Lys Met Ala Glu Ala Tyr Ser Glu Ile Gly Met Lys Gly Glu
                485                 490                 495

Arg Arg Arg Gly Lys Gly His Asp Gly Leu Tyr Gln Gly Leu Ser Thr
            500                 505                 510

Ala Thr Lys Asp Thr Tyr Asp Ala Leu His Met Gln Ala Leu Pro Pro
        515                 520                 525

Arg

<210> SEQ ID NO 120
<211> LENGTH: 249
<212> TYPE: PRT
<213> ORGANISM: Artificial Sequence
<220> FEATURE:
<223> OTHER INFORMATION: Synthetic

<400> SEQUENCE: 120

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Ile Trp Asp Asp Gly Ser Asn Lys Tyr Tyr Val Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp Asp Tyr Tyr Gly Ser Gly Ser Phe Asn Ser Tyr Tyr Gly
            100                 105                 110
Thr Asp Val Trp Gly Gln Gly Thr Thr Val Thr Val Ser Ser Gly Gly
        115                 120                 125
Gly Gly Ser Gly Gly Gly Gly Ser Gly Gly Gly Gly Ser Glu Ile Val
    130                 135                 140
Leu Thr Gln Ser Pro Ala Thr Leu Ser Leu Ser Pro Gly Glu Arg Ala
145                 150                 155                 160
Thr Leu Ser Cys Arg Ala Ser Gln Ser Val Ser Ile Tyr Leu Ala Trp
                165                 170                 175
Tyr Gln Gln Lys Pro Gly Gln Ala Pro Arg Leu Leu Ile Tyr Asp Ala
            180                 185                 190
Ser Asn Arg Ala Thr Gly Ile Pro Ala Arg Phe Ser Gly Ser Gly Ser
        195                 200                 205
Gly Thr Asp Phe Thr Leu Thr Ile Ser Ser Leu Glu Pro Glu Asp Phe
    210                 215                 220
Ala Val Tyr Tyr Cys Gln Gln Arg Ser Asn Trp Pro Pro Phe Thr Phe
225                 230                 235                 240
Gly Pro Gly Thr Lys Val Asp Ile Lys
                245
```

<210> SEQ ID NO 121
<211> LENGTH: 249
<212> TYPE: PRT
<213> ORGANISM: Artificial Sequence
<220> FEATURE:
<223> OTHER INFORMATION: Synthetic

<400> SEQUENCE: 121

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Ile Trp Asp Asp Gly Ser Asn Lys Tyr Tyr Val Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp Asp Tyr Tyr Gly Ser Gly Ser Phe Asn Ser Tyr Tyr Gly
```

```
            100                 105                 110
Thr Asp Val Trp Gly Gln Gly Thr Thr Val Thr Val Ser Ser Gly Gly
            115                 120                 125

Gly Gly Ser Gly Gly Gly Ser Gly Gly Gly Ser Glu Ile Val
        130                 135             140

Leu Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ile Tyr Leu Ala Trp
                165                 170                 175

Tyr Gln Gln Lys Pro Gly Gln Ala Pro Arg Leu Leu Ile Tyr Asp Ala
            180                 185                 190

Ser Asn Arg Ala Thr Gly Ile Pro Ala Arg Phe Ser Gly Ser Gly Ser
        195                 200                 205

Gly Thr Asp Phe Thr Leu Thr Ile Ser Ser Leu Glu Pro Glu Asp Phe
    210                 215                 220

Ala Val Tyr Tyr Cys Gln Gln Arg Ser Asn Trp Pro Pro Phe Thr Phe
225                 230                 235                 240

Gly Pro Gly Thr Lys Val Asp Ile Lys
                245

<210> SEQ ID NO 122
<211> LENGTH: 249
<212> TYPE: PRT
<213> ORGANISM: Artificial Sequence
<220> FEATURE:
<223> OTHER INFORMATION: Synthetic

<400> SEQUENCE: 122

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Tyr Tyr Gly Ser Gly Ser Phe Asn Ser Tyr Tyr Gly
            100                 105                 110

Thr Asp Val Trp Gly Gln Gly Thr Thr Val Thr Val Ser Ser Gly Gly
            115                 120                 125

Gly Gly Ser Gly Gly Gly Ser Gly Gly Gly Ser Glu Ile Val
        130                 135             140

Leu Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ile Tyr Leu Ala Trp
                165                 170                 175

Tyr Gln Gln Lys Pro Gly Gln Ala Pro Arg Leu Leu Ile Tyr Asp Ala
            180                 185                 190

Ser Asn Arg Ala Thr Gly Ile Pro Ala Arg Phe Ser Gly Ser Gly Ser
        195                 200                 205

Gly Thr Asp Phe Thr Leu Thr Ile Ser Ser Leu Glu Pro Glu Asp Phe
```

```
                210                 215                 220
Ala Val Tyr Tyr Cys Gln Gln Arg Ser Asn Trp Pro Pro Phe Thr Phe
225                 230                 235                 240

Gly Pro Gly Thr Lys Val Asp Ile Lys
                245

<210> SEQ ID NO 123
<211> LENGTH: 249
<212> TYPE: PRT
<213> ORGANISM: Artificial Sequence
<220> FEATURE:
<223> OTHER INFORMATION: Synthetic

<400> SEQUENCE: 123

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Asp Asp Gly Ser Asn Lys Tyr Tyr Val Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Tyr Tyr Gly Ser Gly Ser Phe Asn Ser Tyr Tyr Gly
                100                 105                 110

Thr Asp Val Trp Gly Gln Gly Thr Thr Val Thr Val Ser Ser Gly Gly
            115                 120                 125

Gly Gly Ser Gly Gly Gly Ser Gly Gly Gly Ser Glu Ile Val
        130                 135                 140

Leu Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ile Tyr Leu Ala Trp
                165                 170                 175

Tyr Gln Gln Lys Pro Gly Gln Ala Pro Arg Leu Leu Ile Tyr Asp Ala
            180                 185                 190

Ser Asn Arg Ala Thr Gly Ile Pro Ala Arg Phe Ser Gly Ser Gly Ser
        195                 200                 205

Gly Thr Asp Phe Thr Leu Thr Ile Ser Ser Leu Glu Pro Glu Asp Phe
    210                 215                 220

Ala Val Tyr Tyr Cys Gln Gln Arg Ser Asn Trp Pro Pro Phe Thr Phe
225                 230                 235                 240

Gly Pro Gly Thr Lys Val Asp Ile Lys
                245

<210> SEQ ID NO 124
<211> LENGTH: 249
<212> TYPE: PRT
<213> ORGANISM: Artificial Sequence
<220> FEATURE:
<223> OTHER INFORMATION: Synthetic

<400> SEQUENCE: 124

Gln Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Asn Lys Tyr Tyr Val Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Asp Tyr Tyr Gly Ser Gly Ser Phe Asn Ser Tyr Tyr Gly
            100                 105                 110

Thr Asp Val Trp Gly Gln Gly Thr Thr Val Thr Val Ser Ser Gly Gly
        115                 120                 125

Gly Gly Ser Gly Gly Gly Ser Gly Gly Gly Ser Glu Ile Val
130                 135                 140

Leu Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ile Tyr Leu Ala Trp
                165                 170                 175

Tyr Gln Gln Lys Pro Gly Gln Ala Pro Arg Leu Leu Ile Tyr Asp Ala
            180                 185                 190

Ser Asn Arg Ala Thr Gly Ile Pro Ala Arg Phe Ser Gly Ser Gly Ser
        195                 200                 205

Gly Thr Asp Phe Thr Leu Thr Ile Ser Ser Leu Glu Pro Glu Asp Phe
210                 215                 220

Ala Val Tyr Tyr Cys Gln Gln Arg Ser Asn Trp Pro Pro Phe Thr Phe
225                 230                 235                 240

Gly Pro Gly Thr Lys Val Asp Ile Lys
                245

<210> SEQ ID NO 125
<211> LENGTH: 249
<212> TYPE: PRT
<213> ORGANISM: Artificial Sequence
<220> FEATURE:
<223> OTHER INFORMATION: Synthetic

<400> SEQUENCE: 125

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Asn Lys Tyr Tyr Val Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Asp Tyr Tyr Gly Ser Gly Ser Phe Asn Ser Tyr Tyr Gly
            100                 105                 110

Thr Asp Val Trp Gly Gln Gly Thr Thr Val Thr Val Ser Ser Gly Gly
        115                 120                 125
```

Gly Gly Ser Gly Gly Gly Ser Gly Gly Gly Ser Glu Ile Val
            130                 135                 140

Leu Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ile Tyr Leu Ala Trp
                165                 170                 175

Tyr Gln Gln Lys Pro Gly Gln Ala Pro Arg Leu Leu Ile Tyr Asp Ala
            180                 185                 190

Ser Asn Arg Ala Thr Gly Ile Pro Ala Arg Phe Ser Gly Ser Gly Ser
        195                 200                 205

Gly Thr Asp Phe Thr Leu Thr Ile Ser Ser Leu Glu Pro Glu Asp Phe
    210                 215                 220

Ala Val Tyr Tyr Cys Gln Gln Arg Ser Asn Trp Pro Pro Phe Thr Phe
225                 230                 235                 240

Gly Pro Gly Thr Lys Val Asp Ile Lys
                245

<210> SEQ ID NO 126
<211> LENGTH: 249
<212> TYPE: PRT
<213> ORGANISM: Artificial Sequence
<220> FEATURE:
<223> OTHER INFORMATION: Synthetic

<400> SEQUENCE: 126

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Tyr Tyr Gly Ser Gly Ser Phe Asn Ser Tyr Tyr Gly
            100                 105                 110

Thr Asp Val Trp Gly Gln Gly Thr Thr Val Thr Val Ser Ser Gly Gly
        115                 120                 125

Gly Gly Ser Gly Gly Gly Ser Gly Gly Gly Ser Glu Ile Val
    130                 135                 140

Leu Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ile Tyr Leu Ala Trp
                165                 170                 175

Tyr Gln Gln Lys Pro Gly Gln Ala Pro Arg Leu Leu Ile Tyr Asp Ala
            180                 185                 190

Ser Asn Arg Ala Thr Gly Ile Pro Ala Arg Phe Ser Gly Ser Gly Ser
        195                 200                 205

Gly Thr Asp Phe Thr Leu Thr Ile Ser Ser Leu Glu Pro Glu Asp Phe
    210                 215                 220

Ala Val Tyr Tyr Cys Gln Gln Arg Ser Asn Trp Pro Pro Phe Thr Phe
225                 230                 235                 240

-continued

```
Gly Pro Gly Thr Lys Val Asp Ile Lys
            245

<210> SEQ ID NO 127
<211> LENGTH: 249
<212> TYPE: PRT
<213> ORGANISM: Artificial Sequence
<220> FEATURE:
<223> OTHER INFORMATION: Synthetic

<400> SEQUENCE: 127

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Tyr Tyr Gly Ser Gly Ser Phe Asn Ser Tyr Tyr Gly
            100                 105                 110

Thr Asp Val Trp Gly Gln Gly Thr Thr Val Thr Val Ser Ser Gly Gly
        115                 120                 125

Gly Gly Ser Gly Gly Gly Gly Ser Gly Gly Gly Gly Ser Glu Ile Val
    130                 135                 140

Leu Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ile Tyr Leu Ala Trp
                165                 170                 175

Tyr Gln Gln Lys Pro Gly Gln Ala Pro Arg Leu Leu Ile Tyr Asp Ala
            180                 185                 190

Ser Asn Arg Ala Thr Gly Ile Pro Ala Arg Phe Ser Gly Ser Gly Ser
        195                 200                 205

Gly Thr Asp Phe Thr Leu Thr Ile Ser Ser Leu Glu Pro Glu Asp Phe
    210                 215                 220

Ala Val Tyr Tyr Cys Gln Gln Arg Ser Asn Trp Pro Pro Phe Thr Phe
225                 230                 235                 240

Gly Pro Gly Thr Lys Val Asp Ile Lys
            245

<210> SEQ ID NO 128
<211> LENGTH: 249
<212> TYPE: PRT
<213> ORGANISM: Artificial Sequence
<220> FEATURE:
<223> OTHER INFORMATION: Synthetic

<400> SEQUENCE: 128

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45
```

Ala Val Ile Trp Asp Asp Gly Ser Asn Lys Tyr Tyr Val Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Asp Tyr Tyr Gly Ser Gly Ser Phe Asn Ser Tyr Tyr Gly
            100                 105                 110

Thr Asp Val Trp Gly Gln Gly Thr Thr Val Thr Val Ser Ser Gly Gly
            115                 120                 125

Gly Gly Ser Gly Gly Gly Ser Gly Gly Gly Ser Glu Ile Val
130                 135                 140

Leu Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ile Tyr Leu Ala Trp
                165                 170                 175

Tyr Gln Gln Lys Pro Gly Gln Ala Pro Arg Leu Leu Ile Tyr Asp Ala
            180                 185                 190

Ser Asn Arg Ala Thr Gly Ile Pro Ala Arg Phe Ser Gly Ser Gly Ser
            195                 200                 205

Gly Thr Asp Phe Thr Leu Thr Ile Ser Ser Leu Glu Pro Glu Asp Phe
            210                 215                 220

Ala Val Tyr Tyr Cys Gln Gln Arg Ser Asn Trp Pro Pro Phe Thr Phe
225                 230                 235                 240

Gly Pro Gly Thr Lys Val Asp Ile Lys
                245

<210> SEQ ID NO 129
<211> LENGTH: 248
<212> TYPE: PRT
<213> ORGANISM: Artificial Sequence
<220> FEATURE:
<223> OTHER INFORMATION: Synthetic

<400> SEQUENCE: 129

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
            35                  40                  45

Ala Val Ile Trp Asp Asp Gly Ser Asn Lys Tyr Tyr Val Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Asp Tyr Tyr Gly Ser Gly Ser Phe Asn Ser Tyr Tyr Gly
            100                 105                 110

Thr Asp Val Trp Gly Gln Gly Thr Thr Val Thr Val Ser Ser Gly Gly
            115                 120                 125

Gly Gly Ser Gly Gly Gly Gly Ser Gly Gly Gly Ser Glu Ile Val
130                 135                 140

Leu Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ile Tyr Leu Ala Trp
            165                 170                 175

Tyr Gln Gln Lys Pro Gly Gln Ala Pro Arg Leu Leu Ile Tyr Asp Ala
        180                 185                 190

Ser Asn Arg Ala Thr Gly Ile Pro Ala Arg Phe Ser Gly Ser Gly Ser
    195                 200                 205

Gly Thr Asp Phe Thr Leu Thr Ile Ser Ser Leu Glu Pro Glu Asp Phe
    210                 215                 220

Ala Val Tyr Tyr Cys Gln Gln Arg Ser Asn Trp Pro Pro Phe Thr Phe
225                 230                 235                 240

Gly Pro Gly Thr Lys Val Asp Ile
            245

<210> SEQ ID NO 130
<211> LENGTH: 249
<212> TYPE: PRT
<213> ORGANISM: Artificial Sequence
<220> FEATURE:
<223> OTHER INFORMATION: Synthetic

<400> SEQUENCE: 130

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Asp Tyr Tyr Gly Ser Gly Ser Phe Asn Ser Tyr Tyr Gly
        100                 105                 110

Thr Asp Val Trp Gly Gln Gly Thr Thr Val Thr Val Ser Ser Gly Gly
    115                 120                 125

Gly Gly Ser Gly Gly Gly Ser Gly Gly Gly Ser Glu Ile Val
130                 135                 140

Leu Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ile Tyr Leu Ala Trp
            165                 170                 175

Tyr Gln Gln Lys Pro Gly Gln Ala Pro Arg Leu Leu Ile Tyr Asp Ala
        180                 185                 190

Ser Asn Arg Ala Thr Gly Ile Pro Ala Arg Phe Ser Gly Ser Gly Ser
    195                 200                 205

Gly Thr Asp Phe Thr Leu Thr Ile Ser Ser Leu Glu Pro Glu Asp Phe
    210                 215                 220

Ala Val Tyr Tyr Cys Gln Gln Arg Ser Asn Trp Pro Pro Phe Thr Phe
225                 230                 235                 240

Gly Pro Gly Thr Lys Val Asp Ile Lys
            245

<210> SEQ ID NO 131

```
<211> LENGTH: 249
<212> TYPE: PRT
<213> ORGANISM: Artificial Sequence
<220> FEATURE:
<223> OTHER INFORMATION: Synthetic

<400> SEQUENCE: 131

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Tyr Tyr Gly Ser Gly Ser Phe Asn Ser Tyr Tyr Gly
            100                 105                 110

Thr Asp Val Trp Gly Gln Gly Thr Thr Val Thr Val Ser Gly Gly
        115                 120                 125

Gly Gly Ser Gly Gly Gly Ser Gly Gly Gly Ser Glu Ile Val
    130                 135                 140

Leu Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ile Tyr Leu Ala Trp
            165                 170                 175

Tyr Gln Gln Lys Pro Gly Gln Ala Pro Arg Leu Leu Ile Tyr Asp Ala
        180                 185                 190

Ser Asn Arg Ala Thr Gly Ile Pro Ala Arg Phe Ser Gly Ser Gly Ser
    195                 200                 205

Gly Thr Asp Phe Thr Leu Thr Ile Ser Ser Leu Glu Pro Glu Asp Phe
210                 215                 220

Ala Val Tyr Tyr Cys Gln Gln Arg Ser Asn Trp Pro Pro Phe Thr Phe
225                 230                 235                 240

Gly Pro Gly Thr Lys Val Asp Ile Lys
                245

<210> SEQ ID NO 132
<211> LENGTH: 249
<212> TYPE: PRT
<213> ORGANISM: Artificial Sequence
<220> FEATURE:
<223> OTHER INFORMATION: Synthetic

<400> SEQUENCE: 132

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
```

```
65                  70                  75                  80
Leu Gln Met Asn Ser Leu Arg Ala Glu Asp Thr Ala Val Tyr Tyr Cys
                85                  90                  95

Ala Arg Asp Asp Tyr Tyr Gly Ser Gly Ser Phe Asn Ser Tyr Tyr Gly
                100                 105                 110

Thr Asp Val Trp Gly Gln Gly Thr Thr Val Thr Val Ser Ser Gly Gly
                115                 120                 125

Gly Gly Ser Gly Gly Gly Ser Gly Gly Gly Ser Glu Ile Val
            130                 135                 140

Leu Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ile Tyr Leu Ala Trp
                165                 170                 175

Tyr Gln Gln Lys Pro Gly Gln Ala Pro Arg Leu Leu Ile Tyr Asp Ala
                180                 185                 190

Ser Asn Arg Ala Thr Gly Ile Pro Ala Arg Phe Ser Gly Ser Gly Ser
                195                 200                 205

Gly Thr Asp Phe Thr Leu Thr Ile Ser Ser Leu Glu Pro Glu Asp Phe
                210                 215                 220

Ala Val Tyr Tyr Cys Gln Gln Arg Ser Asn Trp Pro Pro Phe Thr Phe
225                 230                 235                 240

Gly Pro Gly Thr Lys Val Asp Ile Lys
                245

<210> SEQ ID NO 133
<211> LENGTH: 249
<212> TYPE: PRT
<213> ORGANISM: Artificial Sequence
<220> FEATURE:
<223> OTHER INFORMATION: Synthetic

<400> SEQUENCE: 133

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
                35                  40                  45

Ala Val Ile Trp Asp Asp Gly Ser Asn Lys Tyr Tyr Val Asp Ser Val
                50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Tyr Tyr Gly Ser Gly Ser Phe Asn Ser Tyr Tyr Gly
                100                 105                 110

Thr Asp Val Trp Gly Gln Gly Thr Thr Val Thr Val Ser Ser Gly Gly
                115                 120                 125

Gly Gly Ser Gly Gly Gly Ser Gly Gly Gly Ser Glu Ile Val
            130                 135                 140

Leu Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ile Tyr Leu Ala Trp
                165                 170                 175

Tyr Gln Gln Lys Pro Gly Gln Ala Pro Arg Leu Leu Ile Tyr Asp Ala
```

```
                180                 185                 190
Ser Asn Arg Ala Thr Gly Ile Pro Ala Arg Phe Ser Gly Ser Gly Ser
            195                 200                 205

Gly Thr Asp Phe Thr Leu Thr Ile Ser Ser Leu Glu Pro Glu Asp Phe
        210                 215                 220

Ala Val Tyr Tyr Cys Gln Gln Arg Ser Asn Trp Pro Pro Phe Thr Phe
225                 230                 235                 240

Gly Pro Gly Thr Lys Val Asp Ile Lys
            245

<210> SEQ ID NO 134
<211> LENGTH: 249
<212> TYPE: PRT
<213> ORGANISM: Artificial Sequence
<220> FEATURE:
<223> OTHER INFORMATION: Synthetic

<400> SEQUENCE: 134

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Asp Tyr Tyr Gly Ser Gly Ser Phe Asn Ser Tyr Tyr Gly
        100                 105                 110

Thr Asp Val Trp Gly Gln Gly Thr Thr Val Thr Val Ser Ser Gly Gly
    115                 120                 125

Gly Gly Ser Gly Gly Gly Gly Ser Gly Gly Gly Gly Ser Glu Ile Val
        130                 135                 140

Leu Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ile Tyr Leu Ala Trp
            165                 170                 175

Tyr Gln Gln Lys Pro Gly Gln Ala Pro Arg Leu Leu Ile Tyr Asp Ala
        180                 185                 190

Ser Asn Arg Ala Thr Gly Ile Pro Ala Arg Phe Ser Gly Ser Gly Ser
            195                 200                 205

Gly Thr Asp Phe Thr Leu Thr Ile Ser Ser Leu Glu Pro Glu Asp Phe
        210                 215                 220

Ala Val Tyr Tyr Cys Gln Gln Arg Ser Asn Trp Pro Pro Phe Thr Phe
225                 230                 235                 240

Gly Pro Gly Thr Lys Val Asp Ile Lys
            245
```

MASKED CHIMERIC ANTIGEN RECEPTOR SPECIFIC TO TYROSINE-PROTEIN KINASE LIKE 7 (PTK7) AND IMMUNE CELLS EXPRESSING SUCH

CROSS REFERENCE TO RELATED APPLICATIONS

This application claims the benefit of the filing date of U.S. Provisional Application No. 63/020,794, filed May 6, 2020, the entire contents of which are incorporated by reference herein.

SEQUENCE LISTING

The application contains a Sequence Listing that has been filed electronically in the form of a text file, created May 14, 2021, and named "095136-0247-022US1_SUBSEQ.TXT" (287,436 bytes), the contents of which are incorporated by reference herein in their entirety

BACKGROUND OF THE INVENTION

Chimeric antigen receptor (CAR) T-cell therapy uses genetically-modified T cells to more specifically and efficiently target and kill cancer cells. After T cells have been collected from the blood, the cells are engineered to express CARs on their surface. The CARs may be introduced into the T cells using CRISPR/Cas9 gene editing technology. When these CAR T cells are injected into a patient, the receptors enable the T cells to kill cancer cells.

Protein tyrosine kinase 7 (PTK7), also known as colon carcinoma kinase 4 (CCK4), is a receptor protein tyrosine kinase that is involved in non-canonical Wnt signaling and comprises an extracellular domain. While PTK7 lacks detectable catalytic tyrosine kinase activity, it comprises signal transduction activity and is presumed to function in cellular adhesion. It is further thought that PTK7 is a marker for tumor progression in cancer, as it is expressed in various cancer cell lines, for example, colon and breast cancer cell lines.

SUMMARY OF THE INVENTION

The present disclosure is based, at least in part, on the development of mask peptides that block binding of an anti-PTK7 antibody to the PTK7 antigen. Masked anti-PTK7 antibodies comprising such a mask peptide showed reduced binding activity to the PTK7 antigen and the binding activity was resumed upon removal of the mask peptide via protease cleavage. Further, T cells expressing a masked anti-PTK7 chimeric antigen receptor successfully inhibited tumor growth as observed in an animal model. Such T cells are expected to show promising anti-tumor effect with reduced toxicity.

Accordingly, one aspect of the present disclosure provides a masked chimeric antigen receptor (CAR) specific to tyrosine-protein kinase-like 7 (PTK7), the masked CAR comprising: (i) an extracellular antigen binding domain, which comprises a single chain variable fragment (scFv) that binds PTK7 and a mask peptide linked to the N-terminus of the scFv via a protease cleavage site; and one or more intracellular signaling domains. In some embodiments, the mask peptide can be 13-25 amino acids in length.

In some embodiments, the mask peptide comprises the amino acid sequence selected from the group consisting of:

(a)
(SEQ ID NO: 1)
EVAPGKRWFYNHVKQVPHLV, (b)
(SEQ ID NO: 2)
HEEVHMRPNKLSLTWAYTGPQLR, and
(c) $X_1CX_2X_3X_4X_5X_6X_7X_8X_9X_{10}X_{11}X_{12}X_{13}$, in which $X_1$ is V, W, or absent; $X_2$ is T, H, or Y; $X_3$ is M, F, Y, I, or H; $X_4$ is P, G, or V; $X_5$ is P, N, S, Y, K, L, V, or A; $X_6$ is S, T, W, A, H, R, or Q; $X_7$ is P, T, V, H, I, M, A, F, or W; $X_8$ R, M, A, H, V, Y, or absent; $X_9$ is S, Q, Y, T, P, A, M, or I; $X_{10}$ is K, R, I, C, S, Q, H, or absent; $X_{11}$ is V, T, R, L, F, W, or A; $X_{12}$ is I, F, L, W, or H; and $X_{13}$ is C, I, or M.

In some examples, the mask peptide comprises the amino acid sequence of (c), which can be one of the following:

(c1)
(SEQ ID NO: 3)
CTMPPSPRSKVIC, (c2)
(SEQ ID NO: 4)
CTFPNTTMQRTFC, (c3)
(SEQ ID NO: 5)
CTYPSWVAYIRFC, (c4)
(SEQ ID NO: 6)
VCTYPPAHRTRFC, (c5)
(SEQ ID NO: 7)
CTMPYHIHSIGLC, (c6)
(SEQ ID NO: 8)
WCTIPSSMSIRLC, (c7)
(SEQ ID NO: 9)
CHIGKRPVPCLWI, (c8)
(SEQ ID NO: 10)
CYIGLRMVPCFHM, (c9)
(SEQ ID NO: 11)
CTMPSHAVASFLC, (c10)
(SEQ ID NO: 12)
CTMPVHTYSQWLC, (c11)
(SEQ ID NO: 13)
CTYPPRFHMHWLC,
or (c12)
(SEQ ID NO: 14)
CTHVAQWAIKAFC.

In specific examples, the mask peptide can be one of the following:

(a)
EVAPGKRWFYNHVKQVPHLV, (SEQ ID NO: 1)

(b)
HEEVHMRPNKLSLTWAYTGPQLR, (SEQ ID NO: 2)

(c1)
CTMPPSPRSKVIC, (SEQ ID NO: 3)

(c2)
CTFPNTTMQRTFC, (SEQ ID NO: 4)

(c3)
CTYPSWVAYIRFC, (SEQ ID NO: 5)

(c4)
VCTYPPAHRTRFC, (SEQ ID NO: 6)

(c5)
CTMPYHIHSIGLC, (SEQ ID NO: 7)

(c6)
WCTIPSSMSIRLC, (SEQ ID NO: 8)

(c7)
CHIGKRPVPCLWI, (SEQ ID NO: 9)

(c8)
CYIGLRMVPCFHM, (SEQ ID NO: 10)

(c9)
CTMPSHAVASFLC, (SEQ ID NO: 11)

(C10)
CTMPVHTYSQWLC, (SEQ ID NO: 12)

(c11)
CTYPPRFHMHWLC, (SEQ ID NO: 13)
or (c12)
CTHVAQWAIKAFC. (SEQ ID NO: 14)

In some embodiments, the mask peptide may be removable by protease cleavage at the protease cleavage site. In some examples, the protease cleavage site is a cleavage site of a matrix metalloproteinase (MMP), for example, comprising the motif of PLGLA (SEQ ID NO: 15).

In some embodiments, the mask peptide can be linked to the protease cleavage site via a first peptide linker. In some embodiments, the protease cleavage site is linked to the N-terminus of the heavy chain or the light chain of the anti-PTK7 antibody via a second peptide linker. Either the first peptide linker or the second peptide linker, or both can be G/S peptide linkers. In some examples, the mask peptide is linked to the scFv that binds PFK7 in a formula of: $M-L_1-P-L_2-scFv$, in which M represents the mask peptide, $L_1$ and $L_2$ represents the first and second peptide linkers, and P represents the protease cleavage site.

In some embodiments, the scFv that binds PTK7 comprises a heavy chain variable domain ($V_H$), which comprises the same heavy chain complementary determining regions (CDRs) as the heavy chain CDRs of antibody Ab181. Alternatively or in addition, n the anti-PTK7 antibody comprises a light chain variable domain ($V_L$), which comprises the same light chain complementary determining regions (CDRs) as the light chain CDRs of antibody Ab181. In some examples, the scFv that binds PTK7 comprises the same $V_H$ as antibody Ab181 and/or the same $V_L$ as antibody Ab181. In some specific examples, the extracellular antigen binding domain comprises the amino acid sequence selected from the group consisting of SEQ ID NOs: 120-134.

Any of the masked anti-PTK7 CARs disclosed herein may comprise one or more intracellular signaling domains, which optionally may comprises a co-stimulatory domain, a CD3ζ cytoplasmic signaling domain, or a combination thereof. In some examples, the co-stimulatory domain is a CD28 co-stimulatory domain. In other examples, the co-stimulatory domain is a 4-1BB co-stimulatory domain. Any of the masked anti-PTK7 CARs disclosed herein may further comprises a transmembrane domain located between the extracellular antigen binding domain and the one or more intracellular signaling domains. In some examples, the transmembrane domain is a CD8 transmembrane domain. In addition, the masked CAR may further comprises a signal peptide at the N-terminus of the masked CAR.

In specific examples, the masked anti-PTK7 CAR disclosed herein may comprise the amino acid sequence of one of SEQ ID NOs: 106-119, for example, SEQ ID NOs: 91-105.

Also provided herein are a nucleic acid, comprising a nucleotide sequence encoding any of the masked anti-PTK7 CARs disclosed herein.

In another aspect, the present disclosure features a genetically engineered T cell, comprising a nucleic acid encoding any one of the basked anti-PTK7 CAR disclosed herein and expressing the masked CAR encoded by the nucleic acid. In some embodiments, the genetically engineered T cell may further comprises a disrupted TRAC gene, a disrupted B2M gene, or a combination thereof. In some examples, the genetically engineered T cell may comprise a disrupted TRAC gene, in which the nucleic acid encoding the masked CAR is inserted, thereby disrupting expression of the TRAC gene.

In some embodiments, the genetically engineered T cell comprises a disrupted TRAC gene, which comprises a deletion of a fragment comprising the amino acid sequence of SEQ ID NO: 40. The nucleic acid encoding the masked CAR can be inserted at the site of the deletion in the TRAC gene. In some examples, the nucleic acid encoding the masked CAR may replace a fragment comprising SEQ ID NO: 40 in the disrupted TRAC gene.

In addition, the present disclosure provides a population of genetically engineered T cells, comprising T cells that express a masked anti-PTK7 CAR, for example, those disclosed herein. In some embodiments, the genetically engineered T cells may have a disrupted TRAC gene, a disrupted B2M gene, or a combination thereof. In some examples, the T cells may have a disrupted TRAC gene, in which a nucleic acid encoding the masked CAR is inserted, thereby disrupting expression of the TRAC gene.

In some embodiments, the genetically engineered T cells comprises a disrupted TRAC gene, which comprises a deletion of a fragment comprising the amino acid sequence of SEQ ID NO: 40. The nucleic acid encoding the masked CAR may be inserted at the site of the deletion in the TRAC gene. In some examples, the nucleic acid encoding the masked CAR may replace a fragment comprising SEQ ID NO: 40 in the disrupted TRAC gene.

In some embodiments, the population of genetically engineered T cells as disclosed herein may comprise T cells, which collectively expresses the masked CAR, have the disrupted TRAC gene, and have the disrupted B2M gene.

In another aspect, provided herein is a method for treating cancer in a subject, comprising administering to a subject in need thereof an effective amount of any of the populations of genetically engineered T cells disclosed herein. In some embodiments, the subject is a human cancer patient having a cancer that comprises PTK+ cancer cells and presents a protease that recognizes the protease cleavage site in the masked CAR. In some examples, the subject can be a human cancer patient having a cancer selected from the group consisting of non-small cell lung cancer, colon cancer, ovarian cancer, and breast cancer, which optionally is triple-negative breast cancer.

Also within the scope of the present disclosure are pharmaceutical compositions providing a population of genetically engineered T cells as disclosed herein for use in treating the target disease as also disclosed herein (e.g., cancer), or use of the population of genetically engineered T cells for manufacturing a medicament for use in treating the target disease.

Moreover, the present disclosure provides a method for producing genetically engineered CAR-T cells, comprising: (a) delivering to T cells a nucleic acid encoding any of the masked CARs disclosed herein, and (b) producing genetically engineered CAR-T cells expressing the masked CAR.

In some embodiments, step (a) can be performed by a process comprising delivering to the T cells: (i) a RNA-guided nuclease, (ii) a first guide RNA (gRNA) targeting a site in a TRAC gene, and (iii) a vector comprising a left homology arm, the nucleic acid encoding the masked CAR, and a right homology arm. The left homology arm and the right homology arm may be homologous to a genomic site of interest (e.g., a TRAC gene locus), thereby produce genetically engineered CAR-T cells having a disrupted TRAC gene and the nucleic acid encoding the masked CAR inserted at the genomic site of interest. In some examples, the left homology arm is homologous to the TRAC gene locus left to the site targeted by the first gRNA, and the right homology arm is homologous to the TRAC gene locus right to the site targeted by the first gRNA.

In some examples, step (a) may further comprise delivering to the T cells a second guide RNA targeting a site in a B2M gene. In some examples, the RNA-guided nuclease is a Cas9 nuclease, optionally a *S. pyogenes* Cas9 nuclease. In some examples, the vector is an AAV vector.

In some embodiments, the RNA-guided nuclease, the first gRNA targeting the TRAC gene, and optionally the second gRNA targeting the B2M gene, can be delivered to the T cells in a ribonucleoprotein (RNP) complex. In some examples, the RNP complex and the vector can be delivered to the T cells by electroporation.

A population of genetically engineered T cells produced by any of the methods disclosed herein is also within the scope of the present disclosure.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The following drawings form part of the present specification and are included to further demonstrate certain aspects of the present disclosure, which can be better understood by reference to the drawing in combination with the detailed description of specific embodiments presented herein.

FIG. 1A: a graph showing binding curves of masked anti-PTK7 antibodies to PTK7 positive cells. FIG. 1B: a graph showing apparent $K_D$ values of masked anti-PTK7 antibody.

FIGS. 2A-2F: graphs showing binding curves of masked anti-PTK7 antibodies to PTK7 positive cells in the absence and the presence of MMP14. FIG. 2G: a graph showing apparent KD of the indicated masked anti-PTK7 antibody in the absence and the presence of MMP14.

FIGS. 4A and 4B includes a graph showing cell killing of PTK7 expressing cells by masked anti-PTK7 CAR T cells. FIG. 4A: SaOS-2 cells. FIG. 4B: MCF-7 cells.

FIGS. 5A-5D include data showing results from testing masked anti-PTK7 CAR T cells for cytokine secretion in the presence of PTK7 expressing cells. FIG. 5A: a graph showing IFNγ levels from masked anti-PTK7 CAR T cells co-cultured with PTK7+ cells (SaOS-2 cells) at the indicated ratios. FIG. 5B: a graph showing IFNγ levels from masked anti-PTK7 CAR T cells co-cultured with PTK7+ cells (MCF-7 cells) at the indicated ratios. FIG. 5C: a graph showing IFNγ levels from masked anti-PTK7 CAR T cells co-cultured with PTK7-cells (A498 cells) at the indicated ratios. FIG. 5D: a graph showing IL-2 levels from masked anti-PTK7 CAR T cells co-cultured with PTK7+ cells (SaOS-2 cells) at the indicated ratios.

FIG. 6A: a graph showing tumor volume. FIG. 6B: a graph showing percent change in body weight. 1E7 and 3E6 refer to the two doses, $1 \times 10^7$ and $3 \times 10^6$ used in this study.

DETAILED DESCRIPTION OF THE INVENTION

Figure 1A:
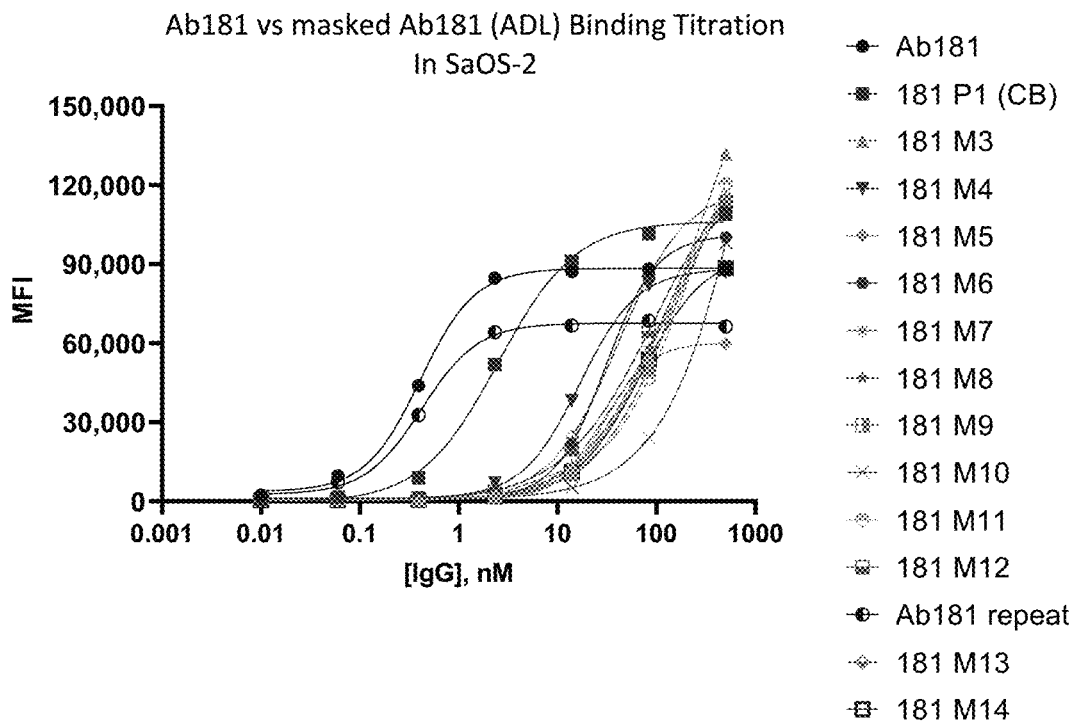
FIGS. 1A-1B include data showing results from testing binding of masked anti-PTK7 antibodies to PTK7 positive cells (SaOS-2 cells; osteosarcoma).

Multiple tumor-associated antigen targets have been progressed into clinical trials, chosen predominantly using the logic that expression in cancer tissues should be selective over normal tissues to avoid toxicity. PTK7 is reported to express on various of cancer cells and thus could serve as a potential tumor treatment target. However, excessive expression of PTK7 was also found in normal tissues, including lung, smooth muscle, stomach, kidney and bladder. Accordingly, there is a need to develop technology to reduce attack of normal tissues and cells in anti-PTK7-medicated tumor therapy.

The present disclosure is based, at least in part, on the development of masked anti-PTK7 CAR (a.k.a., masked CAR or mCAR), which comprises a mask peptide that inhibits (completely or partially) binding of the CAR to the PTK7 antigen. The mask peptide is designed to be removable, for example, via protease cleavage, at a desired site (e.g., at a tumor site). Thus, the masked anti-PTK7 CAR has reduced or no binding activity to the PTK7 antigen until the masked peptide is removed at the desired site. Accordingly, the masked anti-PTK7 CAR would have low or no cytotoxicity against normal cells and tissues, thereby addressing the potential toxicity concerns associated with conventional anti-PTK7 therapy.

Described herein are masked chimeric antigen receptors (CARs) specific to PTK7 (anti-PTK7 CAR), nucleic acids encoding such, genetically engineered T cells expressing such, therapeutic applications of such genetically engineered T cells, as well as methods for producing genetically engineered T cells expressing the masked CAR and the T cells thus produced.

I. Masked Chimeric Antigen Receptor Specific to PTK7

A chimeric antigen receptor (CAR), as used herein, refers to an artificial immune cell receptor that is engineered to recognize and bind to an antigen expressed by undesired cells, for example, disease cells such as cancer cells. A CAR polypeptide can be introduced into immune cells such as T cells for surface expression to produce CAR T cell. CARs have the ability to redirect T-cell specificity and reactivity toward a selected target in a non-MHC-restricted manner. The non-MHC-restricted antigen recognition gives CAR-T cells the ability to recognize an antigen independent of antigen processing, thus bypassing a major mechanism of tumor escape. Moreover, when expressed on T-cells, CARs advantageously do not dimerize with endogenous T-cell receptor (TCR) alpha and beta chains.

There are various designs of CARs, each of which contains different components. In some embodiments, CARs may join an antibody-derived scFv to the CD3zeta (CD3ζ) intracellular signaling domain of the T-cell receptor through hinge and transmembrane domains. In some embodiments, CARs incorporate an additional co-stimulatory domain, e.g., CD28, 4-1BB (41BB), or ICOS, to supply a costimulatory signal. In other embodiments, CARs contain two costimulatory domains (e.g., a combination of CD27, CD28, 4-1BB, ICOS, or OX40) fused with the TCR CD3ζ chain. Maude et al., Blood. 2015; 125(26):4017-4023; Kakarla and Gottschalk, Cancer J. 2014; 20(2):151-155). Any of the various generations of CAR constructs is within the scope of the present disclosure.

In some instances, a CAR can be a fusion polypeptide comprising an extracellular antigen binding domain that recognizes a target antigen (e.g., a single chain variable fragment (scFv) of an antibody or other antibody fragment) and an intracellular domain comprising a signaling domain of the T-cell receptor (TCR) complex (e.g., CD3ζ) and, in most cases, a co-stimulatory domain. (Enblad et al., Human Gene Therapy. 2015; 26(8):498-505). A CAR construct may further comprise a hinge and transmembrane domain between the extracellular domain and the intracellular domain. The masked anti-PTK7 CAR disclosed herein further comprises a mask peptide linked to the N-terminus of the extracellular antigen binding domain. In some instances, a signal peptide may be located at the N-terminus of the masked CAR to facilitate cell surface expression. Examples of signal peptides include MLLLVTSLLLCELPHPAFLLIP (SEQ ID NO: 16) and MALPVTALLLPLALLLHAARP (SEQ ID NO: 17). Other signal peptides may be used.

The masked anti-PTK7 chimeric antigen receptor (CAR) disclosed herein, a.k.a., masked anti-PTK7 CAR, comprises a mask peptide linked to an extracellular antigen binding domain (e.g., a single chain variable fragment or scFv) specific to a PTK7 antigen (e.g., the human PTK7 antigen). The mask peptide inhibits, completely or partially, the binding of the extracellular antigen binding domain to the PTK7 antigen. The mask peptide is linked to the extracellular antigen binding domain in a manner that it can be released under certain conditions, for example, via protease cleavage.

(a) Mask Peptide

As used herein, a "mask peptide" for use in constructing a masked anti-PTK7 CAR can be a peptide capable of inhibiting, e.g., completely or partially, the binding of the CAR comprising such to the PTK7 antigen. For example, a mask peptide may reduce the binding activity of a masked anti-PTK7 CAR comprising such by at least 2-fold (e.g., at least 5-fold, at least 10-fold, at least 50-fold, at least 100-fold, at least 200-fold, at least 300-fold, at least 400-fold, at least 500-fold, at least 800-fold, at least 1,000-fold, at least 2,000-fold, at least 3,000-fold, at least 4,000-fold, or at least 5,000 fold) as compared with the same, unmasked anti-PTK7 CAR. In some embodiments, a mask peptide may substantially inhibit the binding activity of the masked anti-PTK7 CAR comprising such, leading to substantially no binding of the masked anti-PTK7 CAR to the PTK7 antigen, for example, undetectable binding by a conventional assay or very low binding that would be deemed biologically insignificant to those skilled in the art.

Any of the mask peptides disclosed herein may contain about 5-25 amino acid residues, for example, about 7-25 amino acid residues. In some examples, the mask peptides may have 13-25 amino acid residues in length, for example, 13, 14, 15, 16, 17, 18, 19, 20, 21, 22, 23, 24, or 25 amino acid residues in length. In some specific examples, the mask peptides disclosed herein may have 13 amino acid residues in length. In other specific examples, the mask peptides disclosed herein may have 20 amino acid residues in length. In yet other specific examples, the mask peptides disclosed herein may have 23 amino acid residues in length.

In some embodiments, the mask peptide disclosed herein may comprise the amino acid sequence of SEQ ID NO:1 or SEQ ID NO:2. See Table 4 below. In other embodiments, the mask peptide disclosed herein may comprise an amino acid sequence that share substantially homology to SEQ ID NO:1 or SEQ ID NO:2, for example, at least 80%, at least 85%, at least 90%, or at least 95% homology to SEQ ID NO:1 or SEQ ID NO:2.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word-length=3 to obtain amino acid sequences homologous to the protein molecules of interest. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

In some examples, the mask peptide disclosed herein may comprise an amino acid sequence having no more than 5 amino acid variations (e.g., containing 5, 4, 3, 2, or 1 amino acid variation) relative to SEQ ID NO:1 or SEQ ID NO:2. In some instances, such amino acid variations can be amino acid residue substitutions, for example, conservative amino acid residue substitutions.

As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In some embodiments, the mask peptide disclosed herein may comprise a motif of $X_1CX_2X_3X_4X_5X_6X_7X_8X_9X_{10}X_{11}X_{12}X_{13}$, in which $X_1$ is V, W, or absent; $X_2$ is T, H, or Y; $X_3$ is M, F, Y, I, or H; $X_4$ is P, G, or V; $X_5$ is P, N, S, Y, K, L, V, or A; $X_6$ is S, T, W, A, H, R, or Q; $X_7$ is P, T, V, H, I, M, A, F, or W; $X_8$ R, M, A, H, V, Y, or absent; $X_9$ is S, Q, Y, T, P, A, M, or I; $X_{10}$ is K, R, I, C, S, Q, H, or absent; $X_{11}$ is V, T, R, L, F, W, or A; $X_{12}$ is I, F, L, W, or H; and $X_{13}$ is C, I, or M.

In some examples, $X_1$ is V, W, or absent, $X_2$ is T, $X_3$ is M, F, Y, or I; $X_4$ is P; $X_5$ is P, N, S, Y, or V; $X_6$ is S, T, W, A, H, or R; $X_7$ is P, T, V, H, I, M, A, or F; $X_8$ R, M, A, H, V, Y, or absent; $X_9$ is S, Q, Y, T, A, or M; $X_{10}$ is K, R, I, S, Q, H, or absent; $X_{11}$ is V, T, R, F, or W; $X_{12}$ is I, F, or L; and $X_{13}$ is C.

In some embodiments, $X_1$ is absent; $X_2$ is H, or Y; $X_3$ is I; $X_4$ is G; $X_5$ is K, or L; $X_6$ is R; $X_7$ is P, or M; $X_8$ is V; $X_9$ is P; $X_{10}$ is C; $X_{11}$ is L, or F; $X_{12}$ is W or H; and $X_{13}$ is I, or M.

In some examples, the mask peptide may comprise the amino acid sequence of any one of SEQ ID NOs:3-14. In other examples, the mask peptide disclosed herein may comprise an amino acid sequence that share substantially homology to any one of SEQ ID NOs: 3-14, for example, at least 70%, at least 75%, at least 80%, at least 85%, or at least 90% homology to any one of SEQ ID NOs:3-14. Alternatively or in addition, the mask peptide disclosed herein may comprise an amino acid sequence having no more than 4 amino acid variations (e.g., containing 4, 3, 2, or 1 amino acid variation) relative to any one of SEQ ID NOs: 3-14. In some instances, such amino acid variations can be amino acid residue substitutions, for example, conservative amino acid residue substitutions.

In some examples, the mask peptide disclosed herein can be one of SEQ ID NOs:1-14. In some examples, the mask peptide can be a fragment of any one of SEQ ID NOs:1-14, which may have at least 5 consecutive amino acid residues (e.g., at least 6, at least 7, at least 8, at least 9, at least 10, or more).

Any of the mask peptides disclosed here may be linked to the N-terminus of the extracellular antigen binding domain of any anti-PTK7 CAR also disclosed here. A cleavage site such as a protease cleavage site can be located between the mask peptide and the extracellular antigen domain. A cleavage site as used herein refers to a peptide motif, which can be cleaved under certain conditions, thereby separating its N-terminal fragment from its C-terminal fragment. By including a cleavage site between the mask peptide and the CAR, the mask peptide can be removed at the cleavage site under the designed conditions, thereby releasing the fully functional anti-PTK7 CAR.

In some embodiments, the cleavage site is a protease cleavage site, where a protease cuts. Selection of a suitable protease cleavage site would depend on the desired action site of the anti-PTK7 CAR. For example, when a tumor site is the desired action site, a cleavage site of a protease specific to the tumor used for constructing a mask anti-PTK7 CAR intended to act at the tumor site. A protease specific to a tumor refers to any protease that has an elevated level and/or activity at the tumor site as relative to normal tissues.

In some examples, the protease cleavage site can be a cleavage site of a matrix metalloproteinase (MMP). In specific examples, the protease cleavage site can be a cleavage site of MMP14, for example, a motif of PLGLA (SEQ ID NO:15). In other examples, the protease cleavage site can be a cleavage site for a serine or cysteine protease. In specific examples, the protease cleavage site can be a cleavage site for matriptase, e.g., a cleavage site having a motif of LSGRSDNH (SEQ ID NO:18). In other specific examples, the protease cleavage site can be a cleavage site for urokinase-type plasminogen activator (uPA), e.g., a cleavage site having a motif of TGRGPSWV (SEQ ID NO: 19). Additional information regarding tumor-specific proteases and corresponding cleavage sites is known in the art, for example, disclosed in Vasiljeva et al., *Scientific Reports*, 10:5894, 2020, the relevant disclosures of which are incorporated by reference for the subject matter and purpose referenced herein.

In some instances, one or more amino acid residues can be added to the N-terminus of the mask peptide to maintain or improve stability of the peptide. In one example, the dipeptide QG can be added to the N-terminus of a mask peptide (e.g., a mask peptide comprising the amino acid sequence of one of SEQ ID NOs: 3-14). Without being bound by theory, the Glutamine residue (particularly when it is located at the N-terminus) could spontaneously forms pyroglutamate, which helps protect the N-terminus against proteolysis.

Any of the mask peptides disclosed herein (with or without the additional amino acid residues noted above) may be linked to the N-terminus of a protease cleavage site (e.g., those disclosed herein such as the MMP14 cleavage site). In some examples, the mask peptide is linked directly to the N-terminus of the protease cleavage site. In other examples, the mask peptide can be linked to the N-terminus of the protease cleavage site via a peptide linker. The protease cleavage site can be linked to the N-terminus of the extracellular antigen binding domain (e.g., a scFv fragment) of the anti-PTK CAR as disclosed herein. In some examples, the protease cleavage site can be linked directly to the N-terminus of the extracellular antigen binding domain. In other examples, the protease cleavage site can be linked to the N-terminus of the extracellular antigen binding domain via a peptide linker. In some examples, a same peptide linker may be used between the mask peptide and the protease cleavage site and between the protease cleavage site and the extracellular antigen binding domain. In other examples, different peptide linkers can be used.

In specific examples, a mask peptide as disclosed herein may be linked to the extracellular antigen binding domain (e.g., a scFv fragment) in a formula of M-$L_1$-P-$L_2$-scFv, in which M represents the mask peptide, $L_1$ and $L_2$ represents peptide linkers, and P represents the protease cleavage site. $L_1$ and $L_2$ may be identical in some instances. In other instances, $L_1$ and $L_2$ can be different.

Any peptide linkers known in the art for use in linking two peptide or polypeptide fragments in a fusion polypeptide can be used in making the masked anti-PTK7 CAR disclosed herein. Such peptide linkers typically are enriched with flexible amino acid residues, for example, Gly and Ser (G/S rich linkers), so that the fragments flanking the linker can move freely relative to one another. The peptide linkers for use in the masked anti-PTK7 CAR may contain about 5-20 amino acid residues in length. When two linkers are used ($L_1$ and $L_2$ disclosed herein), the two linkers may be of the same length. Alternatively, they may have different lengths. Exemplary G/S rich linkers include, but are not limited to, GSSGGSGGSGGSGGG (SEQ ID NO: 20), GGSSG (SEQ ID NO: 21), a peptide containing one or multiple copies of GGGGS (SEQ ID NO: 22), or a peptide containing GS repeats.

(b) Antigen Extracellular Binding Domain

The extracellular antigen binding domain is the region of any masked anti-PTK7 CARs disclosed herein that is exposed to the extracellular fluid when the CAR is expressed on cell surface. In some embodiments, the antigen binding domain can be a single-chain variable fragment (scFv, which may include an antibody heavy chain variable region ($V_H$) and an antibody light chain variable region ($V_L$) (in either orientation). In some instances, the $V_H$ and $V_L$ fragment may be linked via a peptide linker. The linker, in some embodiments, includes hydrophilic residues with stretches of glycine and serine for flexibility as well as stretches of glutamate and lysine for added solubility. The scFv fragment retains the antigen-binding specificity of the parent antibody, from which the scFv fragment is derived. In some embodiments, the scFv may comprise humanized $V_H$ and/or $V_L$ domains. In other embodiments, the $V_H$ and/or $V_L$ domains of the scFv are fully human.

The extracellular antigen-binding domain in the CAR polypeptide disclosed herein is specific to PTK7 (e.g., human PTK7). In some examples, the extracellular antigen binding domain may comprise a scFv extracellular domain capable of binding to the PTK7 antigen. The anti-PTK7 scFv may be derived from Antibody Ab181.

In some embodiments, an anti-PTK7 scFv derived from Ab181 may comprise a heavy chain variable domain ($V_H$) having the same heavy chain complementary determining regions (CDRs) as those in Antibody Ab181 and/or a light chain variable domain ($V_L$) having the same light chain CDRs as those in Ab181. Two antibodies having the same $V_H$ and/or $V_L$ CDRs means that their CDRs are identical when determined by the same approach (e.g., the Kabat approach, the Chothia approach, the AbM approach, the Contact approach, or the IMGT approach as known in the art. See, e.g., Kabat, E.A., et al. (1991) Sequences of Proteins of Immunological Interest, Fifth Edition, U.S. Department of Health and Human Services, NIH Publication No. 91-3242, Chothia et al., (1989) Nature 342:877; Chothia, C. et al. (1987) J. Mol. Biol. 196:901-917, Al-lazikani et al (1997) J. Molec. Biol. 273:927-948; and Almagro, J. Mol. Recognit. 17:132-143 (2004). See also the world wide web at hgmp.mrc.ac.uk and bioinf.org.uk/abs. The heavy chain and light chain CDRs of Ab181, and its $V_H$ and $V_L$ sequences are provided in Table 1 below.

In other embodiments, an anti-PTK7 scFv derived from Ab181 may be a functional variant of Ab181. Such a functional variant is substantially similar to Ab181, both structurally and functionally. A functional variant comprises substantially the same $V_H$ and $V_L$ CDRs as Ab181. For example, it may comprise only up to 8 (e.g., 8, 7, 6, 5, 4, 3, 2, or 1) amino acid residue variations in the total CDR regions relative to those in AB181 and binds the same epitope of PTK7 with substantially similar affinity (e.g., having a $K_D$ value in the same order). In some instances, the functional variants may have the same heavy chain CDR3 as Ab181, and optionally the same light chain CDR3 as Ab181. Such an anti-PTK7 scFv may comprise a $V_H$ fragment having CDR amino acid residue variations (e.g., up to 5, for example, 5, 4, 3, 2, and 1) in only the heavy chain CDR1 and/or CDR2 as compared with the $V_H$ of Ab181. Alternatively or in addition, the anti-scFv antibody may further comprise a $V_L$ fragment having CDR amino acid residue variations (e.g., up to 5, for example, 5, 4, 3, 2, and 1) in only the light chain CDR1 and/or CDR2 as compared with the $V_L$ of Ab181. In some examples, the amino acid residue variations can be conservative amino acid residue substitutions.

In some embodiments, the anti-PTK7 scFv derived from Ab181 may be in the format of, from N-terminus to C-terminus, $V_H$-linker-$V_L$. In some examples, The anti-PTK7 scFv comprises a $V_H$ fragment of SEQ ID NO: 29 and a $V_L$ fragment of SEQ ID NO: 30. In specific examples, the anti-PTK7 scFv in any of the masked anti-PTK7 CAR may comprise the amino acid sequence of SEQ ID NO: 31.

(c) Transmembrane Domain

The masked anti-PTK7 CAR polypeptide disclosed herein may contain a transmembrane domain, which can be a hydrophobic alpha helix that spans the membrane. As used herein, a "transmembrane domain" refers to any protein structure that is thermodynamically stable in a cell membrane, preferably a eukaryotic cell membrane. The transmembrane domain can provide stability of the CAR containing such.

In some embodiments, the transmembrane domain of a CAR as provided herein can be a CD8 transmembrane domain. In other embodiments, the transmembrane domain can be a CD28 transmembrane domain. In yet other embodiments, the transmembrane domain is a chimera of a CD8 and CD28 transmembrane domain. Other transmembrane domains may be used as provided herein. In one specific example, the transmembrane domain in the anti-PTK7 CAR is a CD8c transmembrane domain having the amino acid sequence of SEQ ID NO: 36.

(d) Hinge Domain

In some embodiments, a hinge domain may be located between an extracellular domain (comprising the antigen binding domain) and a transmembrane domain of a CAR, or between a cytoplasmic domain and a transmembrane domain of the CAR. A hinge domain can be any oligopeptide or polypeptide that functions to link the transmembrane domain to the extracellular domain and/or the cytoplasmic domain in the polypeptide chain. A hinge domain may function to provide flexibility to the CAR, or domains thereof, or to prevent steric hindrance of the CAR, or domains thereof.

In some embodiments, a hinge domain may comprise up to 300 amino acids (e.g., 10 to 100 amino acids, or 5 to 20 amino acids). In some embodiments, one or more hinge domain(s) may be included in other regions of a CAR. In some embodiments, the hinge domain may be a CD8 hinge domain. Other hinge domains may be used.

(e) Intracellular Signaling Domains Any of the masked anti-PTK7 CAR constructs disclosed herein contain one or more intracellular signaling domains (e.g., CD3ζ, and optionally one or more co-stimulatory domains), which are the functional end of the receptor. Following antigen recognition, receptors cluster and a signal is transmitted to the cell.

CD3ζ is the cytoplasmic signaling domain of the T cell receptor complex. CD3ζ contains three (3) immunoreceptor tyrosine-based activation motif (ITAM)s, which transmit an activation signal to the T cell after the T cell is engaged with a cognate antigen. In many cases, CD3ζ provides a primary T cell activation signal but not a fully competent activation signal, which requires a co-stimulatory signaling. In some examples, the masked anti-PTK7 CAR construct disclosed herein comprise a CD3ζ cytoplasmic signaling domain, which may have the amino acid sequence of SEQ ID NO: 39.

In some embodiments, the masked anti-PTK7 CAR polypeptides disclosed herein may further comprise one or more co-stimulatory signaling domains. For example, the co-stimulatory domains of CD28 and/or 4-1BB may be used to transmit a full proliferative/survival signal, together with the primary signaling mediated by CD3ζ. In some examples, the CAR disclosed herein comprises a CD28 co-stimulatory molecule, for example, a CD28 co-stimulatory signaling domain having the amino acid sequence of SEQ ID NO: 37. In other examples, the CAR disclosed herein comprises a 4-1BB co-stimulatory molecule, for example, a 4-1BB co-stimulatory signaling domain having the amino acid sequence of SEQ ID NO: 38.

In specific examples, an anti-PTK7 CAR disclosed herein may include a CD3 signaling domain (e.g., SEQ ID NO: 39) and a CD28 co-stimulatory domain (e.g., SEQ ID NO: 37).

It should be understood that methods described herein encompasses more than one suitable CAR that can be used to produce genetically engineered T cells expressing the CAR, for example, those known in the art or disclosed herein. Examples can be found in, e.g., International Patent Application No. PCT/IB2019/059585, filed Nov. 7, 2019 and U.S. patent application Ser. No. 16/677,207, filed Nov. 7, 2020, the relevant disclosures of each of the prior applications are incorporated by reference herein for the purpose and subject matter referenced herein.

In specific examples, the anti-PTK7 CAR disclosed herein may comprise any one of the amino acid sequences of SEQ ID NO: 32-33. See Table 1 below Amino acid sequences of the components of exemplary anti-PTK7 CARs are provided in Table 1 below.

TABLE 1

Anti-PTK7 CAR Components

| Component | Sequence | SEQ ID NO |
|---|---|---|
| Ab181 VH CDR1 | SYGMH | 23 |
| Ab181 VH CDR2 | VIWDDGSNKYYVDSVKG | 24 |
| Ab181 VH CDR3 | DDYYGSGSFNSYYGTDV | 25 |
| Ab181 VL CDR1 | RASQSVSIYLA | 26 |
| Ab181 VL CDR2 | DASNRAT | 27 |
| Ab181 VL CDR3 | QQRSNWPPFT | 28 |
| Ab181 V$_H$ CDRs - in bold | QVQLVESGGGVVQPGRSLRLSCAASGFTFSSYGMHWVRQAPGKGLEWVAVIWDDGSNKYYVDSVKGRFTISRDNSKNTLYLQMNSLRAEDTAVYYCARDDDYYGSGSFNSYYGTDVWGQGTTVTVSS | 29 |
| Ab181 V$_L$ CDRs - in bold | EIVLTQSPATLSLSPGERATLSCRASQSVSIYLAWYQQKPGQAPRLLIYDASNRATGIPARFSGSGSGTDFTLTISSLEPEDFAVYYCQQRSNWPPFTFGPGTKVDIK | 30 |
| Ab181 scFv (linker underlined) | QVQLVESGGGVVQPGRSLRLSCAASGFTFSSYGMHWVRQAPGKGLEWVAVIWDDGSNKYYVDSVKGRFTISRDNSKNTLYLQMNSLRAEDTAVYYCARDDYYGSGSFNSYYGTDVWGQGTTVTVSS<u>GGGGSGGGGSGGGGS</u>EIVLTQSPATLSLSPGERATLSCRASQSVSIYLAWYQQKPGQAPRLLIYDASNRATGIPARFSGSGSGTDFTLTISSLEPEDFAVYYCQQRSNWPPFTFGPGTKVDIK | 31 |
| Anti-PTK7 CAR CD28 co-stim | MALPVTALLLPLALLLHAARPQVQLVESGGGVVQPGRSLRLSCAASGFTFSSYGMHWVRQAPGKGLEWVAVIWDDGSNKYYVDSVKGRFTISRDNSKNTLYLQMNSLRAEDTAVYYCARDDYYGSGSFNSYYGTDVWGQGTTVTVSSGGGGSGGGGSGGGGSEIVLTQSPATLSLSPGERATLSCRASQSVSIYLAWYQQKPGQAPRLLIYDASNRATGIPARFSGSGSGTDFTLTISSLEPEDFAVYYCQQRSNWPPFTFGPGTKVDIKSAAAFVPVFLPAKPTTTPAPRPPTPAPTIASQPLSLRPEACRPAAGGAVHTRGLDFACDIYIWAPLAGTCGVLLLSLVITLYCNHRNRSKRSRLLHSDYMNMTPRRPGPTRKHYQPYAPPRDFAAYRSRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | 32 |

TABLE 1-continued

Anti-PTK7 CAR Components

| Component | Sequence | SEQ ID NO |
|---|---|---|
| Anti-PTK7 CAR 41BB co-stim | MALPVTALLLPLALLLHAARPQVQLVESGGGVVQPGRSLRLSCAAS GFTFSSYGMHWVRQAPGKGLEWVAVIWDDGSNKYYVDSVKGRFTIS RDNSKNTLYLQMNSLRAEDTAVYYCARDDYYGSGSFNSYYGTDVWG QGTTVTVSSGGGGSGGGGSGGGGSEIVLTQSPATLSLSPGERATLS CRASQSVSIYLAWYQQKPGQAPRLLIYDASNRATGIPARFSGSGSG TDFTLTISSLEPEDFAVYYCQQRSNWPPFTFGPGTKVDIKSAAAFV PVFLPAKPTTTPAPRPPTPAPTIASQPLSLRPEACRPAAGGAVHTR GLDFACDIYIWAPLAGTCGVLLLSLVITLYCNHRNRKRGRKKLLYI FKQPFMRPVQTTQEEDGCSCRFPEEEEGGCELRVKFSRSADAPAYQ QGQNQLYNELNLGRREEYDVLDKRRGRDPEMGGKPRRKNPQEGLYN ELQKDKMAEAYSEIGMKGERRRGKGHDGLYQGLSTATKDTYDALHM QALPPR | 33 |
| CD8 signal peptide | MALPVTALLLPLALLLHAARP | 34 |
| CD8a transmembrane + 5' Linker (underlined) | SAAAFVPVFLPAKPTTTPAPRPPTPAPTIASQPLSLRPEACRPAAG GAVHTRGLDFACDIYIWAPLAGTCGVLLLSLVITLYCNHRNR | 35 |
| CD8a transmembrane (without linker) | FVPVFLPAKPTTTPAPRPPTPAPTIASQPLSLRPEACRPAAGGAVH TRGLDFACDIYIWAPLAGTCGVLLLSLVITLYCNHRNR | 36 |
| CD28 co-stimulatory | SKRSRLLHSDYMNMTPRRPGPTRKHYQPYAPPRDFAAYRS | 37 |
| 41BB co-stimulatory | KRGRKKLLYIFKQPFMRPVQTTQEEDGCSCRFPEEEEGGCEL | 38 |
| CD3ζ | RVKFSRSADAPAYQQGQNQLYNELNLGRREEYDVLDKRRGRDPEMG GKPRRKNPQEGLYNELQKDKMAEAYSEIGMKGERRRGKGHDGLYQG LSTATKDTYDALHMQALPPR | 39 |

Also within the scope of the present disclosure are nucleic acids coding for any of the masked anti-PTK7 CAR constructs disclosed herein. The nucleic acids may be located in a suitable vector, for example, a viral vector such as an AAV vector. Host cells comprising such a nucleic acid or a vector are also within the scope of the present disclosure.

II. Genetically Engineered T Cells Expressing Masked Anti-PTK7 CAR

Another aspect of the present disclosure provides a genetically engineered T cell or a population of genetically engineered T cells expressing a masked anti-PTK7 CAR such as those disclosed herein. In some embodiments, the T cells are human T cells. An expression cassette for producing the masked anti-PTK7 CAR may be inserted in a genomic site of interest. In addition to the nucleotide sequence encoding the masked anti-PTK7 CAR, the expression cassette may further comprise a promoter in operable linkage to the CAR coding sequence and optionally one or more regulatory elements for modulating expression of the CAR. Examples include enhancers, silencers, transcriptional factor binding site, polyadenylation signal sequence, or any combination thereof.

Any of the genetically engineered T cells expressing a masked anti-PTK7 CAR may comprise one or more additional genetic modifications. In some embodiments, the genetically engineered T cells expressing a masked anti-PTK7 CAR may further have a disrupted TRAC gene, a disrupted B2M gene, or a combination thereof. The disruption of the TRAC locus results in loss of expression of the T cell receptor (TCR) and is intended to reduce the probability of Graft versus Host Disease (GvHD), while the disruption of the β2M locus results in lack of expression of the major histocompatibility complex type I (MHC I) proteins and is intended to improve persistence by reducing the probability of host rejection.

As used herein, the term "a disrupted gene" refers to a gene containing one or more mutations (e.g., insertion, deletion, or nucleotide substitution, etc.) relative to the wild-type counterpart so as to substantially reduce or completely eliminate the activity of the encoded gene product. The one or more mutations may be located in a non-coding region, for example, a promoter region, a regulatory region that regulates transcription or translation; or an intron region. Alternatively, the one or more mutations may be located in a coding region (e.g., in an exon). In some instances, the disrupted gene does not express or expresses a substantially reduced level of the encoded protein. In other instances, the disrupted gene expresses the encoded protein in a mutated form, which is either not functional or has substantially reduced activity. In some embodiments, a disrupted gene is a gene that does not encode functional protein. In some embodiments, a cell that comprises a disrupted gene does not express (e.g., at the cell surface) a detectable level (e.g. by antibody, e.g., by flow cytometry) of the protein encoded by the gene. A cell that does not express a detectable level of the protein may be referred to as a knockout cell. For example, a cell having a β2M gene edit may be considered a β2M knockout cell if β2M protein cannot be detected at the cell surface using an antibody that specifically binds β2M protein.

In some embodiments, a disrupted gene may be described as comprising a mutated fragment relative to the wild-type counterpart. The mutated fragment may comprise a deletion, a nucleotide substitution, an addition, or a combination thereof. In other embodiments, a disrupted gene may be described as having a deletion of a fragment that is present in the wild-type counterpart. In some instances, the 5' end of the deleted fragment may be located within the gene region targeted by a designed guide RNA such as those disclosed herein (known as on-target sequence) and the 3' end of the deleted fragment may go beyond the targeted region. Alternatively, the 3' end of the deleted fragment may be located within the targeted region and the 5' end of the deleted fragment may go beyond the targeted region.

In some instances, the disrupted TRAC gene in the genetically engineered T cells disclosed herein may comprise a deletion, for example, a deletion of a fragment in Exon 1 of the TRAC gene locus. In some examples, the disrupted TRAC gene comprises a deletion of a fragment comprising the nucleotide sequence of SEQ ID NO: 40, which is the target site of TRAC guide RNA TA-1. See Table 2 below. In some examples, the fragment of SEQ ID NO: 40 may be replaced by a nucleic acid encoding the masked anti-PTK7 CAR.

The disrupted B2M gene in the genetically engineered T cells disclosed herein may be generated using the CRISPR/Cas technology. In some examples, a B2M gRNA provided in Table 2 may be used. The disrupted B2M gene may comprise a nucleotide sequence of any one of SEQ ID NOs: 60-65.

In some embodiments, provided herein is a population of genetically engineered immune cells (e.g., T cells such as human T cells), which collectively (i.e., in the whole cell population) express any of the masked anti-PYK7 CAR disclosed herein (e.g., the masked anti-PTK7 CAR comprising the amino acid sequence of SEQ ID NO: 106-119, e.g., SEQ ID NOs: 91-105), a disrupted TRAC gene, and a disrupted B2M gene as also disclosed herein. The nucleic acid encoding the masked anti-PTK7 CAR can be inserted in a genomic site of interest, for example, in the disrupted TRAC gene, thereby disrupting expression of the TRAC gene. In some examples, the CAR-coding sequence can be inserted at the site of SEQ ID NO: 40, e.g., replacing a fragment in the TRAC gene that comprise SEQ ID NO: 40.

The population of genetically engineered T cells disclosed herein may be a heterogeneous cell population comprising T cells having one or more of the genetic modifications disclosed herein, for example, expressing the masked anti-PTK7 CAR, having a disrupted TRAC gene, having a disrupted B2M gene, or a combination thereof.

In some examples, at least 30% of a population of the genetically engineered T cells express a detectable level of the masked anti-PTK7 CAR. For example, at least 40%, at least 50%, at least 60%, at least 70%, at least 75%, at least 80%, at least 85%, at least 90%, or at least 95% of the genetically engineered T cells express a detectable level of the masked anti-PTK7 CAR.

In some embodiments, at least 30% of the T cells in the population of genetically engineered T cells may not express a detectable level of β2M surface protein. For example, at least 40%, at least 50%, at least 60%, at least 70% or more of the T cells in the population may not express a detectable level of β2M surface protein.

Alternatively or in addition, at least 50% of the T cells in the population of genetically engineered T cells may not express a detectable level of TCR surface protein. For example, at least 60%, at least 70%, at least 80%, at least 90%, at least 95% or more of the T cells in the population may not express a detectable level of TCR surface protein.

In some embodiments, a substantial percentage of the cells in the population of genetically engineered T cells may comprise more than one gene edit, which results in a certain percentage of cells not expressing more than one gene and/or protein. For example, at least 50% of the cells in the population of genetically engineered T cells may not express a detectable level of two surface proteins, e.g., does not express a detectable level of β2M and TRAC proteins. In some examples, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the cells in the population do not express a detectable level of TRAC and B2M surface proteins.

In some embodiments, a substantial percentage of the cells in the population of genetically engineered T cells may express any of the masked anti-PTK7 CAR, have a disrupted TRAC gene, and a disrupted B2M gene. The expression cassette coding for the masked anti-PTK7 CAR may be inserted in the disrupted TRAC gene, thereby disrupting its expression. In some examples, the disrupted TRAC gene comprises a deletion of a fragment comprising the nucleotide sequence of SEQ ID NO: 40. The CAR expression cassette may be inserted at the deletion site, for example, replacing the fragment comprising SEQ ID NO: 40.

III. Preparation of Genetically Engineered Immune Cells

Any suitable gene editing methods known in the art can be used for making the genetically engineered immune cells (e.g., T cells such as human T cells expressing a masked anti-PTK7 CAR) disclosed herein, for example, nuclease-dependent targeted editing using zinc-finger nucleases (ZFNs), transcription activator-like effector nucleases (TALENs), or RNA-guided CRISPR-Cas9 nucleases (CRISPR/Cas9; Clustered Regular Interspaced Short Palindromic Repeats Associated 9). In specific examples, the genetically engineered immune cells such as T cells are produced by the CRISPR technology in combination with homologous recombination using an adeno-associated viral vector (AAV) as a donor template.

(i) CRISPR-Cas9-Mediated Gene Editing System

The CRISPR-Cas9 system is a naturally-occurring defense mechanism in prokaryotes that has been repurposed as an RNA-guided DNA-targeting platform used for gene editing. It relies on the DNA nuclease Cas9, and two noncoding RNAs, crisprRNA (crRNA) and trans-activating RNA (tracrRNA), to target the cleavage of DNA. CRISPR is an abbreviation for Clustered Regularly Interspaced Short Palindromic Repeats, a family of DNA sequences found in the genomes of bacteria and archaea that contain fragments of DNA (spacer DNA) with similarity to foreign DNA previously exposed to the cell, for example, by viruses that have infected or attacked the prokaryote. These fragments of DNA are used by the prokaryote to detect and destroy similar foreign DNA upon re-introduction, for example, from similar viruses during subsequent attacks. Transcription of the CRISPR locus results in the formation of an RNA molecule comprising the spacer sequence, which associates with and targets Cas (CRISPR-associated) proteins able to recognize and cut the foreign, exogenous DNA. Numerous types and classes of CRISPR/Cas systems have been described (see, e.g., Koonin et al., (2017) Curr Opin Microbiol 37:67-78).

crRNA drives sequence recognition and specificity of the CRISPR-Cas9 complex through Watson-Crick base pairing typically with a 20 nucleotide (nt) sequence in the target DNA. Changing the sequence of the 5' 20 nt in the crRNA allows targeting of the CRISPR-Cas9 complex to specific loci. The CRISPR-Cas9 complex only binds DNA sequences that contain a sequence match to the first 20 nt of the crRNA, if the target sequence is followed by a specific short DNA motif (with the sequence NGG) referred to as a protospacer adjacent motif (PAM).

TracrRNA hybridizes with the 3' end of crRNA to form an RNA-duplex structure that is bound by the Cas9 endonuclease to form the catalytically active CRISPR-Cas9 complex, which can then cleave the target DNA.

Once the CRISPR-Cas9 complex is bound to DNA at a target site, two independent nuclease domains within the Cas9 enzyme each cleave one of the DNA strands upstream of the PAM site, leaving a double-strand break (DSB) where both strands of the DNA terminate in a base pair (a blunt end).

After binding of CRISPR-Cas9 complex to DNA at a specific target site and formation of the site-specific DSB, the next key step is repair of the DSB. Cells use two main DNA repair pathways to repair the DSB: non-homologous end joining (NHEJ) and homology-directed repair (HDR).

NHEJ is a robust repair mechanism that appears highly active in the majority of cell types, including non-dividing cells. NHEJ is error-prone and can often result in the removal or addition of between one and several hundred nucleotides at the site of the DSB, though such modifications are typically <20 nt. The resulting insertions and deletions (indels) can disrupt coding or noncoding regions of genes. Alternatively, HDR uses a long stretch of homologous donor DNA, provided endogenously or exogenously, to repair the DSB with high fidelity. HDR is active only in dividing cells, and occurs at a relatively low frequency in most cell types. In many embodiments of the present disclosure, NHEJ is utilized as the repair operant.

(a) Cas9

In some embodiments, the Cas9 (CRISPR associated protein 9) endonuclease is used in a CRISPR method for making the genetically engineered T cells as disclosed herein. The Cas9 enzyme may be one from *Streptococcus pyogenes*, although other Cas9 homologs may also be used. It should be understood, that wild-type Cas9 may be used or modified versions of Cas9 may be used (e.g., evolved versions of Cas9, or Cas9 orthologues or variants), as provided herein. In some embodiments, Cas9 comprises a *Streptococcus pyogenes*-derived Cas9 nuclease protein that has been engineered to include C- and N-terminal SV40 large T antigen nuclear localization sequences (NLS). The resulting Cas9 nuclease (sNLS-spCas9-sNLS) is a 162 kDa protein that is produced by recombinant *E. coli* fermentation and purified by chromatography. The spCas9 amino acid sequence can be found as UniProt Accession No. Q99ZW2, which is provided herein as SEQ ID NO: 69 provided in Table 2 below.

(b) Guide RNAs (gRNAs)

CRISPR-Cas9-mediated gene editing as described herein includes the use of a guide RNA or a gRNA. As used herein, a "gRNA" refers to a genome-targeting nucleic acid that can direct the Cas9 to a specific target sequence within a TRAC gene or a β2M gene for gene editing at the specific target sequence. A guide RNA comprises at least a spacer sequence that hybridizes to a target nucleic acid sequence within a target gene for editing, and a CRISPR repeat sequence.

An exemplary gRNA targeting a TRAC gene is provided in SEQ ID NO: 42 or 45. See Table 2 below. See also WO 2019/097305A2, the relevant disclosures of which are incorporated by reference herein for the subject matter and purpose referenced herein. Other gRNA sequences may be designed using the TRAC gene sequence located on chromosome 14 (GRCh38: chromosome 14: 22,547,506-22,552,154; Ensembl; ENSG00000277734). In some embodiments, gRNAs targeting the TRAC genomic region and Cas9 create breaks in the TRAC genomic region resulting Indels in the TRAC gene disrupting expression of the mRNA or protein.

An exemplary gRNA targeting a β2M gene is provided in SEQ ID NO: 58 or 59. See Table 2 below. See also WO 2019/097305A2, the relevant disclosures of which are incorporated by reference herein for the purpose and subject matter referenced herein. Other gRNA sequences may be designed using the β2M gene sequence located on Chromosome 15 (GRCh38 coordinates: Chromosome 15: 44,711, 477-44,718,877; Ensembl: ENSG00000166710). In some embodiments, gRNAs targeting the β2M genomic region and RNA-guided nuclease create breaks in the β2M genomic region resulting in Indels in the β2M gene disrupting expression of the mRNA or protein.

In Type II systems, the gRNA also comprises a second RNA called the tracrRNA sequence. In the Type II gRNA, the CRISPR repeat sequence and tracrRNA sequence hybridize to each other to form a duplex. In the Type V gRNA, the crRNA forms a duplex. In both systems, the duplex binds a site-directed polypeptide, such that the guide RNA and site-direct polypeptide form a complex. In some embodiments, the genome-targeting nucleic acid provides target specificity to the complex by virtue of its association with the site-directed polypeptide. The genome-targeting nucleic acid thus directs the activity of the site-directed polypeptide.

As is understood by the person of ordinary skill in the art, each guide RNA is designed to include a spacer sequence complementary to its genomic target sequence. See Jinek et al., Science, 337, 816-821 (2012) and Deltcheva et al., Nature, 471, 602-607 (2011).

In some embodiments, the genome-targeting nucleic acid (e.g., gRNA) is a double-molecule guide RNA. In some embodiments, the genome-targeting nucleic acid (e.g., gRNA) is a single-molecule guide RNA.

A double-molecule guide RNA comprises two strands of RNA molecules. The first strand comprises in the 5' to 3' direction, an optional spacer extension sequence, a spacer sequence and a minimum CRISPR repeat sequence. The second strand comprises a minimum tracrRNA sequence (complementary to the minimum CRISPR repeat sequence), a 3' tracrRNA sequence and an optional tracrRNA extension sequence.

A single-molecule guide RNA (referred to as a "sgRNA") in a Type II system comprises, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension may comprise elements that contribute additional functionality (e.g., stability) to the guide RNA. The single-molecule guide linker links the minimum CRISPR repeat and the minimum tracrRNA sequence to form a hairpin structure. The optional tracrRNA extension comprises one or more hairpins. A single-molecule guide RNA in a Type V system comprises, in the 5' to 3' direction, a minimum CRISPR repeat sequence and a spacer sequence.

The "target sequence" is in a target gene that is adjacent to a PAM sequence and is the sequence to be modified by Cas9. The "target sequence" is on the so-called PAM-strand in a "target nucleic acid," which is a double-stranded molecule containing the PAM-strand and a complementary non-PAM strand. One of skill in the art recognizes that the gRNA spacer sequence hybridizes to the complementary sequence located in the non-PAM strand of the target nucleic acid of interest. Thus, the gRNA spacer sequence is the RNA equivalent of the target sequence.

For example, if the TRAC target sequence is 5'-AGAGCAACAGTGCTGTGGCC-3' (SEQ ID NO: 40), then the gRNA spacer sequence is AGAGCAACAGUGCU-GUGGCC-3' (SEQ ID NO: 43). In another example, if the (32M target sequence is 5'-GCTACTCTCTCTTTCTGGCC-3' (SEQ ID NO: 54), then the gRNA spacer sequence is 5'-GCUACUCUCUCUUUCUGGCC-3' (SEQ ID NO: 56). The spacer of a gRNA interacts with a target nucleic acid of interest in a sequence-specific manner via hybridization (i.e., base pairing). The nucleotide sequence of the spacer thus varies depending on the target sequence of the target nucleic acid of interest.

In a CRISPR/Cas system herein, the spacer sequence is designed to hybridize to a region of the target nucleic acid that is located 5' of a PAM recognizable by a Cas9 enzyme used in the system. The spacer may perfectly match the target sequence or may have mismatches. Each Cas9 enzyme has a particular PAM sequence that it recognizes in a target DNA. For example, *S. pyogenes* recognizes in a target nucleic acid a PAM that comprises the sequence 5'-NRG-3', where R comprises either A or G, where N is any nucleotide and N is immediately 3' of the target nucleic acid sequence targeted by the spacer sequence.

In some embodiments, the target nucleic acid sequence has 20 nucleotides in length. In some embodiments, the target nucleic acid has less than 20 nucleotides in length. In some embodiments, the target nucleic acid has more than 20 nucleotides in length. In some embodiments, the target nucleic acid has at least: 5, 10, 15, 16, 17, 18, 19, 20, 21, 22, 23, 24, 25, 30 or more nucleotides in length. In some embodiments, the target nucleic acid has at most: 5, 10, 15, 16, 17, 18, 19, 20, 21, 22, 23, 24, 25, 30 or more nucleotides in length. In some embodiments, the target nucleic acid sequence has 20 bases immediately 5' of the first nucleotide of the PAM. For example, in a sequence comprising 5'-NNNNNNNNNNNNNNNNNNNNNRG-3', the target nucleic acid can be the sequence that corresponds to the Ns, wherein N can be any nucleotide, and the underlined NRG sequence is the *S. pyogenes* PAM. Examples are provided as SEQ ID NOs: 41 and 55.

The guide RNA disclosed herein may target any sequence of interest via the spacer sequence in the crRNA. In some embodiments, the degree of complementarity between the spacer sequence of the guide RNA and the target sequence in the target gene can be about 60%, 65%, 70%, 75%, 80%, 85%, 90%, 95%, 97%, 98%, 99%, or 100%. In some embodiments, the spacer sequence of the guide RNA and the target sequence in the target gene is 100% complementary. In other embodiments, the spacer sequence of the guide RNA and the target sequence in the target gene may contain up to 10 mismatches, e.g., up to 9, up to 8, up to 7, up to 6, up to 5, up to 4, up to 3, up to 2, or up to 1 mismatch.

Non-limiting examples of gRNAs that may be used as provided herein are provided in WO 2019/097305A2, and WO2019/215500, the relevant disclosures of each of which are herein incorporated by reference for the purposes and subject matter referenced herein. For any of the gRNA sequences provided herein, those that do not explicitly indicate modifications are meant to encompass both unmodified sequences and sequences having any suitable modifications.

The length of the spacer sequence in any of the gRNAs disclosed herein may depend on the CRISPR/Cas9 system and components used for editing any of the target genes also disclosed herein. For example, different Cas9 proteins from different bacterial species have varying optimal spacer sequence lengths. Accordingly, the spacer sequence may have 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 nucleotides in length. In some embodiments, the spacer sequence may have 18-24 nucleotides in length. In some embodiments, the targeting sequence may have 19-21 nucleotides in length. In some embodiments, the spacer sequence may comprise 20 nucleotides in length.

In some embodiments, the gRNA can be a sgRNA, which may comprise a 20 nucleotide spacer sequence at the 5' end of the sgRNA sequence. In some embodiments, the sgRNA may comprise a less than 20 nucleotide spacer sequence at the 5' end of the sgRNA sequence. In some embodiments, the sgRNA may comprise a more than 20 nucleotide spacer sequence at the 5' end of the sgRNA sequence. In some embodiments, the sgRNA comprises a variable length spacer sequence with 17-30 nucleotides at the 5' end of the sgRNA sequence.

In some embodiments, the sgRNA comprises no uracil at the 3' end of the sgRNA sequence. In other embodiments, the sgRNA may comprise one or more uracil at the 3' end of the sgRNA sequence. For example, the sgRNA can comprise 1-8 uracil residues, at the 3' end of the sgRNA sequence, e.g., 1, 2, 3, 4, 5, 6, 7, or 8 uracil residues at the 3' end of the sgRNA sequence.

Any of the gRNAs disclosed herein, including any of the sgRNAs, may be unmodified. Alternatively, it may contain one or more modified nucleotides and/or modified backbones. For example, a modified gRNA such as a sgRNA can comprise one or more 2'-O-methyl phosphorothioate nucleotides, which may be located at either the 5' end, the 3' end, or both.

In certain embodiments, more than one guide RNAs can be used with a CRISPR/Cas nuclease system. Each guide RNA may contain a different targeting sequence, such that the CRISPR/Cas system cleaves more than one target nucleic acid. In some embodiments, one or more guide RNAs may have the same or differing properties such as activity or stability within the Cas9 RNP complex. Where more than one guide RNA is used, each guide RNA can be encoded on the same or on different vectors. The promoters used to drive expression of the more than one guide RNA is the same or different.

It should be understood that more than one suitable Cas9 and more than one suitable gRNA can be used in methods described herein, for example, those known in the art or disclosed herein. In some embodiments, methods comprise a Cas9 enzyme and/or a gRNA known in the art. Examples can be found in, e.g., WO 2019/097305A2, and WO2019/215500, the relevant disclosures of each of which are herein incorporated by reference for the purposes and subject matter referenced herein.

Table 2 below provides exemplary components for gene editing of TRAC and B2M genes.

TABLE 2

Exemplary Components for Genetic Modification of TRAC and B2M Genes

| Description | Sequence | SEQ ID NO |
|---|---|---|
| TRAC target sequence | AGAGCAACAGTGCTGTGGCC | 40 |
| TRAC target sequence with (PAM) | 5'-AGAGCAACAGTGCTGTGGCC (TGG)-3' | 41 |
| TRAC sgRNA (TA-1) unmodified | AGAGCAACAGUGCUGUGGCCguuuuagagcuagaaauagcaaguuaaaauaaggcuaguccguuaucaacuugaaaaaguggcaccgagucggugcUUUU | 42 |
| TRAC sgRNA spacer unmodified | AGAGCAACAGUGCUGUGGCC | 43 |
| TRAC sgRNA spacer modified | A*G*A*GCAACAGUGCUGUGGCC | 44 |
| TRAC sgRNA (TA-1) modified | A*G*A*GCAACAGUGCUGUGGCCguuuuagagcuagaaauagcaaguuaaaauaaggcuaguccguuaucaacuugaaaaaguggcaccgagucggugcU*U*U*U | 45 |
| TRAC gene-edit | AAGAGCAACAAATCTGACT | 46 |
| TRAC gene-edit | AAGAGCAACAGTGCTGTGCCTGGAGCAACAAATCTGACT AAGAGCAACAAATCTGACT | 47 |
| TRAC gene-edit | AAGAGCAACAGTGCTGGAGCAACAAATCTGACT AAGAGCAACAAATCTGACT | 48 |
| TRAC gene-edit | AAGAGCAACAGTGCCTGGAGCAACAAATCTGACT AAGAGCAACAAATCTGACT | 49 |
| TRAC gene-edit | AAGAGCAACAGTGCTGACTAAGAGCAACAAATCTGACT | 50 |
| TRAC gene-edit | AAGAGCAACAGTGCTGTGGGCCTGGAGCAACAAATCTGACT AAGAGCAACAAATCTGACT | 51 |
| TRAC gene-edit | AAGAGCAACAGTGCTGGCCTGGAGCAACAAATCTGACT AAGAGCAACAAATCTGACT | 52 |
| TRAC gene-edit | AAGAGCAACAGTGCTGTGTGCCTGGAGCAACAAATCTGACT AAGAGCAACAAATCTGACT | 53 |
| B2M target sequence | GCTACTCTCTCTTTCTGGCC | 54 |
| B2M target sequence with (PAM) | GCTACTCTCTCTTTCTGGCC (TGG) | 55 |
| 56B2M sgRNA spacer unmodified | GCUACUCUCUCUUUCUGGCC | 56 |
| B2M sgRNA spacer modified | G*C*U*ACUCUCUCUUUCUGGCC | 57 |
| B2M sgRNA unmodified | GCUACUCUCUCUUUCUGGCCguuuuagagcuagaaauagcaaguuaaaauaaggcuaguccguuaucaacuugaaaaaguggcaccgagucggugcUUUU | 58 |
| B2M sgRNA modified | G*C*U*ACUCUCUCUUUCUGGCCguuuuagagcuagaaauagcaaguuaaaauaaggcuaguccguuaucaacuugaaaaaguggcaccgagucggugcU*U*U*U | 59 |
| B2M gene-edit | CGTGGCCTTAGCTGTGCTCGCGCTACTCTCTCTTTCTGCCTGGAGGCTATCCAGCGTGAGTCTCTCCTACCCTCCCGCT | 60 |
| B2M gene-edit | CGTGGCCTTAGCTGTGCTCGCGCTACTCTCTCTTTCGCCTGGAGGCTATCCAGCGTGAGTCTCTCCTACCCTCCCGCT | 61 |
| B2M gene-edit | CGTGGCCTTAGCTGTGCTCGCGCTACTCTCTCTTTCTGGAGGCTATCCAGCGTGAGTCTCTCCTACCCTCCCGCT | 62 |
| B2M gene-edit | CGTGGCCTTAGCTGTGCTCGCGCTACTCTCTCTTTCTGGATAGCCTGGAGGCTATCCAGCGTGAGTCTCTCCTACCCTCCCGCT | 63 |

TABLE 2-continued

Exemplary Components for Genetic Modification of TRAC and B2M Genes

| Description | Sequence | SEQ ID NO |
|---|---|---|
| B2M gene-edit | CGTGGCCTTAGCTGTGCTCGCGCTATCCAGCGTGAGTCTCTCCT ACCCTCCCGCT | 64 |
| B2M gene-edit | CGTGGCCTTAGCTGTGCTCGCGCTACTCTCTCTTTCTGTGGCCT GGAGGCTATCCAGCGTGAGTCTCTCCTACCCTCCCGCT | 65 |
| sgRNA | nnnnnnnnnnnnnnnnnnnnguuuuagagcuagaaauagcaagu uaaaauaaggcuaguccguuaucaacuugaaaaaguggcaccga gucggugcuuuu | 66 |
| sgRNA | nnnnnnnnnnnnnnnnnnnnguuuuagagcuagaaauagcaagu uaaaauaaggcuaguccguuaucaacuugaaaaaguggcaccga gucggugc | 67 |
| sgRNA | n$_{(17-30)}$guuuuagagcuagaaauagcaaguuaaaauaaggcuagu ccguuaucaacuugaaaaaguggcaccgagucggugcu$_{(1-8)}$ | 68 |
| spCas9 | MDKKYSIGLDIGTNSVGWAVITDEYKVPSKKFKVLGNTDRHSIK KNLIGALLFDSGETAEATRLKRTARRRYTRRKNRICYLQEIFSN EMAKVDDSFFHRLEESFLVEEDKKHERHPIFGNIVDEVAYHEKY PTIYHLRKKLVDSTDKADLRLIYLALAHMIKFRGHFLIEGDLNP DNSDVDKLFIQLVQTYNQLFEENPINASGVDAKAILSARLSKSR RLENLIAQLPGEKKNGLFGNLIALSLGLTPNFKSNFDLAEDAKL QLSKDTYDDDLDNLLAQIGDQYADLFLAAKNLSDAILLSDILRV NTEITKAPLSASMIKRYDEHHQDLTLLKALVRQQLPEKYKEIFF DQSKNGYAGYIDGGASQEEFYKFIKPILEKMDGTEELLVKLNRE DLLRKQRTFDNGSIPHQIHLGELHAILRRQEDFYPFLKDNREKI EKILTFRIPYYVGPLARGNSRFAWMTRKSEETITPWNFEEVVDK GASAQSFIERMTNFDKNLPNEKVLPKHSLLYEYFTVYNELTKVK YVTEGMRKPAFLSGEQKKAIVDLLFKTNRKVTVKQLKEDYFKKI ECFDSVEISGVEDRFNASLGTYHDLLKIIKDKDFLDNEENEDIL EDIVLTLTLFEDREMIEERLKTYAHLFDDKVMKQLKRRRYTGWG RLSRKLINGIRDKQSGKTILDFLKSDGFANRNFMQLIHDDSLTF KEDIQKAQVSGQGDSLHEHIANLAGSPAIKKGILQTVKVVDELV KVMGRHKPENIVIEMARENQTTQKGQKNSRERMKRIEEGIKELG SQILKEHPVENTQLQNEKLYLYYLQNGRDMYVDQELDINRLSDY DVDHIVPQSFLKDDSIDNKVLTRSDKNRGKSDNVPSEEVVKKMK NYWRQLLNAKLITQRKFDNLTKAERGGLSELDKAGFIKRQLVET RQITKHVAQILDSRMNTKYDENDKLIREVKVITLKSKLVSDFRK DFQFYKVREINNYHHAHDAYLNAVVGTALIKKYPKLESEFVYGD YKVYDVRKMIAKSEQEIGKATAKYFFYSNIMNFFKTEITLANGE IRKRPLIETNGETGEIVWDKGRDFATVRKVLSMPQVNIVKKTEV QTGGFSKESILPKRNSDKLIARKKDWDPKKYGGFDSPTVAYSVL VVAKVEKGKSKKLKSVKELLGITIMERSSFEKNPIDFLEAKGYK EVKKDLIIKLPKYSLFELENGRKRMLASAGELQKGNELALPSKY VNFLYLASHYEKLKGSPEDNEQKQLFVEQHKHYLDEIIEQISEF SKRVILADANLDKVLSAYNKHRDKPIREQAENIIHLFTLTNLGA PAAFKYFDTTIDRKRYTSTKEVLDATLIHQSITGLYETRIDLSQ LGGD | 69 |

*indicates a nucleotide with a 2'-O-methyl phosphorothioate modification.
"n" refers to the spacer sequence at the 5' end.

(ii) AAV Vectors for Delivery of CAR Constructs to T Cells

A nucleic acid encoding any of the masked anti-PTK7 CAR constructs as disclosed herein can be delivered to a cell using an adeno-associated virus (AAV). AAVs are small viruses which integrate site-specifically into the host genome and can therefore deliver a transgene, such as CAR. Inverted terminal repeats (ITRs) are present flanking the AAV genome and/or the transgene of interest and serve as origins of replication. Also present in the AAV genome are rep and cap proteins which, when transcribed, form capsids which encapsulate the AAV genome for delivery into target cells. Surface receptors on these capsids which confer AAV serotype, which determines which target organs the capsids will primarily bind and thus what cells the AAV will most efficiently infect. There are twelve currently known human AAV serotypes. In some embodiments, the AAV for use in delivering the CAR-coding nucleic acid is AAV serotype 6 (AAV6).

Adeno-associated viruses are among the most frequently used viruses for gene therapy for several reasons. First, AAVs do not provoke an immune response upon administration to mammals, including humans. Second, AAVs are effectively delivered to target cells, particularly when consideration is given to selecting the appropriate AAV serotype. Finally, AAVs have the ability to infect both dividing and non-dividing cells because the genome can persist in the host cell without integration. This trait makes them an ideal candidate for gene therapy.

A nucleic acid encoding the masked anti-PTK7 CAR can be designed to insert into a genomic site of interest in the host T cells. In some embodiments, the target genomic site can be in a safe harbor locus.

In some embodiments, a nucleic acid encoding the masked anti-PTK7 CAR (e.g., via a donor template, which can be carried by a viral vector such as an adeno-associated viral (AAV) vector) can be designed such that it can insert into a location within a TRAC gene to disrupt the TRAC gene in the genetically engineered T cells and express the CAR polypeptide. Disruption of TRAC leads to loss of function of the endogenous TCR. For example, a disruption in the TRAC gene can be created with an endonuclease such as those described herein and one or more gRNAs targeting one or more TRAC genomic regions. Any of the gRNAs specific to a TRAC gene and the target regions can be used for this purpose, e.g., those disclosed herein.

In some examples, a genomic deletion in the TRAC gene and replacement by a CAR coding segment can be created by homology directed repair or HDR (e.g., using a donor template, which may be part of a viral vector such as an adeno-associated viral (AAV) vector). In some embodiments, a disruption in the TRAC gene can be created with an endonuclease as those disclosed herein and one or more gRNAs targeting one or more TRAC genomic regions, and inserting a CAR coding segment into the TRAC gene.

A donor template as disclosed herein can contain a coding sequence for a CAR. In some examples, the CAR-coding sequence may be flanked by two regions of homology to allow for efficient HDR at a genomic location of interest, for example, at a TRAC gene using CRISPR-Cas9 gene editing technology. In this case, both strands of the DNA at the target locus can be cut by a CRISPR Cas9 enzyme guided by gRNAs specific to the target locus. HDR then occurs to repair the double-strand break (DSB) and insert the donor DNA coding for the CAR. For this to occur correctly, the donor sequence is designed with flanking residues which are complementary to the sequence surrounding the DSB site in the target gene (hereinafter "homology arms"), such as the TRAC gene. These homology arms serve as the template for DSB repair and allow HDR to be an essentially error-free mechanism. The rate of homology directed repair (HDR) is a function of the distance between the mutation and the cut site so choosing overlapping or nearby target sites is important. Templates can include extra sequences flanked by the homologous regions or can contain a sequence that differs from the genomic sequence, thus allowing sequence editing.

Alternatively, a donor template may have no regions of homology to the targeted location in the DNA and may be integrated by NHEJ-dependent end joining following cleavage at the target site.

A donor template can be DNA or RNA, single-stranded and/or double-stranded, and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al., (1987) Proc. Natl. Acad. Sci. USA 84:4959-4963; Nehls et al., (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A donor template can be introduced into a cell as part of a vector molecule having additional sequences such as, for example, replication origins, promoters and genes encoding antibiotic resistance. Moreover, a donor template can be introduced into a cell as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLY)).

A donor template, in some embodiments, can be inserted at a site nearby an endogenous promoter (e.g., downstream or upstream) so that its expression can be driven by the endogenous promoter. In other embodiments, the donor template may comprise an exogenous promoter and/or enhancer, for example, a constitutive promoter, an inducible promoter, or tissue-specific promoter to control the expression of the CAR gene. In some embodiments, the exogenous promoter is an EF1α promoter. Other promoters may be used.

Furthermore, exogenous sequences may also include transcriptional or translational regulatory sequences, for example, promoters, enhancers, insulators, internal ribosome entry sites, sequences encoding 2A peptides and/or polyadenylation signals.

Table 3 below provides exemplary donor template components for inserting a nucleic acid encoding a masked anti-PTK7 CAR in the TRAC gene locus. An exemplary donor structure may comprise, from 5' end to 3' end: TRAC[LHA]-EF1a[promoter]-masked CAR-polyA-TRAC[RHA].

TABLE 3

Sequences of Donor Template Components

| Name | Sequence | SEQ ID NO |
|---|---|---|
| TRAC-LHA | GAGATGTAAGGAGCTGCTGTGACTTGCTCAAGGCCTTATATCGAGTAAACGGTAG TGCTGGGGCTTAGACGCAGGTGTTCTGATTTATAGTTCAAAACCTCTATCAATGA GAGAGCAATCTCCTGGTAATGTGATAGATTTCCCAACTTAATGCCAACATACCAT AAACCTCCCATTCTGCTAATGCCCAGCCTAAGTTGGGGAGACCACTCCAGATTCC AAGATGTACAGTTTGCTTTGCTGGGCCTTTTTCCCATGCCTGCCTTTACTCTGCC AGAGTTATATTGCTGGGGTTTTGAAGAAGATCCTATTAAATAAAAGAATAAGCAG TATTATTAAGTAGCCCTGCATTTCAGGTTTCCTTGAGTGGCAGGCCAGGCCTGGC CGTGAACGTTCACTGAAATCATGGCCTCTTGGCCAAGATTGATAGCTTGTGCCTG TCCCTGAGTCCCAGTCCATCACGAGCAGCTGGTTTCTAAGATGCTATTTCCCGTA TAAAGCATGAGACCGTGACTTGCCAGCCCCACAGAGCCCCGCCCTTGTCCATCAC TGGCATCTGGACTCCAGCCTGGGTTGGGGCAAAGAGGGAAATGAGATCATGTCCT AACCCTGATCCTCTTGTCCCACAGATATCCAGAACCCTGACCCTGCCGTGTACCA GCTGAGAGACTCTAAATCCAGTGACAAGTCTGTCTGCCTATTCACCGATTTTGAT TCTCAAACAAATGTGTCACAAAGTAAGGATTCTGATGTGTATATCACAGACAAAA CTGTGCTAGACATGAGGTCTATGGACTTCA | 70 |

TABLE 3-continued

Sequences of Donor Template Components

| Name | Sequence | SEQ ID NO |
|---|---|---|
| EF1α promoter | GGCTCCGGTGCCCGTCAGTGGGCAGAGCGCACATCGCCCACAGTCCCCGAGAAGT<br>TGGGGGGAGGGGTCGGCAATTGAACCGGTGCCTAGAGAAGGTGGCGCGGGGTAAA<br>CTGGGAAAGTGATGTCGTGTACTGGCTCCGCCTTTTTCCCGAGGGTGGGGGAGAA<br>CCGTATATAAGTGCAGTAGTCGCCGTGAACGTTCTTTTTCGCAACGGGTTTGCCG<br>CCAGAACACAGGTAAGTGCCGTGTGTGGTCCCGCGGGCCTGGCCTCTTTACGGG<br>TTATGGCCCTTGCGTGCCTTGAATTACTTCCACTGGCTGCAGTACGTGATTCTTG<br>ATCCCGAGCTTCGGGTTGGAAGTGGGTGGGAGAGTTCGAGGCCTTGCGCTTAAGG<br>AGCCCCTTCGCCTCGTGCTTGAGTTGAGGCCTGGCCTGGGCGCTGGGGCCGCCGC<br>GTGCGAATCTGGTGGCACCTTCGCGCCTGTCTCGCTGCTTTCGATAAGTCTCTAG<br>CCATTTAAAATTTTTGATGACCTGCTGCGACGCTTTTTTTCTGGCAAGATAGTCT<br>TGTAAATGCGGGCCAAGATCTGCACACTGGTATTTCGGTTTTTGGGGCCGCGGGC<br>GGCGACGGGGCCCGTGCGTCCCAGCGCACATGTTCGGCGAGGCGGGGCCTGCGAG<br>CGCGGCCACCGAGAATCGGACGGGGGTAGTCTCAAGCTGGCCGGCCTGCTCTGGT<br>GCCTGGCCTCGCGCCGCCGTGTATCGCCCCGCCCTGGGCGGCAAGGCTGGCCCGG<br>TCGGCACCAGTTGCGTGAGCGGAAAGATGGCCGCTTCCCGGCCCTGCTGCAGGGA<br>GCTCAAAATGGAGGACGCGGCGCTCGGGAGAGCGGGCGGGTGAGTCACCCACACA<br>AAGGAAAAGGGCCTTTCCGTCCTCAGCCGTCGCTTCATGTGACTCCACGGAGTAC<br>CGGGCGCCGTCCAGGCACCTCGATTAGTTCTCGAGCTTTTGGAGTACGTCGTCTT<br>TAGGTTGGGGGAGGGGTTTTATGCGATGGAGTTTCCCCACACTGAGTGGGTGGA<br>GACTGAAGTTAGGCCAGCTTGGCACTTGATGTAATTCTCCTTGGAATTTGCCCTT<br>TTTGAGTTTGGATCTTGGTTCATTCTCAAGCCTCAGACAGTGGTTCAAAGTTTTT<br>TTCTTCCATTTCAGGTGTCGTGA | 71 |
| Synthetic poly(A) signal | AATAAAATCGCTATCCATCGAAGATGGATGTGTGTTGGTTTTTTGTGTG | 72 |
| TRAC-RHA | TGGAGCAACAAATCTGACTTTGCATGTGCAAACGCCTTCAACAACAGCATTATTC<br>CAGAAGACACCTTCTTCCCCAGCCCAGGTAAGGGCAGCTTTGGTGCCTTCGCAGG<br>CTGTTTCCTTGCTTCAGGAATGGCCAGGTTCTGCCCAGAGCTCTGGTCAATGATG<br>TCTAAAACTCCTCTGATTGGTGGTCTCGGCCTTATCCATTGCCACCAAAACCCTC<br>TTTTTACTAAGAAACAGTGAGCCTTGTTCTGGCAGTCCAGAGAATGACACGGGAA<br>AAAAGCAGATGAAGAGAAGGTGGCAGGAGAGGGCACGTGGCCCAGCCTCAGTCTC<br>TCCAACTGAGTTCCTGCCTGCCTGCCTTTGCTCAGACTGTTTGCCCCTTACTGCT<br>CTTCTAGGCCTCATTCTAAGCCCCTTCTCCAAGTTGCCTCTCCTTATTTCTCCCT<br>GTCTGCCAAAAAATCTTTCCCAGCTCACTAAGTCAGTCTCACGCAGTCACTCATT<br>AACCCACCAATCACTGATTGTGCCGGCACATGAATGCACCAGGTGTTGAAGTGGA<br>GGAATTAAAAAGTCAGATGAGGGGTGTGCCCAGAGGAAGCACCATTCTAGTTGGG<br>GGAGCCCATCTGTCAGCTGGGAAAAGTCCAAATAACTTCAGATTGGAATGTGTTT<br>TAACTCAGGGTTGAGAAAACAGCTACCTTCAGGACAAAAGTCAGGGAAGGGCTCT<br>CTGAAGAAATGCTACTTGAAGATACCAGCCCTACCAAGGGCAGGGAGAGGACCCT<br>ATAGAGGCCTGGGACAGGAGCTCAATGAGAAAGG | 73 |

To prepare the genetically engineered immune cells (e.g., T cells disclosed herein), immune cells such as T cells from a suitable source may be obtained, e.g., blood cells from a human donor, who may be a healthy donor or a patient need CAR-T cell therapy. The genetically engineered cells can be made using blood cells from one or more healthy human donors. Manufacturing from healthy donor cells minimizes the risk of unintentionally transducing malignant lymphoma/leukemia cells and potentially may improve the functionality of the CAR T cells. The components of the CRISPR system (e.g., Cas9 protein and the gRNAs), optionally the AAV donor template, may be delivered into the host immune cells via conventional approaches. In some examples, the Cas9 and the gRNAs can form a ribonucleoprotein complex (RNP), which can be delivered to the host immune cells by electroporation. Optionally, the AAV donor template may be delivered to the immune cells concurrently with the RNP complex. Alternatively, delivery of the RNPs and the AAV donor template can be performed sequentially. In some examples, the T cells may be activated prior to delivery of the gene editing components.

After delivery of the gene editing components and optionally the donor template, the cells may be recovered and expanded in vitro. Gene editing efficiency can be evaluated using routine methods for confirm knock-in of the masked anti-PTK7 CAR and knock-out of the target genes (e.g., TRAC, B2M, or both). In some examples, TCRαβ+ T cells may be removed.

IV. Treatment Methods and Compositions

In another aspect, provided herein are therapeutic applications of any of the genetically engineered immune cells such as T cells disclosed herein that express a masked anti-PTK7 CAR. Such therapeutic applications include eliminating disease cells expressing PTK7, for example, PTK7+ cancer cells.

Any of the genetically engineered immune cells such as T cells as disclosed herein (e.g., those expressing a masked anti-PTK7 CAR as also disclosed herein and having one or more additional genetic edits such as a disrupted TRAC gene and/or a disrupted B2M gene) may be formulated in a pharmaceutical composition, which may further comprise one or more pharmaceutically acceptable excipients. Such pharmaceutical compositions are also within the scope of the present disclosure. The pharmaceutical compositions can be used in therapeutic applications, for example, cancer treatment in human patients, which is also disclosed herein.

As used herein, the term "pharmaceutically acceptable" refers to those compounds, materials, compositions, and/or dosage forms which are, within the scope of sound medical judgment, suitable for use in contact with the tissues, organs, and/or bodily fluids of the subject without excessive toxicity, irritation, allergic response, or other problems or complications commensurate with a reasonable benefit/risk ratio. As used herein, the term "pharmaceutically acceptable carrier" refers to solvents, dispersion media, coatings, antibacterial agents, antifungal agents, isotonic and absorption delaying agents, or the like that are physiologically compatible. The compositions can include a pharmaceutically acceptable salt, e.g., an acid addition salt or a base addition salt. See, e.g., Berge et al., (1977) J Pharm Sci 66:1-19.

In some embodiments, the pharmaceutical composition further comprises a pharmaceutically acceptable salt. Non-limiting examples of pharmaceutically acceptable salts include acid addition salts (formed from a free amino group of a polypeptide with an inorganic acid, or an organic acid. In some embodiments, the salt formed with the free carboxyl groups is derived from an inorganic base, or an organic base. In some embodiments, the pharmaceutical composition disclosed herein comprises a population of the genetically engineered CAR-T cells expressing a masked anti-PTK7 CAR as disclosed herein suspended in a cryopreservation solution (e.g., CryoStor® C55).

In some embodiments, any of the genetically engineered T cells expressing a masked anti-PTK7 CAR as disclosed herein can be used for reducing or eliminating disease cells expressing PTK7 and thus treating diseases involving such disease cells. For example, the treatment method disclosed herein may be applied to patients (e.g., human patients) having a cancer, particularly a cancer that presents an elevated level of a protease (e.g., protein level or bioactivity level) relative to normal tissues. To treat such a cancer, genetically engineered T cells expressing a masked anti-PTK CAR that comprise a protease cleavage site recognizable by the protease presented at the cancer site can be used.

Non-limiting target cancer (e.g., solid tumors) include pancreatic cancer, gastric cancer, ovarian cancer, colon cancer, uterine cancer, breast cancer (e.g., triple-negative cancer), esophageal cancer, prostate cancer, testicular cancer, thyroid cancer, nasopharyngeal cancer, non-small cell lung (NSCLC), glioblastoma, neuronal, soft tissue sarcomas, melanoma. In other examples, the target cancer is leukemia, for example, Adult acute myeloid leukemia (AML).

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity or prolonging survival. Alleviating the disease or prolonging survival does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

To perform the method disclosed herein, an effective amount of the genetically engineered T cells expressing a masked anti-PTK7 CAR and optionally one or more additional genetic modifications (e.g., disrupted TRAC gene and/or disrupted B2M gene) can be administered to a subject in need of the treatment (e.g., a human patient having a target cancer as disclosed herein). A subject may be any subject for whom diagnosis, treatment, or therapy is desired. In some embodiments, the subject is a mammal. In some embodiments, the subject is a human.

As used herein, "an effective amount" refers to the amount of each active agent required to confer therapeutic effect on the subject, either alone or in combination with one or more other active agents. Determination of whether an amount of the antibody achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

In some embodiments, an effective amount refers to the amount of a population of genetically engineered T cells as disclosed herein needed to prevent or alleviate at least one or more signs or symptoms of a medical condition (e.g., cancer), and relates to a sufficient amount of a composition to provide the desired effect, e.g., to treat a subject having a medical condition. An effective amount also includes an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate effective amount can be determined by one of ordinary skill in the art using routine experimentation.

For use in the various aspects described herein, an effective amount of cells (e.g., engineered T cells) may comprise at least $5\times10^5$ cells, at least $1\times10^6$ cells, at least $5\times10^6$ cells, at least $1\times10^7$ cells, or at least $5\times10^7$ cells.

In some examples, the genetically engineered T cells are derived from the patient to be treated, i.e., the cells are autologous cells; that is, the engineered T cells are obtained or isolated from a subject and administered to the same subject.

In other examples, the genetically engineered T cells are derived from one or more donors (e.g., healthy human donors) for allogeneic adoptive cell therapy. Allogeneic refers to a cell, cell population, or biological samples comprising cells, obtained from one or more different donors of the same species, where the genes at one or more loci are not identical to the recipient. For example, an engineered T cell population being administered to a subject can be derived from one or more unrelated donors, or from one or more non-identical siblings. A donor is an individual who is not the subject being treated. In some embodiments, a donor is an individual who does not have or is not suspected of having the cancer being treated.

In some embodiments, multiple donors, e.g., two or more donors, are used. In some examples described herein, the cells are expanded in culture prior to administration to a subject in need thereof.

The step of administering may include the placement (e.g., transplantation) of cells, e.g., engineered T cells, into a subject, by a method or route that results in at least partial localization of the introduced cells at a desired site, such as tumor, such that a desired effect(s) is produced. Engineered T cells can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the life time of the subject, i.e., long-term engraftment. For example, in some aspects described herein, an effective amount of engineered T cells is administered via a systemic route of administration, such as an intraperitoneal or intravenous route.

Modes of administration include injection, infusion, instillation, or ingestion. Injection includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the route is intravenous.

In some embodiments, engineered T cells are administered systemically, which refers to the administration of a population of cells other than directly into a target site, tissue, or organ, such that it enters, instead, the subject's circulatory system and, thus, is subject to metabolism and other like processes.

Any subjects (e.g., human patients) suitable for the treatment methods disclosed herein may receive a lymphodepleting therapy to reduce or deplete the endogenous lymphocyte of the subject. Lymphodepletion refers to the destruction of endogenous lymphocytes and/or T cells, which is commonly used prior to immunotransplantation and immunotherapy. Lymphodepletion can be achieved by irradiation and/or chemotherapy. A "lymphodepleting agent" can be any molecule capable of reducing, depleting, or eliminating endogenous lymphocytes and/or T cells when administered to a subject. In some embodiments, the lymphodepleting agents are administered in an amount effective in reducing the number of lymphocytes by at least 10%, 20%, 30%, 40%, 50%, 60%, 70%, 80%, 90%, 95%, 96%, 96%, 97%, 98%, or at least 99% as compared to the number of lymphocytes prior to administration of the agents. In some embodiments, the lymphodepleting agents are administered in an amount effective in reducing the number of lymphocytes such that the number of lymphocytes in the subject is below the limits of detection. In some embodiments, the subject is administered at least one (e.g., 2, 3, 4, 5 or more) lymphodepleting agents.

In some embodiments, the lymphodepleting agents are cytotoxic agents that specifically kill lymphocytes. Examples of lymphodepleting agents include, without limitation, fludarabine, cyclophosphamide, bendamustin, 5-fluorouracil, gemcitabine, methotrexate, dacarbazine, melphalan, doxorubicin, vinblastine, cisplatin, oxaliplatin, paclitaxel, docetaxel, irinotecan, etoposide phosphate, mitoxantrone, cladribine, denileukin diftitox, or DAB-IL2. In some instances, the lymphodepleting agent may be accompanied with low-dose irradiation. The lymphodepletion effect of the conditioning regimen can be monitored via routine practice.

The efficacy of a treatment as disclosed herein can be determined by the skilled clinician. A treatment can be considered "effective treatment," if any one or all of the signs or symptoms of, as but one example, levels of functional target are altered in a beneficial manner (e.g., increased by at least 10%), or other clinically accepted symptoms or markers of disease (e.g., cancer) are improved or ameliorated. Efficacy can also be measured by failure of a subject to worsen as assessed by hospitalization or need for medical interventions (e.g., progression of the disease is halted or at least slowed). Methods of measuring these indicators are known to those of skill in the art and/or described herein. Treatment efficacy includes, but are not limited to, (1) inhibiting the disease, e.g., arresting, or slowing the progression of symptoms; or (2) relieving the disease, e.g., causing regression of symptoms; and (3) preventing or reducing the likelihood of the development of symptoms.

V. Kit for CAR-T Cell Therapy

The present disclosure also provides kits for use of a population of genetically engineered immune cells such as T cells that express a masked anti-PTK7 CAR and optionally have one or more additional genetic modifications such as disrupted TRAC and/or disrupted B2M as described herein in methods for treating a target disease, e.g., a cancer such as those disclosed herein. Such kits may include one or more containers comprising a first pharmaceutical composition that comprises one or more lymphodepleting agents, and a second pharmaceutical composition that comprises any nucleic acid or population of genetically engineered T cells (e.g., those described herein), and a pharmaceutically acceptable carrier.

In some embodiments, the kit can comprise instructions for use in any of the methods described herein. The included instructions can comprise a description of administration of the first and/or second pharmaceutical compositions to a subject to achieve the intended activity in a human patient. The kit may further comprise a description of selecting a human patient suitable for treatment based on identifying whether the human patient is in need of the treatment. In some embodiments, the instructions comprise a description of administering the first and second pharmaceutical compositions to a human patient who is in need of the treatment.

The instructions relating to the use of a population of genetically engineered T cells described herein generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert. The label or package insert indicates that the population of genetically engineered T cells is used for treating, delaying the onset, and/or alleviating a cancer in a subject.

The kits provided herein are in suitable packaging. Suitable packaging includes, but is not limited to, vials, bottles, jars, flexible packaging, and the like. Also contemplated are packages for use in combination with a specific device, such as an inhaler, nasal administration device, or an infusion device. A kit may have a sterile access port (for example, the container may be an intravenous solution bag or a vial having a stopper pierceable by a hypodermic injection needle). The container may also have a sterile access port. At least one active agent in the pharmaceutical composition is a population of the genetically engineered T cells as disclosed herein.

Kits optionally may provide additional components such as buffers and interpretive information. Normally, the kit comprises a container and a label or package insert(s) on or associated with the container. In some embodiment, the disclosure provides articles of manufacture comprising contents of the kits described above.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology*, Humana Press; *Cell Biology: A Laboratory Notebook* (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); *DNA Cloning: A practical Approach*, Volumes I and II (D. N. Glover ed. 1985); *Nucleic Acid Hybridization* (B. D. Hames & S. J. Higgins eds. (1985»; *Transcription and Translation* (B. D. Hames & S. J. Higgins, eds. (1984»; *Animal Cell Culture* (R. I. Freshney, ed. (1986»; *Immobilized Cells and Enzymes* (IRL Press, (1986»; and B. Perbal, *A practical Guide To Molecular Cloning* (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Identification of Masking Peptides Specific for Anti-PTK7 Antibody Ab181

This example describes the identification of masking peptides capable of blocking anti-PTK7 antibody Ab181 from binding to the PTK7 antigen using two different phage display screen assays. Screen 1 used a peptide library format of $X_{15}/X_{19}$ peptides. Screen 2 used a peptide library format of $X_nCX_nCX_n$ peptides. Both Screen 1 and Screen 2 used a series of rounds of selection with increasing stringency to identify specific peptide binders.

Screen 1 generated 2 unique peptide sequences (Table 4) for testing as masking peptides for antibodies and CARs. Screen 2 yielded a total of 27 unique peptide sequences, from which 12 unique peptide sequences (Table 5) were selected for testing based on levels of sequence enrichment and performance in the validation assays after screening.

TABLE 4

Unique peptide sequences that mask the binding domain of Ab181 identified in Screen 1.

| Mask name | Sequence | SEQ ID NO: |
|---|---|---|
| P1 | EVAPGKRWFYNHVKQVPHLV | 1 |
| P2 | HEEVHMRPNKLSLTWAYTGPQLR | 2 |

TABLE 5

Unique peptide sequences that mask the binding domain of Ab181 identified in Screen 2.

| Mask name | Family | Selected shortlist | Sequence | SEQ ID NO: |
|---|---|---|---|---|
| M3 | 1 | CSP_R2_38 | CTMPPSPRSKVIC | 3 |
| M4 | 1 | CSP_R2_29 | CTFPNTTMQRTFC | 4 |
| M5 | 1 | CSP_R2_10 | CTYPSWVAYIRFC | 5 |
| M6 | 1 | CSP_R2_2 | VCTYPPAHRTRFC | 6 |
| M7 | 1 | CSP_R2_28 | CTMPYHIHSIGLC | 7 |
| M8 | 1 | CSP_R2_19 | WCTIPSSMSIRLC | 8 |
| M9 | 2 | CSP_R2_22 | CHIGKRPVPCLWI | 9 |
| M10 | 2 | CSP_R2_39 | CYIGLRMVPCFHM | 10 |
| M11 | 1 | CSP_R3P2_25 | CTMPSHAVASFLC | 11 |
| M12 | 1 | CSP_R3P3_53 | CTMPVHTYSQWLC | 12 |
| M13 | 1 | CSP_R3P2_26 | CTYPPRFHMHWLC | 13 |
| M14 | 3 | CSP_R2_25 | CTHVAQWAIKAFC | 14 |

Example 2: Engineering Masked Antibody and Masked CAR Constructs

Masked antibodies and masked CARs were designed using the sequences identified in the phage display library screens described in Example 1. For masked antibody constructs, the masking peptide was added to the Ab181 IgG1kappa heavy chain (HC) by a flexible linker sequence that also contained the substrate sequence (PLGLA; SEQ ID NO: 15) for Matrix Metalloproteinase (MMP) cleavage (Table 6). Masked CARs were designed by including the masking peptide sequence linked via the flexible PLGLA-substrate linker to the scFv of PTK7 CAR CTX-181, keeping the other elements of the CTX-181 sequence the same as the unmasked CAR (Table 7).

TABLE 6

Masked antibody sequences.

| Antibody | Heavy chain Sequence | Light chain sequence |
| --- | --- | --- |
| Ab181 | QVQLVESGGGVVQPGRSLRLSCAASGFTFSS YGMHWVRQAPGKGLEWVAVIWDDGSNKYYVD SVKGRFTISRDNSKNTLYLQMNSLRAEDTAV YYCARDDYYGSGSFNSYYGTDVWGQGTTVTV SSASTKGPSVFPLAPSSKSTSGGTAALGCLV KDYFPEPVTVSWNSGALTSGVHTFPAVLQSS GLYSLSSVVTVPSSSLGTQTYICNVNHKPSN TKVDKKVEPKSCDKTHTCPPCPAPELLGGPS VFLFPPKPKDTLMISRTPEVTCVVVDVSHED PEVKFNWYVDGVEVHNAKTKPREEQYNSTYR VVSVLTVLHQDWLNGKEYKCKVSNKALPAPI EKTISKAKGQPREPQVYTLPPSRDELTKNQV SLTCLVKGFYPSDIAVEWESNGQPENNYKTT PPVLDSDGSFFLYSKLTVDKSRWQQGNVFSC SVMHEALHNHYTQKSLSLSPGK (SEQ ID NO: 75) | EIVLTQSPATLSLSPGERATLSCRASQSVS IYLAWYQQKPGQAPRLLIYDASNRATGIPA RFSGSGSGTDFTLTISSLEPEDFAVYYCQQ RSNWPPFTFGPGTKVDIKRTVAAPSVFIFP PSDEQLKSGTASVVCLLNNFYPREAKVQWK VDNALQSGNSQESVTEQDSKDSTYSLSSTL TLSKADYEKHKVYACEVTHQGLSSPVTKSF NRGEC (SEQ ID NO: 74) |
| Ab181.P1 | EVAPGKRWFYNHVKQVPHLVGSSGGSGGSGGSGG GPLGLAGGSSGQVQLVESGGGVVQPGRSLRLSCA ASGFTFSSYGMHWVRQAPGKGLEWVAVIWDDGSN KYYVDSVKGRFTISRDNSKNTLYLQMNSLRAEDT AVYYCARDDYYGSGSFNSYYGTDVWGQGTTVTVS SASTKGPSVFPLAPSSKSTSGGTAALGCLVKDYF PEPVTVSWNSGALTSGVHTFPAVLQSSGLYSLSS VVTVPSSSLGTQTYICNVNHKPSNTKVDKKVEPK SCDKTHTCPPCPAPELLGGPSVFLFPPKPKDTLM ISRTPEVTCVVVDVSHEDPEVKFNWYVDGVEVHN AKTKPREEQYNSTYRVVSVLTVLHQDWLNGKEYK CKVSNKALPAPIEKTISKAKGQPREPQVYTLPPS RDELTKNQVSLTCLVKGFYPSDIAVEWESNGQPE NNYKTTPPVLDSDGSFFLYSKLTVDKSRWQQGNV FSCSVMHEALHNHYTQKSLSLSPGK (SEQ ID NO: 76) | Same as Ab181 |
| Ab181.P2 | HEEVHMRPNKLSLTWAYTGPQLRGSSGGSGGSGG SGGGPLGLAGGSSGQVQLVESGGGVVQPGRSLRL SCAASGFTFSSYGMHWVRQAPGKGLEWVAVIWDD GSNKYYVDSVKGRFTISRDNSKNTLYLQMNSLRA EDTAVYYCARDDYYGSGSFNSYYGTDVWGQGTTV TVSSASTKGPSVFPLAPSSKSTSGGTAALGCLVK DYFPEPVTVSWNSGALTSGVHTFPAVLQSSGLYS LSSVVTVPSSSLGTQTYICNVNHKPSNTKVDKKV EPKSCDKTHTCPPCPAPELLGGPSVFLFPPKPKD TLMISRTPEVTCVVVDVSHEDPEVKFNWYVDGVE VHNAKTKPREEQYNSTYRVVSVLTVLHQDWLNGK EYKCKVSNKALPAPIEKTISKAKGQPREPQVYTL PPSRDELTKNQVSLTCLVKGFYPSDIAVEWESNG QPENNYKTTPPVLDSDGSFFLYSKLTVDKSRWQQ GNVFSCSVMHEALHNHYTQKSLSLSPGK (SEQ ID NO: 77) | Same as Ab181 |
| Ab181.M3 | QGCTMPPSPRSKVICGSSGGSGGSGGSGGGPLGL AGGSSGQVQLVESGGGVVQPGRSLRLSCAASGFT FSSYGMHWVRQAPGKGLEWVAVIWDDGSNKYYVD SVKGRFTISRDNSKNTLYLQMNSLRAEDTAVYYC ARDDYYGSGSFNSYYGTDVWGQGTTVTVSSASTK GPSVFPLAPSSKSTSGGTAALGCLVKDYFPEPVT VSWNSGALTSGVHTFPAVLQSSGLYSLSSVVTVP SSSLGTQTYICNVNHKPSNTKVDKKVEPKSCDKT HTCPPCPAPELLGGPSVFLFPPKPKDTLMISRTP EVTCVVVDVSHEDPEVKFNWYVDGVEVHNAKTKP REEQYNSTYRVVSVLTVLHQDWLNGKEYKCKVSN KALPAPIEKTISKAKGQPREPQVYTLPPSRDELT KNQVSLTCLVKGFYPSDIAVEWESNGQPENNYKT TPPVLDSDGSFFLYSKLTVDKSRWQQGNVFSCSV MHEALHNHYTQKSLSLSPGK (SEQ ID NO: 78) | Same as Ab181 |

TABLE 6-continued

Masked antibody sequences.

| Antibody | Heavy chain Sequence | Light chain sequence |
|---|---|---|
| Ab181.M4 | QGCTFPNTTMQRTFCGSGGSGGSGGSGGGPLGL AGGSSGQVQLVESGGGVVQPGRSLRLSCAASGFT FSSYGMHWVRQAPGKGLEWVAVIWDDGSNKYYVD SVKGRFTISRDNSKNTLYLQMNSLRAEDTAVYYC ARDDYYGSGSFNSYYGTDVWGQGTTVTVSSASTK GPSVFPLAPSSKSTSGGTAALGCLVKDYFPEPVT VSWNSGALTSGVHTFPAVLQSSGLYSLSSVVTVP SSSLGTQTYICNVNHKPSNTKVDKKVEPKSCDKT HTCPPCPAPELLGGPSVFLFPPKPKDTLMISRTP EVTCVVVDVSHEDPEVKFNWYVDGVEVHNAKTKP REEQYNSTYRVVSVLTVLHQDWLNGKEYKCKVSN KALPAPIEKTISKAKGQPREPQVYTLPPSRDELT KNQVSLTCLVKGFYPSDIAVEWESNGQPENNYKT TPPVLDSDGSFFLYSKLTVDKSRWQQGNVFSCSV MHEALHNHYTQKSLSLSPGK (SEQ ID NO: 79) | Same as Ab181 |
| Ab181.M5 | QGCTYPSWVAYIRFCGSGGSGGSGGSGGGPLGL AGGSSGQVQLVESGGGVVQPGRSLRLSCAASGFT FSSYGMHWVRQAPGKGLEWVAVIWDDGSNKYYVD SVKGRFTISRDNSKNTLYLQMNSLRAEDTAVYYC ARDDYYGSGSFNSYYGTDVWGQGTTVTVSSASTK GPSVFPLAPSSKSTSGGTAALGCLVKDYFPEPVT VSWNSGALTSGVHTFPAVLQSSGLYSLSSVVTVP SSSLGTQTYICNVNHKPSNTKVDKKVEPKSCDKT HTCPPCPAPELLGGPSVFLFPPKPKDTLMISRTP EVTCVVVDVSHEDPEVKFNWYVDGVEVHNAKTKP REEQYNSTYRVVSVLTVLHQDWLNGKEYKCKVSN KALPAPIEKTISKAKGQPREPQVYTLPPSRDELT KNQVSLTCLVKGFYPSDIAVEWESNGQPENNYKT TPPVLDSDGSFFLYSKLTVDKSRWQQGNVFSCSV MHEALHNHYTQKSLSLSPGK (SEQ ID NO: 80) | Same as Ab181 |
| Ab181.M6 | QGVCTYPPAHRTRFCGSGGSGGSGGSGGGPLGL AGGSSGQVQLVESGGGVVQPGRSLRLSCAASGFT FSSYGMHWVRQAPGKGLEWVAVIWDDGSNKYYVD SVKGRFTISRDNSKNTLYLQMNSLRAEDTAVYYC ARDDYYGSGSFNSYYGTDVWGQGTTVTVSSASTK GPSVFPLAPSSKSTSGGTAALGCLVKDYFPEPVT VSWNSGALTSGVHTFPAVLQSSGLYSLSSVVTVP SSSLGTQTYICNVNHKPSNTKVDKKVEPKSCDKT HTCPPCPAPELLGGPSVFLFPPKPKDTLMISRTP EVTCVVVDVSHEDPEVKFNWYVDGVEVHNAKTKP REEQYNSTYRVVSVLTVLHQDWLNGKEYKCKVSN KALPAPIEKTISKAKGQPREPQVYTLPPSRDELT KNQVSLTCLVKGFYPSDIAVEWESNGQPENNYKT TPPVLDSDGSFFLYSKLTVDKSRWQQGNVFSCSV MHEALHNHYTQKSLSLSPGK (SEQ ID NO: 81) | Same as Ab181 |
| Ab181.M7 | QGCTMPYHIHSIGLCGSGGSGGSGGSGGGPLGL AGGSSGQVQLVESGGGVVQPGRSLRLSCAASGFT FSSYGMHWVRQAPGKGLEWVAVIWDDGSNKYYVD SVKGRFTISRDNSKNTLYLQMNSLRAEDTAVYYC ARDDYYGSGSFNSYYGTDVWGQGTTVTVSSASTK GPSVFPLAPSSKSTSGGTAALGCLVKDYFPEPVT VSWNSGALTSGVHTFPAVLQSSGLYSLSSVVTVP SSSLGTQTYICNVNHKPSNTKVDKKVEPKSCDKT HTCPPCPAPELLGGPSVFLFPPKPKDTLMISRTP EVTCVVVDVSHEDPEVKFNWYVDGVEVHNAKTKP REEQYNSTYRVVSVLTVLHQDWLNGKEYKCKVSN KALPAPIEKTISKAKGQPREPQVYTLPPSRDELT KNQVSLTCLVKGFYPSDIAVEWESNGQPENNYKT TPPVLDSDGSFFLYSKLTVDKSRWQQGNVFSCSV MHEALHNHYTQKSLSLSPGK (SEQ ID NO: 82) | Same as Ab181 |
| Ab181.M8 | QGWCTIPSSMSIRLCGSGGSGGSGGSGGGPLGL AGGSSGQVQLVESGGGVVQPGRSLRLSCAASGFT FSSYGMHWVRQAPGKGLEWVAVIWDDGSNKYYVD SVKGRFTISRDNSKNTLYLQMNSLRAEDTAVYYC ARDDYYGSGSFNSYYGTDVWGQGTTVTVSSASTK GPSVFPLAPSSKSTSGGTAALGCLVKDYFPEPVT VSWNSGALTSGVHTFPAVLQSSGLYSLSSVVTVP | Same as Ab181 |

TABLE 6-continued

Masked antibody sequences.

| Antibody | Heavy chain Sequence | Light chain sequence |
|---|---|---|
| | SSSLGTQTYICNVNHKPSNTKVDKKVEPKSCDKT<br>HTCPPCPAPELLGGPSVFLFPPKPKDTLMISRTP<br>EVTCVVVDVSHEDPEVKFNWYVDGVEVHNAKTKP<br>REEQYNSTYRVVSVLTVLHQDWLNGKEYKCKVSN<br>KALPAPIEKTISKAKGQPREPQVYTLPPSRDELT<br>KNQVSLTCLVKGFYPSDIAVEWESNGQPENNYKT<br>TPPVLDSDGSFFLYSKLTVDKSRWQQGNVFSCSV<br>MHEALHNHYTQKSLSLSPGK<br>(SEQ ID NO: 83) | |
| Ab181.M9 | QGCHIGKRPVPCLWIGSSGGSGGSGGSGGGPLGL<br>AGGSSGQVQLVESGGGVVQPGRSLRLSCAASGFT<br>FSSYGMHWVRQAPGKGLEWVAVIWDDGSNKYYVD<br>SVKGRFTISRDNSKNTLYLQMNSLRAEDTAVYYC<br>ARDDYYGSGSFNSYYGTDVWGQGTTVTVSSASTK<br>GPSVFPLAPSSKSTSGGTAALGCLVKDYFPEPVT<br>VSWNSGALTSGVHTFPAVLQSSGLYSLSSVVTVP<br>SSSLGTQTYICNVNHKPSNTKVDKKVEPKSCDKT<br>HTCPPCPAPELLGGPSVFLFPPKPKDTLMISRTP<br>EVTCVVVDVSHEDPEVKFNWYVDGVEVHNAKTKP<br>REEQYNSTYRVVSVLTVLHQDWLNGKEYKCKVSN<br>KALPAPIEKTISKAKGQPREPQVYTLPPSRDELT<br>KNQVSLTCLVKGFYPSDIAVEWESNGQPENNYKT<br>TPPVLDSDGSFFLYSKLTVDKSRWQQGNVFSCSV<br>MHEALHNHYTQKSLSLSPGK<br>(SEQ ID NO: 84) | Same as Ab181 |
| Ab181.M10 | QGCYIGLRMVPCFHMGSSGGSGGSGGSGGGPLGL<br>AGGSSGQVQLVESGGGVVQPGRSLRLSCAASGFT<br>FSSYGMHWVRQAPGKGLEWVAVIWDDGSNKYYVD<br>SVKGRFTISRDNSKNTLYLQMNSLRAEDTAVYYC<br>ARDDYYGSGSFNSYYGTDVWGQGTTVTVSSASTK<br>GPSVFPLAPSSKSTSGGTAALGCLVKDYFPEPVT<br>VSWNSGALTSGVHTFPAVLQSSGLYSLSSVVTVP<br>SSSLGTQTYICNVNHKPSNTKVDKKVEPKSCDKT<br>HTCPPCPAPELLGGPSVFLFPPKPKDTLMISRTP<br>EVTCVVVDVSHEDPEVKFNWYVDGVEVHNAKTKP<br>REEQYNSTYRVVSVLTVLHQDWLNGKEYKCKVSN<br>KALPAPIEKTISKAKGQPREPQVYTLPPSRDELT<br>KNQVSLTCLVKGFYPSDIAVEWESNGQPENNYKT<br>TPPVLDSDGSFFLYSKLTVDKSRWQQGNVFSCSV<br>MHEALHNHYTQKSLSLSPGK<br>(SEQ ID NO: 85) | Same as Ab181 |
| Ab181.M11 | QGCTMPSHAVASFLCGSSGGSGGSGGSGGGPLGL<br>AGGSSGQVQLVESGGGVVQPGRSLRLSCAASGFT<br>FSSYGMHWVRQAPGKGLEWVAVIWDDGSNKYYVD<br>SVKGRFTISRDNSKNTLYLQMNSLRAEDTAVYYC<br>ARDDYYGSGSFNSYYGTDVWGQGTTVTVSSASTK<br>GPSVFPLAPSSKSTSGGTAALGCLVKDYFPEPVT<br>VSWNSGALTSGVHTFPAVLQSSGLYSLSSVVTVP<br>SSSLGTQTYICNVNHKPSNTKVDKKVEPKSCDKT<br>HTCPPCPAPELLGGPSVFLFPPKPKDTLMISRTP<br>EVTCVVVDVSHEDPEVKFNWYVDGVEVHNAKTKP<br>REEQYNSTYRVVSVLTVLHQDWLNGKEYKCKVSN<br>KALPAPIEKTISKAKGQPREPQVYTLPPSRDELT<br>KNQVSLTCLVKGFYPSDIAVEWESNGQPENNYKT<br>TPPVLDSDGSFFLYSKLTVDKSRWQQGNVFSCSV<br>MHEALHNHYTQKSLSLSPGK<br>(SEQ ID NO: 86) | Same as Ab181 |
| Ab181.M12 | QGCTMPVHTYSQWLCGSSGGSGGSGGSGGGPLGL<br>AGGSSGQVQLVESGGGVVQPGRSLRLSCAASGFT<br>FSSYGMHWVRQAPGKGLEWVAVIWDDGSNKYYVD<br>SVKGRFTISRDNSKNTLYLQMNSLRAEDTAVYYC<br>ARDDYYGSGSFNSYYGTDVWGQGTTVTVSSASTK<br>GPSVFPLAPSSKSTSGGTAALGCLVKDYFPEPVT<br>VSWNSGALTSGVHTFPAVLQSSGLYSLSSVVTVP<br>SSSLGTQTYICNVNHKPSNTKVDKKVEPKSCDKT<br>HTCPPCPAPELLGGPSVFLFPPKPKDTLMISRTP<br>EVTCVVVDVSHEDPEVKFNWYVDGVEVHNAKTKP<br>REEQYNSTYRVVSVLTVLHQDWLNGKEYKCKVSN<br>KALPAPIEKTISKAKGQPREPQVYTLPPSRDELT | Same as Ab181 |

TABLE 6-continued

Masked antibody sequences.

| Antibody | Heavy chain Sequence | Light chain sequence |
|---|---|---|
| | KNQVSLTCLVKGFYPSDIAVEWESNGQPENNYKT TPPVLDSDGSFFLYSKLTVDKSRWQQGNVFSCSV MHEALHNHYTQKSLSLSPGK (SEQ ID NO: 87) | |
| Ab181.M13 | QGCTYPPRFHMHWLCGSSGGSGGSGGSGGGPLGL AGGSSGQVQLVESGGGVVQPGRSLRLSCAASGFT FSSYGMHWVRQAPGKGLEWVAVIWDDGSNKYYVD SVKGRFTISRDNSKNTLYLQMNSLRAEDTAVYYC ARDDYYGSGSFNSYYGTDVWGQGTTVTVSSASTK GPSVFPLAPSSKSTSGGTAALGCLVKDYFPEPVT VSWNSGALTSGVHTFPAVLQSSGLYSLSSVVTVP SSSLGTQTYICNVNHKPSNTKVDKKVEPKSCDKT HTCPPCPAPELLGGPSVFLFPPKPKDTLMISRTP EVTCVVVDVSHEDPEVKFNWYVDGVEVHNAKTKP REEQYNSTYRVVSVLTVLHQDWLNGKEYKCKVSN KALPAPIEKTISKAKGQPREPQVYTLPPSRDELT KNQVSLTCLVKGFYPSDIAVEWESNGQPENNYKT TPPVLDSDGSFFLYSKLTVDKSRWQQGNVFSCSV MHEALHNHYTQKSLSLSPGK (SEQ ID NO: 88) | Same as Ab181 |
| Ab181.M14 | QGCTHVAQWAIKAFCGSSGGSGGSGGSGGGPLGL AGGSSGQVQLVESGGGVVQPGRSLRLSCAASGFT FSSYGMHWVRQAPGKGLEWVAVIWDDGSNKYYVD SVKGRFTISRDNSKNTLYLQMNSLRAEDTAVYYC ARDDYYGSGSFNSYYGTDVWGQGTTVTVSSASTK GPSVFPLAPSSKSTSGGTAALGCLVKDYFPEPVT VSWNSGALTSGVHTFPAVLQSSGLYSLSSVVTVP SSSLGTQTYICNVNHKPSNTKVDKKVEPKSCDKT HTCPPCPAPELLGGPSVFLFPPKPKDTLMISRTP EVTCVVVDVSHEDPEVKFNWYVDGVEVHNAKTKP REEQYNSTYRVVSVLTVLHQDWLNGKEYKCKVSN KALPAPIEKTISKAKGQPREPQVYTLPPSRDELT KNQVSLTCLVKGFYPSDIAVEWESNGQPENNYKT TPPVLDSDGSFFLYSKLTVDKSRWQQGNVFSCSV MHEALHNHYTQKSLSLSPGK (SEQ ID NO: 89) | Same as Ab181 |

The mask peptide in each of the masked antibodies (Table 6) or masked CARs (Table 7) is in boldface and underlined. The heavy chain and light chain complementary determining regions in the parent Ab181 (following the Kabat numbering scheme) are boldfaced and italicized. See also Table 1 above. The signal sequence in the CAR sequences (Table 7) are italicized and the extracellular antigen-binding domain (not including the signal peptide) in each CAR construct is underlined.

TABLE 7

Masked CAR sequences.

| Masked CAR | CAR Sequence |
|---|---|
| CTX181 (unmasked CAR) | *MALPVTALLLPLALLLHAARP*QVQLVESGGGVVQPGRSLRLSCAASGFTFSSYGMHWVRQAPGKG LEWVAVIWDDGSNKYYVDSVKGRFTISRDNSKNTLYLQMNSLRAEDTAVYYCARDDYYGSGSFNS YYGTDVWGQGTTVTVSSGGGGSGGGGSGGGGSEIVLTQSPATLSLSPGERATLSCRASQSVSIYL AWYQQKPGQAPRLLIYDASNRATGIPARFSGSGSGTDFTLTISSLEPEDFAVYYCQQRSNWPPFT FGPGTKVDIKSAAAFVPVFLPAKPTTTPAPRPPTPAPTIASQPLSLRPEACRPAAGGAVHTRGLD FACDIYIWAPLAGTCGVLLLSLVITLYCNHRNRKRGRKKLLYIFKQPFMRPVQTTQEEDGCSCRF PEEEEGGCELRVKFSRSADAPAYQQGQNQLYNELNLGRREEYDVLDKRRGRDPEMGGKPRRKNPQ EGLYNELQKDKMAEAYSEIGMKGERRRGKGHDGLYQGLSTATKDTYDALHMQALPPR (with signal peptide SEQ ID NO: 90; with no signal peptide SEQ ID NO: 105; Extracellular domain SEQ ID NO: 120) |
| CTX181.P1 | *MALPVTALLLPLALLLHAARP*EVAPGKRWFYNHVKQVPHLVGSSGGSGGSGGSGGGPLGLAGGSS GQVQLVESGGGVVQPGRSLRLSCAASGFTFSSYGMHWVRQAPGKGLEWVAVIWDDGSNKYYVDSV KGRFTISRDNSKNTLYLQMNSLRAEDTAVYYCARDDYYGSGSFNSYYGTDVWGQGTTVTVSSGGG GSGGGGSGGGGSEIVLTQSPATLSLSPGERATLSCRASQSVSIYLAWYQQKPGQAPRLLIYDASN RATGIPARFSGSGSGTDFTLTISSLEPEDFAVYYCQQRSNWPPFTFGPGTKVDIKSAAAFVPVFL PAKPTTTPAPRPPTPAPTIASQPLSLRPEACRPAAGGAVHTRGLDFACDIYIWAPLAGTCGVLLL SLVITLYCNHRNRKRGRKKLLYIFKQPFMRPVQTTQEEDGCSCRFPEEEEGGCELRVKFSRSADA PAYQQGQNQLYNELNLGRREEYDVLDKRRGRDPEMGGKPRRKNPQEGLYNELQKDKMAEAYSEIG MKGERRRGKGHDGLYQGLSTATKDTYDALHMQALPPR (with signal peptide SEQ ID NO: 91; with no signal peptide SEQ ID NO: 106; Extracellular domain SEQ ID NO: 121) |

TABLE 7-continued

Masked CAR sequences.

| Masked CAR | CAR Sequence |
|---|---|

CTX181.P2  *MALPVTALLLPLALLLHAARP*__HEEVHMRPNKLSLTWAYTGPQLR__GSSGGSGGSGGGSGPLGLAGG
GSQVQLVESGGGVVQPGRSLRLSCAASGFTFSSYGMHWVRQAPGKGLEWVAVIWDDGSNKYYVDS
VKGRFTISRDNSKNTLYLQMNSLRAEDTAVYYCARDDYYGSGSFNSYYGTDVWGQGTTVTVSSGG
GGSGGGGSGGGGSEIVLTQSPATLSLSPGERATLSCRASQSVSIYLAWYQQKPGQAPRLLIYDAS
NRATGIPARFSGSGSGTDFTLTISSLEPEDFAVYYCQQRSNWPPFTFGPGTKVDIKSAAAFVPVF
LPAKPTTTPAPRPPTPAPTIASQPLSLRPEACRPAAGGAVHTRGLDFACDIYIWAPLAGTCGVLL
LSLVITLYCNHRNRSKRSRLLHSDYMNMTPRRPGPTRKHYQPYAPPRDFAAYRSRVKFSRSADAP
AYQQGQNQLYNELNLGRREEYDVLDKRRGRDPEMGGKPRRKNPQEGLYNELQKDKMAEAYSEIGM
KGERRRGKGHDGLYQGLSTATKDTYDALHMQALPPR
(with signal peptide SEQ ID NO: 92; with no signal peptide SEQ ID
NO: 107; Extracellular domain SEQ ID NO: 122)

CTX181.M3  *MALPVTALLLPLALLLHAARPQG*__CTMPPSPRSKVIC__GSSGGSGGSGGSGGGPLGLAGGSSGQVQL
VESGGGVVQPGRSLRLSCAASGFTFSSYGMHWVRQAPGKGLEWVAVIWDDGSNKYYVDSVKGRFT
ISRDNSKNTLYLQMNSLRAEDTAVYYCARDDYYGSGSFNSYYGTDVWGQGTTVTVSSGGGGSGGG
GSGGGGSEIVLTQSPATLSLSPGERATLSCRASQSVSIYLAWYQQKPGQAPRLLIYDASNRATGI
PARFSGSGSGTDFTLTISSLEPEDFAVYYCQQRSNWPPFTFGPGTKVDIKSAAAFVPVFLPAKPT
TTPAPRPPTPAPTIASQPLSLRPEACRPAAGGAVHTRGLDFACDIYIWAPLAGTCGVLLLSLVIT
LYCNHRNRSKRSRLLHSDYMNMTPRRPGPTRKHYQPYAPPRDFAAYRSRVKFSRSADAPAYQQGQ
NQLYNELNLGRREEYDVLDKRRGRDPEMGGKPRRKNPQEGLYNELQKDKMAEAYSEIGMKGERRR
GKGHDGLYQGLSTATKDTYDALHMQALPPR
(with signal peptide SEQ ID NO: 93; with no signal peptide SEQ ID
NO: 108; Extracellular domain SEQ ID NO: 123)

CTX181.M4  *MALPVTALLLPLALLLHAARPQG*__CTFPNTTMQRTFC__GSSGGSGGSGGSGGGPLGLAGGSSGQVQL
VESGGGVVQPGRSLRLSCAASGFTFSSYGMHWVRQAPGKGLEWVAVIWDDGSNKYYVDSVKGRFT
ISRDNSKNTLYLQMNSLRAEDTAVYYCARDDYYGSGSFNSYYGTDVWGQGTTVTVSSGGGGSGGG
GSGGGGSEIVLTQSPATLSLSPGERATLSCRASQSVSIYLAWYQQKPGQAPRLLIYDASNRATGI
PARFSGSGSGTDFTLTISSLEPEDFAVYYCQQRSNWPPFTFGPGTKVDIKSAAAFVPVFLPAKPT
TTPAPRPPTPAPTIASQPLSLRPEACRPAAGGAVHTRGLDFACDIYIWAPLAGTCGVLLLSLVIT
LYCNHRNRSKRSRLLHSDYMNMTPRRPGPTRKHYQPYAPPRDFAAYRSRVKFSRSADAPAYQQGQ
NQLYNELNLGRREEYDVLDKRRGRDPEMGGKPRRKNPQEGLYNELQKDKMAEAYSEIGMKGERRR
GKGHDGLYQGLSTATKDTYDALHMQALPPR
(with signal peptide SEQ ID NO: 94; with no signal peptide SEQ ID
NO: 109; Extracellular domain SEQ ID NO: 124)

CTX181.M5  *MALPVTALLLPLALLLHAARPQG*__CTYPSWVAYIRFC__GSSGGSGGSGGSGGGPLGLAGGSSGQVQL
VESGGGVVQPGRSLRLSCAASGFTFSSYGMHWVRQAPGKGLEWVAVIWDDGSNKYYVDSVKGRFT
ISRDNSKNTLYLQMNSLRAEDTAVYYCARDDYYGSGSFNSYYGTDVWGQGTTVTVSSGGGGSGGG
GSGGGGSEIVLTQSPATLSLSPGERATLSCRASQSVSIYLAWYQQKPGQAPRLLIYDASNRATGI
PARFSGSGSGTDFTLTISSLEPEDFAVYYCQQRSNWPPFTFGPGTKVDIKSAAAFVPVFLPAKPT
TTPAPRPPTPAPTIASQPLSLRPEACRPAAGGAVHTRGLDFACDIYIWAPLAGTCGVLLLSLVIT
LYCNHRNRSKRSRLLHSDYMNMTPRRPGPTRKHYQPYAPPRDFAAYRSRVKFSRSADAPAYQQGQ
NQLYNELNLGRREEYDVLDKRRGRDPEMGGKPRRKNPQEGLYNELQKDKMAEAYSEIGMKGERRR
GKGHDGLYQGLSTATKDTYDALHMQALPPR
(with signal peptide SEQ ID NO: 95; with no signal peptide SEQ ID
NO: 110; Extracellular domain SEQ ID NO: 125)

CTX181.M6  *MALPVTALLLPLALLLHAARP*QGV__CTYPPAHRTRFC__GSSGGSGGSGGSGGGPLGLAGGSSGQVQL
VESGGGVVQPGRSLRLSCAASGFTFSSYGMHWVRQAPGKGLEWVAVIWDDGSNKYYVDSVKGRFT
ISRDNSKNTLYLQMNSLRAEDTAVYYCARDDYYGSGSFNSYYGTDVWGQGTTVTVSSGGGGSGGG
GSGGGGSEIVLTQSPATLSLSPGERATLSCRASQSVSIYLAWYQQKPGQAPRLLIYDASNRATGI
PARFSGSGSGTDFTLTISSLEPEDFAVYYCQQRSNWPPFTFGPGTKVDIKSAAAFVPVFLPAKPT
TTPAPRPPTPAPTIASQPLSLRPEACRPAAGGAVHTRGLDFACDIYIWAPLAGTCGVLLLSLVIT
LYCNHRNRSKRSRLLHSDYMNMTPRRPGPTRKHYQPYAPPRDFAAYRSRVKFSRSADAPAYQQGQ
NQLYNELNLGRREEYDVLDKRRGRDPEMGGKPRRKNPQEGLYNELQKDKMAEAYSEIGMKGERRR
GKGHDGLYQGLSTATKDTYDALHMQALPPR
(with signal peptide SEQ ID NO: 96; with no signal peptide SEQ ID
NO: 111; Extracellular domain SEQ ID NO: 126)

CTX181.M7  *MALPVTALLLPLALLLHAARPQG*__CTMPYHIHSIGLC__GSSGGSGGSGGSGGGPLGLAGGSSGQVQL
VESGGGVVQPGRSLRLSCAASGFTFSSYGMHWVRQAPGKGLEWVAVIWDDGSNKYYVDSVKGRFT
ISRDNSKNTLYLQMNSLRAEDTAVYYCARDDYYGSGSFNSYYGTDVWGQGTTVTVSSGGGGSGGG
GSGGGGSEIVLTQSPATLSLSPGERATLSCRASQSVSIYLAWYQQKPGQAPRLLIYDASNRATGI
PARFSGSGSGTDFTLTISSLEPEDFAVYYCQQRSNWPPFTFGPGTKVDIKSAAAFVPVFLPAKPT
TTPAPRPPTPAPTIASQPLSLRPEACRPAAGGAVHTRGLDFACDIYIWAPLAGTCGVLLLSLVIT
LYCNHRNRSKRSRLLHSDYMNMTPRRPGPTRKHYQPYAPPRDFAAYRSRVKFSRSADAPAYQQGQ
NQLYNELNLGRREEYDVLDKRRGRDPEMGGKPRRKNPQEGLYNELQKDKMAEAYSEIGMKGERRR
GKGHDGLYQGLSTATKDTYDALHMQALPPR
(with signal peptide SEQ ID NO: 97; with no signal peptide SEQ ID
NO: 112; Extracellular domain SEQ ID NO: 127)

TABLE 7-continued

Masked CAR sequences.

Masked CAR  CAR Sequence

CTX181.M8   MALPVTALLLPLALLLHAARPQGWCTIPSSMSIRLCGSSGGSGGSGGSGGGPLGLAGGSSGQVQL
            VESGGGVVQPGRSLRLSCAASGFTFSSYGMHWVRQAPGKGLEWVAVIWDDGSNKYYVDSVKGRFT
            ISRDNSKNTLYLQMNSLRAEDTAVYYCARDDYYGSGSFNSYYGTDVWGQGTTVTVSSGGGGSGGG
            GSGGGGSEIVLTQSPATLSLSPGERATLSCRASQSVSIYLAWYQQKPGQAPRLLIYDASNRATGI
            PARFSGSGSGTDFTLTISSLEPEDFAVYYCQQRSNWPPFTFGPGTKVDIKSAAAFVPVFLPAKPT
            TTPAPRPPTPAPTIASQPLSLRPEACRPAAGGAVHTRGLDFACDIYIWAPLAGTCGVLLLSLVIT
            LYCNHRNRSKRSLLHSDYMNMTPRRPGPTRKHYQPYAPPRDFAAYRSRVKFSRSADAPAYQQGQ
            NQLYNELNLGRREEYDVLDKRRGRDPEMGGKPRRKNPQEGLYNELQKDKMAEAYSEIGMKGERRR
            GKGHDGLYQGLSTATKDTYDALHMQALPPR
            (with signal peptide SEQ ID NO: 98; with no signal peptide SEQ ID
            NO: 113; Extracellular domain SEQ ID NO: 128)

CTX181.M9   MALPVTALLLPLALLLHAARPQGCHIGKRPVPCLWIGSSGGSGGSGGSGGGPLGLAGGSSGQVQL
            VESGGGVVQPGRSLRLSCAASGFTFSSYGMHWVRQAPGKGLEWVAVIWDDGSNKYYVDSVKGRFT
            ISRDNSKNTLYLQMNSLRAEDTAVYYCARDDYYGSGSFNSYYGTDVWGQGTTVTVSSGGGGSGGG
            GSGGGGSEIVLTQSPATLSLSPGERATLSCRASQSVSIYLAWYQQKPGQAPRLLIYDASNRATGI
            PARFSGSGSGTDFTLTISSLEPEDFAVYYCQQRSNWPPFTFGPGTKVDIKSAAAFVPVFLPAKPT
            TTPAPRPPTPAPTIASQPLSLRPEACRPAAGGAVHTRGLDFACDIYIWAPLAGTCGVLLLSLVIT
            LYCNHRNRSKRSLLHSDYMNMTPRRPGPTRKHYQPYAPPRDFAAYRSRVKFSRSADAPAYQQGQ
            NQLYNELNLGRREEYDVLDKRRGRDPEMGGKPRRKNPQEGLYNELQKDKMAEAYSEIGMKGERRR
            GKGHDGLYQGLSTATKDTYDALHMQALPPR
            (with signal peptide SEQ ID NO: 99; with no signal peptide SEQ ID
            NO: 114; Extracellular domain SEQ ID NO: 129)

CTX181.M10  MALPVTALLLPLALLLHAARPQGCYIGLRMVPCFHMGSSGGSGGSGGSGGGPLGLAGGSSGQVQL
            VESGGGVVQPGRSLRLSCAASGFTFSSYGMHWVRQAPGKGLEWVAVIWDDGSNKYYVDSVKGRFT
            ISRDNSKNTLYLQMNSLRAEDTAVYYCARDDYYGSGSFNSYYGTDVWGQGTTVTVSSGGGGSGGG
            GSGGGGSEIVLTQSPATLSLSPGERATLSCRASQSVSIYLAWYQQKPGQAPRLLIYDASNRATGI
            PARFSGSGSGTDFTLTISSLEPEDFAVYYCQQRSNWPPFTFGPGTKVDIKSAAAFVPVFLPAKPT
            TTPAPRPPTPAPTIASQPLSLRPEACRPAAGGAVHTRGLDFACDIYIWAPLAGTCGVLLLSLVIT
            LYCNHRNRSKRSLLHSDYMNMTPRRPGPTRKHYQPYAPPRDFAAYRSRVKFSRSADAPAYQQGQ
            NQLYNELNLGRREEYDVLDKRRGRDPEMGGKPRRKNPQEGLYNELQKDKMAEAYSEIGMKGERRR
            GKGHDGLYQGLSTATKDTYDALHMQALPPR
            (with signal peptide SEQ ID NO: 100; with no signal peptide SEQ
            ID NO: 115; Extracellular domain SEQ ID NO: 130)

CTX181.M11  MALPVTALLLPLALLLHAARPQGCTMPSRAVASFLCGSSGGSGGSGGSGGGPLGLAGGSSGQVQL
            VESGGGVVQPGRSLRLSCAASGFTFSSYGMHWVRQAPGKGLEWVAVIWDDGSNKYYVDSVKGRFT
            ISRDNSKNTLYLQMNSLRAEDTAVYYCARDDYYGSGSFNSYYGTDVWGQGTTVTVSSGGGGSGGG
            GSGGGGSEIVLTQSPATLSLSPGERATLSCRASQSVSIYLAWYQQKPGQAPRLLIYDASNRATGI
            PARFSGSGSGTDFTLTISSLEPEDFAVYYCQQRSNWPPFTFGPGTKVDIKSAAAFVPVFLPAKPT
            TTPAPRPPTPAPTIASQPLSLRPEACRPAAGGAVHTRGLDFACDIYIWAPLAGTCGVLLLSLVIT
            LYCNHRNRSKRSLLHSDYMNMTPRRPGPTRKHYQPYAPPRDFAAYRSRVKFSRSADAPAYQQGQ
            NQLYNELNLGRREEYDVLDKRRGRDPEMGGKPRRKNPQEGLYNELQKDKMAEAYSEIGMKGERRR
            GKGHDGLYQGLSTATKDTYDALHMQALPPR
            (with signal peptide SEQ ID NO: 101; with no signal peptide SEQ
            ID NO: 116; Extracellular domain SEQ ID NO: 131)

CTX181.M12  MALPVTALLLPLALLLRAARPQGCTMPVHTYSQWLCGSSGGSGGSGGSGGGPLGLAGGSSGQVQL
            VESGGGVVQPGRSLRLSCAASGFTFSSYGMHWVRQAPGKGLEWVAVIWDDGSNKYYVDSVKGRFT
            ISRDNSKNTLYLQMNSLRAEDTAVYYCARDDYYGSGSFNSYYGTDVWGQGTTVTVSSGGGGSGGG
            GSGGGGSEIVLTQSPATLSLSPGERATLSCRASQSVSIYLAWYQQKPGQAPRLLIYDASNRATGI
            PARFSGSGSGTDFTLTISSLEPEDFAVYYCQQRSNWPPFTFGPGTKVDIKSAAAFVPVFLPAKPT
            TTPAPRPPTPAPTIASQPLSLRPEACRPAAGGAVHTRGLDFACDIYIWAPLAGTCGVLLLSLVIT
            LYCNHRNRSKRSLLHSDYMNMTPRRPGPTRKHYQPYAPPRDFAAYRSRVKFSRSADAPAYQQGQ
            NQLYNELNLGRREEYDVLDKRRGRDPEMGGKPRRKNPQEGLYNELQKDKMAEAYSEIGMKGERRR
            GKGHDGLYQGLSTATKDTYDALHMQALPPR
            (with signal peptide SEQ ID NO: 102; with no signal peptide SEQ
            ID NO: 117; Extracellular domain SEQ ID NO: 132)

CTX181.M13  MALPVTALLLPLALLLRAARPQGCTYPPRFMHHWLCGSSGGSGGSGGSGGGPLGLAGGSSGQVQL
            VESGGGVVQPGRSLRLSCAASGFTFSSYGMHWVRQAPGKGLEWVAVIWDDGSNKYYVDSVKGRFT
            ISRDNSKNTLYLQMNSLRAEDTAVYYCARDDYYGSGSFNSYYGTDVWGQGTTVTVSSGGGGSGGG
            GSGGGGSEIVLTQSPATLSLSPGERATLSCRASQSVSIYLAWYQQKPGQAPRLLIYDASNRATGI
            PARFSGSGSGTDFTLTISSLEPEDFAVYYCQQRSNWPPFTFGPGTKVDIKSAAAFVPVFLPAKPT
            TTPAPRPPTPAPTIASQPLSLRPEACRPAAGGAVHTRGLDFACDIYIWAPLAGTCGVLLLSLVIT
            LYCNHRNRSKRSLLHSDYMNMTPRRPGPTRKHYQPYAPPRDFAAYRSRVKFSRSADAPAYQQGQ
            NQLYNELNLGRREEYDVLDKRRGRDPEMGGKPRRKNPQEGLYNELQKDKMAEAYSEIGMKGERRR
            GKGHDGLYQGLSTATKDTYDALHMQALPPR
            (with signal peptide SEQ ID NO: 103; with no signal peptide SEQ
            ID NO: 118; Extracellular domain SEQ ID NO: 133)

TABLE 7-continued

Masked CAR sequences.

| Masked CAR | CAR Sequence |
|---|---|
| CTX181.M14 | *MALPVTALLLPLALLLRAARP*QGCTHVAQWAIKAFCGSSGGSGGSGGSGGGPLGLAGGSSGQVQL<br>VESGGGVVQPGRSLRLSCAASGFTFSSYGMHWVRQAPGKGLEWVAVIWDDGSNKYYVDSVKGRFT<br>ISRDNSKNTLYLQMNSLRAEDTAVYYCARDDYYGSGSFNSYYGTDVWGQGTTVTVSSGGGGSGGG<br>GSGGGGSEIVLTQSPATLSLSPGERATLSCRASQSVSIYLAWYQQKPGQAPRLLIYDASNRATGI<br>PARFSGSGSGTDFTLTISSLEPEDFAVYYCQQRSNWPPFTFGPGTKVDIKSAAAFVPVFLPAKPT<br>TTPAPRPPTPAPTIASQPLSLRPEACRPAAGGAVHTRGLDFACDIYIWAPLAGTCGVLLLSLVIT<br>LYCNHRNRSKRSRLLHSDYMNMTPRRPGPTRKHYQPYAPPRDFAAYRSRVKFSRSADAPAYQQGQ<br>NQLYNELNLGRREEYDVLDKRRGRDPEMGGKPRRKNPQEGLYNELQKDKMAEAYSEIGMKGERRR<br>GKGHDGLYQGLSTATKDTYDALHMQALPPR<br>(with signal peptide SEQ ID NO: 104; with no signal peptide SEQ ID NO: 119; Extracellular domain SEQ ID NO: 134) |

Figure 1B:
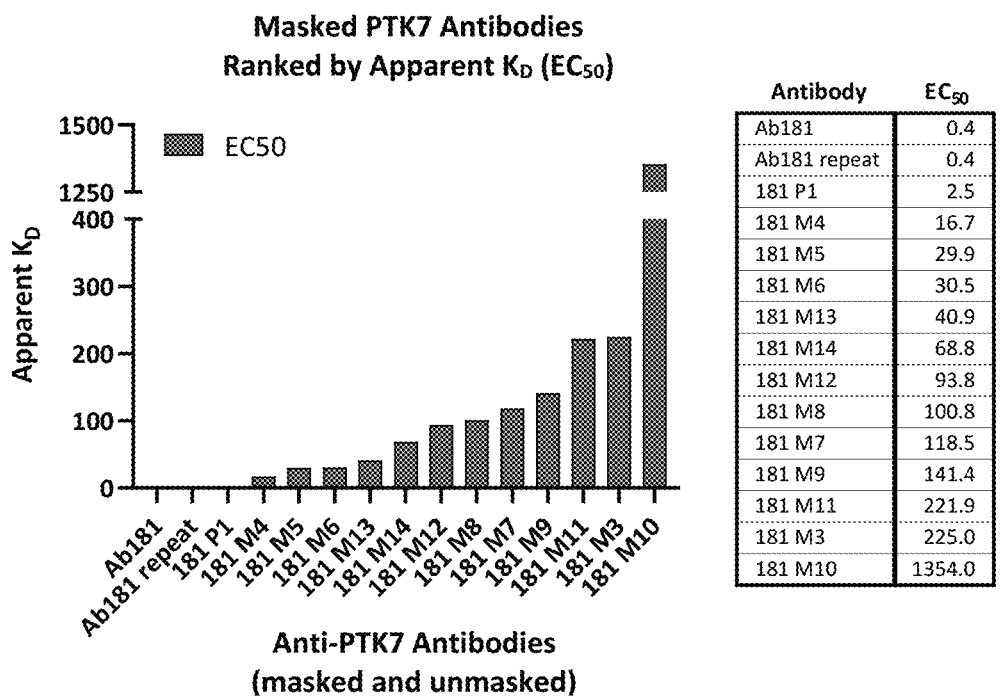

Example 3: Determining Binding Affinities of Masked Anti-PTK7 Antibodies and Reversal of Binding Inhibition by MMP14 Treatment To test the ability of the different masking peptides to mask and/or inhibit binding of the anti-PTK7 antibody, binding titration assay were performed on PTK7 positive cell line SaOS-2 (osteosarcoma). Cells were plated (0.2×10$^6$ cells/per well) and incubated with a dose titration (500 nM to 0.011 nM) of the antibodies listed in Table 6. Cells were incubated with antibodies for 30 minutes at 4° C. followed by washing and incubation with a universal secondary antibody, mouse anti-human.Fc conjugated to APC (Biolegend cat #409305) for another 30 minutes at 4° C. Following washing, cells were fixed in a fixation buffer (IC Fixation Buffer, eBioscience cat #00-8222-49) at a 1:1 ratio, total volume of 200 μL, and run on a flow cytometer (Novocyte), collecting 10,000 events per well. Percent positive cells were calculated according to baselines set by no antibody controls (0 nM), and geometric Mean Fluorescent Intensities (MFI) of the total singlet cell populations were used to establish binding titration curves using 4-parameter nonlinear regression formula (Prism Graphpad) (FIG. 1A). Apparent EC$_{50}$ values were calculated from binding curves, and masking peptides were ranked in order of lowest to highest EC$_{50}$ as shown in FIG. 1B.

These results demonstrate the range of binding affinities of the different masking peptides in masked antibody format, which enables the masking peptides in masked antibody format to be used to inhibit binding of Ab181 to antigen PTK7 on target cells.

Figure 2A:
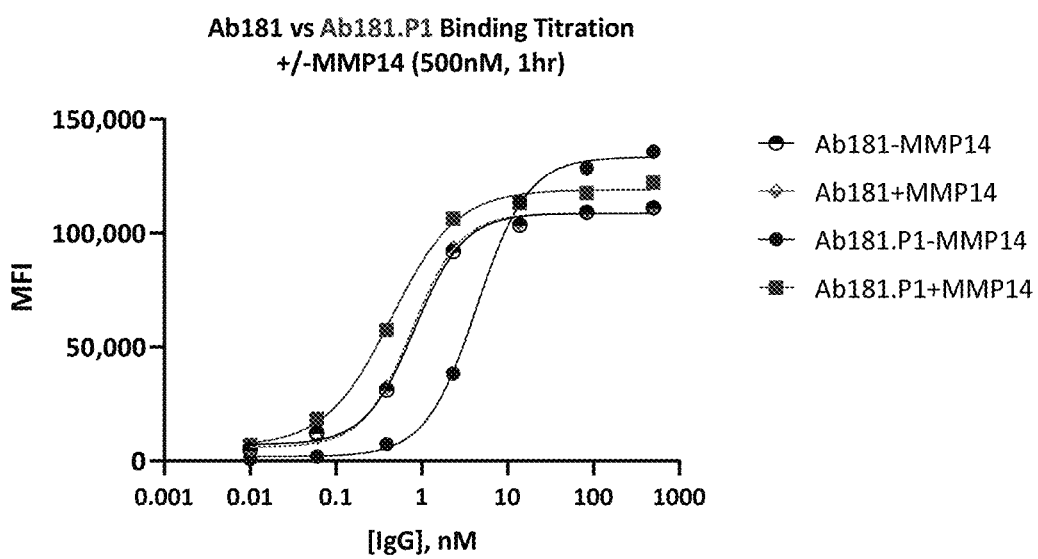
FIGS. 2A-2G include data showing that masking peptides inhibit binding of anti-PTK7 antibodies to PTK7 positive cells (SaOS-2 cells; osteosarcoma). The binding inhibition of masked anti-PTK7 antibodies is disrupted by treatment of the masked antibody with MMP, the protease that cleaves the linker connecting the masking peptide to the antibody.
Figure 2B:
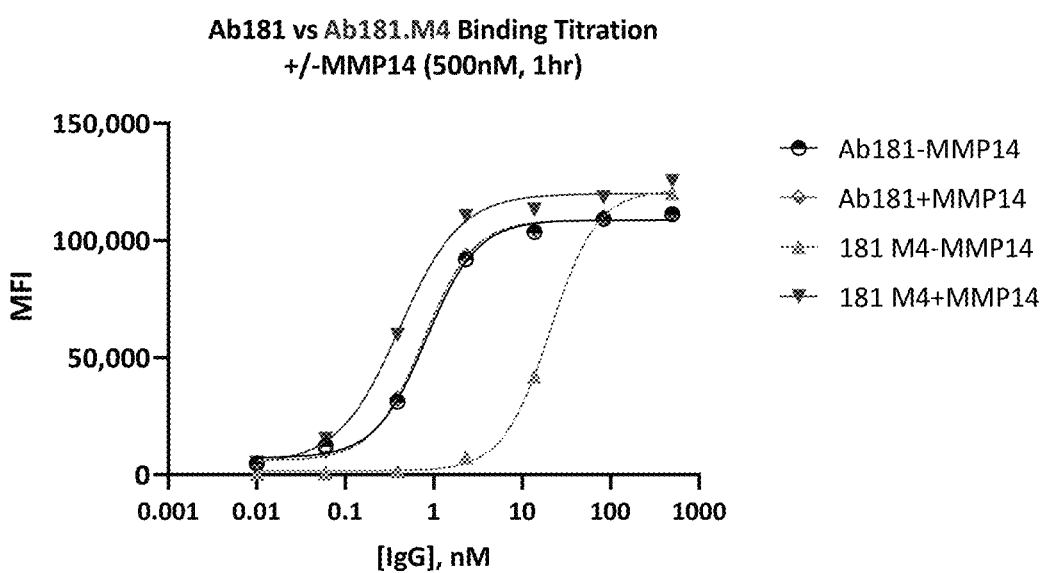
Figure 2C:
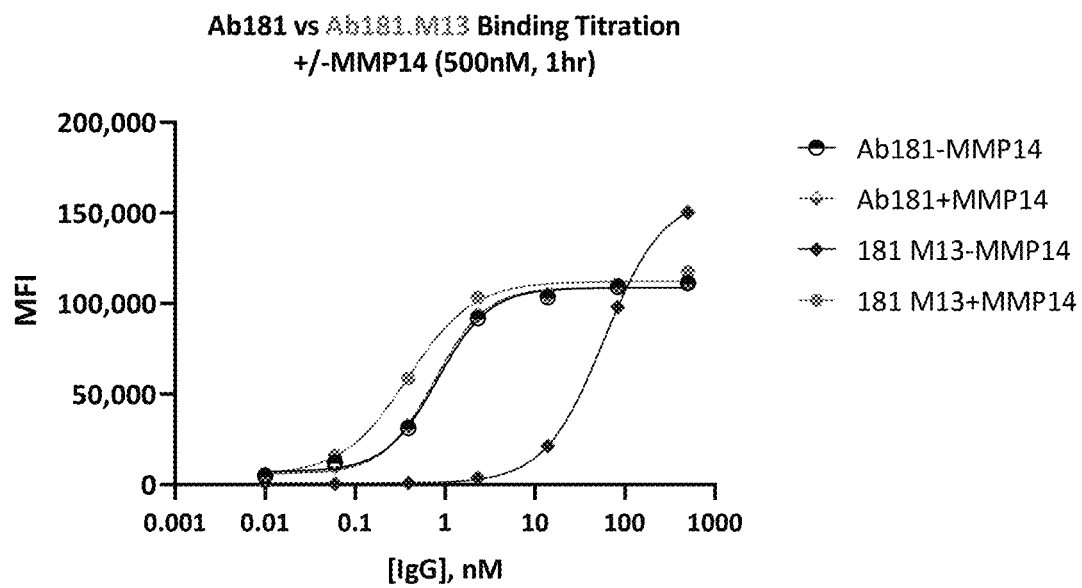
Figure 2D:
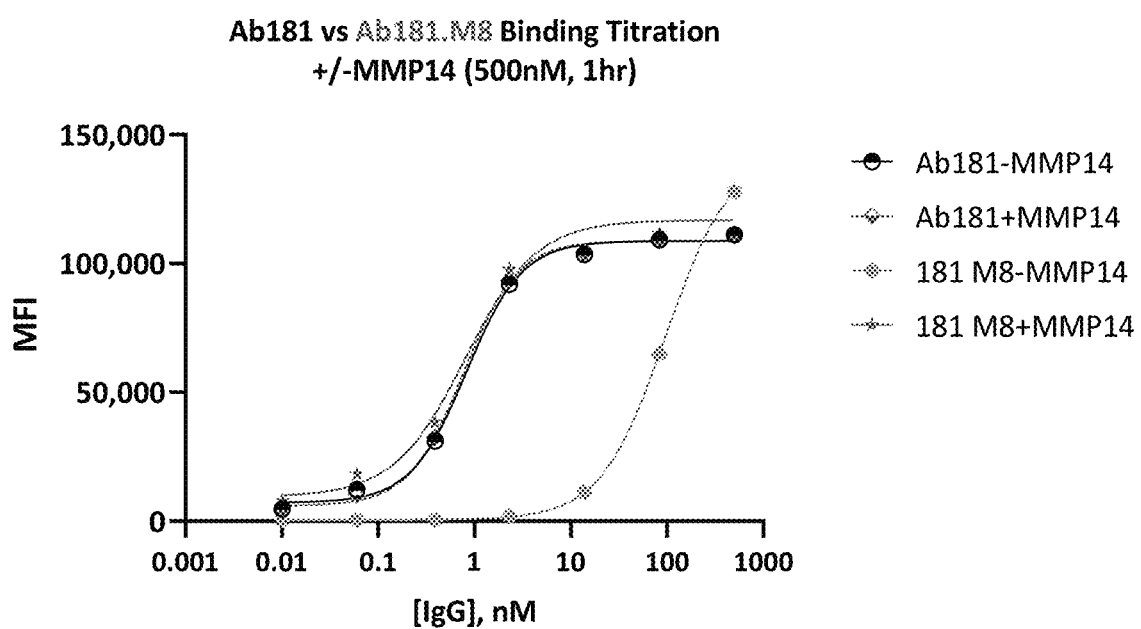
Figure 2E:
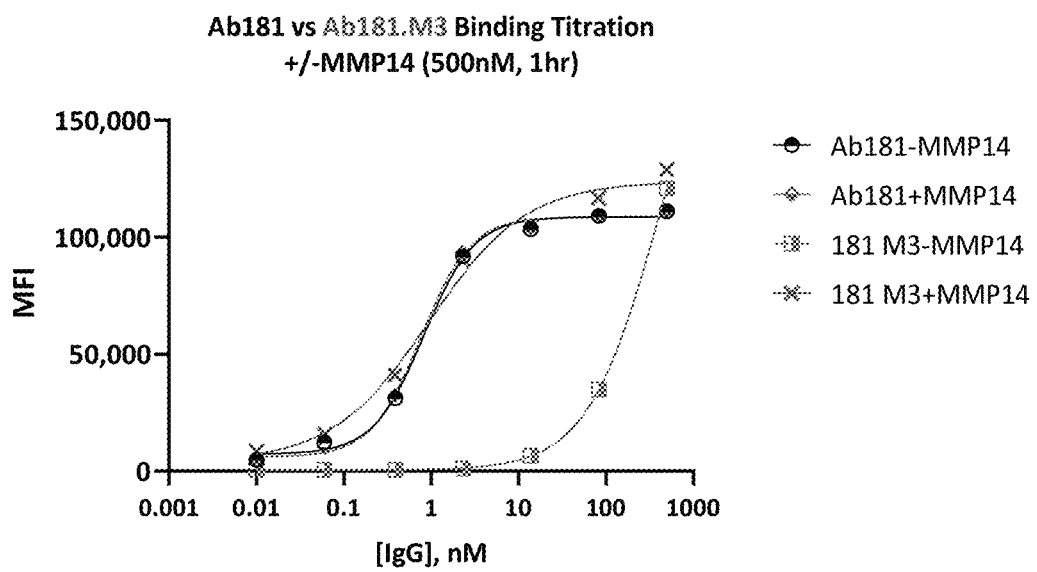
Figure 2F:
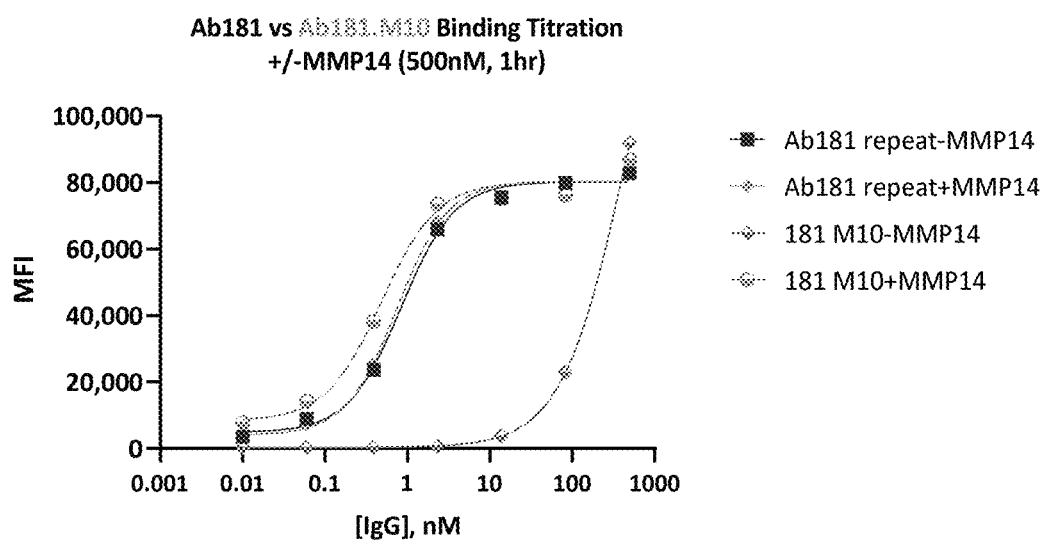
Figure 2G:
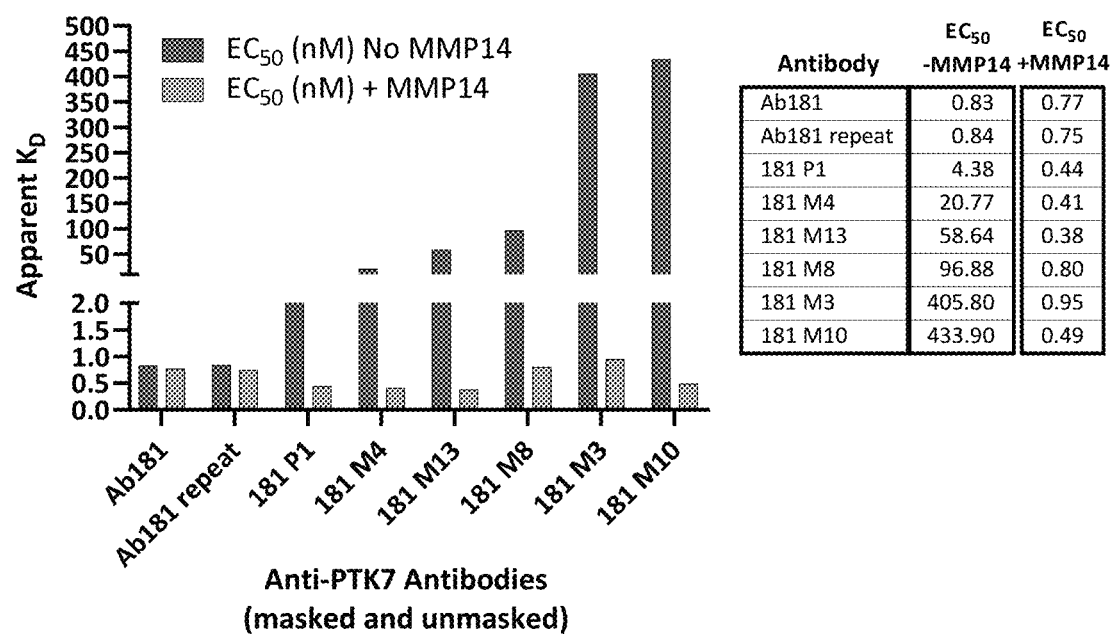

In addition to assessing the strength of the masking peptides for inhibiting antibody binding to PTK7 on the cell surface, it was demonstrated that this inhibition was reversible when the masked antibody was treated with MMP, the protease that cleaves the linker connecting the masking peptide to the antibody. MMP2, MMP 9 and MMP 14 were tested for the ability to cleave this sequence using in vitro binding assays. MMP14 provided more robust cleavage than MMP2 and MMP9, and therefore mask reversal studies were performed using MMP14. A subset of masked antibodies (6) were selected from the 14 candidates based on binding curve profile, sequence similarity, and apparent EC$_{50}$. Masked and unmasked antibodies were each incubated with 500 nM MMP14 (Enzo Biosciences Cat #ALX-201-098-C010) for 1 hour at room temperature before being used in a dose titration assay, alongside untreated antibodies, as described in Example 1. Binding titration curves (FIGS. 2A-2E) and apparent EC$_{50}$ values (FIG. 2G) were calculated as described in Example 1.

These results demonstrated that MMP14 treatment of the masked antibodies led to effective reversal of their masking effect, regardless of the strength of the masking peptide, thereby highlighting that the masking peptide activity can be regulated.

Example 4: CAR Expression and Detection in Masked CAR T Cells

Activated primary human T cells were electroporated with Cas9:gRNA RNP complexes and adeno-associated adenoviral vectors (AAVs) to generate TRAC$^-$/β2M$^-$/anti-PTK7 CAR$^+$ or TRAC$^-$/β2M$^-$/masked-anti-PTK7 CAR$^+$ T cells. Recombinant AAV serotype 6 (AAV6) comprising one of the nucleotide sequences encoding an anti-PTK7 CAR (SEQ ID NO: 90 in Table 7 above) or masked anti-PTK7 CARs (masked CARs; SEQ ID NO: 91-104 in Table 7 above) were delivered with Cas9:sgRNA RNPs (1 μM Cas9, 5 μM gRNA) to activated allogeneic human T cells. In some examples, a sgRNA targeting a TRAC gene site (e.g., SEQ ID NO: 40) and/or a sgRNA targeting a β2M site (e.g., SEQ ID NO: 54), either modified or unmodified, may be used.

Figure 3:
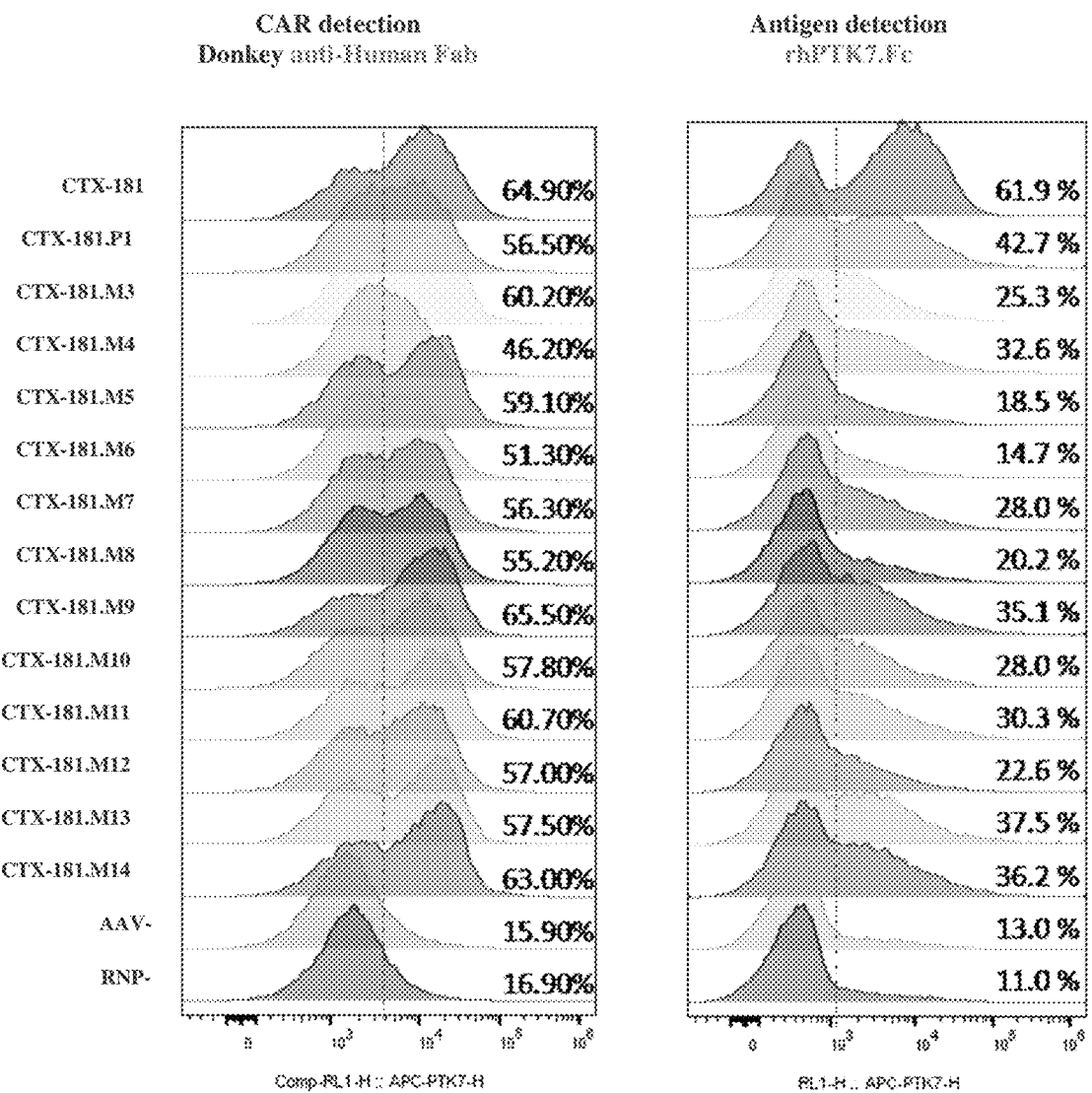
FIG. 3 includes flow cytometry data showing that anti-PTK7 CAR and masked anti-PTK7 CARs have similar surface expression but masking peptides on masked CARs reduce binding to soluble antigen PTK7.

About one (1) week post electroporation, cells were processed for flow cytometry to assess TRAC and β2M knockout levels, and anti-PTK7 CAR/masked anti-PTK7 CAR expression levels on the cell surface of the edited cell population (FIG. 3). For all CAR T cells and TRAC$^-$/β2M$^-$ control cells tested, >90% of viable cells lacked expression of TCR and >65% lacked expression of β2M. Live CAR T cells were gated by their forward scatter (FSC) and side scatter (SSC) profiles, and with 7-AAD dye (BD Biosciences cat #559925). The cells were then stained with a panel of antibodies indicated in Table 8.

TABLE 8

CAR T cell surface expression antibody panel.

| Antibody | Company | Catalogue # | Clone | Fluor | Dilution |
|---|---|---|---|---|---|
| IgG, F(ab')$_2$ fragment specific | Jackson Immunoresearch | 109-006-097 | polyclonal | Biotinylated; detected with SA-APC | 1:20 |

TABLE 8-continued

CAR T cell surface expression antibody panel.

| Antibody | Company | Catalogue # | Clone | Fluor | Dilution |
|---|---|---|---|---|---|
| TCRαβ | Miltenyi | 130-099-661 | BW242/412 | PE | 1:100 |
| β2M | Biolegend | 316318 | 2M2 | PECy7 | 1:100 |
| CD8 | Biolegend | 344742 | SK1 | BV605 | 1:100 |
| CD4 | Biolegend | 300546 | RPA-T4 | BV510 | 1:100 |
| Streptavidin-APC (SA-APC) | eBioscience through ThermoFisher | 17-4317-82 | N/A | APC | 1:100 |
| 7-AAD | BD Biosciences | 559925 | N/A | PerCP range | 1:500 |

In addition to detecting surface CAR expression, the ability of the CAR T cells and masked CAR T cells to detect target antigen was also determined. Live CAR T cells were gated by their forward scatter (FSC) and side scatter (SSC) profiles, and with DAPI dye (Invitrogen, catalog #: D3571). The cells were then stained with 10 μg/mL recombinant human PTK7.Fc (R and D Systems, catalog #9799-TK Lot DHMCO219041) as described above in Example 3, and with mouse anti-human.Fc conjugated to APC (Biolegend cat #409305) as secondary antibody for detection (FIG. 3). Percent positive populations for surface CAR expression and antigen detection are shown in Table 9.

TABLE 9

CAR surface expression and antigen detection levels for anti-PTK7 CARs and Masked anti-PTK7 CARs.

| CAR Construct | % CAR Expression | % Antigen detection |
|---|---|---|
| CTX181 | 64.9 | 61.9 |
| CTX181.P1 | 56.5 | 42.7 |
| CTX181.M3 | 60.2 | 25.3 |
| CTX181.M4 | 46.2 | 32.6 |
| CTX181.M5 | 59.1 | 18.5 |
| CTX181.M6 | 51.3 | 14.7 |
| CTX181.M7 | 56.3 | 28.0 |
| CTX181.M8 | 55.2 | 20.2 |
| CTX181.M9 | 65.5 | 35.1 |
| CTX181.M10 | 57.8 | 28.0 |
| CTX181.M11 | 60.7 | 30.3 |
| CTX181.M12 | 57.0 | 22.6 |
| CTX181.M13 | 57.5 | 37.5 |
| CTX181.M14 | 63.0 | 36.2 |
| AAV negative | 15.9 | 13.0 |
| RNP negative | 16.9 | 11.0 |

Taken together, these results show that CAR and masked CAR constructs were expressed at similar levels on the surface of T cells, and that masked CARs were able to mask/inhibit binding to target antigen PTK7.Fc compared to the unmasked CAR CTX181. These results were consistent with the range of masking affinities observed with masked antibody binding to target cells, and demonstrated that masking the CAR affected binding to target, but not expression of the CAR on T cells.

Example 5: Cell Killing Function of Masked CAR T Cells

A cell killing (cytotoxicity) assay was used to assess the ability of the TRAC⁻/β2M⁻/anti-PTK7 CAR T cells and masked CAR T cells (TRAC⁻/β2M⁻/masked anti-PTK7 CAR T cells) to cause cellular lysis in osteosarcoma, breast cancer and adherent kidney carcinoma cell lines (SaOS-2, MCF7 & A498, respectively), which express PTK7 to varying degrees. Adherent cells were seeded in 96-well plates at 12,500 or 25,000 cells per well and incubated overnight at 37° C. During the following day, CAR T cells and masked CAR T cells were added to the wells containing target cells at ratios of 1:0.5 or 1:1 effector:target cell. AAV negative (TRAC⁻/β2M⁻) and RNP negative (unedited) T cells were used as a negative control. After approximately 20 hours, 120 μL of supernatant was removed for cytokine quantification. T cells were removed from the culture by aspiration and 100 μL Cell titer-Glo (Promega) was added to each well of the plate to assess the number of remaining viable cells. The amount of light emitted from each well was then quantified using a plate reader.

The anti-PTK7 CAR and masked anti-PTK7 CAR T cells showed a range of cytotoxic activity against both SaOS-2 (high PTK7; FIG. 4A) and MCF-7 (medium PTK7; FIG. 4B) cells, and showed an insignificant effect on A498 cells that express little to no PTK7. Unmasked anti-PTK7 CAR T cells (CTX181 cells) were used as a control. Masked CAR T cells were ranked according to their cytotoxicity against SaOS-2 cells (Table 10), which revealed that in vitro potency appeared to trend with the level of masking observed with soluble recombinant human PTK7.Fc as shown in Table 9. These results suggest that the cytotoxic effects of unmasked anti-PTK7 CAR T cells can be inhibited by the masking peptides disclosed herein.

TABLE 10

Ranking of Masked Anti-PTK7 CARs based on % cytotoxicity in SaOS-2 cells at E:T = 1:0.5 ratio.

| Sample | % Cell killing at E:T = 1:0.5 | % Cell killing at E:T = 1:1 |
|---|---|---|
| CTX-181 | 97.1 | 96.6 |
| CTX-181.P1 | 92.7 | 79.1 |
| CTX-181-M4 | 78.4 | 54.6 |
| CTX-181-M13 | 68.6 | 41.3 |
| CTX-181-M14 | 52.8 | 29.5 |
| CTX-181-M9 | 43.3 | 31.9 |
| CTX-181-M6 | 42.4 | 13.9 |
| CTX-181-M3 | 39.0 | 17.8 |
| CTX-181-M7 | 37.5 | 10.2 |
| CTX-181-M10 | 32.7 | 25.8 |
| CTX-181-M5 | 29.6 | −0.8 |
| CTX-181-M12 | 29.5 | 18.5 |
| CTX-181-M11 | 20.1 | 12.7 |
| CTX-181-M8 | 15.4 | 3.9 |
| AAV- | −7.0 | −18.2 |
| RNP- | −7.1 | −13.1 |

Example 6: Effector Cytokine Secretion of Masked CAR T Cells

Functional activity of masked CAR T cells was further assessed using cytokine release assays for Interferon gamma (IFNγ) and Interleukin-2 (IL2) Unmasked anti-PTK7 CAR T cells (CTX181 T cells) were used as a control. T cells were incubated with target cells SaOS-2, MCF7 & A498, that express PTK7 to varying degrees at cellular ratios as described in Example 5. After 20 hours, supernatant media from the co-cultured cells were collected and the levels of IFNγ and IL2 were measured using an ELISA (RD Systems) following the manufacturer's instructions. The MILLIPLEX kit (Millipore, catalog #HCYTOMAG-60K) using magnetic microspheres, HCYIFNG-MAG (Millipore, catalog #HCYIFNG-MAG) and HIL2-MAG (Millipore, catalog #HIL2-MAG), respectively, was used to quantify IFNγ and IL-2 secretion in samples from the cytotoxicity assay. The assay was conducted following manufacturer's protocol.

Figure 5B:
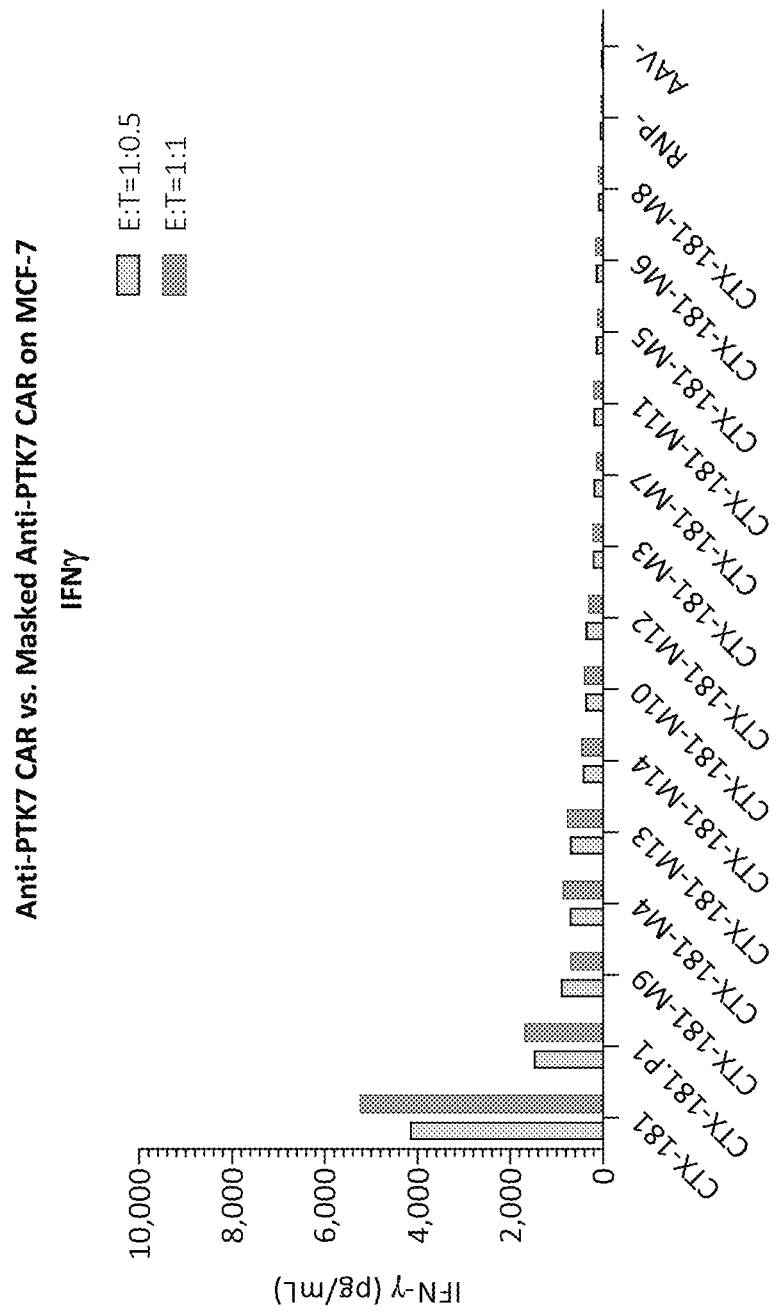

Results showed that anti-PTK7 CAR T cells and masked anti-PTK7 CAR T cells, when co-cultured at a 1:0.5 or 1:1 effector:target cell ratio, secreted IFNγ in the presence of PTK7 expressing cancer cell lines SaOS-2 (FIG. 5A and Table 11) and MCF7 (FIG. 5B). Little to no IFNγ was secreted by anti-PTK7 CAR T cells and masked anti-PTK7 CAR T cells in the presence of A498 (a low to negative PTK7 expressing cell line) (FIG. 5C). Low IL2 levels were detected from SaOS-2 cultures incubated with masked CAR T cells, and no significant differences were observed between the masked CAR constructs (FIG. 5D). The control cells TCR−/β2M− (AAV negative) and non-edited (RNP negative) showed no specific IFNγ or IL2 secretory response in the presence of any of the cancer cell lines listed.

TABLE 11

Ranking of Masked Anti-PTK7 CARs based on IFNγ secretion in SaOS-2 cells at E:T = 1:0.5 ratio.

| Sample | IFNγ (pg/mL) at E:T = 1:0.5 | IFNγ (pg/mL) at E:T = 1:1 |
| --- | --- | --- |
| CTX-181 | 22,298.0 | 34,931.0 |
| CTX-181.P1 | 13,629.0 | 20,498.0 |
| CTX-181-M4 | 9,554.0 | 13,206.0 |
| CTX-181-M13 | 4,860.0 | 6,172.0 |
| CTX-181-M9 | 4,364.0 | 4,611.0 |
| CTX-181-M12 | 2,422.2 | 1,766.2 |
| CTX-181-M10 | 2,113.0 | 1,877.3 |
| CTX-181-M14 | 1,756.7 | 1,925.2 |
| CTX-181-M7 | 885.4 | 829.7 |
| CTX-181-M11 | 883.9 | 886.9 |
| CTX-181-M3 | 833.0 | 798.6 |
| CTX-181-M6 | 734.9 | 715.1 |
| CTX-181-M5 | 522.7 | 459.2 |
| CTX-181-M8 | 400.2 | 442.8 |
| RNP− | 184.2 | 125.1 |
| AAV− | 165.8 | 96.7 |

Taken together, the functional assays described herein demonstrated that anti-PTK7 CAR T cells were cytotoxic towards and secreted IFNγ in the presence of PTK7 expressing cells, and that masked anti-PTK7 CAR T cells showed varying decreased levels of these activities in vitro. Accordingly, the functional effects of anti-PTK7 CAR T cells may be inhibited using the masking peptides disclosed herein.

Example 7: In Vivo Efficacy of Anti-PTK7 CAR T Cells and Masked Anti-Ptk7 CAR T Cells in Xenograft Mouse Models Previous in vivo xenograft studies have consistently shown transient body weight loss and higher levels of CAR T cells in mice treated with the anti-PTK7 CAR suggesting that the anti-PTK7 CAR recognizes an antigen in the mouse, which resulted in CAR T cell proliferation. This observation indicated that cross reactivity occurred between murine PTK7 expressed in mouse tissues and the anti-PTK7 CAR. This example tests the ability of the masked CAR T format would mitigate the toxicities observed with the unmasked anti-CAR T cells, and hence alleviate on-target/off-tissue toxicities.

The efficacy of anti-PTK7 CAR T cells and masked anti-PTK7 CAR T cells were tested in vivo using a human pancreatic Hs766T tumor xenograft mouse model. Mice were dosed with anti-PTK7 CAR T cells or masked anti-PTK7 CAR T cells when tumors (cell lines injected subcutaneous into right flank) reached an average of 55 mm$^3$. In the studies described herein, 5 female (5-8 weeks) NOG mice were dosed at a single time point IV with TRAC−/β2M−/anti-PTK7 CAR T cells, CTX181 or TRAC−/β2M−/masked anti-PTK7 CAR T cells, CTX181.P1 (generated as previously described above), at two dose levels ($1\times10^7$ cells/mouse and $3\times10^6$ cells/mouse). Body weight (recorded daily for first 9 days post dosing, then 2× weekly) and tumor volume were measured. Studies were terminated when tumors reached endpoint size (2000 mm$^3$ for Hs766T) or 90 days, whichever occurred first. Mice were housed and monitored under pathogen free conditions and IACUC standards.

Figure 6A:
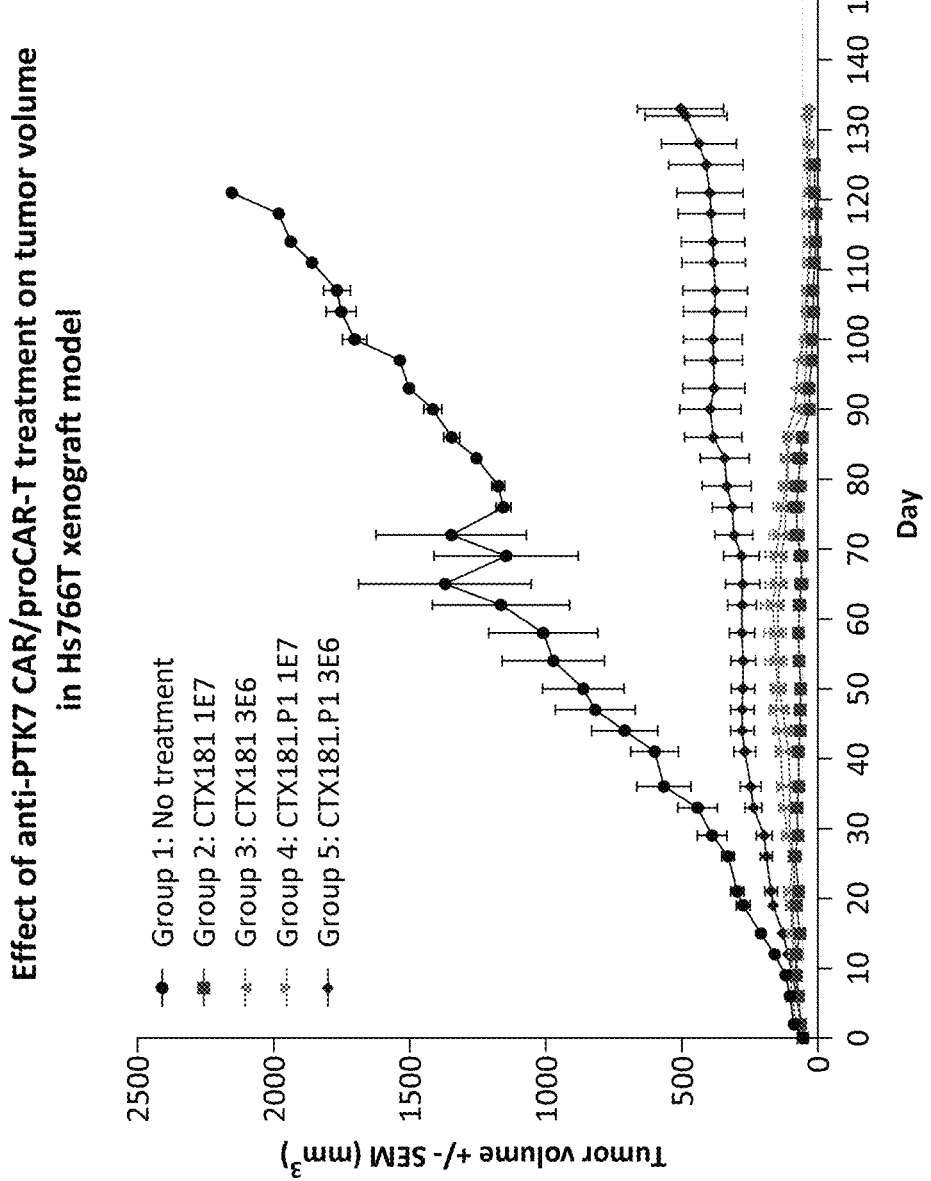
FIGS. 6A-6B includes graphs showing results from testing masked anti-PTK7 CAR T cells in a human pancreatic Hs766T tumor xenograft mouse model.
Figure 6B:
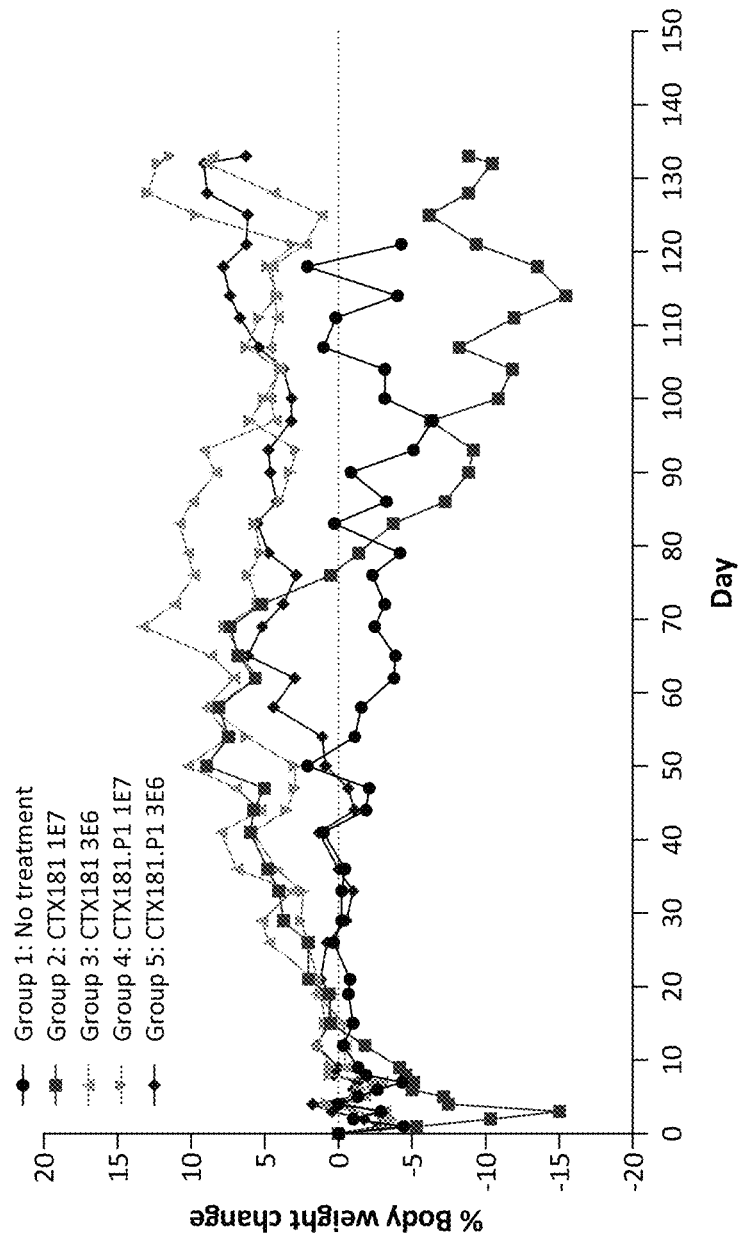

Both anti-PTK7 CAR T cells (CTX181) and masked anti-PTK7 CAR T cells (CTX181.P1) were efficacious in reducing tumor burden in the Hs766T pancreatic cancer xenograft model, with different dose levels showing varying degrees of potency (FIG. 6A). Unexpectedly, both higher and lower dose levels of masked anti-PTK7 CAR T cells were able to mitigate acute and latent toxicities observed with the higher dose of anti-PTK7 CAR T cells (CTX181), suggesting that the masked CAR strategy may be effective in reducing on-target/off-tissue toxicities (FIG. 6B).

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A masked chimeric antigen receptor (CAR) specific to tyrosine-protein kinase-like 7 (PTK7), the masked CAR comprising:
   (i) an extracellular antigen binding domain, which comprises a single chain variable fragment (scFv) that binds PTK7 and a mask peptide linked to the N-terminus of the scFv via a protease cleavage site; and
   (ii) one or more intracellular signaling domains,
      wherein the mask peptide comprises the amino acid sequence selected from the group consisting of:

(a)
   EVAPGKRWFYNHVKQVPHLV, (SEQ ID NO: 1)

(b)
   HEEVHMRPNKLSLTWAYTGPQLR, (SEQ ID NO: 2)

and (c) $X_1CX_2X_3X_4X_5X_6X_7X_8X_9X_{10}X_{11}X_{12}X_{13}$, in which $X_1$ is V, W, or absent; $X_2$ is T, H, or Y; $X_3$ is M, F, Y, I, or H; $X_4$ is P, G, or V; $X_5$ is P, N, S, Y, K, L, V, or A; $X_6$ is S, T, W, A, H, R, or Q; $X_7$ is P, T, V, H, I, M, A, F, or W; $X_8$ is R, M, A, H, V, Y, or absent; $X_9$ is S, Q, Y, T, P, A, M, or I; $X_{10}$ is K, R, I, C, S, Q, H, or absent; $X_{11}$ is V, T, R, L, F, W, or A; $X_{12}$ is I, F, L, W, or H; and $X_{13}$ is C, I, or M.

2. The masked CAR of claim 1, wherein the mask peptide comprises the amino acid sequence of (c), which is:

(c1)
   CTMPPSPRSKVIC, (SEQ ID NO: 3)

(c2)
   CTFPNTTMQRTFC, (SEQ ID NO: 4)

(c3)
   CTYPSWVAYIRFC, (SEQ ID NO: 5)

(c4)
   VCTYPPAHRTRFC, (SEQ ID NO: 6)

(c5)
   CTMPYHIHSIGLC, (SEQ ID NO: 7)

(c6)
   WCTIPSSMSIRLC, (SEQ ID NO: 8)

(c7)
   CHIGKRPVPCLWI, (SEQ ID NO: 9)

(c8)
   CYIGLRMVPCFHM, (SEQ ID NO: 10)

(c9)
   CTMPSHAVASFLC, (SEQ ID NO: 11)

(c10)
   CTMPVHTYSQWLC, (SEQ ID NO: 12)

(c11)
   CTYPPRFHMHWLC, (SEQ ID NO: 13)

or (c12)
   CTHVAQWAIKAFC. (SEQ ID NO: 14)

3. The masked CAR of claim 1, wherein the mask peptide is 13-25 amino acids in length.

4. The masked CAR of claim 1, wherein the mask peptide is:

(a)
   EVAPGKRWFYNHVKQVPHLV, (SEQ ID NO: 1)

(b)
   HEEVHMRPNKLSLTWAYTGPQLR, (SEQ ID NO: 2)

(c1)
   CTMPPSPRSKVIC, (SEQ ID NO: 3)

(c2)
   CTFPNTTMQRTFC, (SEQ ID NO: 4)

(c3)
   CTYPSWVAYIRFC, (SEQ ID NO: 5)

(c4)
   VCTYPPAHRTRFC, (SEQ ID NO: 6)

(c5)
   CTMPYHIHSIGLC, (SEQ ID NO: 7)

(c6)
   WCTIPSSMSIRLC, (SEQ ID NO: 8)

(c7)
   CHIGKRPVPCLWI, (SEQ ID NO: 9)

(c8)
   CYIGLRMVPCFHM, (SEQ ID NO: 10)

(c9)
   CTMPSHAVASFLC, (SEQ ID NO: 11)

(c10)
   CTMPVHTYSQWLC, (SEQ ID NO: 12)

(c11)
   CTYPPRFHMHWLC, (SEQ ID NO: 13)

or (c12)
   CTHVAQWAIKAFC. (SEQ ID NO: 14)

5. The masked CAR of claim 1, wherein the mask peptide is removable by protease cleavage at the protease cleavage site.

6. The masked CAR of claim 1, wherein the protease cleavage site is a cleavage site of a matrix metalloproteinase (MMP).

7. The masked CAR of claim 6, wherein the protease cleavage site is a MMP14 cleavage site, which comprises the motif of PLGLA (SEQ ID NO: 15).

8. The masked CAR of claim 1, wherein the mask peptide is linked to the protease cleavage site via a first peptide linker.

9. The masked CAR of claim 1, wherein the protease cleavage site is linked to the N-terminus of the heavy chain or the light chain of the anti-PTK7 antibody via a peptide linker.

10. The masked CAR of claim 8, wherein the first peptide linker is a G/S peptide linkers.

11. The masked CAR of claim 8, wherein the mask peptide is linked to the scFv that binds PFK7 in a formula of: $M-L_1-P-L_2$-scFv, in which M represents the mask peptide, $L_1$ and $L_2$ represents the first and second peptide linkers, and P represents the protease cleavage site.

12. The masked CAR of claim 1, wherein the scFv that binds PTK7 comprises a heavy chain variable domain ($V_H$), which comprises a $V_H$ CDR1 sequence of SEQ ID NO: 23, a $V_H$ CDR2 sequence of SEQ ID NO: 24, and a $V_H$ CDR3 sequence of SEQ ID NO: 25; and/or wherein the anti-PTK7 antibody comprises a light chain variable domain ($V_L$), which comprises a $V_L$ CDR1 sequence of SEQ ID NO: 26, a $V_L$ CDR2 sequence of SEQ ID NO: 27 and a $V_L$ CDR3 sequence of SEQ ID NO: 28.

13. The masked CAR of claim 12, wherein the scFv that binds PTK7 comprises a $V_H$ sequence of SEQ ID NO: 29 and a $V_L$ sequence of SEQ ID NO: 30.

14. The masked CAR of claim 12, wherein the extracellular antigen binding domain comprises the amino acid sequence selected from the group consisting of SEQ ID NOs: 120-134.

15. The masked CAR of claim 1, wherein the one or more intracellular signaling domains comprises a co-stimulatory domain, a CD3CΘ cytoplasmic signaling domain, or a combination thereof.

16. The masked CAR of claim 15, wherein the co-stimulatory domain is a CD28 co-stimulatory domain or a 4-1BB co-stimulatory domain.

17. The masked CAR of claim 15, which further comprises a transmembrane domain located between the extracellular antigen binding domain and the one or more intracellular signaling domains.

18. The masked CAR of claim 17, wherein the transmembrane domain is a CD8 transmembrane domain.

19. The masked CAR of claim 1, which further comprises a signal peptide at the N-terminus of the masked CAR.

20. The masked CAR of claim 1, which comprises the amino acid sequence selected from the group consisting of SEQ ID NOs: 106-119.

21. A nucleic acid, comprising a nucleotide sequence encoding a masked CAR of claim 1.

22. A genetically engineered T cell, comprising the nucleic acid of claim 21 and expressing the masked CAR encoded by the nucleic acid.

23. The genetically engineered T cell of claim 22, wherein the T cell further comprises a disrupted TRAC gene, a disrupted B2M gene, or a combination thereof.

24. The genetically engineered T cell of claim 21, wherein the T cell comprises a disrupted TRAC gene, in which the nucleic acid encoding the masked CAR is inserted, thereby disrupting expression of the TRAC gene.

25. The genetically engineered T cell of claim 23, wherein the T cell comprises a disrupted TRAC gene, which comprises a deletion of a fragment comprising the nucleic acid sequence of SEQ ID NO: 40.

26. The genetically engineered T cell of claim 25, wherein the nucleic acid encoding the masked CAR is inserted at the site of the deletion in the disrupted TRAC gene.

27. The genetically engineered T cell of claim 26, wherein the nucleic acid encoding the masked CAR replaces a fragment comprising SEQ ID NO: 40 in the disrupted TRAC gene.

28. A population of genetically engineered T cells, comprising T cells that express the masked CAR of claim 1.

29. A method for producing genetically engineered CAR-T cells, comprising:
    (a) delivering to T cells a nucleic acid encoding a masked CAR set forth in claim 1; and
    (b) producing genetically engineered CAR-T cells expressing the masked CAR.

30. A population of genetically engineered T cells, produced by a method of claim 29.

* * * * *